US012779177B2

(12) United States Patent
Jaros et al.

(10) Patent No.: US 12,779,177 B2
(45) Date of Patent: Nov. 3, 2026

(54) EXTENDED DWELL AND MIDLINE CATHETERS AND RELATED METHODS

(71) Applicant: B. Braun Melsungen AG, Melsungen (DE)

(72) Inventors: Dominik Jaros, Felsberg (DE); Helmut Freigang, Körle (DE); Guido Eikelmann, Baunatal (DE); Johannes Bolz, Kassel (DE); Lilian Zhi Ling Lew, Penang (MY); Teng Lip Khoo, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 1016 days.

(21) Appl. No.: 17/633,079

(22) PCT Filed: Aug. 28, 2020

(86) PCT No.: PCT/EP2020/074081
§ 371 (c)(1),
(2) Date: Feb. 4, 2022

(87) PCT Pub. No.: WO2021/038041
PCT Pub. Date: Mar. 4, 2021

(65) Prior Publication Data

US 2022/0331562 A1 Oct. 20, 2022

Related U.S. Application Data

(60) Provisional application No. 62/893,382, filed on Aug. 29, 2019.

(51) Int. Cl.

| | |
|---|---|
| ***A61M 25/06*** | (2006.01) |
| ***A61M 5/14*** | (2006.01) |
| ***A61M 25/00*** | (2006.01) |

(52) U.S. Cl.
CPC .......... *A61M 25/0606* (2013.01); *A61M 5/14* (2013.01); *A61M 25/0009* (2013.01);
(Continued)

(58) Field of Classification Search
CPC .......... A61M 25/0606; A61M 25/0009; A61M 25/0017; A61M 25/0023; A61M 25/0043;
(Continued)

(56) References Cited

U.S. PATENT DOCUMENTS

| | | |
|---|---|---|
| 5,704,914 A | 1/1998 | Stocking et al. |
| 6,749,588 B1 | 6/2004 | Howell et al. |

(Continued)

FOREIGN PATENT DOCUMENTS

| | | |
|---|---|---|
| AU | 2020338266 B2 | 11/2025 |
| CN | 101104094 A | 1/2008 |

(Continued)

OTHER PUBLICATIONS

China Application No. 202080075730.1, Second Office Action dated Jul. 8, 2024, pp. 1-15.

(Continued)

*Primary Examiner* — Tasnim Mehjabin Ahmed
(74) *Attorney, Agent, or Firm* — Alumen IP Law PC

(57) ABSTRACT

Extended dwell catheter assemblies each with a housing having an interior having a catheter assembly located therein, which can include a catheter tube and a needle. The catheter tube of the catheter assembly can be placed into a vein of a patient, with or without a guidewire, and then the extended dwell catheter assembly can be activated to separate into two or more housing components or by opening a gate to enable separation of the catheter assembly from the housing. A needle guard can be included to cover the needle tip of the needle from unintended needlesticks.

27 Claims, 78 Drawing Sheets

(52) U.S. Cl.
CPC .... *A61M 25/0017* (2013.01); *A61M 25/0023* (2013.01); *A61M 25/0043* (2013.01); *A61M 25/0068* (2013.01); *A61M 25/0084* (2013.01); *A61M 25/0097* (2013.01); *A61M 25/0612* (2013.01); *A61M 25/0618* (2013.01); *A61M 25/0693* (2013.01)

(58) Field of Classification Search
CPC .......... A61M 25/0068; A61M 25/0084; A61M 25/0097; A61M 25/0612; A61M 25/0618; A61M 25/0693; A61M 5/14
See application file for complete search history.

(56) References Cited

U.S. PATENT DOCUMENTS

| | | | |
|---|---|---|---|
| 8,465,441 B2 | 6/2013 | Srivatsa et al. | |
| 2006/0100585 A1 | 5/2006 | Wang | |
| 2007/0270758 A1 | 11/2007 | Hanner et al. | |
| 2018/0133438 A1* | 5/2018 | Hulvershorn | A61M 25/0606 |
| 2018/0154112 A1 | 6/2018 | Chan et al. | |

FOREIGN PATENT DOCUMENTS

| | | | |
|---|---|---|---|
| CN | 107073242 | A | 8/2017 |
| CN | 107205704 | A | 9/2017 |
| CN | 108136160 | A | 6/2018 |
| DE | 90 03 085 | U1 | 5/1990 |
| DE | 0545671 | A1 | 6/1993 |
| EP | 3693051 | A1 | 8/2020 |
| JP | 2013-529111 | A | 7/2013 |
| KR | 101814552 | B1 | 1/2018 |
| TW | 201700121 | A | 1/2017 |
| WO | 2011/143621 | A1 | 11/2011 |
| WO | WO 2016/187063 | A1 | 11/2016 |
| WO | WO 2018/157339 | A1 | 9/2018 |
| WO | WO 2018/170349 | A1 | 9/2018 |
| WO | WO 2019/124422 | A1 | 6/2019 |

OTHER PUBLICATIONS

International Preliminary Report on Patentability (Chapter I) on corresponding PCT application (PCT/EP2020/074081) from International Searching Authority (EPO) dated Mar. 10, 2022.
JP Patent Application No. 2022-513333 First Office Action (dated May 14, 2024).
Japanese Patent Application No. 2022-513333, Decision of Rejection dated Feb. 25, 2025, pp. 1-3.
Singapore Patent Application No. 11202201221T, Written Opinion dated Nov. 28, 2024, pp. 1-8.
International Search Report and Written Opinion on corresponding PCT application (PCT/EP2020/074081) from International Searching Authority (EPO) dated Dec. 17, 2020.
China Application No. 202080075730.1, Notification to Grant, dated Sep. 13, 2024, pp. 1-7.
Second Written Opinion for Singaporean Patent Application 11202201221T (dated Feb. 26, 2026).
Examiner's Report, JP Patent Application No. 2022-513333, dated Sep. 9, 2025, pp. 1-4.
First Examination Report, AU Patent Application No. 2020338266, dated Jun. 26, 2025, pp. 1-3.
Notification of Reasons for Refusal, JP Patent Application No. 2025-104620, dated Jan. 6, 2026, pp. 1-9.
EP Patent Application No. 20 767 987.9, Office Action dated Mar. 20, 2025, pp. 1-9.

* cited by examiner

EXTENDED DWELL AND MIDLINE CATHETERS AND RELATED METHODS

FIELD OF ART

The disclosed invention generally relates to needle devices and intravenous (IV) infusion devices, including IV catheters. In particular, IV catheter assemblies having a one-handed operation for actuation are disclosed.

BACKGROUND

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing to the catheter. Blood control catheters include an internal blood control valve that is opened by the insertion of a male Luer or another object into a proximal end of the catheter adapter. Non-limiting examples of blood control valves are disclosed in United States Patent Application Publication No. 2011/0046570, filed Aug. 20, 2009, titled "Systems and Methods for Providing a Flushable Catheter Assembly." Following placement of the catheter into the vasculature of a patient, an IV fluid source can be connected to the catheter adapter or catheter hub, opening the blood control valve. Thus connected, fluid from the IV source can begin flow into a patient through the catheter.

As is well known in the art, typical blood pressure is 10 to 20 centimeters of water. Infusion bags are usually placed about 100 cm above the patient's heart to direct flow into the patient. At roughly that height, the pressure exerted by the fluid from the infusion bag is much greater than the blood pressure of the patient and therefore can flow into the patient.

For patients with different to access veins, extended dwell catheters can be used to aid in Difficult Intravenous Access (DIVA). An extended dwell catheter is a midline catheter that may be considered a peripherally inserted catheter. However, a typical midline catheter is configured to be inserted in a larger vein than those used for standard I.V. therapy. The recommended insertion site for the midline catheter is the basilic, cephalic, or median vein in the antecubital fossa. For DIVA patients, a physician can use visualization equipment to aid in identification of deep veins for catheter access. In that case, an extended dwell catheter will provide a longer length and a more flexible catheter for insertion into the patient. With the addition of a guidewire, this can help to reduce the chances of the catheter becoming kinked.

SUMMARY

Extended dwell catheter assemblies are described. Each extended dwell catheter assembly comprises a housing having an interior having a catheter assembly located therein, which can comprise a needle, needle hub, catheter, and catheter tube. The catheter tube of the catheter assembly can be placed into a vein of a patient, with or without a guidewire, and then the extended dwell catheter assembly can be activated to separate the housing into two or more housing components to enable separation of the catheter assembly from the housing. A needle guard can be included with the catheter assembly to cover the needle tip of the needle from unintended needlesticks.

An extended dwell catheter assembly in accordance with aspects of the invention can comprise: a housing comprising a first frame attached to a second frame and having an interior space, said housing having a distal opening and a proximal opening; a catheter assembly located in the interior space of the housing, said catheter assembly comprising a catheter tube attached to a catheter hub and a needle attached to a needle hub, wherein the needle and the catheter hub project out the distal opening of the housing and the needle hub projects out the proximal opening of the housing, and wherein the catheter hub is slidable within the interior space of the housing from a proximal position to a distal position within the interior space; an upper seam located between the first frame and the second frame along a first side and a lower seam located between the first frame and the second frame along a second side; and wherein the first frame and the second frame are separable from one another along the upper seam and the lower seam. The upper seam is located above, elevation-wise, the lower seam.

The catheter hub can comprise an interior cavity and wherein a needle guard can be located in the interior cavity of the catheter hub.

The needle guard can include a proximal and two arms. The two arms can intersect one another in a ready to use position and an activated position or protected position when viewing the needle guard from a side.

A valve and a valve opener can be located inside the interior of the catheter hub.

The second frame can comprise a plurality of male detents and wherein each detent comprises a tip pointing in a distal direction.

The second frame can comprise a plurality of male detents and wherein each detent can comprise a tip pointing in a proximal direction.

The first frame and the second frame can have lower wall structures that engage one another along respective joining edges.

The first frame and the second frame can to wall structures that do not join to define a lengthwise housing opening.

The distal opening of the housing can be round can be formed from two partial cutouts, one cutout formed from the first frame and one cutout formed from the second frame.

The needle hub can have a flange extension located in an opening of the housing and an edge of the opening can limit distal movement of the needle hub.

The needle hub can have a flange defining a plane that is located orthogonally to the needle, and wherein the flange is located in a channel of the housing.

The housing can comprise a base end and wherein the base end can comprise a plurality of sides. The plurality of sides can define a square or a rectangular shape when viewing along an end view.

The housing can separate into a first frame and a second from. The first frame and the second frame can separate by separating male detents from female receiving slots or female engagement slots.

The first frame and second frame can separate from one another by applying a compressive force on a first or top lever and applying a proximally directed force concurrently while applying a compressive force on a bottom lever and applying a distally directed force.

The first frame and the second frame can separate from one another, or at least the proximal ends of the first frame and the second frame can separate from one another, by sliding a catheter hub along a distal direction within the interior space of the housing to push against one or two activation ramps located within the interior space.

The first frame can comprise a plurality of engagement slots sized and shaped to receive a plurality of male detents.

A first lever and a second lever can be provided with the housing, the first and second levers can project from different surfaces of the housing.

The first lever can attach to a three-sided cutout on the second frame.

The second lever can comprise a curved proximally facing surface.

The second frame can comprise a plurality of slots and the first frame can comprise a plurality of tabs.

The plurality of tabs can engage the plurality of slots. The engagement can be friction fit or interference fit. The engagement can comprise a positive engagement.

The first frame can comprise an end cap component comprising a tab and the second frame can comprise a recess, and wherein the tab of the end cap component can engage the recess.

The end cap component located at the distal end of the first frame can be understood as a gate that can close to hold a catheter hub inside the housing and that can swing open to allow the catheter hub to separate from the housing. Similarly, an end cap component can locate at the distal end of the second frame and can be understood as a gate that can close to hold a catheter hub inside the housing and that can swing open to allow the catheter hub to separate from the housing. Together, the two gates on the two frames can both open to crease a large access opening to enable the catheter hub to separate from the housing. The two gates are rotatable or pivotable about the living hinges.

The recess of the second frame can be located on an end cap component.

The end cap component of the first frame can attach to a wall of the first frame by a living hinge.

The end cap component of the second frame can attach to a wall of the second frame by a living hinge.

The housing can have two living hinges including a first living hinge and a second living hinge, the first frame can swing about the first living hinge and the second frame can swing about the second living hinge.

A further aspect of the invention incudes an extended dwell catheter assembly comprising: a housing comprising a first frame attached to a second frame and having an interior space, said housing having a distal opening and a proximal opening; a catheter assembly located in the interior space of the housing, said catheter assembly comprising a catheter tube attached to a catheter hub and a needle attached to a needle hub, wherein the needle and catheter hub project out the distal opening of the housing and the needle hub projects out the proximal opening of the housing, and wherein the catheter hub is slidable within the interior space of the housing from a proximal position to a distal position within the interior space; and a first lever projects in a first radial direction of the housing and a second lever projects in a second radial direction of the housing, said second radial direction being opposite the first radial direction.

A plurality of male detents can attach to a plurality of engaging sockets to secure the first frame to the second frame.

A still yet further aspect of the invention is an extended dwell catheter assembly comprising: a housing comprising a first frame attached to a second frame and having an interior space, said housing having a distal opening and a proximal opening; a catheter assembly located in the interior space of the housing, said catheter assembly comprising a catheter tube attached to a catheter hub and a needle attached to a needle hub, wherein the needle and catheter hub project out the distal opening of the housing and the needle hub projects out the proximal opening of the housing, and wherein the catheter hub is slidable within the interior space of the housing from a proximal position to a distal position within the interior space; a first end cap component attached to a wall of the first frame by a first living hinge; and a second end cap component attached to a wall of the second frame by a second living hinge.

A plurality of tabs can engage a plurality of slots to secure the first frame to the second frame.

A tab adapter having a body, a channel, a first opening, and a second opening can be provided for use with a catheter hub. The tab adapter can attach to an exterior of the catheter hub.

A push tab of a catheter hub can be located inside an interior of a body of a tab adapter.

An extended dwell catheter assembly comprising: a housing comprising a first frame attached to a second frame and having an interior space, said housing having a distal opening and a proximal opening; a catheter assembly located in the interior space of the housing, said catheter assembly comprising a catheter tube attached to a catheter hub and a needle attached to a needle hub, wherein the needle and the catheter tube project out the distal opening of the housing and the needle hub projects out the proximal opening of the housing, and wherein the catheter hub is slidable within the interior space of the housing from a proximal position to a distal position within the interior space; an upper seam located between the first frame and the second frame along a first side of the housing and a lower seam located between the first frame and the second frame along a second side of the housing; and wherein the first frame and the second frame are separable from one another along the upper seam and the lower seam. The upper seam is located above, elevation-wise, the lower seam.

An extended dwell catheter assembly comprising: a housing comprising a first frame attached to a second frame and having an interior space, said housing having a distal opening and a proximal opening; a catheter assembly located in the interior space of the housing, said catheter assembly comprising a catheter tube attached to a catheter hub and a needle attached to a needle hub, wherein the needle and catheter tube project out the distal opening of the housing and the needle hub projects out the proximal opening of the housing, and wherein the catheter hub is slidable within the interior space of the housing from a proximal position to a distal position within the interior space; and a first lever projects in a first radial direction of the housing and a second lever projects in a second radial direction of the housing, said second radial direction being opposite the first radial direction.

An extended dwell catheter assembly comprising: a housing comprising a first frame attached to a second frame and having an interior space, said housing having a distal opening and a proximal opening; a catheter assembly located in the interior space of the housing, said catheter assembly comprising a catheter tube attached to a catheter hub and a needle attached to a needle hub, wherein the needle and catheter tube project out the distal opening of the housing and the needle hub projects out the proximal opening of the housing, and wherein the catheter hub is slidable within the interior space of the housing from a proximal position to a distal position within the interior space; a first end cap component attached to a wall of the first frame by a first living hinge; and a second end cap component attached to a wall of the second frame by a second living hinge.

A still further aspect of the invention is an extended dwell catheter assembly comprising: a housing comprising a first frame and a second frame and having an interior space, said housing having a distal opening and a proximal opening; a catheter assembly located in the interior space of the housing, said catheter assembly comprising a catheter tube attached to a catheter hub and a needle attached to a needle hub, wherein the needle and catheter tube project out the distal opening of the housing and the needle hub projects out the proximal opening of the housing in a read to use position.

Wherein the catheter hub is slidable within the interior space of the housing from a proximal position to a distal position within the interior space.

A gate assembly comprising first gate and a second gate, wherein the first gate has a key fitted into an opening of the first frame and the second gate has a key fitted into an opening of the second frame.

The first gate can be pivotable or rotatable about a hinge and the second gate can be pivotable or rotatable about a hinge. The hinge can be a living hinge. Both hinges can be living hinges.

The key that is fitted into the opening of the first frame can have a gate sidewall and a flange. There can be more than one flange extending from a planar surface of the gate sidewall to define the gate.

The two keys can be located on opposite sides of a nose end having a bore. The opposite sides can be understood as being on different sides of an axis defined by the bore.

The opening on the frame that the key is fitted into can be formed by a first wall slab and a second wall slap. Each of the two wall slaps can have edges. The two wall slabs can connect along one or more of the edges. At least one edge on one wall slap can connect directly to the other edge of the other wall slap. Two of the edges, one on each wall slap for a total of two, can connect via a rib. One of the first and second wall slabs can be shaped, such as having angles, curves, a contour etc., and not merely a planar wall.

A tab adapter comprising a body having a first opening, a second opening, and a channel, and wherein the tab adapter can connect to the catheter hub. For example, the tab adapter can straddle the exterior of the catheter hub. The catheter hub can be located at least partially within the channel of the tab adapter. A push tab on the catheter hub can project into an interior of the tab adapter. The tab adapter can have a shaped proximally facing surface. The shaped proximally facing surface can resemble a curved ramp. Optionally, it can resemble a straight ramp. The shaped surface can provide a convenient contact point for a user or practitioner to push against to move the catheter hub from a proximal position to a distal position within the interior of the housing. Projections or gripping features can provide on the proximally facing surface.

The distally facing surface of the tab adapter can have a curved or contoured surface. The shaped distally facing surface can resemble a curved ramp. Optionally, it can resemble a straight ramp. Optionally the surface can include projections or gripping features.

A top surface and two side surfaces of the distally facing surface can converge to a tip. The tip can be a narrow tip. The tip can have an end tip. The end tip can have an arrow shape. The end tip can be used to push against a gate assembly. The end tip can push against an abutting edge of the gate assembly. The abutting edge of the gate assembly can have two adjacent edges having a seam therebetween. The two adjacent edges can separate at the seam, such as when pushed by the end tip.

An extension having a narrow tip can be provided for use with the end tip of the distally facing surface of the tab adapter. The extension and the end tip of the distally facing surface can be called an actuating end. The end tip of the extension can have an arrow shape. The end tip of the extension can be distal of the end tip of the distally facing surface. The extension can be located below, elevation-wise, the distally facing surface.

The tab adapter can have to side surface portions. The two side surface portions can define a width of the tab adapter. The width can be thought of as being orthogonal to the lengthwise direction of the tab adapter. A projection can extend from the surface of each of the two side surface portions. Each projection can further push against the gate assembly after the two gates of the gate assembly are opened by the actuating end.

The body of the tab adapter can comprise an actuating end comprising a tip end.

The tip end can locate at a distal end of a distally facing surface, and wherein the tab adapter can further comprise an extension having a tip end located below, elevation-wise, the tip end of the distally facing surface.

The gate assembly can comprise two adjacent edge sections bisected by a seam and defining an abutting edge. The two adjacent edge sections can separate at the seam.

The gate assembly comprises a hook arm engaging a female detent. The hook arm can be located on the first gate and the female detent located on the second gate. The arrangement can reverse. The hook arm can have a stem, rod, or stub-like structure with a notch or curve at an end forming the hook arm.

The first gate can attach to the second gate by a tie strip. The tie strip can be omitted.

Each gate can have a male detent or a stub for frictionally engaging a receiving slot on the opposite gate. Each gate can have both a male detent or a stub and a receiving slot.

A cylindrical nose section can be provided on the gate assembly defining a bore.

The gate assembly can have a base wall having a guide opening. The guide opening can have a smaller diameter than the diameter of the bore. The guide opening can support a catheter tube having a needle located inside the lumen of the catheter tube.

A still further aspect of the invention is an extended dwell catheter assembly comprising: a housing comprising a first frame attached to a second frame and having an interior space, said housing having a distal opening and a proximal opening; a catheter assembly located in the interior space of the housing, said catheter assembly comprising a catheter tube attached to a catheter hub and a needle attached to a needle hub, wherein the needle and the catheter tube project out the distal opening of the housing and the needle hub projects out the proximal opening of the housing, and wherein the catheter hub is slidable within the interior space of the housing from a proximal position to a distal position within the interior space; an upper seam located between the first frame and the second frame along a first side of the housing and a lower seam located between the first frame and the second frame along a second side of the housing, the upper seam located above, elevation-wise, the lower seam; and wherein the first frame and the second frame are separable from one another along the upper seam and the lower seam.

The catheter hub can comprise an interior cavity and wherein a needle guard comprising a proximal wall and two arms can be located in the interior cavity of the catheter hub.

The first frame or the second frame can comprise a plurality of tabs and the other one of the first frame or the second frame can comprise a plurality of receiving slots engaging the plurality of tabs.

The housing can comprise a base end comprising a plurality of side walls. There can be four side walls defining a square or a rectangular cross-section. In other examples, the base end can have a round or oval cross-section.

A first lever and a second lever can be provided with the housing, the first and second levers can project from different surfaces of base end of the housing. The projection of the first and second levers can be radial of a lengthwise axis of the housing.

The first lever can be attached to a three-sided cut-out on the second frame.

The second lever can comprise a curved proximally facing surface.

The housing can comprise a body opening and wherein a push tab on the catheter hub can be located in the body opening.

The push tab can slide from a proximal position to a distal position within the body opening.

The first lever and the second lever can move relative to one another to separate the first frame and the second frame.

The first frame can comprise a gate having a living hinge and the second frame can comprise gate having a living hinge.

A tab can engage a recess to engage the two end cap components together.

The first frame can have an activation structure and the second frame can have an activation structure and wherein a gap defined by the two activation structures can be sized and shaped to be pushed by the catheter hub to separate the first frame from the second frame.

A tab adapter can be fitted around the catheter hub.

The tab adapter can be fitted over a push tab on the catheter hub.

A guidewire assembly with a guidewire can extend through the needle.

Aspects of the invention can further include a method of manufacturing an extended dwell catheter assembly. The method can comprise: forming a housing, the housing comprising a first frame attached to a second frame and having an interior space, said housing having a distal opening and a proximal opening, an upper seam located between the first frame and the second frame along a first side of the housing and a lower seam located between the first frame and the second frame along a second side of the housing, the upper seam located above, elevation-wise, the lower seam; placing a catheter assembly in the interior space of the housing, said catheter assembly comprising a catheter tube attached to a catheter hub and a needle attached to a needle hub, wherein the needle and the catheter tube project out the distal opening of the housing and the needle hub projects out the proximal opening of the housing, and wherein the catheter hub is slidable within the interior space of the housing from a proximal position to a distal position within the interior space; and wherein the first frame and the second frame are separable from one another along the upper seam and the lower seam.

The first frame and the second frame can be separable by moving the first frame in a first direction and the second frame in a second direction.

The first frame and the second frame can be separable by advancing the catheter hub in a distal direction to push apart two activation structures located inside the interior space of the housing.

The catheter hub is separable from the housing by displacing two end cap components about two living hinges.

A still yet further aspect of the invention is an extended dwell catheter assembly comprising: a housing comprising a first frame attached to a second frame and having an interior space, said housing having a distal opening and a proximal opening; a catheter assembly located in the interior space of the housing, said catheter assembly comprising a catheter tube attached to a catheter hub and a needle attached to a needle hub, wherein the needle and the catheter tube project out the distal opening of the housing and the needle hub projects out the proximal opening of the housing, and wherein the catheter hub is slidable within the interior space of the housing from a proximal position to a distal position within the interior space; and a gate assembly attached to the housing, the gate assembly comprising a first gate attached to a living hinge and a second gate attached to a living hinge; wherein the two gates are rotatable about the two living hinges to open the two gates for separating the catheter assembly from the housing.

A tie strip can connect the two gates together.

The gate assembly can comprise a key comprising a flange for attaching to a slot on the housing.

Unless a component or structure is described as critical or essential, it may be practiced as optional or with alternatives.

Broadly speaking, extended dwell ("ExD") catheter assemblies described herein each comprises a housing and a catheter assembly. The housing is configured to accommodate the catheter assembly during initial puncture, through catheter advancement, through separation of the catheter hub from the needle hub, and then activating to enable separation of the catheter hub from the housing and allowing the catheter to remain with the patient. Thus, in a ready to use position, the needle tip and catheter tube of the catheter assembly can project out a distal end of the housing and needle hub, or at least the air vent connected to the needle hub, can extend out a proximal opening of the housing.

The housing and the catheter hub can separate through a variety of different mechanisms. For example, the housing can split into two or more housing parts to release the catheter hub, the housing can have parts that swing, rotate or pivot, the housing can have end cap components that swing open to open a gate opening at a distal end of the housing to allow the catheter hub to exit the housing, and the housing can have a gate assembly that attaches to the distal end of the housing and the gate assembly can have one or more gates that swing about a hinge to open, among other options.

The gate assembly can have two gates located on two gate housing bodies that can join and wherein each gate can swing open via a living hinge. The two gates can engage one another during initial assembly with the housing via male detents and receiving slots. The two gates can engage via a hook arm and a female detent. The hook arm and the female detent can be in addition to the male detents and receiving slots or as an alternative.

The unique housing designs allow for use with standard or existing catheter assemblies without the need for, although optional, specifically designed catheters. Thus, standard catheters with extended catheter lengths and midline catheters with approximately 8-10 cm catheter lengths are readily usable with the housings of the present disclosure, with or without a guidewire. The catheters can be supported during cannulation and vascular access by a guide opening. As the catheter hub moves distally to place the catheter tube into the patient, the structure or structures defining the guide opening can separate to allow the catheter hub to pass, as further discussed below. The guide opening can separate by separating the housing into two or more frames or frame sections. The guide opening can separate by opening two gates of a gate assembly located with the housing. The gate assembly can be unitarily formed with the housing or can be separately formed and subsequently attached to the housing.

In an example, the extended dwell or ExD catheter assembly in accordance with aspects of the present invention comprises a housing having a receiving space or interior space having a catheter assembly located therein, which has a catheter tube and a needle located inside the lumen of the catheter tube and extending out a distal end or distal opening of the housing. The catheter hub can be a standard catheter with extended catheter lengths or a midline catheter.

A needle tip of the needle can extend out a distal opening of the catheter tube. The catheter tube can attach to a catheter hub, such as with a bushing or a ferule, and the needle can attach to a needle hub.

The needle hub can extend out a proximal end of the housing. The needle hub can include a vent plug, which can engage the proximal opening of the needle hub, such as in a Luer fit. The vent plug can have a vent filter that allows air to purge but not blood.

Optionally, a guide wire may be incorporated to assist in inserting, positioning, and moving the catheter tube of the ExD catheter assemblies in accordance with aspects of the present invention, as further discussed below.

In an example, the catheter assembly can comprise a first hub or catheter hub having an over-the-needle tube or catheter tube attached thereto and a second hub or needle hub having a needle attached thereto. The first hub or catheter hub can be one-hub structure with a distal opening attached to the catheter tube and a proximal opening having a female Luer. Optionally, the catheter hub can be formed from two hub bodies attached together with one of the two hub bodies having a female Luer.

The catheter tube has a lumen or bore for receiving the needle and has a distal opening or distal end opening and the needle tip of the needle extends distally of the distal opening in a ready to use position, in which the assembly is ready for venipuncture. The catheter assembly used with the housing can also be called a needle assembly as it incorporates a needle with a needle tip.

The needle can include a change in profile located proximally of the needle tip for use with a needle guard. The needle tip extends distally of the distal end opening of the catheter tube or tubing in the ready to use position with the change in profile, if incorporated for use with a needle guard, located proximally of the distal end opening of the catheter tube. The change in profile can be a crimp, a bump, or a material build-up having different profile than other diameter sections of the needle shaft. As used herein, the term proximal is understood to mean an end or side closer to the practitioner and the term distal is the opposite end or side.

The change in profile can be used to interact with a needle guard during retraction of the needle following successful venipuncture, as further discussed below. A vent plug is disposed at the proximal open end of the second hub or needle hub. The vent can have a vent filter at a proximal end thereof, which is conventional. The catheter tube is attached to the first hub or catheter hub by a ferrule or bushing.

The needle guard can be provided in the interior cavity of the first hub or catheter hub for covering the needle tip in the protective position. When incorporated, the needle guard can be one of the needle guards disclosed in U.S. Pat. No. 6,616,630, the contents of which are expressly incorporated herein by reference. In some examples, the needle guard can be omitted. If so, the change in profile on the needle can also be omitted.

In still other examples, a needle guard can be included without also including a change in profile on the needle. In yet other examples, the needle guard can be located in a third housing between the first hub and the second hub. An exemplary needle guard located in a third housing is disclosed in U.S. Pat. No. 8,597,249, the contents of which are expressly incorporated herein by reference. In still other examples, the needle guard can include multiple arms or fingers extending in both a first direction and an opposite second direction as disclosed in U.S. Pat. No. 9,387,307, the contents of which are expressly incorporated herein by reference. For example, the needle guard can include a first protector body surrounded by a second protector body.

In an example, the needle guard can be made from a metal material and can have a resilient portion that can generate a biasing force. The needle guard can comprise a wall surface that is positioned to a side of the needle and is movable distal of the needle tip to guard the needle tip from accidental contact therewith. The wall surface can be a needle trap and can move directly in front or distal of the point of the needle tip.

The needle guard can include a proximal wall and two arms extending distally of the proximal wall. The two arms can intersect one another in the ready to use position and in the protective position in which the needle guard covers the needle tip, as viewed from a side. In some examples, the two arms of the needle guard can extend in a distal direction without intersecting one another.

Two distal walls, one on each arm, can be incorporated to block the needle tip. The two distal walls can be biased outwardly by the needle in the ready to use position and disposed distally of an internal change in profile inside the first hub in the ready to use position. The internal change in profile inside the catheter hub can be a reduced diameter section located next to an inside diameter section of a larger dimension. The elbows on the two arms of the needle guard can have a dimension that is larger than the inside diameter at the internal change in profile to restrict proximal movement of the needle guard from the catheter hub until the two arms are no longer biased outwardly or until the dimension at the two elbows are reduced.

Each distal wall of each arm can include a curved lip to facilitate relative movement between the needle guard and the needle. When in the ready to use position, the dimension measured between the two joints or elbows, at the intersection between each arm and its respective distal wall, can be larger than the inside diameter of the internal change in profile, which can prevent the needle guard from moving proximally thereof due to the relative dimensions. Once the needle tip moves proximally of the two distal walls, the two arms can be allowed to move radially inward and one or both distal walls can close over the needle tip to block the needle tip in a protective position. At this point, the dimension between the two joints or elbows can decrease and is smaller than the internal dimension of the internal change in profile inside the catheter hub, which then allows the needle guard to move proximally and be removed from the catheter hub with the needle. In alternative embodiments, the dimension between the two joints or elbows can be equal to or slightly larger than the internal dimension of the internal change in profile and the needle can still move proximally by flexing or squeezing the two joints to get through the internal change in profile.

The first hub or catheter hub can have a proximal opening having a nose section of the second hub or needle hub disposed therein. The proximal opening of the first hub can have a female Luer for receiving a male Luer tip, such as a syringe, an IV tubing connector, a Luer extension set, etc. External threads can be provided on the exterior surface at the proximal end of the catheter hub for threaded engagement with a threaded collar of a male threaded Luer tip.

A pair of stabilizing wings can extend radially of the first hub to facilitate securement or anchoring of the first hub to a patient following successful venipuncture. Optionally the wings can be omitted. The first hub can embody a standard IV catheter hub without an injection port. In other examples, the first hub can include an injection port or an integrated extension set. If the wings are not present on the first hub or catheter hub, then the bottom of the first hub can have a flattened surface angled at between 2 to 15 degrees from the through axis of the first hub.

The first hub can be removably secured to the second hub by receiving the nose section of the second hub in the proximal opening thereof. A flange or extension can be provided on the second hub and together with the nose section define a gap having part of the first hub located therein.

Optionally the flange or extension can be omitted, and a stub or other surface mating features provided. The stub can be the male part of a key fitting in a gap through or partially into the Luer threads to prohibit rotation of the second hub relative to the first hub. The proximal facing end surface of the first hub abuts the distally facing surface of the step in the outside surface of the second hub which is at the proximal end of the nose section, which is inside the first hub. This abutment can set the amount of protrusion of the needle tip out of the catheter tubing. The stub can be an optional structural feature.

The second hub can have a body having an optional interior cavity having the proximal end of the needle projecting there-into. The interior cavity can function as a primary blood flashback chamber. The proximal opening of the body can have a female Luer for receiving the vent plug or a syringe tip therein and the exterior can have threads or be without threads. In an example, the exterior of the body of the second hub is generally cylindrical and without threads. The first and second hubs can be made from plastic materials, such as by plastic injection.

A push tab can be provided with the first hub or catheter hub. The push tab can be located on an exterior surface of the first hub at a location distal of the exterior threads so as to avoid interfering with the exterior threads. For example, the push tab should be positioned sufficiently distally of the exterior threads and generally at the 12 o'clock position of the catheter hub so that when a threaded male connector, such as a syringe type with a threaded collar, is connected to the threads of the first hub, the push tab does not interfere with the connection. In some examples, the push tab should be positioned sufficiently distally of the exterior threads so that when the push tab is folded over, the push tab does not interfere with the connection.

In some examples, the catheter assembly can incorporate a valve and a valve opener. For example, a valve and a valve opener can both be located within the catheter hub. In use, the valve opener can be pushed distally into the valve to open the one or more slits formed with the valve to open a fluid passage through the valve for fluid flow. An exemplary valved catheter assembly with a valve and a valve opener is disclosed in U.S. Pat. No. 8,333,735, the contents of which are expressly incorporated herein by reference.

The valve opener can have a nose section having a bore and a plunger section located proximally of the nose section. The nose section can be pushed into the valve to open the one or more slits of the valve, such as three slits defining three flaps. The plunger section can comprise two or more plunger components having a gap therebetween. The gap can allow fluid to flow through the plunger components and through the bore in the nose section.

A housing in accordance with aspects of the present ExD catheter assembly comprises a left frame or first frame and a second frame or right frame attached to one another. Each frame comprises a nose portion, a body portion, and a base portion. The two nose portions can join to form a nose end, the two body portions can join to form a body, and the two base portions can join to form a base end.

In an example, the nose end or nose portion is provided with a nose tip having an elongated cylindrical like structure having a bore for accommodating the catheter tube and needle, which is located within the catheter tube. The nose end or nose portion can further include a nose base, which has an enlarged portion formed with the tip, and a tapered distal portion.

A plurality of support ribs or fins can be provided at the intersection between the tip and the nose base of the housing. In other examples, the nose end can be a spherical or rounded dome having an opening to accommodate the catheter tube and needle.

The body of the housing can have an interior space for accommodating a catheter assembly, which can be a catheter assembly as described with reference to FIG. 2 and elsewhere. A body opening or first opening opens into the interior space. The body opening can extend from the nose end to the base end. The body opening can be located between two upper edges of the first and second frames.

In an example, a second opening opposing the first opening can be provided with the body so that the interior space can be accessed from the two body openings. Thus, the body therefore can have a through passage, between the distal end and the proximal end of the housing, defined by the two body openings. In other examples, the body only has a single opening leading to the interior space with the opposing side of the body being solid or is enclosed by wall surfaces of the first frame and the second frame.

When the housing incorporates a single body opening, the opening can be located at the top of the housing, elevation-wise, to allow for viewing by the user as the ExD catheter assembly is being used. Optionally the enclosed side can have small windows or openings for access or venting but not a full opening, like that of the single body opening.

The base or base end of the housing can extend from the body and can have a plurality of sides. The plurality of sides can define a base with a polygonal cross-section. In an example, the base can have four sides defining an interior space, which is open to the interior space of the body. In other examples, the base or base end can embody a generally elongated cylinder or a non-circular cylinder. The four sides can be referred to as first, second, third, and fourth sides. The four sides can also be referred to as the top, bottom, left, and right sides. These specific nomenclatures are given so as to enable calling out a particular side relative to other sides only but are not structurally limiting unless the context indicates otherwise.

The base or base end can have an open proximal end to allow the needle hub to extend proximally thereof, proximal of an end surface, in the ready to use position. The first side and the second side of the base end can each have an opening to allow viewing and accessing the interior space of the base end, such as to facilitate or assist assembling of the catheter assembly therein.

The top side of the base end can be provided with a first or top lever and the bottom side can be provided with a second or bottom lever. When a user simultaneously applies a compressive force and a distally directed force on the top lever and a compressive force and a proximally directed force on the bottom lever, the user can cause the left housing frame and the right housing frame to move relative to one another and the detents on the first frame and second frame to separate. This in turn will allow the housing to separate into separate housing components, e.g., into the left frame and the right frame.

By manipulating the first or top lever and the bottom lever, the user can cause the housing to separate into two or more housing components. The separation of the housing into housing components can then expose the catheter assembly to separate from the housing following successful venipuncture so that the catheter hub can then be secured to an IV line and secured to the patient, such as by using tape or securement dressing.

In other examples, by rearranging the detents or engagement tabs between the left housing frame and the right housing frame, the user can simultaneously apply a compressive force and a proximally directed force on the top lever and a compressive force and a distally directed force on the second or bottom lever to move the two housing sections relative to one another and the detents on the first frame and second frame to separate.

The housing exterior can have a plurality of surface ornamentations, such as on the exterior surface of the left or first frame. A similar set of surface ornamentations can be provided with the right or second frame. A generally planar upper edge can be provided with both body frames. Further, the distal most edge of the top lever can be located proximally of the distal most edge of the bottom lever. This arrangement can be utilized to enable ready grip of the top lever by a thumb and the bottom lever by an outer edge of the index finger to separate the housing into housing components. For example, the index finger can push against the curved proximally facing surface of the bottom lever and pushed distally or in the distal direction. In other examples, the relative arrangements between the top and bottom levers can be altered or arranged differently depending on the detent types or snap connections incorporated to retain the first frame and the second frame together.

The housing can comprise a wall that opposes the body opening along the top side of the housing. A seam can run lengthwise of the housing, which can mark the interface between the left frame and the right frame of the housing along the body and the nose end of the housing. The seam can run from the nose end to and including through the base end of the housing. However, the seam can be non-linear or not extend in a straight line. For example, the seam can be off-axis compared to the straight line defined by the seam along the body and the nose end.

The seam at the base end can be near the edge or intersection of the sides, such as the right side and the bottom side. A plurality of pairs of detents can be incorporated between the left frame and the right frame to secure the two frames together. In an example, a catheter assembly can be located inside the housing before engaging the left frame to the right frame, or vice-versa. Following use, such as following successful venipuncture, the top lever and the second or bottom lever can be actuated to separate the detents to then separate the housing into components, such as to separate the left frame from the right frame, to enable separation of the catheter assembly from the housing.

In an example, the right frame can be provided with the second side and top side or third side at the base portion, which are generally right angle to one another. The first side and the bottom side or fourth side can be provided with the left frame.

To secure the catheter assembly to the right frame, and particularly the needle hub from moving, the lower wall structure or section of the right frame can terminate with a proximal edge that is located along an axial position on the right frame to accommodate the flange or extension on the needle hub. The distal edge of the flange can therefore be delimited from shifting or moving in the distal direction by the proximal edge on the lower wall structure.

To secure the needle hub from moving in the proximal direction, the second side can be provided with a channel and a shoulder on a proximal edge of the channel for retaining the flange on the needle hub. The channel can be located on the second side and the corresponding channel on the first side define a gap or width for accommodating the Luer threads on the catheter hub and the width of the flange on the needle hub.

The non-circular structures for coupling the flange and the groove channel, such as by using multi-sided structures, can prevent the needle hub from rotating while within the space defined by the sides of the base end. This in turn can hold the needle hub in the assembled position so that the needle bevel can be oriented in the desire position without prematurely rotating before performing venipuncture.

The second side of the base portion can have a channel and a shoulder. A plurality of tabs or male detents can be provided at a lower edge of the second side. The tabs can embody a hook-like structure for engaging female detents located on the left or first frame. Optionally, there can be more than two detents or only one detent. Each of the male detents can have a tip pointing in the distal direction for engaging a female detent from a proximal position of the female detent and moving or sliding to a distal position to engage.

For the particular arrangement, the right frame and the detents must travel or move in the proximal direction relative to the left frame to separate the male detents from the female detents on the left frame. In other examples, the male detents on the right frame can point in the proximal direction so that separation of the male and female frames will require movement of the right frame in the distal direction relative to the left frame to separate the male detents from the female detents on the left frame.

Along the top side, a cut-out can be provided for forming the top lever. The cut-out can be provided with three sides with the fourth side being connected to the base of the top lever. The top lever can be formed to project outwardly away from the direction of the lower edge. The top lever can have a tapered or ramped portion and a contact portion. The contact portion can provide a surface for the user to touch or manipulate.

A rib or protrusion can be provided on the underside surface of the top side and can be recessed from a side edge of the top side. The recessed space between the side edge and the protrusion can be sized to accommodate the thickness of the first side of the left frame when the left frame is assembled to the right frame. The rib can be thought of an alignment tab for use to align the first side to the side edge so that upon assembling with the first side, a generally flushed surface is provided between the side edge and the exterior of the first side.

A second rib or protrusion can be spaced from the first rib and be provided on the underside surface of the top side. In an example, the second rib can be aligned to or with the side edge and can be configured to engage a corresponding slot or recess on the left side or first side of the left frame to register the two frames at the base end along an axial direction of the housing.

In an example, the second rib can have an arrow-tip like structure with two tapered edges and an apex therebetween. The arrow-tip like structure can be configured to seat in a corresponding seat on the left side of the left frame and the two tapered surfaces can allow the projection to escape from the corresponding seat by allowing the corresponding tapered surfaces to slide relative to one another when the top lever and the bottom lever are gripped and are caused to slide relative to one another.

A shoulder can be formed on the underside surface of the top wall, just distal of the cutout. The shoulder on the underside surface can be configured to support the flange on the needle hub, similar to the function of the shoulder on the second side.

A tab or detent with a free end pointing in the distal direction can be located on a side edge of the lower wall structure. The tab can engage a corresponding female detent formed with the left frame. In other examples, additional tabs can be provided along the side edge of the lower wall structure.

Two protrusions can be provided with the distal portions of the right frame. As shown, a lower protrusion can be provided on the side edge of the lower wall structure for engaging a slot on the left frame to provide added rigidity along the seam. An upper protrusion can be provided on the side edge of the base for engaging a slot on the left frame to provide added rigidity along an upper seam at the nose end of the housing. The upper seam is located above, elevation-wise, the lower seam.

In an example, the right frame has a bottom wall structure, a top wall structure or section, and a sidewall structure or section, each having a surface. In an example, the upper wall or top wall structure can have a length that extends in the same lengthwise direction as the needle and a width, which is perpendicular or radial of the length. The width of the top wall structure can be smaller in dimension than the width of the bottom wall structure. These different widths between the top and bottom wall structures, for example the top wall structure does not project towards the needle as much as the bottom wall, allow for a gap along the upper portion of the housing and for the bottom to be closed when the first frame is attached to the second frame.

A shoulder can be provided between the upper wall structure and the top wall and a raised stub can be provided distal of the top lever. The step up at the shoulder can provide for a relatively larger interior space at the base end of the housing to accommodate the flange on the needle hub and the Luer threads on the catheter hub. The raised stub can be unconnected to the contact portion of the top lever but can be provided with a tapered surface to mimic the ramp at the base of the top lever, to appear more symmetrical. A gap can be provided between the top lever and the raised stub, which can incorporate spaced apart gripping bumps. The top lever can also incorporate similar spaced apart gripping bumps.

The left frame can be configured to couple to the right frame to form the housing in accordance with aspects of the present invention, shown and described elsewhere. In an embodiment, the first frame can be provided with a nose portion, a body portion, and a base portion. The left frame and the right frame can join to form a nose end, a body, and a base end. In an exemplary embodiment, the lower wall structure can be provided with an engagement slot for engaging the tab or detent and a receiving slot for receiving the projection on the right frame. As further discussed below, the engagement slot can have a detent for receiving a corresponding detent on the right frame. The receiving slot however can embody a simple channel without engagement surfaces for receiving the lower projection on the right frame.

Also shown in FIG. 9, proximal of the body portion 188*a*, is a base portion 190*a*, which has a left or first side 200 and a bottom or fourth side 206 having the bottom lever 216 formed thereon. The first side 200 and the bottom side 206 resemble two wall structures that are placed at right angle to one another with the bottom lever 216 on one of the walls. One or more gripping features 284 can be provided on the exterior of the bottom lever 216.

The engagement slot can have an opening for the tab to enter, a tapered surface, and a tab. The tab on the right frame can enter the opening of the engagement slot and then travel distally to engage the tab of the engagement slot to complete the engagement between the tab and the engagement slot.

To disengage the left and right frames, the tab can move in reverse. The tab can move proximally relative to the engagement slot. The proximal movement can cause the tapered surface of the engagement slot to move against the tapered surface on the tab to impart a pair of component forces that include a radially directed force to cause the left and right frames to move away from one another to separate the tab from the engagement slot. Concurrently, the lower protrusion on the right frame can separate from the receiving slot on the left frame. Similar engagement mechanisms can be provided at the base end of the housing to enable separation of the two frames at the base end.

The bottom or fourth side of the base end can comprise two engagement slots formed at the edge of the bottom side. Each of the engagement slots can comprise an opening for receiving the corresponding tab on the lower edge of the second side of the right frame. A lip can be provided at each engagement slot with a recessed pocket for receiving and engaging the fingers on the corresponding tab. The gap between the finger of the tab and the lower edge can be configured to receive the lip therebetween to engage the tab to the engagement slot.

The engagement slot towards the distal end of the base section can have an opening that is bounded by at least three sides and can be relatively longer than the length of the corresponding tab to permit axial movement of the tab to disengage from the engagement slot. Optionally, the engagement slot at the proximal end of the base section can be bounded by two sides only without a third side to constrain the corresponding tab.

The first side of the base portion can be provided with an opening and two receiving slots for mating or aligning with the rib and the projection on the top wall of the base section of the right frame. The more distal receiving slot can have a recess formed on the interior surface of the first side while the more proximal receiving slot can have a recess formed on the exterior surface of the first side. This arrangement can allow the wall structure of the first side to straddle or pass between the rib and the projection.

Like the right frame, the base portion can be provided with a channel for interacting with the flange on the needle hub. The barrier wall distal of the channel can be provided with a shaped contour for accommodating the catheter hub, when the left frame is attached to the right frame and the catheter hub is located therebetween or is located inside the interior space of the housing.

In use, the ExD catheter assembly can be advanced against a patient, to a selected catheter location, such as a deep or a superficial vein. The user can puncture the targeted vein with guidance from a visualization machine, such as an ultrasound monitor with an ultrasound probe. Primary blood flashback can be observed flowing into the needle hub. Next, the angle of insertion of the ExD catheter assembly can be lowered prior to further advancing the ExD catheter assembly to locate the catheter tube deep into the vein. In some examples, a guide wire dispenser having a guidewire extending through the lumen of the needle may be used with the ExD catheter assembly. For example, a SonoStik® guidewire dispenser having a housing may be placed into the proximal opening of the catheter hub after removal of the vent plug and the guidewire projecting through the lumen of the needle and advanced in a manner known in the industry. The guidewire may be used to guide the catheter tube to a desired treatment location within the body.

The needle and catheter tube can be advanced over the guidewire and stopped at or just before the nose end of the catheter hub contacts the skin. If the ExD catheter assembly is used without a guidewire, then the ExD catheter assembly may be advanced without first advancing the guidewire. The practitioner can then place his or her thumb on the top lever and an index finger against the bottom lever to separate the housing into two or more housing components, such as separate the left frame from the right frame, as described above. Once the housing is separated into smaller components, such as into separate first and second housing frames, the catheter assembly is free from the housing and can separate from the housing. The user can next retract the needle and needle hub from the catheter hub.

For the ExD catheter assemblies and components thereof disclosed hereinafter, it is understood that where a feature is shown but not expressly described and is otherwise the same or similar to the feature or features described elsewhere, such as above with reference to FIGS. 1-14, the disclosed part or parts shown in all the drawing figures but not expressly described because of redundancy and because knowledge is built on a foundation laid by earlier disclosures may nonetheless be understood to be described or taught by the same or similar features expressly set forth in the text for the embodiments in which the feature or features are described. Said differently, subsequent disclosures of the present application are built upon the foundation of earlier disclosures unless the context indicates otherwise. The disclosure is therefore understood to teach a person of ordinary skill in the art the disclosed embodiments and the features of the disclosed embodiments without having to repeat similar components and features in all embodiments since a skilled artisan would not disregard similar structural features having just read about them in several preceding paragraphs nor ignore knowledge gained from earlier descriptions set forth in the same specification. As such, the same or similar features shown in the following ExD catheter assemblies incorporate the teachings of earlier embodiments unless the context indicates otherwise. Therefore, it is contemplated that later disclosed embodiments enjoy the benefit of earlier expressly described embodiments, such as features and structures of earlier described embodiments, unless the context indicates otherwise.

An alternative ExD catheter assembly shares similar aspects with the ExD catheter assembly of FIGS. 1-14, and in particular a similar housing configuration in which a first frame or left frame and a second or right frame are attached to form the housing and can separate to release the catheter hub from the housing. The housing can comprise a nose end, a body, and a base end. The housing has a body opening that opens into an interior space. A catheter assembly can be positioned in the interior space of the housing.

At the distal end, part of the needle, which is attached to a needle hub, and the catheter tube, which is attached to the catheter hub, can project out a distal opening of the housing, at the nose end. Optionally, a guidewire dispenser, such as a SonoStik® guidewire dispenser, can be connected to the proximal opening of the needle hub, after removal of the vent plug.

Each of the two first and second frames can comprise a wall structure comprising a lower wall section, an upper wall section, and a sidewall section. A plurality of projections or ornamentations can be provided on the exterior surface of the sidewall section, which can embody round, elongated, polygonal, or irregular shape projections. The projections can be spaced from one another and be provided for aesthetic and to facilitate gripping the housing on the two sidewalls of the housing.

The base end at the proximal end of the housing can be provided with a plurality of sidewalls, which can include a first or left sidewall, a second or right sidewall opposing the first sidewall, a third or top sidewall, and a fourth or bottom sidewall opposing the third sidewall. The sidewalls at the base end define a generally square or rectangular shaped structure having a hollow interior for accommodating the catheter assembly. In other examples, the sidewalls can define a different shape cross-section, such as oval or round. A seam can pass through both the top sidewall and the bottom sidewall, and through the nose end of the housing.

The first sidewall and the second sidewall can define a width of the housing at the base end. In an example, the width at the base end can be larger than a width of the body immediately distal of the base end. In other examples, the width at the base end and that of the body immediately distal of the base end can be generally the same or equal. The width of the body, measured as a distance between the two sidewall sections of the first and second frames, from either their respective exterior surfaces or interior surfaces, can be generally constant in the distal direction until about the start of the activation area or region of the body, where the body widens in the distal direction to a maximum width at a body distal end. From there, the width can rapidly decrease to a peak or apex, where the distal opening is located.

The activation region of the body can widen so that each of the two frames, or at least one of the two frames, can incorporate an activation structure. The activation ramp can be sized and shaped to interact with the catheter hub to enable separation of the housing into two or more housing components.

A cut-out for receiving the flange extension of the needle hub can be provided at the proximal end of the housing, which is defined by partial cut-outs on the bottom side of the base end and partial cut-outs at the proximal ends of the two frames.

An opening can be provided near the distal end of the housing, at the lower wall of the housing. The opening can be elongated, can have a proximal edge, can have a distal edge, and can have side edges. In other examples, the opening can have different shapes, provided the shape does not interfere with the activation ramp located in the interior of the housing.

A seam can be provided lengthwise of the housing and runs from the distal end to the proximal end and can be non-continuous at the rear opening and at the front opening. At the distal edge of the front opening, an end cap component can be provided at the distal end of each of the left and right frames. Regarding the end cap component of the second frame, the discussions of which applies equally to the end cap component of the first frame, the end cap component can have a lower section, a top section, and a side section. In an example, the side section can have a cut-out, resembling a half-circle, so that two side sections with two cut-outs from two adjacent end cap components can form a through passage or opening to accommodate the needle and catheter tube. The through passage formed by the two cut-outs can provide support and guidance for the needle and the catheter to enable venipuncture of an extended length catheter, with or without a guidewire, and a short midline catheter of about 8-10 cm length without an integrated guidewire.

The lower section of the end cap component can be separated from the lower wall of the housing wall by a gap and the upper or top section of the end cap component can be separated from the upper wall of the housing wall by a gap. Thus, each end cap component can be attached to the remaining part of the respective left and right frames by a material strip or layer, which has a thickness. In an example, the material strip can have the same thickness as the wall thickness of the side section and the front section. In other examples, the material strip can comprise an indentation to thin out the thickness of the material strip so that it is thinner than the thickness of the side section and the front section.

In an example, the material strip that connects the left end cap component to the left frame and the material strip that connects the right end cap component to the right frame can act as a hinge, such as a living hinge. The living hinge can allow the end cap component and the respective frame that it attaches to, i.e., the front-end wall, to pivot, rotate, or swing relative to one another. For example, if the first and second frames separate from one another beginning from the proximal end when the assembly is activated due to the catheter hub pushing against the one or more activation ramps, the first and second frames can swing outwardly away from one another and pivot or rotate about their respective material strip or living hinge. The two end cap components can remain attached to one another as the two frames pivot or rotate about the two living hinges until they too are separated to free the catheter hub from the two frames, as further discussed below.

The second frame can have joining edges where the seams are formed with the joining edges of the first frame. The left frame or first frame and the right frame or second frame can connect to one another along their respective joining edges. Engagement slots, tabs, and/or detents may be used for removable securement of the two frames, as further discussed below. The right frame can have a cutout that forms part of the opening at the bottom or lower side of the housing.

In the figure, the catheter assembly can be situated in the interior space of the housing, which can have a needle and a catheter tube passing through the cut-out, and the catheter hub, or at least the push tab of the catheter hub, positioned distally of the base end. The needle hub and vent plug can project out the proximal opening of the housing, with the flange of the needle hub engaging the housing.

A flange extending from the needle hub, which can have a generally square or rectangular shape contour, can be arranged so that a plane defined by the flange is generally orthogonal to the lengthwise axis of the housing. Portions of the flange that projects outwardly of the exterior profile of the needle hub can engage a groove formed with the plurality sides of the base end, such as with the first side, second side, third side, and fourth side. The groove can be a recessed channel formed into the wall thickness of the plurality of sides of the base end. The groove can be continuously formed across the sides other than where the cut-out is provided at the fourth side for accommodating the flange extension of the needle hub. The groove can be structured to accept, receive, or accommodate the flange on the needle hub, including where the flange transitions between the various sides, such as the intersections of the sides of the flange.

In the ready to use position where the ExD catheter assembly is ready to be used to perform a venipuncture, the needle hub can be held stationary from axial movement by delimiting the flange extension of the needle hub from distal movement via the bottom housing edge at the cut-out of the two bottom wall structures. To delimit the needle hub from moving in the proximal direction, the flange extending from the exterior of the needle hub can be positioned against the proximal lip of the groove of the base end. Further, the non-circular structures for coupling the flange and the groove, such as by using multi-sided structures, can prevent the needle hub from rotating while within the space defined by the sides of the base end. This in turn can hold the needle hub in the assembled position so that the needle bevel can be oriented in the desire position, as assembled, without prematurely rotating before performing venipuncture.

The exterior threads of the catheter hub can comprise a slot for receiving a tab projecting from the interior surface of the top side of the base end. In other examples, the arrangement can be reversed, and the top side can incorporate a slot and the catheter hub can incorporate a tab. In still other examples, detents can be provided between the catheter hub and the housing at other locations along their respective structures to engage the two. The engagement ensures proper alignment between the catheter hub and the housing in the ready to use position and prevents the catheter hub from rotating while engaged to the housing.

The catheter hub can be structured to slide axially in the distal direction within the interior space of the housing following successful placement of the needle and the catheter hub into the vein of a patient while the needle hub remains engaged to the base end of the housing. In an example, the exterior threads are structured to ride on or slide on the interior surfaces of the two lower walls of the housing. For example, a user can push on the push tab to advance the needle hub in the distal direction. The push tab can be located between the two upper wall sections of the two frames. As shown, the upper edge of the push tab can project above the exterior surfaces of the two upper wall sections to present itself for contact and for pushing by a practitioner. In some examples, the push tab can be structured so that the upper edge of the push tab projects further upwardly of the two upper wall sections to present itself as a larger target for pushing by a practitioner.

When the practitioner pushes on the push tab in the distal direction following placement of the catheter tube into the vein, and optionally after advancing a guidewire into the vein to guide the catheter tube, the body of the catheter hub abuts the one or more activation ramps, on the left frame, the right frame, or one of each of the two frames, to cause the two frames to separate starting from the proximal end of the housing. The push tab can be molded with a sufficient length or height to extend above the housing to enable pushing by a practitioner. Optionally, a tab extender can be snap onto a standard push tab to increase the height of the push tab for pushing by a practitioner, as further discussed below.

The second frame can have a base portion having a second side, top side and bottom side. The top side and bottom side can be relatively shorter in length than the second side. The top side and the bottom side of the right frame can be referred to as partial sides as similar top and bottom side sections are carried by the first or left frame such that when two partial top sections are joined at their respective joining edges and the two partial bottom sections are joined at their respective joining edges, they form the top side and bottom side of the base end.

The partial top side section can incorporate a slot and the partial bottom side section can incorporate a slot, at the joining edges. The slots can be generally rectangular in shape with sharp corners or with radiused corners but can instead embody a round shape, a square shape, a star shape, an oval shape, a polygonal shape, or an irregular shape. The slot on the partial top side section and the slot on the partial bottom side section can be located along the same axial position of the lengthwise axis of the right frame. In other examples, they can be axially offset from the same axial position. In an example, the two slots are both located generally along the proximal end of the two joining edges.

The body portion can be located distal of the base portion, which can have a wall with a top wall section, bottom or lower wall section and sidewall section. In an example, two slots, similar to the slots at the base portion, can be provided at the joining edge of the lower wall structure or section. The two slots can have the same shape as the two slots on the base portion or can be different. In an example, one of the two slots on the lower wall section can be located adjacent the housing edge of the bottom cutout and the second slot can be located distally thereof. In other examples, there can be just one slot on the lower wall section, or more than two slots and they can locate elsewhere along the joining edge.

The activation ramp can be located on the interior surface of the sidewall section of the housing wall closer to the distal end than the proximal end, at the activation region of the frame. The activation ramp can have a proximal ramp section, a distal ramp section, and a central ramp section, which can be located between the proximal and distal ramp sections. In an example, the proximal ramp section can comprise a slope that increases from the interior surface of the right frame, which can be viewed as a structure having a surface that extends radially away from the interior surface.

When assembled with the left frame and the assembled housing having a catheter assembly located therein, the proximal ramp section can extend away from the interior surface towards the needle, or towards the lengthwise axis passing through the housing. The lengthwise axis passing through the housing can be considered as a referenced line and the proximal ramp section can be understood as having a surface that is furthest from the referenced line and that gradually moves closer to the referenced line as the ramp approaches the central ramp section.

The central ramp portion can have a surface that is closer to the referenced line than the proximal ramp portion and can comprise a generally flat area or a surface area with a large radius.

The distal ramp portion, in an example, can comprise a slope that decreases from the central ramp portion, which can have a surface that moves away from the referenced line. If the proximal ramp portion has a positive slope, then the distal ramp portion can have a negative slope. Thus, the activation ramp can be considered a sloping structure that increases to a peak or crest at the central ramp section then has a negative slope. In other examples, the distal ramp portion can be constant or flat at the central ramp portion, without any slope. In still other examples, the distal ramp portion can have a positive slope that continues to extend towards the referenced line. Preferably, the distal ramp portion has a negative slope.

When the left and right frames are assembled together to form a housing, the gap between the two adjacent activation ramps, which can be referred to as an activation gap, if two activation ramps are incorporated, or between the activation ramp and the interior surface of the adjacent frame, if only one activation ramp is incorporated, can vary. The activation gap can narrow as it extends from the proximal ramp portion to a narrower point at the central ramp portion, or from two proximal ramp portions to a narrower point at two central ramp portions. As further discussed below, the activation gap can be incorporated as a means for which the catheter hub can advance against to impart a pair of components forces to then separate the housing into two or more housing components.

A recess can be provided with the end cap component of the second or right frame. The recess can have three sides and a fourth side that is opened. Optionally, the recess can embody a four-sided slot, similar to one of the slots of the body section or the base section. The recess at the end cap component can be sized and shaped to receive a corresponding tab on the adjacent end cap component in an interference or snap fit arrangement. In some examples, the location of the recess and of the tab for coupling with the recess can reverse so that the recess can locate on the end cap component of the first or left frame.

The activation ramp can be implemented as two separate activation ramp sections, each with a proximal ramp portion, distal ramp portion, and central ramp portion. The two separate activation ramp sections can operate or function as explained above. A gap or void can be provided at the distal ramp sections of the two ramp sections, formed by the negative slopes of the two distal ramp sections. A small gap can be located between the two ramp sections. In other examples, the activation ramp can be formed as a single ramp structure without a gap. The surface of the activation ramp can be generally flat or can have a large radius to form a slight curve for accommodating the contour of the catheter hub.

As can be visualized, when the second or right frame is coupled to the first or left frame and the catheter hub is advanced distally to abut the two separate activation ramp sections, the nose section of the catheter hub initially abuts the two proximal ramp portions of the two separate activation ramp sections then moves into the gap or void as the nose section continues to move in the distal direction. Then the intermediate portion of the catheter hub, which is larger in diameter or size than the nose section of the catheter hub, moves over the two proximal ramp portions to further expand the two frames away from one another. At this point, the two frames are completely separated from one another except for the engagement at the two end cap components, at the distal end of the housing. If not completely separated proximal of the two end cap components, further movement of the external threads of the catheter hub against the two proximal ramp portions can further expand the two frames away from one another so that the tabs and slots of the two frames completely separate from one another, except for the engagement at the two end cap components. Finally, the last engagement between the recess and the tab on the left frame can separate by physically grasping one of the frames, or both, and pulling one or both frames away from one another. The catheter hub can then be completed, such as connected to a drip line and taped to a patient.

In an example, the recess at the end cap component can have two sidewalls, a bottom wall, and a center wall. In an example, the two sidewalls each can comprise a surface and wherein the two surfaces of the two sidewalls can taper or can converge in the direction of the bottom wall. Thus, the surface of the center wall can be trapezoid in shape. The recess can be tapered and can have a width or gap at the opening of the recess that is larger than the width or gap at the bottom of the recess. This configuration can allow the corresponding tab on the end cap component of the first frame to engage the recess and for the engagement to readily separate to facilitate separation of the two frames at the two end cap components to then separate the catheter hub from the housing of the ExD catheter assembly.

The exterior surface of the second frame can be provided with a plurality of spaced apart projections or ornamentations, similar to the left frame. In an example, the two different sets of projections for the two frames can be the same and can have the same spacing. In other examples, the projections can have different shapes and/or different spacing between two adjacent projections.

In an example, tabs or male detents can be provided on the third side of the base portion at the joining edge and on the fourth side of the base portion at the joining edge to engage the two slots on the base portion of the second frame. Tabs or male detents can also be provided at the joining edge on the lower wall structure or section for engaging the two slots on the lower wall structure of the second frame. Optionally, the two frames can join one another along adjoining seams via welding or adhesive. If welding or adhesive is used, the upper and lower seams at the distal end of the housing attach to one another via detents so that the detents can disengage to open a distal gate opening to then enable separation of the catheter hub from the housing, as further discussed below.

A tab or male detent can be provided at the joining edge of the end cap component of the first frame. The tab can be located on the end cap component at a location to matingly engage the slot on the right frame, when the left and right frames are assembled to form the housing in accordance with aspects of the invention. The tab can be sized and shaped to engage the recess on the end cap component of the second frame. In an example, the engagement between the tab and the recess is a slight interference.

In an example, the engagement between the tab or male detent and the recess at the two end cap components can have a stronger gripping or engagement hold than the engagement between the tabs on the base portion and tabs on the lower wall structure engaging corresponding slots on the second frame 194. This relative engagement force between the engaging pairs of tabs and slots can ensure that when the catheter hub is advanced in the distal direction within the interior space of the housing following initial catheter tube placement, and after advancement of a guidewire when incorporated, upon contact by the catheter hub against the activation ramps, the housing can separate first at the proximal end of the housing before separation at the two end cap components. In other examples, the various pairs of tabs and slots can open generally at about the same time upon contact by the catheter hub against the activation ramps.

The tabs on the base portion of the first frame can be longer than the tabs on the lower wall structure of the body section. The tabs on the base portion can also be longer than the tab on the end cap component. The different lengths of the various tabs can mate or engage with slots having different and corresponding depths to engage to ensure a generally tight seam when the two housing frames are coupled to form the housing. In some examples, each of the left and right frames can have both a slot and a tab to mate with corresponding tabs and slots rather having an arrangement where all the slots are located with one frame and all the tabs are located with another frame.

The exterior surface of the firm can be provided with a plurality of spaced apart projections or ornamentations, similar to that of the second frame. In an example, the two different sets of projections for the two housing frames can be the same and can have the same spacing. In other examples, the projections can have different shapes and/or different spacings between two adjacent projections.

In use, the user can use the ExD catheter assembly in accordance with aspects of the present invention to puncture a targeted vein with guidance from a visualization device, such as an ultrasound monitor using an ultrasound probe. Primary blood flashback can be observed flowing into the needle hub. Next, the angle of insertion of the ExD catheter assembly can be lowered prior to further advancing the ExD catheter assembly to locate the catheter tube deep into the vein. In some examples, a guidewire dispenser having a guidewire extending through the lumen of the needle may be used with the ExD catheter assembly. For example, a SonoStik® guidewire dispenser having a housing may be placed into the proximal opening of the catheter hub after removal of the vent plug and the guidewire projecting through the lumen of the needle and advanced in a manner known in the industry. The guidewire may be used to guide the catheter tube to a desired treatment location within the body.

The needle and catheter tube can advance over the guidewire and stopped at or just before the nose end of the housing contacts the skin. If the ExD catheter assembly is used without a guidewire, then the ExD catheter assembly may be advanced without first advancing the guidewire. The practitioner can then place his or her thumb on the push tab of the catheter hub to advance the catheter hub against the one or more activation ramps on one or both first and second housing frames.

When the catheter hub is pushed in the distal direction until the nose end of the catheter hub pushes against the two activation ramps, a pair of component forces can be generated on each of the two frames. This can then cause the two frames to separate starting at the base end of the housing. As the catheter hub continues to move in the distal direction, the two frames can further separate until the tabs and slots on the base end and the body completely separate from one another. At this point with the tab and the recess on the two end cap components continue to engage, the two frames can pivot at their respective living hinges. The user can then use a free hand while maintaining a grip on the catheter hub to pull on one of the two frames to separate them at their respective end cap components. The catheter hub and the housing can then be free of one another. The user can then finish preparing the catheter hub, such as connecting a drip line to the catheter hub and taping it to a patient to secure the puncture site.

In the alternative implementation of an ExD catheter assembly in accordance with aspects of the invention, the left and right frames, or first and second frames can be secured together with the tabs or male detents engaging the corresponding slots or female detents. In the present embodiment, the engagement between the tabs or male detents and the slots or female detents at the body and at the base can be such that they do not separate upon advancement of the catheter hub in the distal direction within the interior of the housing. For example, the engagement between the tabs and the slots can be with interference and/or with adhesive, bonding or welding. Further, the activation ramps can be omitted from the first and second frames so that radial forces are not generated by the advancing catheter hub to separate the two housing frames. Thus, when the catheter hub is advanced distally to further place the catheter tube into the vein, the catheter hub can reach the void space at the distal end of the body section without imparting any radial forces on the two frames to separate them, without the activation ramps. Instead, the distal abutment of the catheter hub against the gates at the distal end opens the distal gate opening to then permit separation of the catheter hub from the housing.

Upon being pushed distally by the advancing catheter hub, the male detent or tab on the first frame can release or separate from the recess on the second frame. The recess can have open slot. This structure allows the tab and recess at the two end cap components of the left and right frames to separate by allowing the tab to pass through the side opening of the recess without a sidewall rather than the opening proximate the joining edge. The separation at the two end components can therefore occur by simply providing an axial force when pushing the catheter hub in the distal direction against on the two end cap components without having to generate a radial force.

Thus, following cannulation, optionally following guidewire placement and following catheterization, as previously described with the first or prior discussed implementation of the ExD catheter assembly, the catheter hub can advance against the proximally facing surfaces of the two end cap components of the left and right frames. The advancing force of the catheter hub forces the tab to separate from the recess. This separation can be facilitated by the open side between the two sidewalls of the recess at the end cap component of the second or right frame. That is, the tab on the first or left frame can simply slide out through the gap provided by the missing side of the recess between the two sidewalls.

When the tab and the female detent at the two end components separate and the two frames are held secured by the tabs and slots at the body portions and base portions of the two frames, the two end components are forced to swing in the distal direction about the two living hinges.

In an example, the space or distance between the two living hinges is larger than the horizontal dimension or cross-sectional dimension of the catheter hub. Thus, as the two end cap components swing in the distal direction about the two living hinges, a gate with a gap, called a gate opening or distal gate opening as defined by the space provided by the distally swinging end components, opens up to provide clearance for the catheter hub to pass therethrough. The swinging end cap components may be referred to as gates that can swing open to open the distal gate opening. In practice, the opening of the gates to open the gate opening at the distal end allows the catheter hub to separate from the needle hub and the housing through the gate opening or distal gate opening to separate from the needle, the needle hub, the housing, and guidewire and guidewire dispenser if used. The catheter hub can then be secured to a patient for fluid administration. The needle, the needle hub, the housing, and the guidewire and guidewire dispenser if used, can be discarded or disposed of per approved protocol.

Thus, an aspect of the present invention is understood to include an ExD catheter assembly comprising a multi-part housing having an interior space having a catheter assembly located therein; said catheter assembly comprising a catheter tube attached to a catheter hub and a needle attached to a needle hub and extending through the catheter tube with a needle tip extending distally of a distal opening of the catheter tube. Said needle and catheter tube projects through an opening at a distal end of the housing. The distal end can comprise two end cap components removably attached to one another, such as by engaging a male detent and a female detent. The female detent can be a recess with three sidewalls and with at least one open side and one open inlet to the recess. Each end cap component can comprise a gate that is pivotable or rotatable about a living hinge. When the two gates of the two end cap components pivot or rotate open to open the gate opening at the distal end of the housing, the needle hub can move distally past the gate opening to separate from the housing.

The multi-part housing for forming the housing of the ExD catheter assembly can comprise a first frame attached to a second frame. The two frames can have a seam therebetween. The two frames can attach along a joining edge. One of the two frames can comprise a tab or a male detent and the other frame can comprise a corresponding slot or female detent for receiving the male detent to removably secure the two frames together. The distal end of the housing can comprise a seam. The opening at the distal end having the needle and catheter tube project thereto can be formed by two cut-outs on two wall surfaces so that when the two wall surfaces come together, a generally cylindrical guide opening is formed by the two cut-outs. The distal end of the housing can include a living hinge. Preferably there are two living hinges at the distal end of the housing. A gate with a gap can be defined by the distance between the two living hinges. When the tab and the female detent with at least one open side separate from one another, two end cap components can swing distally about the two living hinges to open a gate opening or distal gate opening at the distal end of the housing. The catheter hub can exit the gate opening or distal gate opening and separate from the remaining components of the ExD catheter assembly, which can include a needle, a needle hub, a housing, and a guidewire and a guidewire dispenser if used.

In accordance with additional aspects of the invention, an ExD catheter assembly can include a tab extender or tab adapter attached to the catheter hub and extends orthogonal to the lengthwise axis of the housing through the housing opening so that an upper portion of the tab adapter rises above the top wall structure of the housing to present a surface for pushing or grasping by a practitioner. In an example, the tab adapter is provided to extend the profile of the integrally formed push tab of the catheter hub well above the top wall structure to facilitate operation of the ExD catheter assembly. Alternatively, the push tab can be formed in an extended configuration and extends above the top wall structure of the housing to present itself to be pushed by a practitioner without the separately formed tab adapter.

The tab adapter can be formed from a plastic material, such as by plastic injection molding. The tab adapter can comprise a body having a first end and a second end. The first end can be located above, elevation-wise, the second end. In an example, the body can be formed in-part as a solid structure above an imaginary line and having a tunnel or channel below the imaginary line with an arcuate first opening and an arcuate second opening in communication with one another via the channel. In an alternative embodiment, the body is hollow and is formed with a wall structure having an exterior surface and an interior surface defining an interior space or cavity. The wall thickness between the exterior surface and an interior surface can have a sufficient thickness to provide structural rigidity for carrying a digital load applied by a user to advance the catheter hub.

The tab adapter can be sized and shaped for mounting over the catheter hub. In an example, the tab adapter is configured to seat over the catheter hub and the hub body situated in the channel of the body. The first opening and the second opening of the tab adapter may be sized to fit snugly around the curved body of the catheter hub. Depending on how the tab adapter is situated over the catheter hub, such as by placement or location along the axial position of the catheter hub, the first and second openings of the tab adapter can have the same size or different sizes to fit the particular contour of the catheter hub. In an example, the first and second openings can have a semi-spherical shape, semi-oval or elliptical shape, or an arcuate shape. Preferably, the two openings are sized and shaped to fit snuggly over the catheter hub body and has a gripping force around the hub body. The two openings can have different shapes from one another and can be selected based on the size and contour of the catheter hub body.

When the tab adapter is mounted over the catheter hub, the push tab is configured to fit within the interior space of the body of the tab adapter. To secure against slipping, sliding, or moving relative to the catheter hub when digital pressure is applied to the body, two gripping bars can be provided at the second end of the body, on either side of each of the two openings. The gripping bars can resemble ribs and can be provided with contoured surfaces to snuggly fit against the catheter hub. Relative to the upper part of the two openings, the locations of the gripping bars on the body of the tab adapter should be located so that when mounted to the catheter hub, the two gripping bars are below the centerline of the catheter hub body. The size and shape of the first and second openings and the locations of the two gripping bars are such that the tab adapter fits snuggly and grips the catheter hub body. The adapter may be used by sliding the channel and the two openings over the catheter hub body and ensuring that the push tab on the catheter hub is located within the interior of the tab adapter. The channel can have an open side for placement of the tab adapter onto the catheter hub.

The push tab of the catheter hub can contact the interior surface on the proximal side of the body. Thus, when the tab adapter is pushed in the distal direction by a practitioner, the interior surface of the tab adapter pushes against the proximally facing surface of the push tab to advance the push tab, and hence the catheter hub, in the distal direction. In an example, the interior space of the tab adapter is provided with a socket that receives that push tab in a size-on-size fit or with a slight interference to resist separation from the catheter hub body upon distal advancement of the catheter hub.

In a further example, the first and second frames can attach to one another along a seam by corresponding tabs or male detents and engagement slots. Optionally, the first and second frames can attach to one another along upper and lower seams via adhesive or welding. The catheter hub of the catheter assembly can separate from the housing by incorporating a gate assembly at the distal end of the housing that opens to allow the catheter hub to separate via the gate opening created with the two gates pivot in the distal direction. The housing in the present embodiment can remain attached together and only the gate assembly at the distal opening is actuate-able to allow the catheter hub to separate.

The ExD catheter assembly can comprise a removable protective cap, which is configured to be placed over the needle to cover the needle and the needle tip prior to use. The proximal opening of the protective cap can frictionally engage with the nose section or nose end of the housing.

A tab adapter or tab extender can be positioned over the catheter hub and secured thereto by fitment. A needle hub can extend proximally of the base end, and outside of the housing. A vent plug can attach to the needle hub, which can allow air to vent but captures any blood that may flow inside of the needle hub and the vent plug.

The housing of the present extended dwell catheter assembly can include a nose end or nose section having a tip at an end of two nose portions having an upper seam extending therebetween. The upper seam can extend through the upper part of the nose end. A similar corresponding lower seam can extend through the lower part of the nose end. Each nose portion can be joined to an end cap component of each respective first or second frame. Each nose portion and each end cap component can be referred to as a gate or rotatable gate. The two gates from the two end cap components can be part of a gate assembly. The two gates can swing open to allow the catheter hub to separate from the housing without requiring the first frame and the second frame to separate from one another.

In an example, each of the two first and second frames comprises a wall structure comprising a lower wall section, an upper wall section, and a sidewall section. A plurality of projections or ornamentations can be provided on the exterior surface of the sidewall section, which can embody round, elongated, polygonal, or irregular shape projections. The projections can be spaced from one another and provided for aesthetic and to facilitate gripping the housing on the two sidewalls of the housing. The two housing frames can have an interior for accommodating the catheter assembly having a catheter hub therein.

In an example, a lower elongated opening is not incorporated, unlike the opening of FIG. 16. The lower wall of both housing frames can be solid and can join one another along the seam up to the gap that separates the two end cap components from the remainder of two frames. This arrangement allows the two frames to remain attached to one another while the two end cap components along with the two nose portions of the nose end to swing open about respective living hinges to open a distal gate opening. In other embodiments, two housing frames can be joined to one another up to a lengthwise gap. The lengthwise gap can extend up to and flows or blends into the front gap that allows the two end cap components to swing to open the distal gate opening, as further discussed below. The proximal end of the lengthwise gap can serve as an injection point for the plastic injection gate or inlet.

Optional score lines can be incorporated on the wall surface of each frame. The score lines can be straight, can have curves, or both for aesthetic appeal. Score lines are understood as grooved lines formed into the wall thickness of the lower walls of the two frames. In other examples, the score lines can be omitted.

The two end cap components can attach to the two front end walls via two living hinges. Each of the two end cap components can attach to a nose portion, which combination may be referred to as a gate or rotatable gate. The two gates of the gate assembly can swing open when pushed in a distal direction by distal movement of the catheter hub to open a distal gate opening, which may move when digital pressure is applied to a tab adapter, which is attached to the catheter hub.

A front base wall can be provided proximally and inside the boundary defined by the hollow partial cylinder of each nose portion. Each front base wall can have a cut-out that is sized and shaped to accommodate part of the needle and the catheter tube. When the first and second frames are joined, the two cut-outs from the two front base walls form a perimeter defining an opening sized and shaped to receive the circumference of the combination catheter tube with the needle of the catheter assembly located within the housing. In an example, the perimeter of the two cut-outs may be referred to as a guide opening that guides the combination needle and catheter tube as the combination advances in the distal direction during cannulation and vascular access. The two base walls can have varying thicknesses, measured along the length of the first frame and/or second frame. A male detent can project from a side part of the base wall that is thicker. In other examples, the base wall can have a uniform thickness.

A male detent, which can instead be a stub or stud having an elongated body with a rounded end, can be provided on each of the first and second frames. The male detent of the first frame can be located above, elevation-wise, the needle and/or the catheter tube and extends generally orthogonally to the axis defined by the needle. The male detent of the second frame can be located below, elevation-wise, the needle and extends generally orthogonally to the axis defined by the needle.

The arrangement of the two male detents on the two frames can reverse. In an example, the two male detents can project radially relative to the lengthwise axis of the needle a sufficient amount such that the tip of each male detent extends beyond the half-way mark of the needle diameter and preferably beyond an edge of the needle on the opposite side from which the male detent extends. In other examples, the male detents can extend a shorter length or distance from the respective side from which the male detents extend. The length of the male detents can be selected to vary the amount of engagement with corresponding receiving slots, as further discussed below.

A receiving slot can be provided with the first frame below the male detent. Similarly, a receiving slot can be provided with the second frame above the male detent. Again, the arrangement can reverse. Each receiving slot can comprise wall structures configured to frictionally engage a corresponding male detent located on the opposing frame. Thus, the receiving slot on the first frame can be configured to frictionally engage the male detent on the second frame and the receiving slot on the second frame can be configured to frictionally engage the male detent on the first frame.

In an example, the receiving slot can have a first wall surface and a second wall surface configured to frictionally engagement two surface sections of a male detent to be mated therewith. In an example, the first wall surface and the second wall surface can be arranged generally orthogonally to one another. Preferably, each receiving slot does not have wall surface opposite the second wall surface, which then provides clearance, or a missing wall, for the male detent to separate from the receiving slot when the catheter hub body, such as the nose end of the catheter hub, abuts and pushes against the two base walls in the distal direction. When so pushed, the two gates of the gate assembly can rotate about the two living hinges to open the distal gate opening to then allow the catheter hub to separate from the housing. In an embodiment, each receiving slot can further include a wall surface opposite the respective first wall surface so that each receiving slot can have a three-sided wall structure. Each receiving slot and the rigidity of the end cap component can be sized to grip the corresponding male detent in a slight interference fit.

In use, the user can use the ExD catheter assembly to puncture a targeted vein with guidance from a visualization device, such as an ultrasound monitor using an ultrasound probe, after removing the protective cap. Primary blood flashback can be observed flowing into the needle hub. Next, the angle of insertion of the ExD catheter assembly is lowered prior to further advancing the ExD catheter assembly to locate the catheter tube deep into the vein. In some examples, a guidewire dispenser having a guidewire extending through the lumen of the needle may be used with the ExD catheter assembly. For example, a SonoStik® guidewire dispenser having a housing may be placed into the proximal opening of the catheter hub after removal of the vent plug and the guidewire projecting through the lumen of the needle and advanced in a manner known in the industry. The guidewire may be used to guide the catheter tube to a desired treatment location within the body.

The needle and catheter tube can be advanced over the guidewire and stopped at or just before the nose end of the housing contacts the skin. If the ExD catheter assembly is used without a guidewire, then the ExD catheter assembly may be advanced without first advancing the guidewire. The practitioner can then place his or her thumb on the tab adapter that is engaged to the catheter hub to advance the catheter hub against the gate assembly.

When the catheter hub is pushed in the distal direction such that the nose end of the catheter hub pushes against the two gates of the two end components, the distally directed force is transferred to the gate assembly and overcomes or exceeds the interference and/or friction forces provided by the engagement between the two male detents, or stubs or studs, and the two receiving slots. As the catheter hub continues to move in the distal direction, the two gates can swing in the distal direction about the living hinges. The user can continue to move the catheter hub in the distal direction while applying a proximally directed force to or while applying a steady holding force to the housing to move the needle hub completely through the gate opening provided by the two rotated gates. The catheter hub and the housing can then be free of one another. The user can then finish preparing the catheter hub, such as connecting a drip line to the catheter hub and taping it to a patient to secure the puncture site, and optionally removing the tab adapter from the catheter hub.

A tab adapter in accordance with aspects can be formed from a plastic material, such as by plastic injection molding. The tab adapter can comprise a body having a first end and a second end. The first end can be located above, elevation-wise, the second end. In an example, the body can be formed as a solid structure with a slot to accommodate a push tab extending from the catheter hub and with a hollow tunnel for mounting over the catheter hub body, as further discussed below.

The body can have an exterior surface and an interior surface, a first opening or distal opening and a second opening on the side of the body opposite the first opening. A channel can be provided between the two openings. The channel can have an open side for placement over the catheter hub. The wall thickness between the exterior surface and the interior surface can have a sufficient thickness to provide structural rigidity for carrying a digital load applied by a user to advance the catheter hub.

The body can have a distally facing exterior surface comprising one or more projections or surface features for aesthetic appeal. The distally facing exterior surface can be curved or arcuate. The projections or surface features can optionally be omitted. In other examples, the projections can embody other shapes, such as dimples, round bumps, shaped projections, random projections, etc. The distally facing exterior surface can be located between two side surfaces. In an example, each of the two side surfaces can have a flat or planar wall without varying surface features. In an embodiment, each side surface has a first surface portion, a tapered side surface portion, and a second surface portion. Like the first surface portion, the second surface portion can have a flat or planar wall. The two second surface portions on the two side surfaces can define a width that is larger than the width defined by the two first surface portions. Thus, the width at the first end of the tab adapter can be wider than the width at the second end of the tab adapter.

The distal opening of the tab adapter can have a perimeter defined by a plurality of edge sections or segments. The shape of the perimeter can vary depending on the shape of the catheter hub that the tab adapter is configured to mount to. For example, the shape of the perimeter can have only four side edge sections or can be semi-circular or part circle.

In an example, the proximally facing surface of the tab adapter has a first surface section and a second surface section. The first surface section can be generally planar but is slanted from the planar surface of the second surface section at an inflection line or transition line. The first surface section can incorporate one or more surface features or projections.

The proximal or second opening can have a perimeter defined by a semi-circular or part circle edge. The shape of the perimeter can vary depending on the shape of the catheter hub that the tab adapter is configured to mount to. For example, the shape of the perimeter can be defined by a plurality of edge segments or sections and can vary depending on the shape of the of the catheter hub that the tab adapter is configured to mount to. The first and the second openings should extend more than the half or median line of the catheter hub body to ensure gripping to more than half of the diameter of the catheter hub body. A plurality of ribs can be incorporated in the interior cavity of the tab adapter to provide rigidity.

A catheter hub in accordance with aspects of the invention has a nose section at a distal end and a proximal body section. The nose section can have a generally square shape with rounded corners connecting the four sides. In other examples, the nose section can have other cross-sectional shapes, including generally cylindrical, oval, elliptical, polygonal, etc. The proximal body section is generally round and can be relatively larger in girth or outer contour than the nose section. Thus, a step up or a stepped section can be provided between the nose section and the proximal body section. The openings on the tab adapter can be sized and shaped accordingly to fit with the contour of the catheter hub body.

The tab adapter can be sized and shaped for mounting over the catheter hub. In an example, the tab adapter is configured to seat over the catheter hub and the hub body situated in the channel of the body of the tab adapter. The first opening and the second opening of the tab adapter are sized to fit snugly around the curved body of the catheter hub. Depending on how the tab adapter is situated over the catheter hub, such as by placement or locating along the axial position of the catheter hub, the first and second openings of the tab adapter can have the same size or different sizes to fit the particular contour of the catheter hub.

In an example, the first opening can have a shape that fits snuggly around the generally square cross-section of the nose section and the second opening can have a semi-spherical shape, semi-oval or elliptical shape, or an arcuate shape to fit around the proximal body section. Preferably, the two openings are sized and shaped to fit snuggly over the catheter hub body and has a gripping force around the hub body. The channel located between the two openings has an open side for placement of the tab adapter over a catheter hub.

When mounted over the catheter hub, the push tab of the catheter hub is configured to fit within the interior space of the body. The push tab of the catheter hub can contact the interior surface on the proximal side of the body or can project into a female detent, recess, or socket within the interior for increased securement between the tab adapter and the catheter hub. Thus, in use when the tab adapter is pushed in the distal direction by a practitioner, the interior surface of the tab adapter, or a recess or female detent within the adapter, pushes against the proximally facing surface of the push tab to advance the push tab, and hence the catheter hub, in the distal direction. In other examples, the gripping provided by the openings of the tab adapter against the catheter hub body can also transfer the distally directed force to the catheter hub to advance the catheter hub when the tab adapter is pushed.

An extended dwell catheter assembly provided in accordance with still further aspects of the present invention comprises a housing with a first frame or left frame and a second or right frame attached to form a housing having an interior for accommodating a catheter assembly and allowing the catheter hub to move from a proximal position within the interior to a distal position and then subsequently separating from the housing.

The ExD catheter assembly further comprises a catheter assembly, which can be similar to other catheter assemblies described herein. The catheter assembly is shown located at least partially within the housing. The catheter assembly comprises a catheter hub, a needle hub, and a protective cap covering a needle with a needle tip.

The first and second frames that form the housing can separate to release the catheter hub of the catheter assembly from the housing. The first and second frames can attach to one another along a seam by corresponding tabs or male detents and engagement slots, as previously described, and whereby the engagements can separate.

Optionally, the first and second frames can attach to one another along upper and lower seams via adhesive or welding, in addition to the tabs and detents or as an alternative to using the tabs and detents. Where the two housing frames do not separate, or where the housing can separate into smaller housing components, the housing can be provided with a gate assembly to permit separation of the catheter hub from the housing following cannulation and vascular access.

In alternative embodiments, the housing can be assembled from two housing frames that represent an upper frame and a lower frame, instead of the left frame and the right frame described herein. For example, the upper frame can have a body opening, similar to opening 196 of FIG. 1, and the lower frame can have a closed bottom wall, similar to the closed bottom wall of FIG. 4, that can optionally have one or more small vents or openings. Thus, the seam between the two alternative frames is rotated from the seam shown and described elsewhere.

In still yet another example, the housing can be assembled from two housing frames that represent a front frame and a rear frame, instead of left and right frames or upper and lower frames. In other words, the housing can be assembled along a seam that is located somewhere between the distal end and the proximal end of the housing.

In yet another alternative embodiment, the housing for positioning a catheter hub therein can be unitarily formed and provided with a distal opening and a proximal opening. A gate assembly as described herein can attach to the distal opening and the needle hub, and/or vent plug, can extend out the proximal opening in a ready to use position.

In yet another embodiment, a tab adapter can comprise a body having a first end and a second end. The first end can be located above, elevation-wise, the second end. In an example, the body can be formed as a solid structure with a slot to accommodate a push tab extending from the catheter hub and with a hollow tunnel for mounting over the catheter hub body, as further discussed below.

The body of the adapter can have an exterior surface and an interior surface, a first opening or distal opening and a second opening on the end of the body opposite the first opening. A channel can be provided between the two openings. The channel can have an open side for mounting over a catheter hub. The wall thickness between the exterior surface and the interior surface has a sufficient thickness to provide structural rigidity for carrying a digital load applied by a user to advance the catheter hub.

The body of the tab adapter can have a distally facing exterior surface comprising one or more projections or surface features for aesthetic appeal. The distally facing exterior surface can be arcuate or curved. The projections or surface features can optionally be omitted. In other examples, the projections can embody other shapes, such as dimples, round bumps, shaped projections, random projections, etc.

The distally facing exterior surface can be located between two side surfaces. In an example, each of the two side surfaces can have a flat or planar wall without varying surface features. However, the two side surfaces can curve to provide an end cross-section with curves.

A recessed groove or race can be located between a first surface portion and a second surface portion on each of the two side surfaces of the tab adapter. The two second surface portions of the two side surfaces can be generally planar and parallel to one another, thereby defining a generally constant outside dimension at least along portions of the two side surfaces. The two first surface portions can also be generally parallel to one another. In an example, the two first surface portions of the two side surfaces taper inwardly in the direction from the second end towards the first end.

A projection can be incorporated on at least one of the two side surfaces of the tab adapter and extending radially of the lengthwise axis of the tab adapter. The projection can include ramped surfaces and a planar end surface that intersect with the ramped surfaces. In other examples, the projection can be formed from straight sides and a planar end surface of a semi-spherical dome, or a non-spherical dome. In use, the projection can be arranged to abut or contact the gate assembly at the distal end of the housing to open the gate wider and allow separation between the housing and the catheter hub. In an example, a projection is provided on each of the two side surfaces of the tab adapter so that the gate assembly can be abutted by both projections.

The distal opening of the tab adapter can have a perimeter defined by a plurality of edge sections or segments. The shape of the perimeter can vary depending on the shape of the catheter hub that the tab adapter is configured to mount to or mount on. For example, the shape of the perimeter can have only four side edge sections or can be semi-circular or part circle or any corresponding shape of the catheter hub outer contour. However, the shape of the perimeter does not have to precisely conform to the contour of the catheter hub in order for the tab adapter to be used with the catheter hub and secured thereto by fitment.

In an example, the proximally facing surface of the tab adapter has a first surface section and a second surface section. The first surface section can be generally curved, arcuate, or slanted, such as a ramp having a wall that is mostly vertical or extending upwardly. The second surface section can be curved or arcuate and mostly horizontal or flat. The first surface section and the second surface section connect or joined to one another and together resemble a jump or a ramp, similar to the arcuate exterior surface of the distally facing surface. The first surface section of the proximally facing surface can incorporate one or more surface features or projections.

In an example, the proximal or second opening of the tab adapter can have a perimeter defined by a semi-circular or part circle edge. The shape of the perimeter of the second opening can vary depending on the shape of the catheter hub that the tab adapter is configured to mount to or mount on. For example, the shape of the perimeter can be defined by a plurality of edge segments or sections and can vary depending on the shape of the of the catheter hub that the tab adapter is configured to mount to or mount on.

In some examples, the shape of the perimeter of the second opening does not have to precisely conform to the contour of the catheter hub in order for the tab adapter to be used with the catheter hub. The perimeters of the first and second openings can be the same or can differ from one another. The first and the second openings should extend more than the half or median line of the catheter hub body to ensure gripping to more than half of the diameter of the catheter hub body.

In an embodiment, the distally facing exterior surface of the tab adapter is provided with a narrowed tip narrows down to a smaller tip having a tip end that resembles a spear or arrow. Thus, the distally facing surface and the two side surfaces of the tab adapter can converge to define an acute tip that is somewhat pointed but that flares out to resemble a wide arrow. Just below, elevation-wise, the tip of the distally facing exterior surface, an extension is provided. In an example, the extension can be molded as an elongated stem or bar formed with the body of the tab adapter. The extension can have side edges and a bottom edge having an elongated shape with a narrowing tip. The narrowing tip or tip end of the extension can be located distally of the tip end of the distally facing exterior surface. In an alternative embodiment, the extension may be omitted. The extension can be unitarily formed with the tab adapter and can share one of the side edges with the underside surface of the tab adapter.

An actuating end of the tab adapter can include one or the other or both the narrowing tip or tip end of the extension and the narrowing tip or tip end of the distally facing surface. The actuating end can be provided at the distal end of the tab adapter. The actuating end can be configured to separate the two gates of the gate assembly located at the distal end of the housing to then provide clearance for the catheter hub, which is attached to the tab adapter, to separate from the housing following successful venipuncture.

In an example, the gate assembly can comprise a nose end having a tip. The nose end can be hollow and define a bore. The gate assembly can further comprise an upper seam and a lower seam, which allows the gate assembly to separate at the upper and lower seams and swing distally about two pivotable or rotatable hinges, as further discussed below. The upper seam extends through the upper part of the nose end. A similar corresponding lower seam can extend through the lower part of the nose end. The upper seam is located above, elevation-wise, the lower seam.

The gate assembly can be clam-shape or clam-shell shape and comprises a body having a first gate and a second gate, which can be combined to form an assembled gate assembly in accordance with aspects of the invention. In an example, the two gates can be formed by molding, such as plastic injection molding, and can include a tie strip for keeping the pair together during manufacturing and assembly. Optionally, the tie strip can be omitted, and other tracking and monitoring may be used to associate the corresponding pair of gates.

Both the first and second gates can have body sections having a barrier wall having wall sections extending proximally thereof and wall sections extending distally thereof. Each gate can further comprise a male detent, or stem or stud, and a receiving slot for engaging the corresponding receiving slot and male detent of the opposing gate. Each receiving slot can have at least one open or missing side so that the mated male detent can swing out through the missing side. For example, each receiving slot can have three sides and can be sized and shaped to receive the male detent in an interference. Thus, when a load is applied to the gate, each male detent can slip past the missing wall of the corresponding receiving slot and allow the gate to swing open, as further discussed below. The first and second gates can swing distally about respective living hinges.

Each gate is provided with a front base wall inside the boundary defined by the hollow partial cylinder of each nose portion or each distal wall. Each front base wall can have a cut-out that is sized and shaped to accommodate part of the needle and the catheter tube. When the first and second frames are joined, the two cut-outs from the two front base walls form a perimeter defining an opening that is sized and shaped to receive the circumference of the combination catheter tube and needle. The opening may be thought of as a guide opening for guiding the catheter tube and needle during advancement of the same during cannulation and vascular access.

In an example, the perimeter of the two cut-outs of the gate assembly may be referred to as a guide opening that guides the combination needle and catheter tube as the combination advances in the distal direction during cannulation and vascular access. The two base walls can have varying thicknesses, measured along the length of the first frame and/or second frame. A male detent can project from a side part of the base wall that is thicker. In other examples, the base wall can have a uniform thickness.

A male detent can be provided on each of the first and second gates. The male detent of each of the first gate and the second gate can be located on the side of the cut-out opposite the receiving slot. In an example, the two male detents can project radially relative to the lengthwise axis of the needle a sufficient amount such that the tip of each male detent extends beyond the half-way mark of the needle diameter and preferably beyond an edge of the needle on the opposite side from which the male detent extends. In other examples, the male detents can extend a shorter length or distance from the respective side from which the male detents extend. The length of the male detents can be selected to vary the amount of engagement with corresponding receiving slots.

Each receiving slot of a gate can comprise wall structures configured to frictionally engage a corresponding male detent located on the opposing gate. The receiving slot on the first gate, which can be located with the first frame or left frame, can be configured to frictionally engage the male detent on the second gate, which can be located with the second frame, and the receiving slot on the second gate is configured to frictionally engage the male detent on the first gate.

In an example, the receiving slot can have a first wall surface and a second wall surface configured to frictionally engage two surface sections of a male detent. In an example, the first wall surface and the second wall surface are arranged generally orthogonally to one another. Preferably, each receiving slot does not have a wall surface opposite the second wall surface, or has a missing wall section so as to define an open slot or channel, which then provides clearance for the male detent to separate from the receiving slot when the tip end of the tab adapter abuts and pushes against the two base walls in the distal direction. When so pushed, the two gates can rotate about the two living hinges to open the gates to then allow the catheter hub to separate from the housing. In an embodiment, each receiving slot can further include a wall surface opposite the respective first wall surface so that each receiving slot has a three-sided wall structure. Each receiving slot can be sized to grip the corresponding male detent in a slight interference fit.

The assembling of the two gates of the gate assembly can be facilitated by a hook arm located on the first gate hooking or latching to a corresponding female detent on the second gate housing. In other examples, the location of the hook arm and the female detent can reverse. Thus, in addition to the friction forces provided by the combination male detents and receiving slots discussed immediately above, the clam-shell or clam-shape structure of the gate assembly can be held together via the hook arm and the female detent. In some examples, the hook arm and female detent can be omitted and the interference between the pair of male detents and receiving slots can increase to provide the required engagement to retain the first and second gates together. In still other examples, positive engagement means, such as barbs, may be incorporated with the pair of male detents and receiving slots to provide added engagement forces.

The combination hook arm and female detent can provide holding forces in the radial direction relative to the axis passing through the bore of the nose end. However, upon being abutted and pushed in the distal direction by the actuating end of the tab adapter, such as by the tip end of the extension on the tab adapter, such as when the tab adapter moves in the distal direction to advance the catheter tube into the vein of a patient as discussed above, the hook arm deforms and separates from the female detent. At about the same time that the hook arm deflects to separate from the female detent, the male detents on the two gates separate from the corresponding receiving slots.

Two of the proximal wall sections that extend proximally of the barrier wall can be referred to as gate sidewalls. In an example, the two gate sidewalls can be pivotably connected to the corresponding barrier walls of the first and second gates. In one example, each pivotable or rotatable connection can be a living hinge, which is understood to mean a unitarily formed thin section or thin plastic strip formed during molding to join two adjacent sections, such as to join the gate sidewall and the barrier wall. The thin plastic strip allows the two joined adjacent sections to pivot or rotate about the living hinge.

Each gate sidewall can be provided with a flange, with more than one flange contemplated, such as two or three spaced apart flanges. Each set of two flanges, or at least one flange, and gate sidewall can define a key for fitting into a slot at the distal end of the housing to retain the gate assembly to the housing. The key can extend from a body section of each gate via a living hinge and the key can attach to the housing to allow the body section to rotate about the living hinge.

The first and second gates can have a seam passing therebetween. When the two gates are pushed in the distal direction to separate, such as by the actuation end of the tab adapter, the separation occurs at the seam. The seam can extend between two adjacent proximal wall sections. These wall sections may be referred to as deflection walls. Each deflection wall can have a proximal edge 638. The proximal edge can have different edge sections. The different edge sections of the proximal edge can have straight edges or curved edges. Two relatively straight edges are joined by an elbow, radius, or angle, can be an acute or an obtuse angle. Two adjacent straight edge sections of the two deflection walls converge at the seam. The two adjacent edge sections at the seam 232, or bisected by the seam, define an abutting edge. The abutting edge is configured to be abutted or pushed by the actuating or actuation end of the tab adapter, such as by the tip end of the distally facing exterior wall surface, when the tab adapter is advanced in the distal direction during use of the ExD catheter assembly.

An extended dwell catheter assembly in accordance with aspects of the invention is understood to include a tab adapter having an actuating end, such as a narrowed tip or a tip end, for pushing against an abutting edge or against a combination hook arm and female detent of a gate assembly. In an example, the tab adapter has both a tip with a tip end located on a distally facing exterior surface and a tip end located on an extension, which is located below, elevation-wise, the exterior surface of the distally facing exterior surface. The two tip ends can be part of an actuation end of the tab adapter. In some examples, the tip end of the distally facing exterior surface is located proximally of the tip end of the extension so that the two tip ends contact two different surfaces along two different planes. In an example, the tip end of the extension is configured to abut a surface that is located distally of a surface to be abutted by the tip end of the distally facing exterior surface.

Movement of the two gates in the closed direction can cause the hook arm to engage the female detent and the two male detents to engage the two receiving slots to enclose the clam-shell shape structure. The two engaged housing sections can engage without added adhesive glue or bonding.

In an example, the housing can be provided with two receiving slots at the distal end, one on the first or left frame and one on the second or right frame. In an example, each receiving slot can be formed by a first wall slab and a second wall slab. The first and second wall slabs of each receiving slot define a hollow space therebetween for receiving a key.

The gate assembly can have a key formed with each of the two gates. In an example, each gate can comprise a gate sidewall having one or more flanges, or projections that project outwardly from the surface of the gate sidewall. The combination gate sidewall and the one or more flanges can define a profile or contour, called a key 633, that is sized and shaped to fit within the hollow space of the receiving slot at the distal end of the housing. Thus, when the gate assembly is assembled to the housing, the two keys 6 on the first and second gates slide into the two receiving slots and are held thereto by frictional, interference, and/or mechanical engagements. Once assembled, the gate assembly is secured to the distal end of the housing with the two gates being pivotable about respective living hinges to swing open, such as to allow a catheter hub assembled to the housing to separate from the housing.

A gap can be provided between the first wall slab and the second wall slab. The gap can be provided to accommodate the wall structure of the gate sidewall, adjacent the living hinge. The gap can be delimited at the end opposite the opening to the hollow space by a rib, which can join the first wall slab and the second wall slab together. The first wall slab can have a contoured wall structure, which can be sized and shaped to receive the profile defined by the at least one flange on the gate sidewall of the gate assembly.

An extended dwell catheter assembly in accordance with aspects of the invention is understood to have a housing molded as a single piece. The housing may be cylindrical-in-part and rectangular-in-part. The rectangular portion of the housing may be a base. In some embodiments, the housing may be entirely cylindrical. A gate opening on top of the housing may bisect the housing lengthwise. Opening the housing by spreading the gate opening may allow a catheter hub to be removed from an interior space of the housing through a body opening.

In some embodiments, the gate opening may be a living hinge. The living hinge may separate when the gate opening is pulled apart with radial force. In some embodiments, the gate opening may be a frangible living hinge. The frangible living hinge may have perforations that facilitate separation of the living hinge and the gate opening when the gate opening is pulled apart.

A lock may serve as additional reinforcement to keep the gate opening intact. The lock may be located on a nose section of the housing between a nose end and the body opening. In some embodiments, there may be a plurality of locks on the gate opening along its length. The lock may be a detent engagement of two sides created by the bisection of the housing by the gate opening. The detent engagement may be disengaged by applying additional radial force on the housing to pull the gate opening apart. A male detent and a female detent of the detent engagement may alternate sides in relation to the gate opening.

The base of the housing may have a top opening extending from a skirt of the base to a proximal end of the housing. The skirt may be rectangular. The skirt may have rounded edges. Other skirt shapes are contemplated, such as round and triangular.

A movable bridge or a plurality of movable bridges may extend over the opening. The movable bridge may have splitting, or moving, edges that may be colinear to the gate opening. In some embodiments, the edges may be connected to each other with a living hinge. In some embodiments, the edges may be connected to each other with a frangible living hinge. The edges may split with application of radial force on the base pointing away from the edges.

The base may have wings extending out from its sides. The wings may be held to advance the catheter assembly towards the patient once the skin is punctured. The wings may have protruding grips for improved handling. The wings may also be pushed downward, meaning opposite direction of the base opening, to exert radial forces on the housing. In some embodiments, pushing down the wings may only exert enough forces to split the movable bridges. In some embodiments, pushing down the wings may split one or more components, including the movable bridges, the gate opening, and unlock the lock. In such embodiments, the ability to split one or more components may depend on the length and/or material properties of the housing. For example, a shorter housing provides a shorter distance for force travel across the length of the housing, in which case less force dissipation occurs between the wings and the nose end. In another example, a housing constructed from a material having lower ductility or hardness may allow one or more of the movable bridges, the gate opening, and the lock to split with more ease.

An extended dwell catheter assembly in accordance with aspects of the invention is understood to have a housing having a base. The base may have a top opening to observe flashback from a needle hub. The housing may additionally have a body opening providing access to an interior space housing a catheter hub. The catheter hub may be pushed to a distal position via a push tab extending from the catheter hub and out of the body opening to fully advance a catheter tube once in the body. The body opening may extend between a skirt of the base and a proximal section cover. The proximal section cover may allow the catheter assembly to be held from a more proximal position in relation to the patient. Hence, larger hands can be accommodated, and availability of more holding positions can provide improved control. The base may be rectangular up until the proximal section cover, which may be cylindrical. In some embodiments, the base may be entirely rectangular or entirely cylindrical.

A gate opening on top of the housing may bisect the housing lengthwise between a nose end and a proximal end. Having the proximal section cover and thus having the gate opening bisect the housing all the way from the nose end to the proximal end may provide added structural reinforcement to the housing. Hence, additional force may be required to spread apart the gate opening than in catheter assemblies without the proximal section cover to remove the catheter hub from the interior space of the housing. In some embodiments, the gate opening may be a living hinge. In some embodiments, the gate opening may be a frangible living hinge.

The proximal section cover may have wings. When the wings are pushed downward, meaning opposite direction of the base opening, to remove the catheter hub, more force may be required than in shorter catheter assemblies without the proximal section cover because the wings and the nose end are further apart than in such catheter assemblies, and the gate opening continues to bisect the housing proximal to the base opening unlike in such assemblies. In some embodiments, if added reinforcement is not desired, the housing may be constructed from a material having lower ductility or hardness than in catheter assemblies without the proximal section cover to allow removal of the catheter hub from the housing with more ease despite the aforementioned constraints.

An extended dwell catheter assembly in accordance with aspects of the invention is understood have a housing constructed from separate parts. The housing may have a first frame and a second frame. The first and second frames may be held together by a hinge or a plurality of hinges. The hinge may be located on the bottom of the housing. The first frame may have a male part of the hinge, and the second frame may have a female part of the hinge. In other embodiments, the first frame may have the female part of the hinge, and the second frame may have the male part of the hinge. A pin may pass through both the male part and the female part. In some embodiments, the male part may be insertable into the female part instead of using the pin.

In some embodiments, the housing may be constructed as a single piece. In such embodiments, the hinge may be a living hinge. In some of such embodiments, the hinge may resemble a conventional hinge, for example hinges generally used in opening and closing doors. The hinge may allow the first frame to open and hang down from the second frame in an open position.

The first and second frames may have an upper seam on top of the housing and a lower seam on the bottom of the housing. The upper and lower seams may bisect the housing. The upper and lower seams may be living hinges, frangible living hinges, or spaced apart. In some embodiments, only the upper seam may be a living hinge or a frangible living hinge. In some of such embodiments, only the lower seam may be a living hinge or a frangible living hinge. In some embodiments, one of the upper and lower seams may be a living hinge while another one of the upper and lower seams may be a frangible living hinge. In some embodiments, one of the upper and lower seams may be a frangible living hinge while another one of the upper and lower seams may be a living hinge. In some embodiments, some parts of the upper and lower seams may be a living hinge and some parts may be a frangible living hinge. The living hinge and/or the frangible living hinge of the upper seam and/or the lower seam may be separated by applying radial forces on the housing directed away from the upper and lower seams to pull down the first frame from a closed state to an open state. The radial forces may be applied by pushing down wings located on a proximal section cover of a base. The upper seam is located above, elevation-wise, the lower seam.

The base of the housing may be separated from rest of the housing by a skirt. In some embodiments, the proximal section cover may be deleted, and the wings may extend out from sides of the base. In some embodiments, the sides may have protrusions to provide improved grip.

In addition to, or in lieu of, the wings, radial forces may be applied by pushing down rails extending out of the housing. The rails may extend from the skirt to the nose section. The rails may extend out widthwise from a body opening providing access to an interior space of the housing. The rails may be supported with a rail leg or rail legs extending between under the rails and the housing.

A lock may serve as additional reinforcement to keep the upper and lower seams intact. The lock may interrupt the upper seam. The lock may be located on a nose section of the housing between a nose end and the body opening. In some embodiments, there may be a plurality of locks. In some embodiments, the lock may be a detent engagement of the first and second frames. In some embodiments, the detent engagement may be disengaged by pushing a tab away from the engagement to lift up and free a male detent from a female detent. The tab may be located on the same frame as the male detent. In some embodiments, the male detent may be on the second frame and the female detent may be on the first frame. In some embodiments, the male detent may be on the first frame and the female detent may be on the second frame.

The tab may have a curved shape resembling a fin. An inner curve of the tab may have a rough surface. The rough surface may provide improved grip. In some embodiments, the tab may be deleted. In such embodiments, the detent engagement may be disengaged by applying additional radial force on the housing when pulling down the first frame from the closed state to the open state.

The catheter hub of the catheter assembly may be pushed to the distal position via a push tab extending from the catheter hub out of the body opening to fully advance a catheter tube once in the body. In the distal position, the catheter hub may be partially covered by the nose section.

Also, in the distal position, the push tab may abut the nose section to stop further movement of the catheter hub into the nose section.

The first frame may open and hang down from the second frame by hinges. The first frame may not contact the second frame at the lower seam except for by the hinges. In embodiments having an upper seam that is a living hinge(s) and/or frangible living hinge(s), the upper seam may be torn open by the application of radial forces on the housing.

A needle hub may be tightly fitted onto the second frame so that the needle hub does not fall out of the interior space once the housing is opened from the first frame. In other embodiments, locations(s) of one, some or all feature(s) and/or component(s) of the housing may be switched to the opposing frame so that the housing can be opened from the second frame.

The catheter hub may be removed from the housing by moving the nose section laterally while holding the catheter hub in place. The catheter hub may then stay attached to the patient. A needle may be exposed when the catheter hub is detached from the assembly. The needle may engage with a needle guard (not shown) located inside the catheter hub as the needle is withdrawn from the catheter hub. The needle guard may prevent needle pokes. The needle, the needle hub, and the housing may then be safely discarded.

An extended dwell catheter assembly in accordance with aspects of the invention is understood to have a housing constructed from a single piece. The housing may have hinges. The hinges may be living hinges. The hinges may not have pins. The housing may have a lock or a plurality of locks to keep the housing closed. The lock may not feature a tab. The housing may be held from a base proximal to the housing. Wings or a proximal section cover may be omitted. Hence, the base may be open at a proximal end. A needle hub may extend out proximally from the base.

An extended dwell catheter assembly in accordance with aspects of the invention is understood to have a housing constructed from separate parts. The housing may have a first frame and a second frame. The first and second frames may be held together by a detent engagement of the first and second frames. The detent engagement may be located on a nose section of the housing between a nose end and a body opening. In some embodiments, there may be a plurality of detent engagements of the first and second frames. In some embodiments, the detent engagement may be disengaged by pressing a button on the housing that disconnects the first and second frames. Once the first and second frames are disconnected, a catheter hub may be freed from an interior space of the housing.

The button may have one or more ramped side surfaces applying radial forces on the housing to disengage the detent engagement when the button is depressed. The button may be housed in a button housing. The button may have a top surface. The top surface may be directly contacted to press down the button. The top surface may be round. Other shapes of the top surface are contemplated, such as oval, square, and rectangle. The button may be located proximal to the body opening on a base of the housing. A needle hub may extend from within the interior space and out of the base. The base may be dimensioned so that more than half of the needle hub is exposed. In some embodiments, the button may be replaced by a latch that is unlatched by applying radial forces on the housing to disengage the detent engagement.

In some embodiments, the male detent of the detent engagement may be on the second frame and the female detent of the detent engagement may be on the first frame. In some embodiments, the male detent may be on the first frame and the female detent may be on the second frame. The catheter hub may be extracted from the housing once the detent engagement is fully disengaged and the first and second frames are fully detached from each other. In some embodiments, the partially disengaged state may be the result of the button being only partially pressed down. In some embodiments, the partially disengaged state may be the result of the button fully pressed down, and the frames may require additional radial force to complete detachment from each other. For example, each one of the frames may be held by one hand and pulled apart from a partially disengaged state.

When the button is depressed, the button housing may separate, a first half of the button housing being on the first frame and a second half of the button housing being on the second frame. The button housing may have one or more ramped sidewalls. Each ramped sidewall may slidably receive each side surface. When the button is depressed, the ramps of the sidewall and the side surface may align so no space is left for the button to move down unless the button housing separates, so each side surface may exert a force on each ramped sidewall.

One or more male tabs and one or more female tabs that can engage with the one or more male tabs may extend from the first and second halves of the button housing. The male tabs may extend from each side surface of the first half, and the female tabs may extend from each side surface of the second half. In other embodiments, the male tabs may extend from each side surface of the second half, and the female tabs may extend from each side surface of the first half. In other embodiments, one of the side surfaces may have the male tab and the other side surface may have the female tab, and one of the side surfaces may have the female tab and the other side surface may have the male tab.

One of the female tabs may be slidably engageable with a recess of the button. When the button is pressed, the male tabs may disengage from the female tabs due to the radial forces applied on the button housing and a roof of the recess pressing down on the female tab, which is then freed from its complementing male tab. In other embodiments, there may be a plurality of recesses that may be slidably engageable with a plurality of female tabs and plurality of recess roofs that may release the plurality of female tabs from male tabs.

The ramped side surfaces of the button may have pins extending out therefrom. The button may attach to the catheter assembly by coupling the pins to seats located inside the button housing. The pins may move up and down within the seats when the button is pressed until the first and second frames separate along with the button to be safely discarded. In some embodiments, the button may be coupled to one of the first and second frames in such a way that the button stays with that frame after the frames separate from each other. By example and not limitation, such a coupling that allows the button to stay with one of the frames may require tight fitment of one of the pins into its complementing seat.

The button may have a ramped rear surface in addition to the ramped side surfaces. In some embodiments, the ramped rear surface may facilitate sliding of the button when pressed. In some embodiments, the ramped rear surface may apply radial forces on the button housing due to the bulk of the button inside the housing changing when pressed. The pins may have legs that extend below the button and connect from underneath the button. The legs may allow for the button to move down evenly when pressed.

An extended dwell catheter assembly in accordance with aspects of the invention is understood to have a housing constructed from separate parts. The housing may have a first frame and a second frame. The first and second frames may be held together by clamp-shaft coupling. The first and second frames may pivot or rotate away from each other at the clamp-shaft coupling to open the housing. The clamp-shaft coupling may be located between upper and lower body openings of the housing and a base of the housing. The base may have ends on each of the first and second frames that proximally curve outward. The curved ends may be used as leverage to be pushed together and open the housing. Once the housing is opened up, a catheter hub located in an interior space of the housing may be removed.

Prior to removal, the catheter hub may be pushed in a distal direction to advance a catheter tube into the patient. The catheter hub may be pushed with a pusher. The pusher may have a T-shape. The pusher may be initially proximal to a push tab of the catheter hub. The pusher may be pushed in a distal direction to engage with the push tab and push the catheter hub to a nose section of the housing. Once the catheter hub is fully advanced, the base may be squeezed from the base ends to open and detach the housing from the catheter hub.

The clamp-shaft coupling may have upper clamp and upper shaft, and lower clamp and lower shaft pairs. The upper and lower clamps may be on alternating frames. Similarly, the upper and lower shafts may be on alternating frames. In some embodiments, the upper and lower clams may be on the same frame and so may the upper and lower shafts. In some embodiments, the clamp-shaft coupling may be replaced with another connection that the first and second frames may pivot from. By example and not limitation, such a connection may be a hinge like a traditional hinge used in opening and closing doors.

The base may have a plurality of grips protruding from each of the first and second frames. The grips may improve gripping when holding the catheter assembly from the base. The grips may be shaped and arranged like gills. The base may also have a second type of grips protruding from each of the first and second frames. The grips may be located more proximally on the housing relative to the grips. The grips may have a circular shape. The grips may have a curved surface that complements fingertips of the user. The grips may allow the user to have improved grip when squeezing the base ends to open the housing.

The pusher may have a pair of legs, one at each end of the hat of its T-shape. The legs may have hook shapes. The hook shape of the legs may slidably engage with tracks of the housing, respectively. The tracks may extend along each side of the upper body opening. The pusher may be slid on the tracks in a distal direction to first engage with the push tab of the catheter hub and then push the catheter hub towards the nose section.

In a fully advanced or distal position, the push tab may be sandwiched between the nose section and the pusher. The pusher may be slid to this position by holding and guiding the pusher from a handle. The handle may be leveled above the legs. The handle being further out from the housing may make it easier to grip the pusher as well as allow the handle of the pusher to sit above the base when in a proximal position. The handle may have protrusions for increased grip.

In the distal position, each leg of the legs may be above a track end of track ends. The track ends may be recesses between the nose section and the tracks on each side of the upper body opening. The track ends may be dimensioned so that the hook-like legs of the pusher do not grab onto the housing and have space to be detached from the housing. The first and second frames may each have grips that extend across the nose section and the base. The grips may be used to hold the catheter assembly with one hand while pushing or removing the pusher with the other hand.

When the housing is opened, the opening between the first and second frames may decrease proximally due to the pivot point clamp-shaft coupling being located in a proximal section of the housing. The pusher and the housing may be discarded, and the catheter hub may be left attached to the patient.

At the most distal end of the housing, a tip may extend out of a nose end. The tip may have two separable sections, one at each of the first and second frames, respectively. The sections may form a double butt lap joint when the housing is closed. The section of the tip may be on top of the section when joined together. In other embodiments, the section may be on top of the section when joined together.

A lock may serve as additional reinforcement to keep the sections joined, and generally the first and second frames intact. The lock may interrupt the upper seam. The lock may be located on the nose section of the housing between the nose end and the upper body opening. In some embodiments, there may be a plurality of locks. In such embodiments, one of the locks may be between the nose end and the lower body opening.

In some embodiments, the lock may be a detent engagement of the first and second frames. In some embodiments, the detent engagement may be disengaged by squeezing the curved based ends together. The resulting radial forces on the housing may lift up and free a male detent from a female detent. In some embodiments, the male detent may be on the second frame and the female detent may be on the first frame. In some embodiments, the male detent may be on the first frame and the female detent may be on the second frame. In embodiments having a plurality of locks, the male and female detents may each alternate between the first and second frames.

There may be another embodiment of the pusher having a distal handle and a proximal handle. The distal and proximal handles may provide multiple options for holding the pusher. Depending on the user's hand size or position of the catheter assembly relative to the user or the patient, holding the pusher from the distal handle or the proximal handle may be easier. The proximal handle may be elevated relative to the distal handle. The elevated position of the proximal handle may allow it to sit on the base of the housing when the pusher is in a proximal position. The distal and proximal handles may be the same size or different sizes. The distal and proximal handles may each have a grip or grips protruding from thereon. The distal handle may have a tip extending distally therefrom. The tip may be curved upwards. The curvature of the tip may allow the user's finger to engage with the distal handle without slipping and leverage the tip when sliding the pusher in a distal direction.

An extended dwell catheter assembly in accordance with aspects of the invention is understood to have a housing that may be constructed from separate parts. The housing may have a first frame and a second frame. The first and second frames may be held together by clamp-shaft coupling. A first arm and a second arm may be pivotably or rotatably attached to the clamp-shaft coupling. The first and second arms may overlap each other. Due to the overlap, the first and second arms may resemble a pair of scissors. The first and second arms may have a distal section and a proximal section. The distal section may be within an interior space of the housing while the proximal section may be extending out of the interior space. The distal section may push the first and second frames apart when the first and second arms pivot away from each other at the clamp-shaft coupling to open the housing when ends of the housing are squeezed. The first and second arms may make opening the housing is easier by providing additional leverage. Lock or locks keeping the first and second frames intact may be easier to unlock due to the radial forces applied on the housing by the first and second arms.

The clamp-shaft coupling may be larger in size than in catheter assemblies without the first and second arms. The larger size may allow for the first and second arms to pivot with less application of force. A plurality of locks is shown, one located on a nose section of the housing between a nose end and an upper body opening and another between the nose end and a lower body opening.

An extended dwell catheter assembly in accordance with aspects of the invention is understood to have a housing constructed from separate parts. The housing may have a first frame and a second frame. The first and second frames may have an upper seam and a lower seam. The upper seam may be at a nose section of the housing. The upper seam may curve out and widen into a body opening.

At the most distal end of the housing, a tip may extend out of a nose end. The tip may have two separable sections, one at each of the first and second frames, respectively. The sections may form two finger joints, one extending from the upper seam and one extending from the lower seam, when the first and second frames are intact.

The first and second frames may be held together by a bottom plate. The bottom plate may have long tabs engageable with slots of the first frame and short tabs engageable with slots of the second frame, respectively. A latch pivotably attachable to the bottom plate and the first frame may pull the bottom plate in a proximal direction when activated, thereby releasing the short tabs from their slots. At the same time, the long tabs may still be engaged to the slots, and thus the second frame may separate from the first frame, which remains attached to the bottom plate and the latch. The latch may go over a base of the housing. A needle hub may be ejected proximally out of the base once a catheter hub is pushed to a distal position.

The long tab and the short tab may be distal to the long tab and the short tab. The long tab and the short tab may extend out of their respective slots out to a first frame distal slot recess and a second frame distal slot recess when engaged with the first and second frames, respectively. The first and second frame distal slot recesses may have the same dimensions. The first and second frame distal slot recesses may have a trapezoidal shape. Other shapes are also contemplated, for example, rectangular, square, and triangular.

The long tab and the short tab may extend out of their respective slots out to a first frame proximal slot recess and a second frame proximal slot recess when engaged with the first and second frames, respectively. The first frame proximal slot recess may be dimensioned larger than the second frame proximal slot recess. The larger dimensions of the first frame proximal slot recess may accommodate the long tab. The first and second frame proximal slot recesses may provide a snug fitment for the tabs. In other embodiments, the first and second frame proximal slot recesses may have the same dimensions. In such embodiments, fitment of the tab may not be snug.

The tabs may have chamfered distal ends. The tabs may have rounded distal ends. In other embodiments, all distal ends may be rounded, chamfered, or squared off. The slots may have widths just enough to accommodate their respective tabs. The tabs may be directly adjacent to the base.

The bottom plate may lay inside an interior space of the housing under the catheter hub. The tabs engageable with the first frame and the tabs engageable with the second frame may be separated by a groove. The groove may run along an entire length of the bottom plate on its surface facing up, or toward the catheter hub when assembled. The latch may pivotably or rotatably connect with the first frame from under the bottom plate. The connection may be facilitated with a connection pin. The connection pin may extend out inwards, or towards the interior space, from a distal bottom corner of a first side of the latch. The connection pin may have a generally cylindrical shape with a protrusion on its outer surface that extends along its length. The protrusion may engage with a slot inside the base of the first frame that limits the rotation of the connection pin to allow the latch to pivot only a certain amount in the proximal direction.

The latch may have a top and a second side. The top may have teeth that extend down from an inside surface facing the base when assembled. The teeth may form a finger joint with an opposing tooth that goes in between the teeth. A first half of the tooth may be on the first frame and a second half may be on the second frame. In some embodiments, there may be a plurality of teeth receivable by multiple sets of the teeth. The top and the first side may extend across an entirety of a height and width of the base. The second side may partially extend across the height of the base. The first side may have a proximal bottom corner. An edge may extend across bottom corners. The edge may be sloped, the proximal bottom corner being higher, elevation-wise, than the distal bottom corner.

The latch may be movably connected to the bottom plate with a shaft extending inwards, or towards the base. The shaft may be cylindrical. The shaft may move laterally in a proximal direction when the latch is pulled in the same direction. The lateral movement of the shaft may be limited by the limited rotation of the connection pin. The first and second sides of the latch may form filleted corners with the top of the latch. In other embodiments, the corners may be straight.

The bottom plate may have a proximal hook attached to the shaft of the latch. When the latch is pulled in a proximal direction, the shaft may pull the bottom plate proximally from the proximal hook. When the bottom plate is pulled in a proximal direction, the short tabs will disengage with their respective slots while the long tabs remain engaged with their respective slots. As a result, the second frame will detach from the first frame, which will remain attached to the latch and the bottom plate. The first and second frames may be separated from the catheter hub, which may remain attached to the patient. The first and second frames may then be discarded.

Methods of making and of using the extended dwell catheter assemblies and components thereof are within the scope of the present invention.

BRIEF DESCRIPTION OF THE DRAWINGS

These and other features and advantages of the present devices, systems, and methods will become appreciated as the same becomes better understood with reference to the specification, claims and appended drawings wherein:

DETAILED DESCRIPTION

The detailed description set forth below in connection with the appended drawings is intended as a description of the presently preferred embodiments of catheter assemblies and components thereof provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Broadly speaking, extended dwell ("ExD") catheter assemblies described herein each comprises a housing and a catheter assembly. The housing is configured to accommodate the catheter assembly during initial puncture, through catheter advancement, through separation of the catheter hub from the needle hub, and then activating to enable separation of the catheter hub from the housing and allowing the catheter to remain with the patient. The housing and the catheter hub can separate through a variety of different mechanisms. For example, the housing can split into two or more housing parts to release the catheter hub, the housing can have parts that swing, rotate, or pivot, the housing can have end cap components that swing open to open the gate opening to allow the catheter hub to exit the housing, and the housing can have a gate assembly that attaches to the distal end of the housing, among other options. The gate assembly can have two gates located on two gate housing bodies that can join and wherein each gate can swing open via a living hinge. The two gates can engage via male detents and receiving slots. The two gates can engage via a hook arm and a female detent. The unique housing designs allow for use with standard or existing catheter assemblies without the need for, although optional, specifically designed catheters. Thus, standard catheters with extended lengths and midline catheters with approximately 8-10 cm catheter lengths are readily usable with the housings of the present disclosure, with or without a guidewire.

Figure 1:
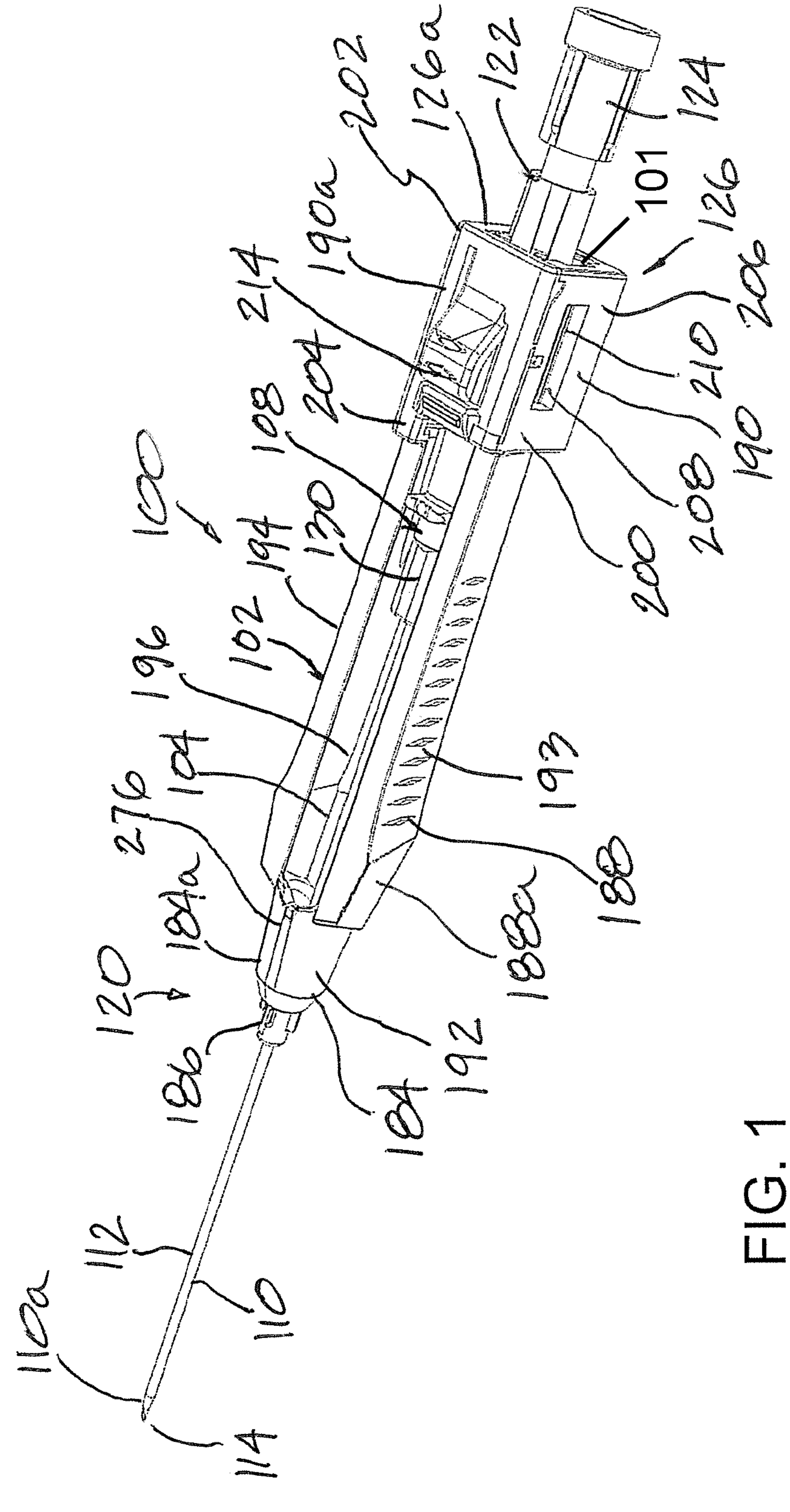
FIG. 1 is a perspective view of an extended dwell catheter assembly provided in accordance with aspects of the present invention.

With reference now to FIG. 1, a perspective view of an exemplary embodiment of an extended dwell catheter assembly 100 in accordance with aspects of the invention is shown. In the example shown, the extended dwell or ExD catheter assembly 100 comprises a housing 102 having a receiving space or interior space 104 having a catheter assembly 108 located therein, which has a catheter tube 110 and a needle 112 located inside the lumen of the catheter tube extending out a distal end 120 of the housing 102. A needle tip 114 of the needle extends out a distal opening 110*a* of the catheter tube 110. The catheter tube 110 is attached to a catheter hub 130 and the needle 112 is attached to a needle hub 122. The needle hub 122 is shown extending out a proximal end 126 of the housing 102. The needle hub 122 can include a vent plug 124, which can engage the proximal opening of the needle hub 122, such as in a Luer fit.

Figure 2:
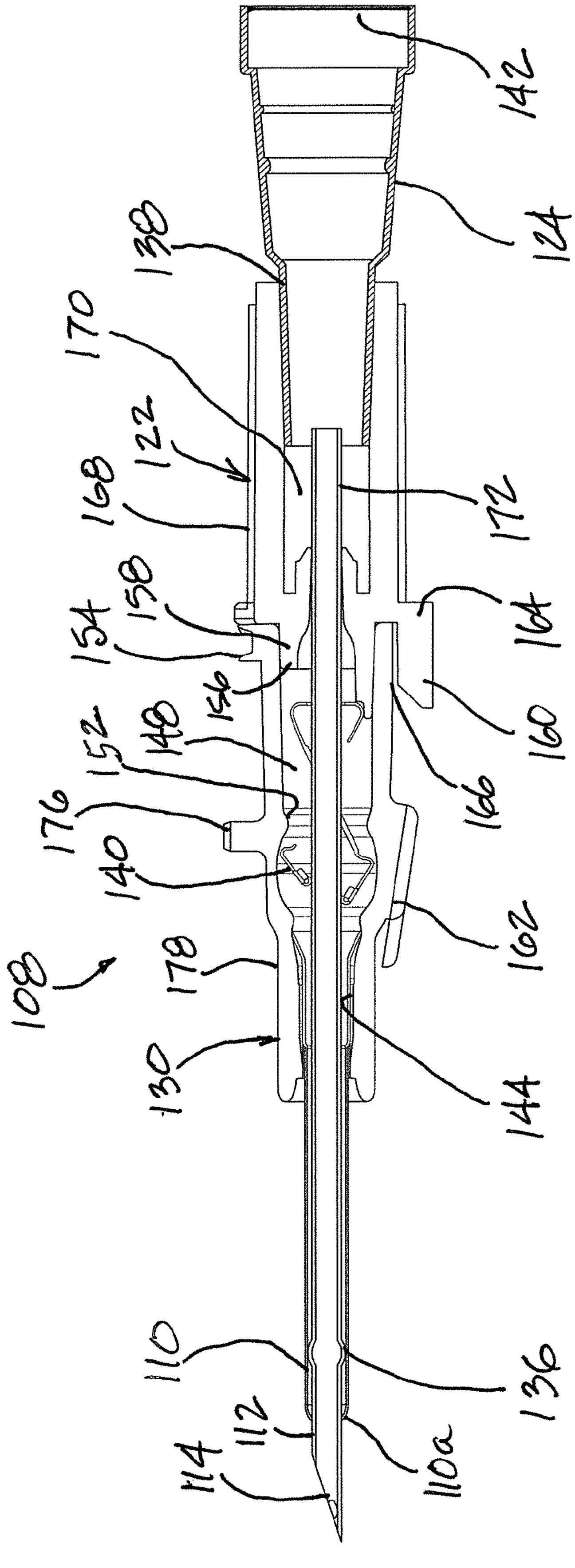
FIG. 2 is cross-section side view of a catheter assembly provided in accordance with aspects of the present invention for use with a multi-part housing.

With reference now to FIG. 2, a cross-sectional side view of the catheter assembly 108 of FIG. 1 is shown outside or away from the housing 102. The presently shown catheter assembly 108 and similar catheter assemblies may be used with the housing 102 to form an ExD catheter assembly in accordance with aspects of the present invention. Optionally, a guide wire may be incorporated to assist in inserting, positioning, and moving a catheter, as further discussed below.

In an example, the catheter assembly 108 comprises a first hub or catheter hub 130 having an over-the-needle tube or catheter tube 110 attached thereto and a second hub or needle hub 122 having a needle 112 attached thereto. The catheter tube 110 has a lumen or bore for receiving the needle 112 and has a distal opening or distal end opening 110*a* and the needle tip 114 of the needle 112 extends distally of the distal opening 110*a* in a ready to use position, in which the assembly is ready for venipuncture. The catheter assembly 108 can also be called a needle assembly.

The needle 112 can include a change in profile 136 located proximally of the needle tip 114 for use with a needle guard. The needle tip 114 extends distally of the distal end opening of the tube or tubing 110 in the ready to use position with the change in profile 136, if incorporated for use with a needle guard, located proximally of the distal end opening 110*a*. The change in profile 136 can be a crimp, a bump, or a material build-up having different profile than other diameter sections of the needle shaft. As used herein, the term proximal is understood to mean an end or side closer to the practitioner and the term distal is the opposite end or side.

The change in profile 136 can be used to interact with a needle guard 140 during retraction of the needle 112 following successful venipuncture, as further discussed below. A vent plug 124 is disposed at the proximal open end 138 of the second hub or needle hub 122. The vent can have a vent filter 142 at a proximal end thereof, which is conventional. As shown, the catheter tube 110 is attached to the first hub or catheter hub 130 by a ferrule or bushing 144.

The needle guard 140 can be provided in the interior cavity 148 of the first hub or catheter hub 130 for covering the needle tip 114 in the protective position. When incorporated, the needle guard 140 can be one of the needle guards disclosed in U.S. Pat. No. 6,616,630, the contents of which are expressly incorporated herein by reference. In some examples, the needle guard 140 can be omitted. If so, the change in profile 136 on the needle can also be omitted. In still other examples, a needle guard can be included without also including a change in profile on the needle. In yet other examples, the needle guard 140 can be located in a third housing between the first hub 130 and the second hub 122. An exemplary needle guard located in a third housing is disclosed in U.S. Pat. No. 8,597,249, the contents of which are expressly incorporated herein by reference. In still other examples, the needle guard can include multiple arms or fingers extending in both a first direction and an opposite second direction as disclosed in U.S. Pat. No. 9,387,307, the contents of which are expressly incorporated herein by reference. For example, the needle guard can include a first protector body surrounded by a second protector body.

In an example, the needle guard can be made from a metal material and can have a resilient portion that can generate a biasing force. The needle guard can comprise a wall surface that is positioned to a side of the needle and is movable distal of the needle tip to guard the needle tip from accidental contact therewith. The wall surface can be a needle trap and can move directly in front or distal of the point of the needle tip.

As shown, the needle guard 140 can include a proximal wall and two arms extending distally of the proximal wall. The two arms can intersect one another in the ready to use position of FIG. 1, and when viewed from the side view of FIG. 1, and in the protective position in which the needle guard covers the needle tip, again as viewed from a side. In some examples, the two arms of the needle guard 140 can extend in a distal direction without intersecting one another. Two distal walls, one on each arm, can be incorporated to block the needle tip. The two distal walls can be biased outwardly by the needle 112 in the ready to use position of FIG. 1 and disposed distally of an internal change in profile 152 inside the first hub 130 in the ready to use position. The internal change in profile 152 can be a reduced diameter section located next to an inside diameter section of a larger dimension. The elbows on the two arms of the needle guard can have a dimension that is larger than the inside diameter at the internal change in profile 152 to restrict proximal movement of the needle guard from the catheter hub until the two arms are no longer biased outwardly or until the dimension at the two elbows are reduced.

Each distal wall of each arm can include a curved lip to facilitate relative movement between the needle guard 140 and the needle 112. When in the ready to use position, the dimension measured between the two joints or elbows, at the intersection between each arm and its respective distal wall, is larger than the inside diameter of the internal change in profile 152, which prevents the needle guard 140 from moving proximally thereof due to the relative dimensions. Once the needle tip 114 moves proximally of the two distal walls, the two arms are allowed to move radially inward and one or both distal walls close over the needle tip to block the needle tip in a protective position. At this point, the dimension between the two joints or elbows decreases and is smaller than the internal dimension of the internal change in profile 152, which then allows the needle guard to move proximally and be removed from the catheter hub with the needle. In alternative embodiments, the dimension between the two joints can be equal to or slightly larger than the internal dimension of the internal change in profile 152 and the needle can still move proximally by flexing or squeezing the two joints to get through the internal change in profile 152.

The first hub 130 has a proximal opening 156 having a nose section 158 of the second hub 122 disposed therein. The proximal opening 156 of the first hub has a female Luer for receiving a male Luer tip, such as a syringe, an IV tubing connector, a Luer extension set, etc. External threads 154 can be provided on the exterior surface at the proximal end for threaded engagement with a threaded collar of a male threaded Luer tip. A pair of stabilizing wings 162 can extend radially of the first hub 130 to facilitate securement or anchoring of the first hub 130 to a patient following successful venipuncture. Optionally the wings can be omitted. The first hub 130 can embody a standard IV catheter hub without an injection port. In other examples, the first hub can include an injection port, or an integrated extension set. If the wings are not present on the first hub or catheter hub 130, then the bottom of the first hub can have a flattened surface angled at between 2 to 15 degrees from the through axis of the first hub.

The first hub 130 is removably secured to the second hub 122 by receiving the nose section 158 of the second hub in the proximal opening 156 thereof. A flange or extension 160 can be provided on the second hub 122 and together with the nose section 158 define a gap 166 having part of the first hub located therein. Optionally the flange or extension 160 can be omitted and a stub 164 or other surface mating features provided. The stub 164 can be the male part of a key fitting in a gap through or partially into the Luer threads to prohibit rotation of the second hub 122 relative to the first hub 130. The proximal facing end surface of the first hub abuts the distally facing surface of the step in the outside surface of the second hub which is at the proximal end of the nose section 158, which is inside the first hub. This abutment can set the amount of protrusion of the needle tip 114 out of the catheter tubing 110*a*. The stub 164 can be an optional structural feature.

The second hub 122 has a body 168 having an optional interior cavity 170 having the proximal end 172 of the needle 112 projecting there-into. The interior cavity 170 can function as a primary blood flashback chamber. The proximal opening 138 of the body 168 can have a female Luer for receiving the vent plug 124 or a syringe tip therein and the exterior can have threads or be without threads. In an example, the exterior of the body 168 of the second hub 122 is generally cylindrical and without threads. The first and second hubs can be made from plastic materials, such as by plastic injection.

A push tab 176 can be provided with the first hub or catheter hub 130. The push tab 176 can be located on an exterior surface 178 of the first hub 130 at a location distal of the exterior threads 154 so as to avoid interfering with the exterior threads. For example, the push tab 176 should be positioned sufficiently distally of the exterior threads 154 so that when a threaded male connector, such as a syringe type with a threaded collar, is connected to the threads of the first hub, the push tab 176 does not interfere with the connection. In some examples, the push tab 176 should be positioned sufficiently distally of the exterior threads 154 so that when the push tab 176 is folded over, the push tab does not interfere with the connection.

In some examples, the catheter assembly 108 can incorporate a valve and a valve opener. For example, a valve and a valve opener can both be located within the catheter hub 130. In use, the valve opener can be pushed distally into the valve to open the one or more slits formed with the valve to open a fluid passage through the valve for fluid flow. An exemplary valved catheter assembly with a valve opener is disclosed in U.S. Pat. No. 8,333,735, the contents of which are expressly incorporated herein by reference. The valve opener can have a nose section having a bore and a plunger section located proximally of the nose section. The nose section can be pushed into the valve to open the one or more slits of the valve, such as three slits defining three flaps. The plunger section can comprise two or more plunger components having a gap therebetween. The gap can allow fluid to flow through the plunger components and through the bore in the nose section.

With reference again to FIG. 1 in addition to FIG. 2, the housing 102 of the present ExD catheter assembly 100 comprises a left frame or first frame 193 and a second frame or right frame 194 attached to one another. Each frame comprises a nose portion 184*a*, a body portion 188*a*, and a base portion 190*a*. The two nose portions 184*a* can join to form a nose end 184, the two body portions 188*a* can join to form a body 188, and the two base portions 190*a* can join to form a base end 190. In an example, the nose end or nose portion 184 is provided with a nose tip 186 having an elongated cylindrical like structure having a bore for accommodating the catheter tube 110 and needle 112, which is located within the catheter tube. The nose end or nose portion 184 can further include a nose base 192, which has an enlarged portion formed with the tip 186, and a tapered distal portion. A plurality of support ribs or fins can be provided at the intersection between the tip 186 and the nose base 192. In other examples, the nose end 184 can be a spherical or rounded dome having an opening to accommodate the catheter tube and needle. In other examples, the nose end 184 can have a different shape, such as resembling a multi-sided structure connected to form an enclosed end with a central opening to accommodate the needle and catheter tube.

The body 188 has an interior space 104 for accommodating a catheter assembly, which can be a catheter assembly as described with reference to FIG. 2. A body opening or first opening 196 opens into the interior space 104. As shown, the body opening 196 extends from the nose end 184 to the base end 190.

In an example, a second opening opposing the first opening 196 is provided with the body 188 so that the interior space 104 can be accessed from the two body openings. Thus, the body therefore can have a through passage defined by the two body openings 196. In other examples, the body 188 only has a single opening 196 leading to the interior space 104 as shown with the opposing side being solid or is enclosed by wall surfaces of the first frame and the second frame. Optionally the enclosed side can have small windows or openings for access or venting but not a full opening, like that of body opening 196.

The base or base end 190 extends from the body 188 and has a plurality of sides. In an example, there can be four sides 200, 202, 204, 206 defining an interior space 208, which is open to the interior space 104 of the body 188. In other examples, the base 190 can embody a generally elongated cylinder or a non-circular cylinder. For discussion purposes, side 204 and side 206 can be identified as the top side and the bottom side, respectively. Side 200 and side 202 can be identified as the left side and the right side, respectively. The sides may also be understood as the first side 200, the second side 202, the third side 204, and the fourth side 206. These specific nomenclatures are given so as to enable calling out a particular side relative to other sides only but are not limiting unless the context indicates otherwise.

The base 190 can have an open proximal end to allow the needle hub 122 to extend proximally thereof, proximal of an end surface 126*a*, in the ready to use position of FIG. 1. As shown, the first side 200 and the second side 202 of the base end 190 can each have an opening 210 to allow viewing and accessing the interior space 208 of the base end 190, such as to facilitate or assist assembling of the catheter assembly 108 therein, as further discussed below.

Figure 3:
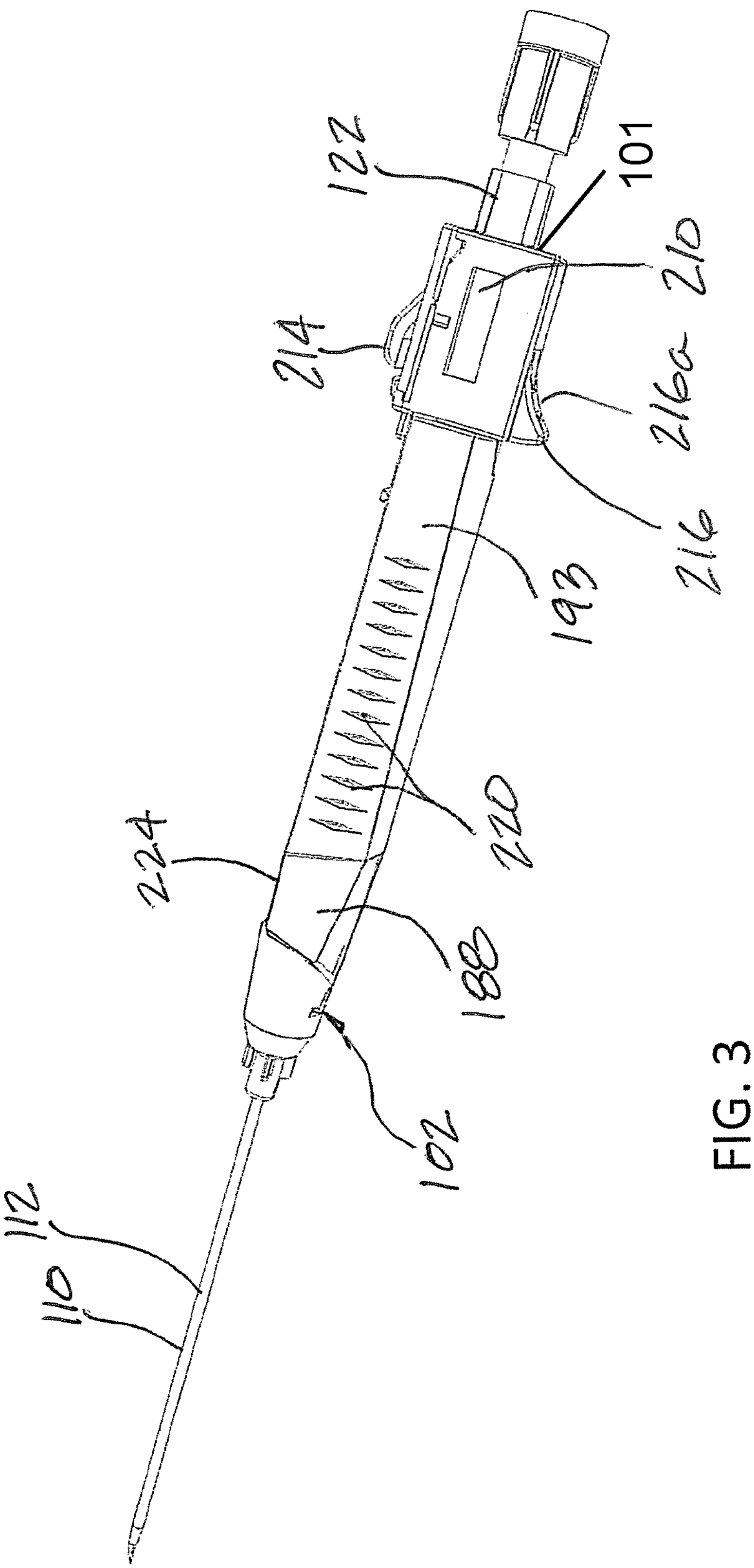
FIG. 3 is a side view of the assembly of FIG. 1

The top side 204 of the base end 190 can be provided with a first lever or top lever 214 and the bottom side 206 is provided with a bottom lever 216 (FIG. 3). As further discussed below, when a user simultaneously applies a compressive force and a distally directed force on the top lever 214 and a compressive force and a proximally directed force on the bottom lever 216, the user can cause the left housing frame 193 and the right housing frame 194 to move relative to one another and the detents on the first frame 193 and second frame 194 to separate and the housing to then separate into separate housing components, i.e., the left frame 193 and the right frame 194. In other words, by manipulating the top lever 214 and the bottom lever 216, the user can cause the housing 102 to separate into two or more housing components. The separation of the housing 102 into housing components can then expose the catheter assembly 108 to separate from the housing 102 following successful venipuncture so that the catheter hub 130 (FIG. 2) can then be secured to an IV line and secured to the patient, such as by using tape or securement dressing. In other examples, by rearranging the detents or engagement tabs between the left housing frame 193 and the right housing frame 194, the user can simultaneously apply a compressive force and a proximally directed force on the first lever or top lever 214 and a compressive force and a distally directed force on the second lever or bottom lever 216 to move the two housing sections relative to one another and the detents on the first frame 193 and second frame 194 to separate.

FIG. 3 is a side view of the ExD catheter assembly 100 of FIG. 1. In the orientation shown, a plurality of surface ornamentations 220 can be seen on the exterior surface of the left or first frame 193, specifically at or on the left body 188. A similar set of surface ornamentations can be provided with the right or second frame 194. A generally planar upper edge 224 is provided with both body frames 193, 194. Further, the distal most edge of the top lever 214 is located proximally of the distal most edge of the second or bottom lever 216. This arrangement is utilized to enable ready grip of the top lever 214 by a thumb and the bottom lever 216 by an outer edge of the index finger to separate the housing 102 into housing components, as further discussed below. For example, the index finger can push against the curved proximally facing surface 216*a* of the bottom lever 216 and pushed distally or in the distal direction.

In other examples, the relative arrangements between the top and bottom levers 214, 216 can be altered or arranged differently depending on the detent types or snap connections incorporated to retain the first frame 193 and the second frame 194 together, as further discussed below.

Figure 4:
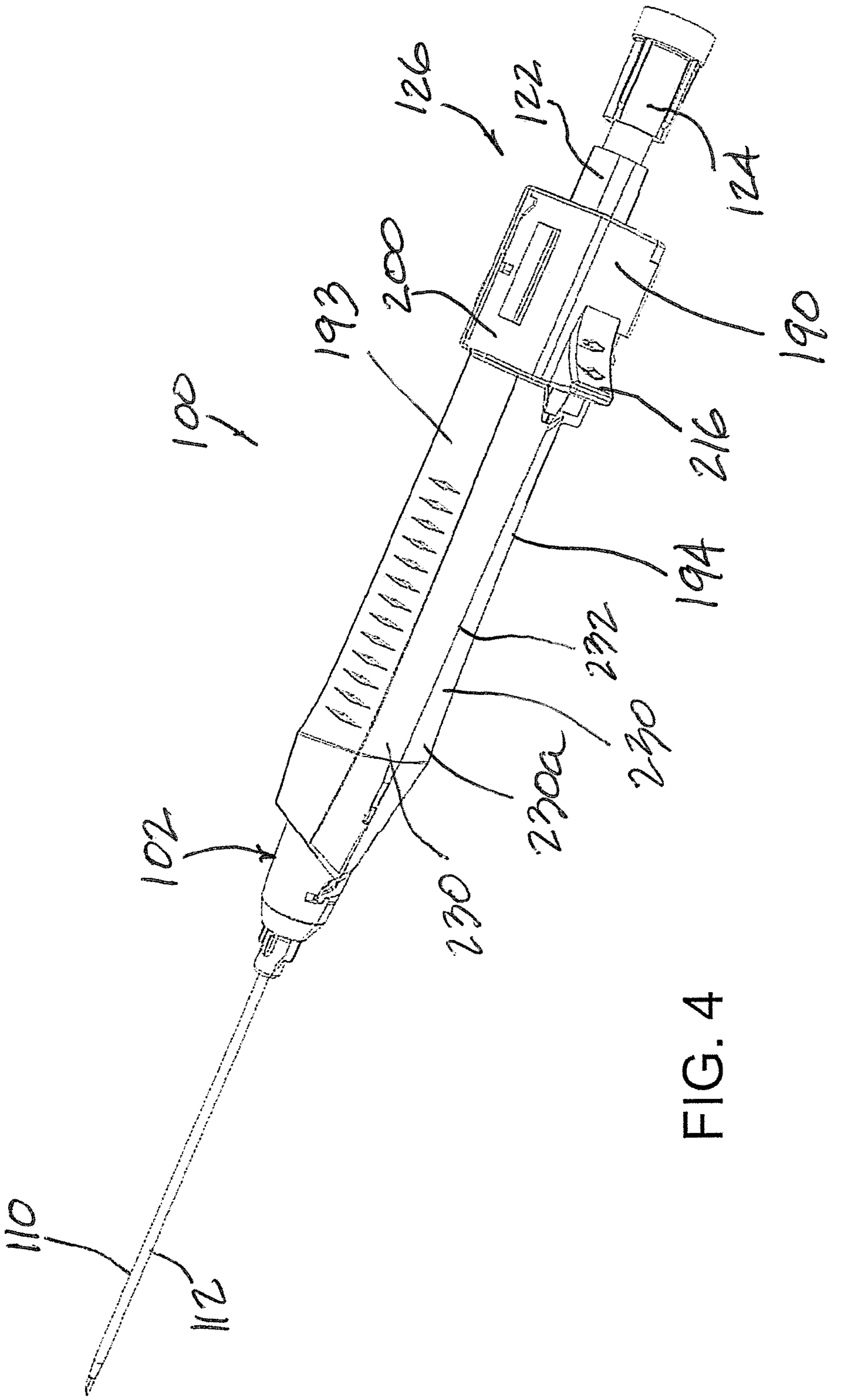
FIG. 4 is a perspective view of the extended dwell catheter assembly of FIG. 1 from a different perspective.

With reference now to FIG. 4, a bottom perspective view of the ExD catheter assembly 100 of FIG. 1 is shown. As shown, the housing 102 comprises a wall 230 that opposes the body opening 196 (FIG. 1) along the top side of the housing, as previously described. A seam 232 runs lengthwise of the housing 102, which marks the interface between the left frame 193 and the right frame 194 of the housing along the body 188 and the nose end 184 of the housing. The seam 232 run from the nose end 184 to and including through the base end 190 of the housing. However, the seam can be non-linear or not in a straight line. For example, the seam 232 can be off-axis compared to the straight line defined by the seam 232 along the body and the nose end. The seam at the base end 190 can be near the edge or intersection of the sides, such as the right side 202 and the bottom side 206. A plurality of pairs of detents can be incorporated between the left frame 193 and the right frame 194 to secure the two frames together as shown in FIG. 4. In an example, a catheter assembly can be located inside the housing 102 before engaging the left frame 193 to the right frame 194, or vice-versa. Following use, such as following successful venipuncture, the top lever 214 (FIG. 1) and the second or bottom lever 216 can be actuated to separate the detents to then separate the housing into components, such as to separate the left frame 193 from the right frame, to enable separation of the catheter assembly from the housing.

Figure 5:
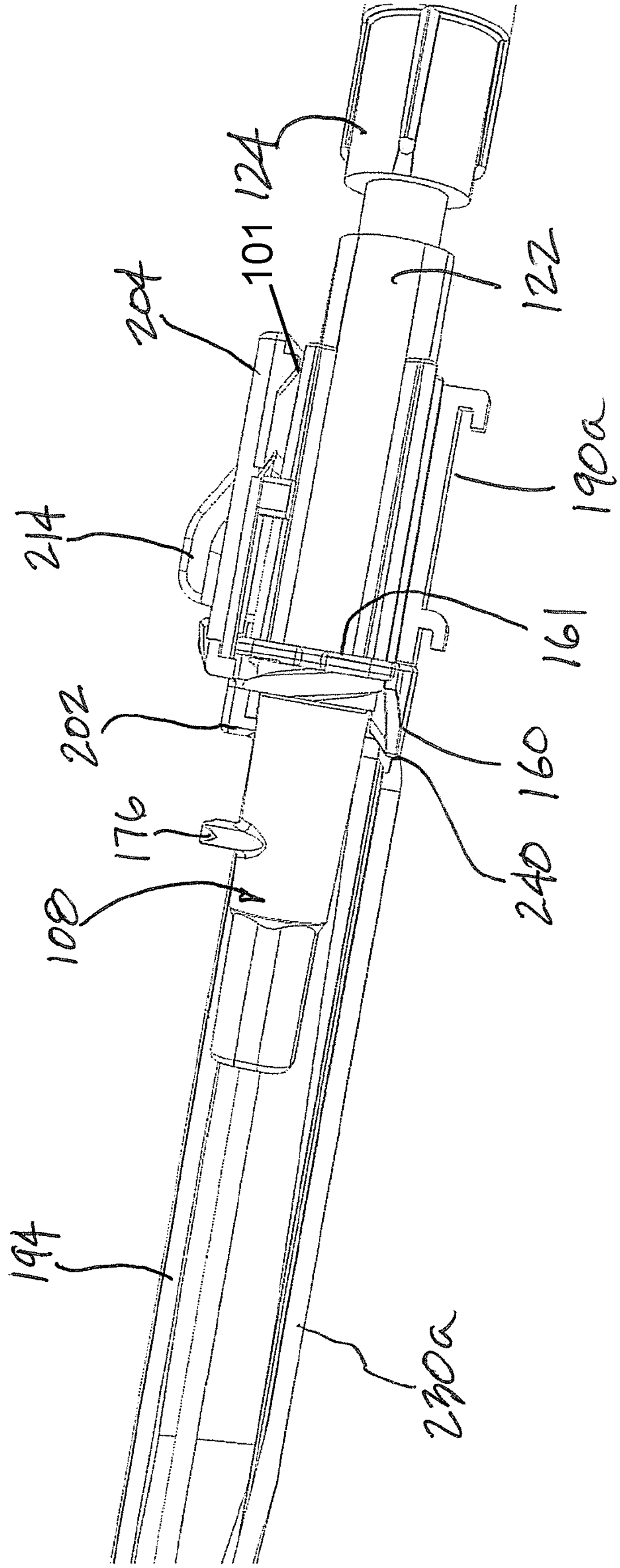
FIG. 5 is a partial perspective view of the extended dwell catheter assembly of FIG. 1 from a different perspective and shown without one of the housing components.

With reference now to FIG. 5, the ExD catheter assembly 100 of FIG. 1 is shown with the first or left frame 193 separated from the right frame 194 and with the catheter assembly 108 retained to the right frame or second frame 194. In an example, the right frame 194 is provided with the second side 202 and top side or third side 204 at the base portion 190*a*, which are generally right angle to one another. The first side 200 and the bottom side or fourth side 206 are provided with the left frame 193, which has been separated from the right frame 194 in the separated view shown.

To secure the catheter assembly 108 to the right frame 194, and particularly the needle hub from moving, the lower wall structure or section 230*a* of the right frame 194 terminates with a proximal edge 240 that is located along an axial position on the right frame to accommodate the flange or extension 160 on the needle hub 122. The distal edge of the flange 160 is therefore delimited from shifting or moving in the distal direction by the proximal edge 240 on the lower wall structure 230*a*. To secure the needle hub 122 from moving in the proximal direction, the second side 202 is provided with a channel 244 and a shoulder 246 (FIG. 6) on a proximal edge of the channel for retaining the flange 161 on the needle hub. The channel 244 located on the second side 202 and the corresponding channel on the first side 200 (FIG. 1) define a gap or width for accommodating the Luer threads 154 on the catheter hub and the width of the flange 161 on the needle hub. Further, the non-circular structures for coupling the flange 161 and the groove channel 244, such as by using multi-sided structures, prevents the needle hub from rotating while within the space defined by the sides of the base end 190. This in turn holds the needle hub in the assembled position so that the needle bevel can be oriented in the desire position without prematurely rotating before performing venipuncture.

Figure 6:
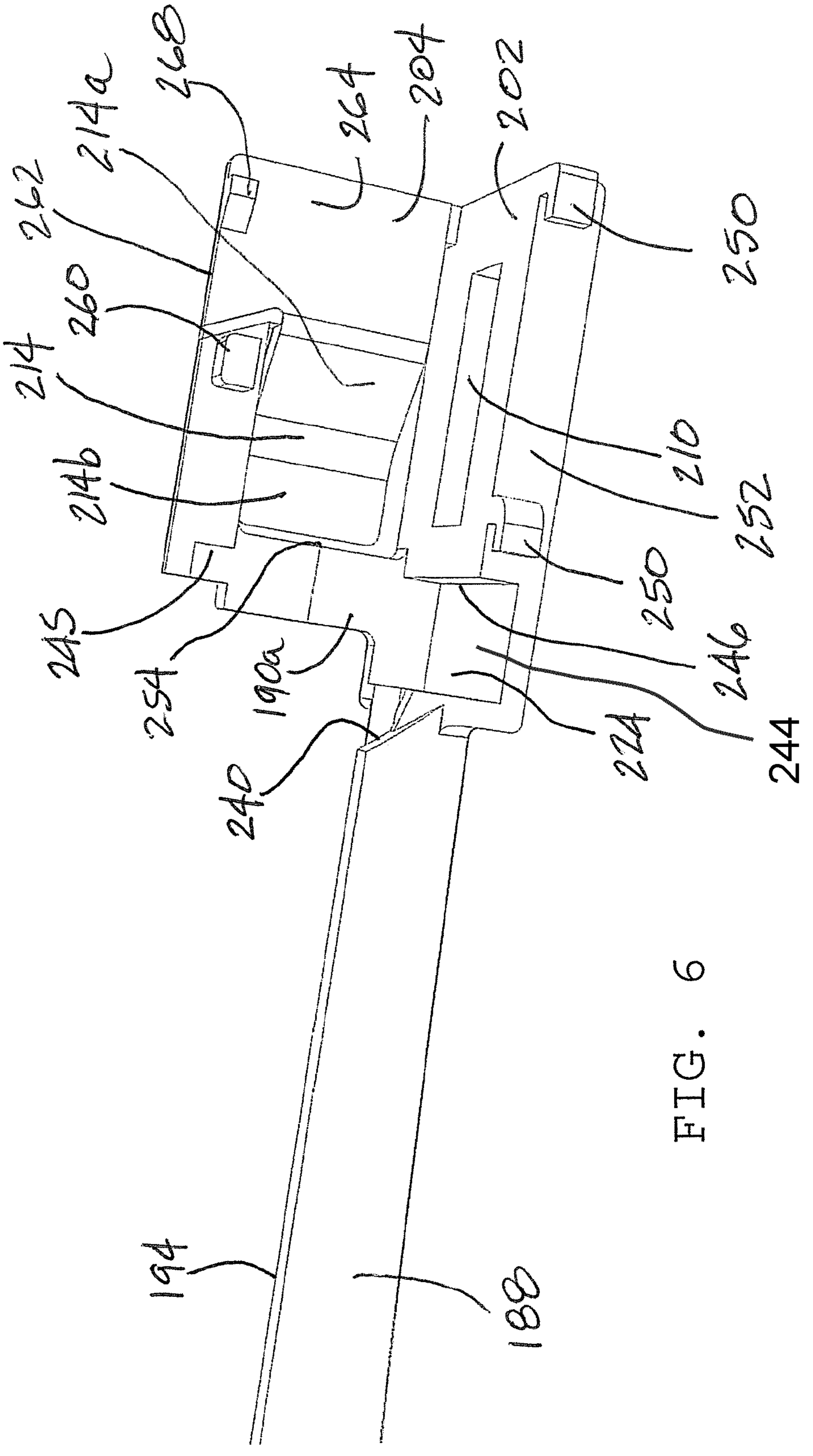
FIG. 6 is a partial perspective view of one of the housing components of the extended dwell catheter assembly of FIG. 1.

FIG. 6 is a blown-up view of the right frame or second frame 194 showing the body 188 of the right frame 194 and the base portion 190*a* of the right frame without the catheter assembly. With continued reference to FIG. 6 and further reference to FIG. 5, the second side 202 of the base portion 190*a* is shown with the channel 244 and the shoulder 246. A plurality of tabs or male detents 250 are provided at a lower edge 252 of the second side 202. In the example shown, the tabs 250 can embody a hook-like structure for engaging female detents located on the left or first frame 193, as further discussed below. Optionally, there can be more than two detents or only one detent 250. Each of the male detents 250 is shown with a tip pointing in the distal direction for engaging a female detent from a proximal position of the female detent and moving or sliding to a distal position to engage. Consequently, the right frame 194 and the detents 250 must travel or move in the proximal direction relative to the left frame 193 to separate the male detents or tabs 250 from the female detents on the left frame, as further discussed below. In other examples, the male detents 250 on the right frame can point in the proximal direction so that separation of the male and female frames will require movement of the right frame in the distal direction relative to the left frame 193 to separate the male detents or tabs 250 from the female detents on the left frame.

Along the top side 204, a cut-out 254 is provided for forming the top lever 214. The cut-out 254 is provided with three sides with the fourth side being connected to the base of the top lever 214. The top lever 214 can be formed to project outwardly away from the direction of the lower edge 252. As shown, the top lever 214 has a tapered or ramped portion 214*a* and a contact portion 214*b*. The contact portion 214*b* provides a surface for the user to touch or manipulate.

A rib or protrusion 260 is provided on the underside surface 264 of the top side 204 and is recessed from a side edge 262 of the top side. The recessed space between the side edge 262 and the protrusion 260 is sized to accommodate the thickness of the first side 200 of the left frame 193 when the left frame is assembled to the right frame 194. The rib 260 can function as an alignment tab for use to align the first side 200 to the side edge 262 so that upon assembling with the first side 200, a generally flushed surface is provided between the side edge 262 and the exterior of the first side 200. Optionally the rib 260 can be omitted.

A second rib or protrusion 268 spaced from the first rib 260 can also be provided on the underside surface 264 of the top side 204. In an example, the second rib 268 is aligned to or with the side edge 262 and is configured to engage a corresponding slot or recess on the left side or first side 200 of the left frame 193 to register the two frames 193, 194 at the base end 190 along an axial direction of the housing 102. In an example, the second rib 268 has an arrow-tip like structure with two tapered edges and an apex therebetween. The arrow-tip like structure is configured to seat in a corresponding seat on the left side 200 of the left frame 193 and the two tapered surfaces allow the projection 268 to escape from the corresponding seat by allowing the corresponding tapered surfaces to slide relative to one another when the top lever 214 and the bottom lever 214 (FIG. 3) are gripped and are caused to slide relative to one another.

Also shown is a shoulder 245 formed on the underside surface 264 of the top wall 204, just distal of the cutout 254. The shoulder 245 on the underside surface is configured to support the flange on the needle hub, similar to the function of the shoulder 246 on the second side 202.

Figure 7:
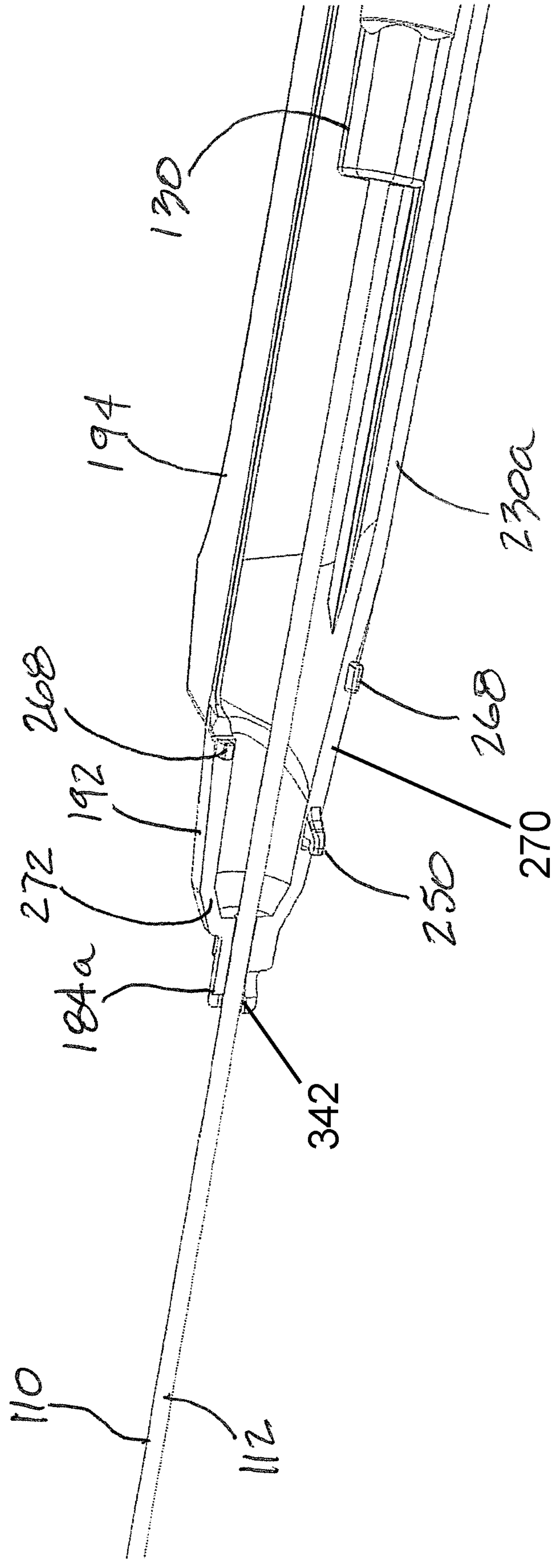
FIG. 7 is partial perspective view of the housing component of FIG. 6 from a different perspective.

FIG. 7 shows the front or distal portions of the right frame 194, shown with a catheter tube extending out the distal opening 342 of the nose portion 184*a*. A tab or detent 250 with a free end pointing in the distal direction is shown located on a side edge 270 of the lower wall structure 230*a*. The tab or male detent 250 can engage a corresponding female detent formed with the left frame 193. In other examples, additional tabs 250 can be provided along the side edge 270 of the lower wall structure.

Two protrusions 268 are provided with the distal portions of the right frame 194. As shown, a lower protrusion 268 is provided on the side edge 270 of the lower wall structure 230*a* for engaging a slot on the left frame to provide added rigidity along the seam 232 (FIG. 4). An upper protrusion 268 is provided on the side edge 272 of the base 192 for engaging a slot on the left frame to provide added rigidity along an upper seam 276 (FIG. 1) at the nose end 184 of the housing 102. Element 232 can generically be referred to as a seam, which can be the upper seam or the lower seam. However, to provide different reference numbers to more easily distinguish between an upper seam and a lower seam, the upper seam can be referred to as 276 and the lower seam as 232.

Figure 8:
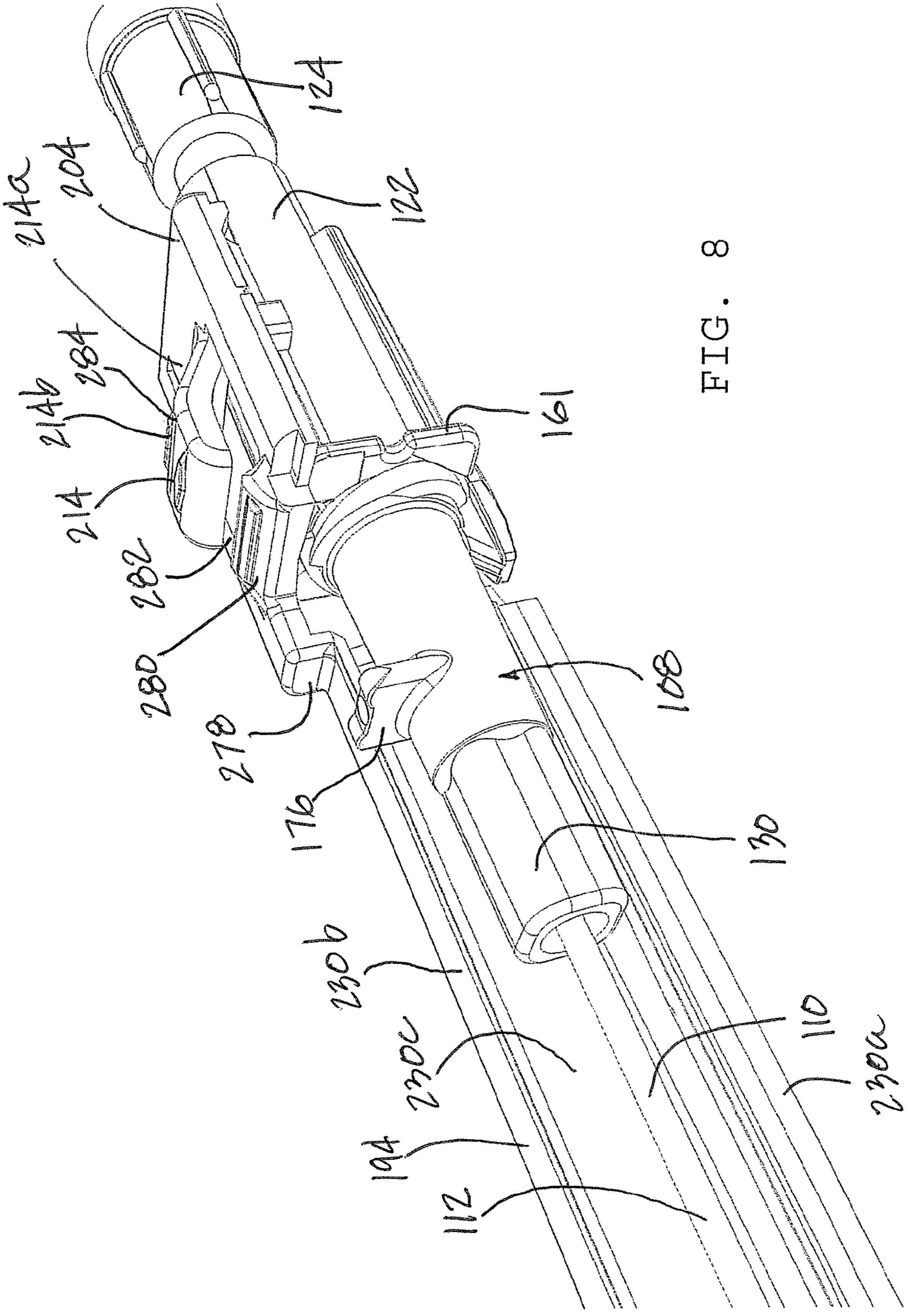
FIG. 8 is a partial perspective view of the extended dwell catheter assembly of FIG. 1 from a different perspective and shown without one of the housing components.

FIG. 8 is a close-up view of the right frame 194 with the catheter assembly 108 attached thereto, similar to FIG. 5. In the orientation shown, the right frame 194 is clearly shown with a bottom wall structure 230*a*, a top wall structure or section 230*b*, and a sidewall structure or section 230*c*, each having a surface. In an example, the upper wall or top wall structure 230*b* has a length that extends in the same lengthwise direction as the needle and a width, which is perpendicular or radial of the length. The width of the top wall structure 230*b* is smaller in dimension than the width of the bottom wall structure 203*a*. These different widths between the top and bottom wall structures, for example the top wall structure 230*b* does not project towards the needle as much as the bottom wall, allow for a gap along the upper portion of the housing and for the bottom to be closed when the first frame is attached to the second frame, as shown in FIG. 4.

A shoulder 278 is provided between the upper wall structure 230*b* and the top side 204 and a raised stub 280 is provided distal of the top lever 214. The step up at the shoulder 278 provides for a relatively larger interior space at the base end of the housing to accommodate the flange on the needle hub 122 and the Luer threads on the catheter hub 130. The raised stub 280 is not connected to the contact portion 214*b* of the top lever 214 but is provided with a tapered surface to mimic the ramp 214*a* at the base of the top lever 214, to appear more symmetrical. A gap 282 is provided between the top lever 214 and the raised stub 280, which can incorporate spaced apart gripping bumps 284. The top lever 214 can also incorporate similar spaced apart gripping bumps 284.

Figure 9:
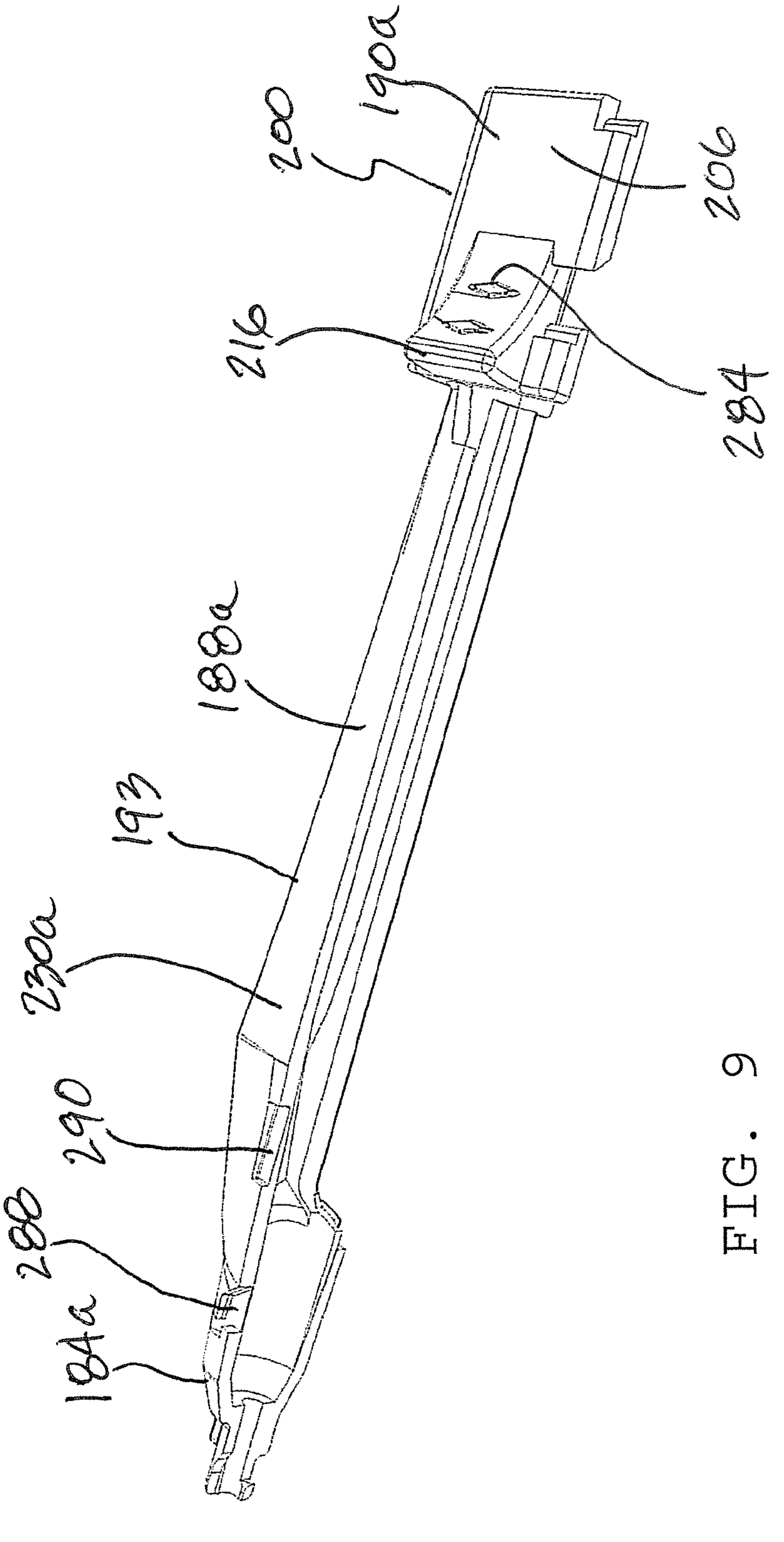
FIG. 9 is a perspective view of one of the housing components of the extended dwell catheter assembly of FIG. 1.

With reference now to FIG. 9, a perspective view of the left frame or first frame 193 is shown, which resembles the right frame 194 with a few exceptions. The left frame 193 is configured to couple to the right frame 194 to form the housing shown in FIG. 1 and elsewhere. In the present embodiment, the first frame 193 is provided with a nose portion 184*a*, a body portion 188*a*, and a base portion 190*a*. The left frame 193 and the right frame 194 can join to form a nose end 184, a body 188, and a base end 190. In the present embodiment, the lower wall structure 230*a* is provided with an engagement slot 288 for engaging the tab or detent 250 (FIG. 7) and a receiving slot 290 for receiving the projection 268 on the right frame 194. As further discussed below, the engagement slot 288 can have a detent for receiving a corresponding detent on the right frame 194. The receiving slot 290 however can embody a simple channel without engagement surfaces for receiving the lower projection 268 on the right frame 194, as further discussed below.

Also shown in FIG. 9, proximal of the body portion 188*a*, is a base portion 190*a*, which has a left or first side 200 and a bottom or fourth side 206 having the second or bottom lever 216 formed thereon. The first side 200 and the bottom side 206 resemble two wall structures that are placed at right angle to one another with the bottom lever 216 on one of the walls. One or more gripping features 284 can be provided on the exterior of the bottom lever 216.

Figure 10:
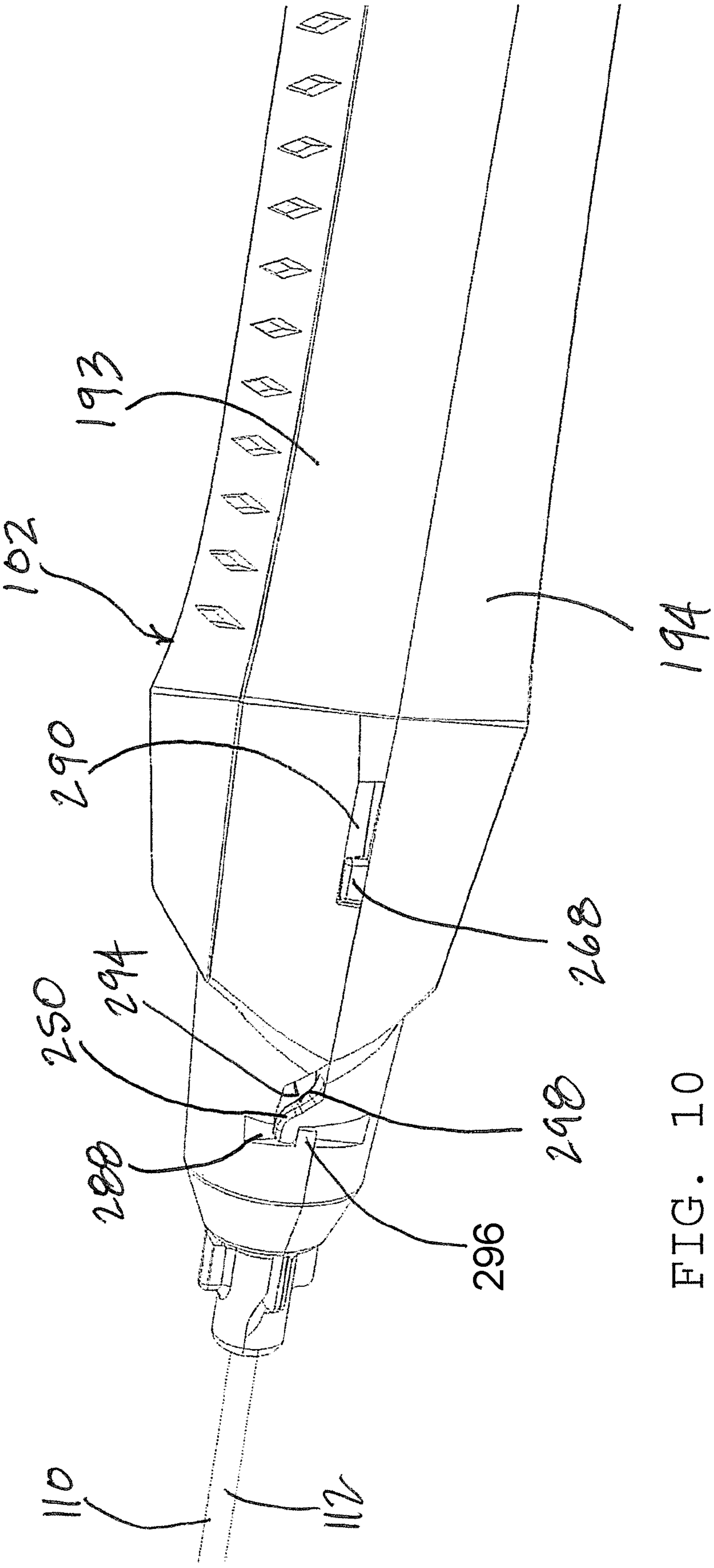
FIG. 10 is a partial perspective view of the extended dwell catheter assembly of FIG. 1 from a different perspective.

With reference now to FIG. 10, a detailed view of the distal portion of the housing 102 showing the left frame 193 attached to the right frame 194 is shown. As shown, the engagement slot 288 has an opening for the tab 250 to enter, which has a tapered surface 294 and a tab 296. The tab 250 on the right frame 194 can enter the opening of the engagement slot 288 and then travel distally to engage the tab 296 of the engagement slot 288 to complete the engagement between the tab 250 and the engagement slot 288.

To disengage the left and right frames, the tab 250 is removed in reverse. The tab 250 can move proximally relative to the engagement slot 288. The proximal movement causes the tapered surface 294 of the engagement slot 288 to move against the tapered surface 298 on the tab 296 to impart a pair of component forces that include a radially directed force to cause the left and right frames to move away from one another to separate the tab 250 from the engagement slot 288. Concurrently, the lower protrusion 268 on the right frame 294 separates from the receiving slot 290 on the left frame 193. Similar engagement mechanisms are provided at the base end 190 of the housing (FIG. 1) to enable separation of the two frames 193, 194 at the base end.

Figure 11:
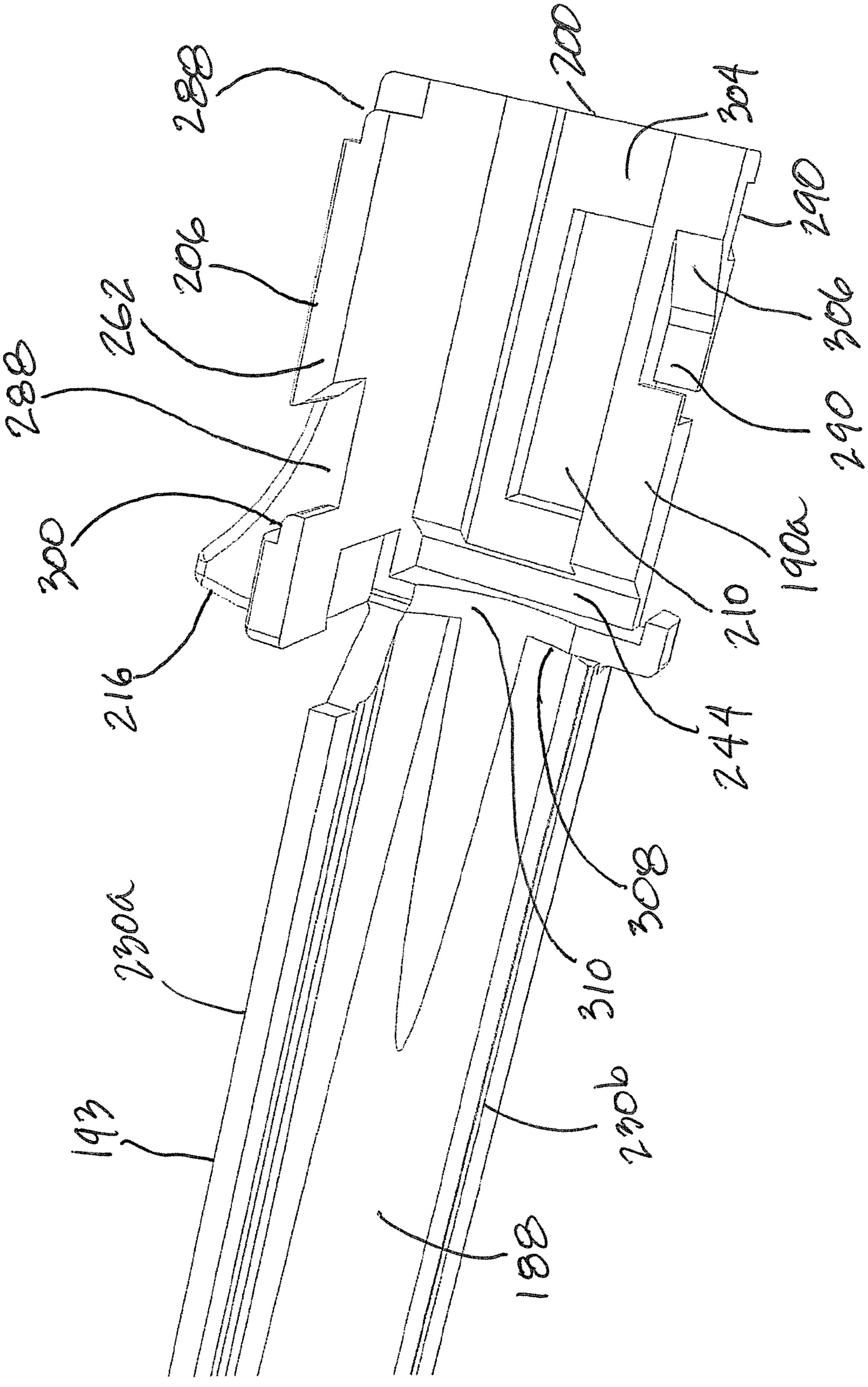
FIG. 11 is a partial perspective view of the housing component of FIG. 9 from a different perspective.

FIG. 11 shows an enlarged view of the left frame 193 at the base portion 190*a*. As shown, the bottom or fourth side 206 of the base end 206 comprises two engagement slots 288 formed at the edge 262 of the bottom side. Each of the engagement slots 288 comprises an opening for receiving the corresponding tab 250 on the lower edge 252 of the second side 202 of the right frame 194 (FIG. 6). A lip 300 is provided at each engagement slot with a recessed pocket for receiving and engaging the fingers on the corresponding tab 250. The gap between the finger of the tab 250 and the lower edge 252 is configured to receive the lip 300 therebetween to engage the tab 250 to the engagement slot. Note that the engagement slot 288 towards the distal end of the base section has an opening that is bounded by at least three sides and is relatively longer than the length of the corresponding tab 250 to permit axial movement of the tab to disengage from the engagement slot. The engagement slot 288 at the proximal end of the base section is bounded by two sides only without a third side to constrain the corresponding tab.

The first side 200 of the base portion 190*a* is provided with an opening 210, as previously described, and two receiving slots 290 for mating or aligning with the rib 260 and the projection 268 on the top wall of the base section of the right frame 194. As shown, the more distal receiving slot 290 has a recess formed on the interior surface 304 of the first side 200 while the more proximal receiving slot 290 has a recess formed on the exterior surface of the first side 200. This arrangement allows the wall structure 306 of the first side 200 to straddle or pass between the rib 260 and the projection 268 as shown with reference to FIG. 6.

Like the right frame 194, the base portion 190*a* is provided with a channel 244 for interacting with the flange on the needle hub. The barrier wall 308 distal of the channel 244 is provided with a shaped contour 310 for accommodating the catheter hub, when the left frame 193 is attached to the right frame 194 and the catheter hub is located therebetween.

Figure 12:
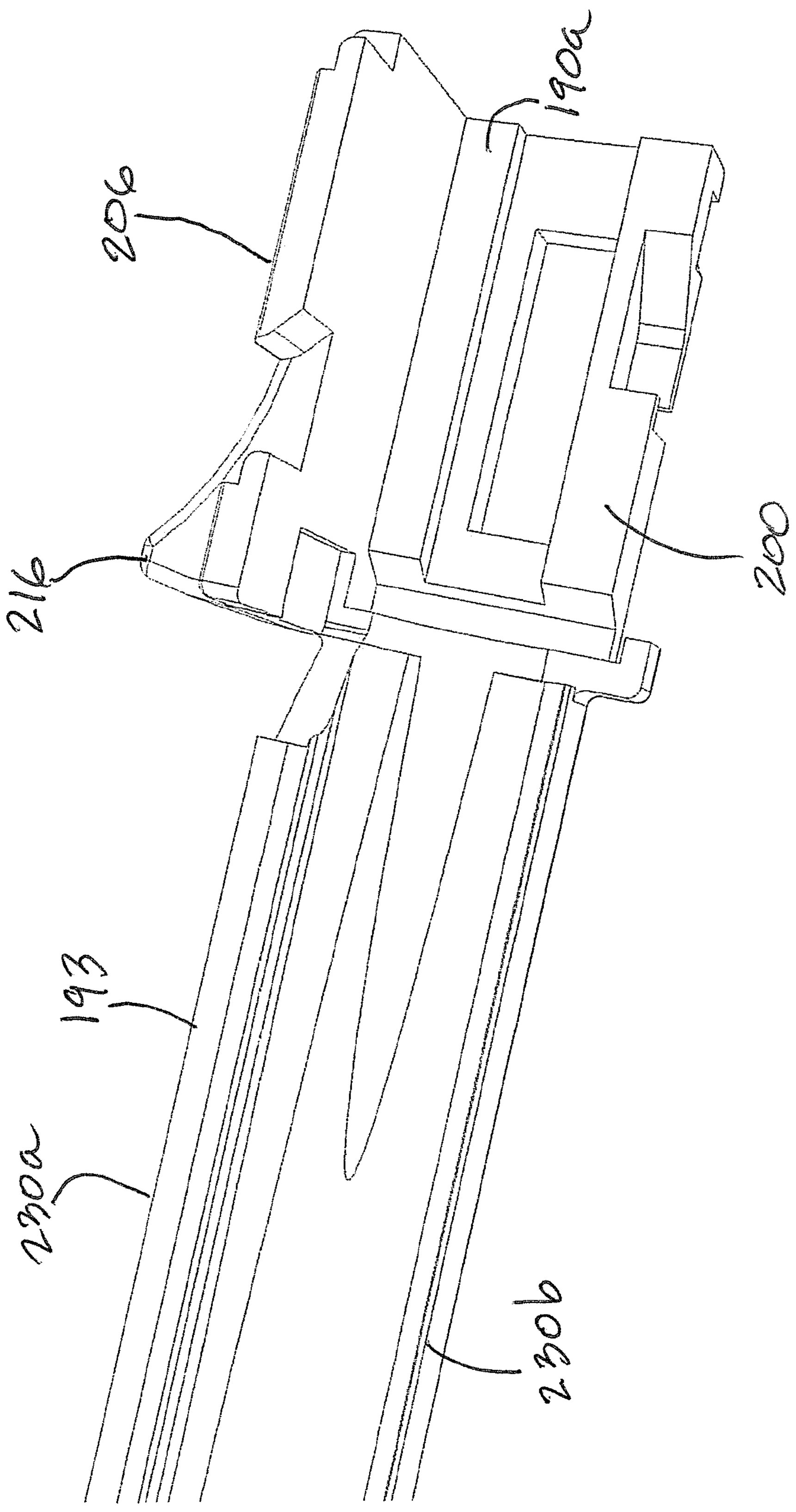
FIG. 12 is a partial perspective view of the housing component of FIG. 9 from a different perspective.

FIG. 12 is a perspective view showing the left frame 193 at the base portion 190*a*, similar to that of FIG. 11 but from a different perspective.

Figure 13:
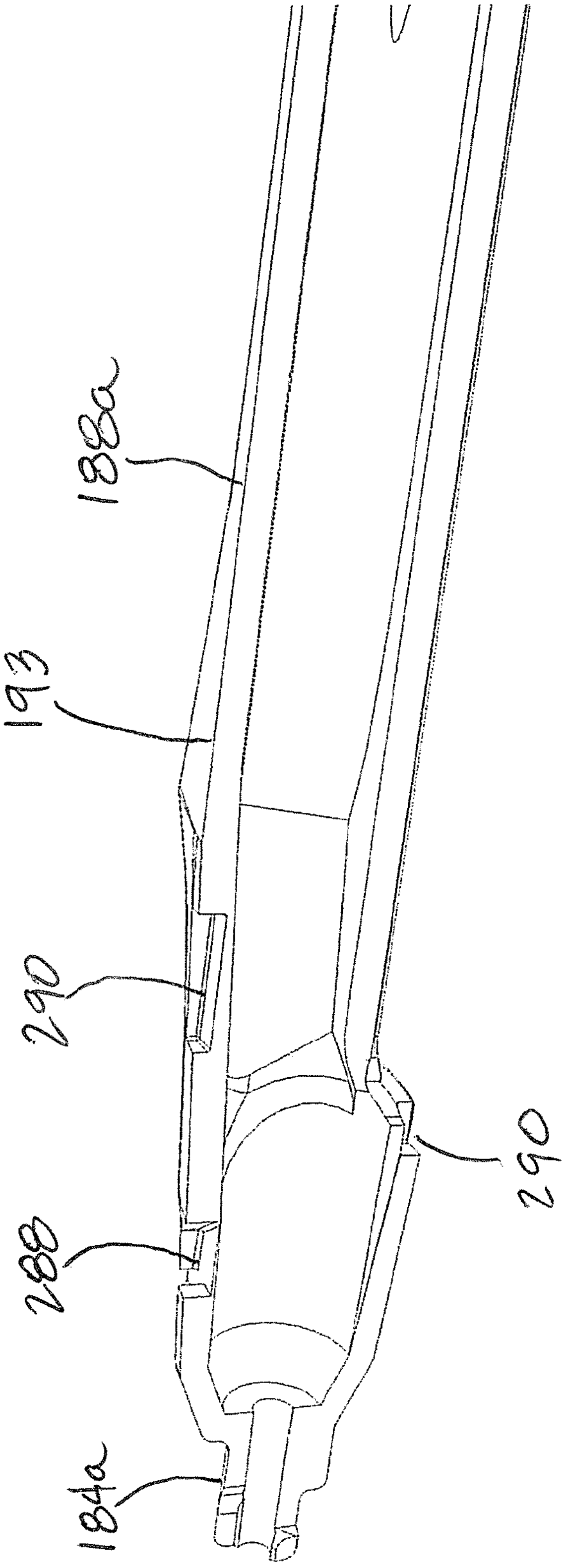
FIG. 13 is a partial perspective view of the housing component of FIG. 9 from a different perspective.

FIG. 13 is a perspective view showing the left frame 193 at body portion 188*a* and the nose portion 184*a*. The present view is similar to the view shown with reference to FIG. 9 but from a different perspective. In the present embodiment, the receiving slot 290 on the nose portion 184*a* for coupling to the upper protrusion 268 of the right frame 194 (FIG. 7) is more clearly shown.

Figure 14:
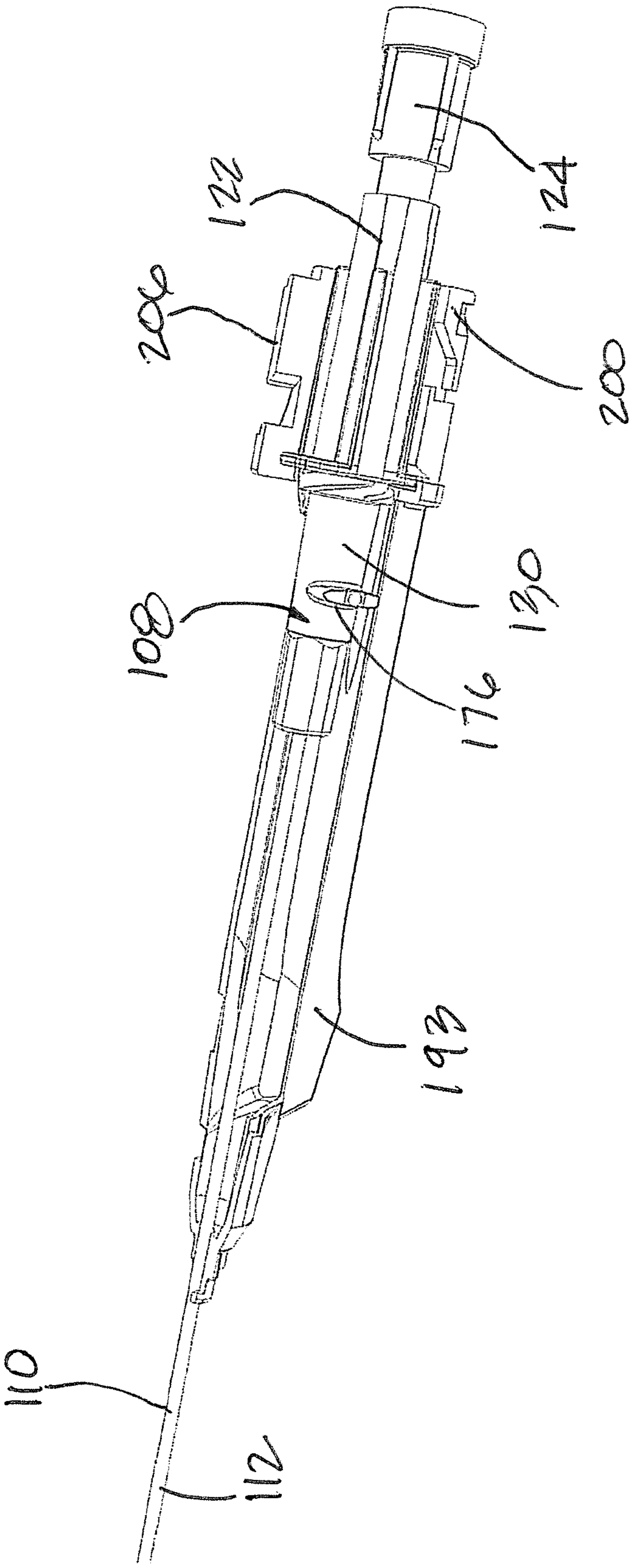
FIG. 14 is a partial perspective view of the extended dwell catheter assembly of FIG. 1 from a different perspective and shown without one of the housing components.

FIG. 14 is a perspective view showing left frame 193 separated from the right frame 194 and with the catheter assembly 108 retained to the left frame 193, to show how the catheter assembly 108 is seated within the shaped profile of the left frame, similar to that discussed with reference to FIG. 5, but with the left frame instead of a right frame 194.

With reference again to FIGS. 1, 5 and 14 and in use, the ExD catheter assembly 100 is advanced against a patient, to a selected catheter location, such as a deep or a superficial vein. The user can puncture the targeted vein with guidance from a visualization machine, such as an ultrasound monitor with an ultrasound probe. Primary blood flashback can be observed flowing into the needle hub 122. Next, the angle of insertion of the ExD catheter assembly 100 is lowered prior to further advancing the ExD catheter assembly 100 to locate the catheter tube deep into the vein. In some examples, a guide wire dispenser having a guidewire extending through the lumen of the needle may be used with the ExD catheter assembly. For example, a SonoStik® guidewire dispenser having a housing may be placed into the proximal opening of the catheter hub after removal of the vent plug 124 and the guidewire projecting through the lumen of the needle and advanced in a manner known in the industry. The guidewire may be used to guide the catheter tube to a desired treatment location within the body. In some examples, the guidewire dispenser may be mounted to the ExD catheter assembly prior to the initial needle insertion and the assembly is without the removable vent plug 124.

The needle and catheter tube are advanced over the guidewire and stopped at or just before the nose end 184 contacts the skin. If the ExD catheter assembly is used without a guidewire, then the ExD catheter assembly may be advanced without first advancing the guidewire. The practitioner can then place his or her thumb on the first or top lever 214 and an index finger against the bottom lever (FIG. 3) to separate the housing 102 (FIG. 1) into two or more housing components, such as separate the left frame 193 from the right frame 194, as described above. Once the housing 102 is separated into smaller components, the catheter assembly 108 is free from the housing. The user can next retract the needle 122 and needle hub 122 from the catheter hub, as previously described with reference to FIG. 2.

For the ExD catheter assemblies and components thereof disclosed hereinafter, it is understood that where a feature is shown but not expressly described and is otherwise the same or similar to the feature or features described elsewhere, such as above with reference to FIGS. 1-14, the disclosed part or parts shown in all the drawing figures but not expressly described because of redundancy and because knowledge is built on a foundation laid by earlier disclosures may nonetheless be understood to be described or taught by the same or similar features expressly set forth in the text for the embodiments in which the feature or features are described. Said differently, subsequent disclosures of the present application are built upon the foundation of earlier disclosures unless the context indicates otherwise. The disclosure is therefore understood to teach a person of ordinary skill in the art the disclosed embodiments and the features of the disclosed embodiments without having to repeat similar components and features in all embodiments since a skilled artisan would not disregard similar structural features having just read about them in several preceding paragraphs nor ignore knowledge gained from earlier descriptions set forth in the same specification. As such, the same or similar features shown in the following ExD catheter assemblies incorporate the teachings of earlier embodiments unless the context indicates otherwise. Therefore, it is contemplated that later disclosed embodiments enjoy the benefit of earlier expressly described embodiments, such as features and structures of earlier described embodiments, unless the context indicates otherwise.

Figure 15:
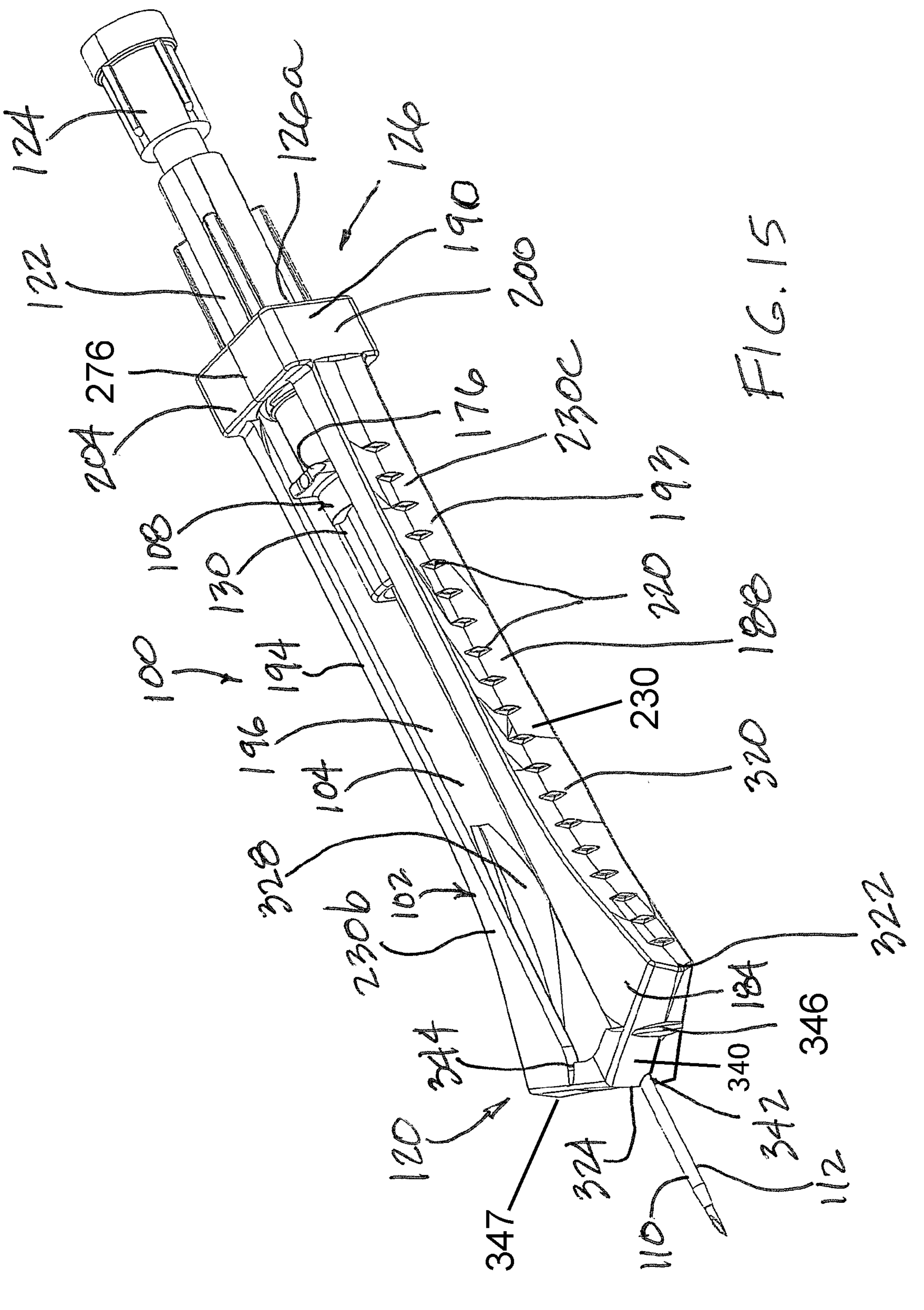
FIG. 15 is a perspective view of an extended dwell catheter assembly provided in accordance with further aspects of the present invention.

With reference now to FIG. 15, an extended dwell catheter assembly 100 provided in accordance with further aspects of the present invention is shown. The present ExD catheter assembly 100 shares similar aspects with the ExD catheter assembly of FIGS. 1-14, and in particular a similar housing 102 configuration in which a first frame or left frame 193 and a second or right frame 194 are attached to form the housing and can separate to release the catheter hub from the housing. As shown, the housing 102 comprises a nose end 184, a body 188, and a base end 190. The housing 102 has a body opening 196 that opens into an interior space 104. A catheter assembly 108 is positioned in the interior space 104. The catheter assembly 108 can be similar to the catheter assembly 108 described elsewhere herein, such as with reference to FIG. 2, and has a needle guard located inside the catheter hub 130 and a needle hub 122 with a vent plug 124 projecting proximally of an end surface 126*a* of the housing 102.

At the distal end 120, part of the needle 112, which is attached to the needle hub 122, and the catheter tube 110, which is attached to the catheter hub 130, projects out a distal opening 342 of the housing, at the nose end 184. Optionally, a guidewire dispenser, such as a SonoStik® guidewire dispenser, can be connected to the proximal opening of the needle hub, after removal of the vent plug 124.

Each of the two first and second frames 193, 194 comprises a wall structure 230 comprising a lower wall section 230*a* (FIG. 16), an upper wall section 230*b*, and a sidewall section 230*c*. A plurality of projections or ornamentations 220 are provided on the exterior surface of the sidewall section 230, which can embody round, elongated, polygonal, or irregular shape projections. The projections 220 can be spaced from one another and provided for aesthetic and to facilitate gripping the housing 102 on the two sidewalls 230*c* of the housing.

The base end 190 at the proximal end 126 of the housing is provided with a plurality of sidewalls, which include a first or left sidewall 200, a second or right sidewall 202 (FIG. 19) opposing the first sidewall, a third or top sidewall 204, and a fourth or bottom sidewall 206 (FIG. 16) opposing the third sidewall. The sidewalls at the base end 190 define a generally square or rectangular shaped cross-sectional structure having a hollow interior for accommodating the catheter assembly 108. In other examples, the sidewalls can define a different shape, such as oval or round. A seam 232 passes through both the top sidewall 204 and the bottom sidewall 206, and through the nose end 184 of the housing 102.

The first sidewall 200 and the second sidewall 202 (FIG. 19) define a width of the housing at the base end 190. In an example, the width at the base end 190 is larger than a width of the body 188 immediately distal of the base end 190. In other examples, the width at the base end 190 and that of the body 188 immediately distal of the base end 190 can be generally the same or equal. The width of the body 188, measured as a distance between the two sidewall sections 230*c* of the first and second frames, from either their respective exterior surfaces or interior surfaces, can be generally constant in the distal direction until about the start of the activation area or region 320 of the body, where the body widens in the distal direction to a maximum width at a body distal end 322. From there, the width rapidly decreases to a peak or apex 324, where the distal opening 342 is located. As further discussed below, the activation region 320 of the body 188 widens so that each of the two frames 193, 194, or at least one of the two frames, can incorporate an activation ramp or structure 328. The activation ramp 328 is sized and shaped to interact with the catheter hub 130 to enable separation of the housing 102 into two or more housing components.

Figure 16:
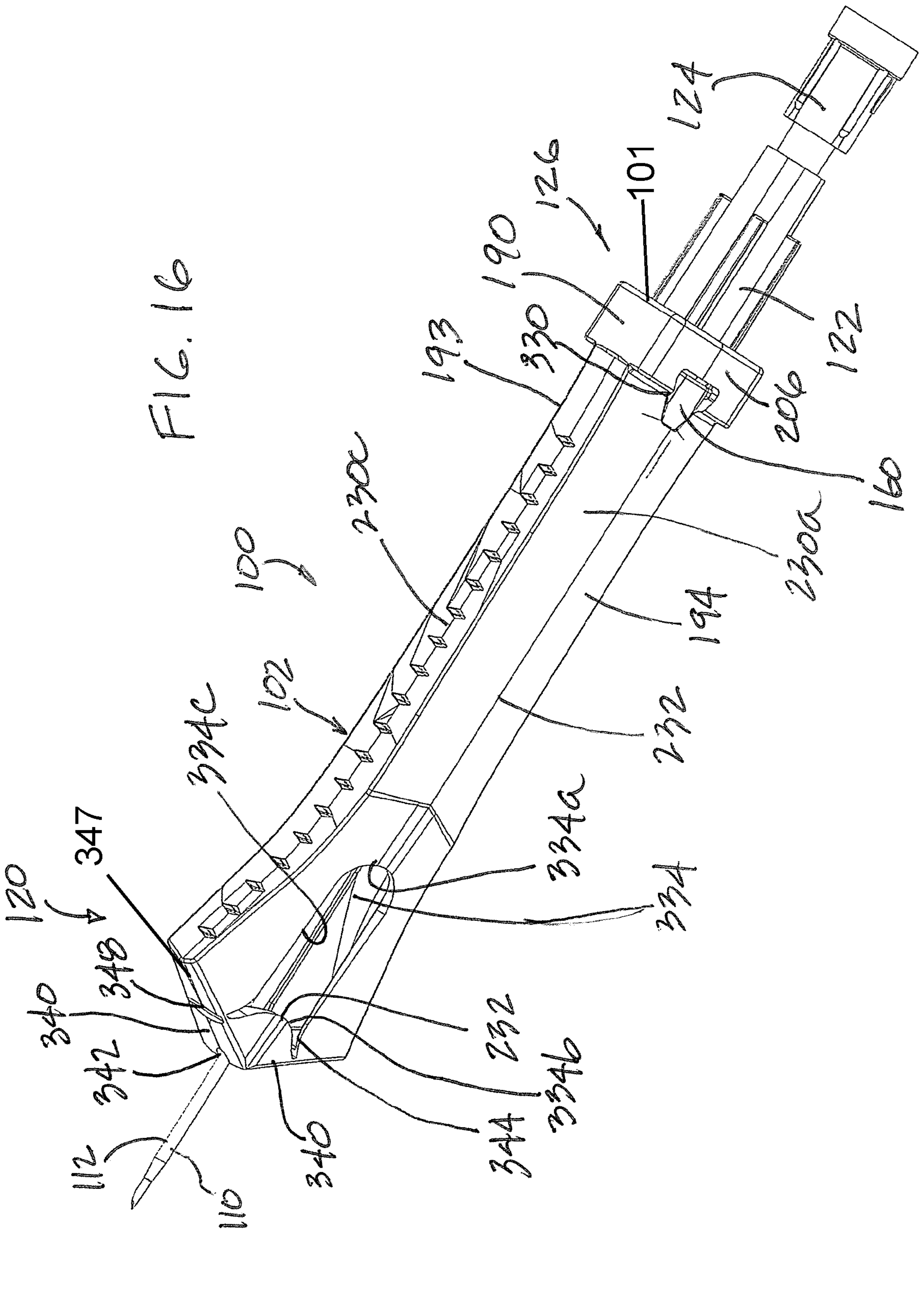
FIG. 16 is a perspective view of the extended dwell catheter assembly of FIG. 15 from another perspective.

FIG. 16 is a perspective view of the ExD catheter assembly 100 of FIG. 15 shown from a different perspective. The two lower wall sections 230*a* on the first frame 193 and the right frame 194 can be seen. A cut-out 330 for receiving the flange extension 160 of the needle hub 122 is provided at the proximal end 126 of the housing 102, which is defined by partial cut-outs on the bottom side 206 of the base end 190 and partial cut-outs at the proximal ends of the two frames 193, 194.

An opening 334 is provided near the distal end 120 of the housing 102, at the lower wall of the housing. The opening 334 can be elongated, can have a proximal edge 334*a*, can have a distal edge 334*b*, and can have side edges 334*c*. In other examples, the opening 334 can have different shapes, provided the shape does not interfere with activation ramp 328 located in the interior of the housing 102.

A seam 232 is provided lengthwise of the housing and runs from the distal end 120 to the proximal end 126 and is non-continuous at the rear opening 330 and at the front opening 334. At the distal edge 334*b* of the front opening 334, an end cap component or gate 340 is provided at the distal end of each of the left and right frames 193, 194. Thus, the housing has two gates or end cap components 340. With particular reference to the end cap component 340 of the second frame 194, the discussions of which applies equally to the end cap component of the first frame 193, the end cap component 340 has a lower section or sidewall 340*a*, a top section or sidewall 340*b* (FIG. 17), and a side section 340*c*. In an example, the side section 340*c* has a cut-out 342*a*, resembling a half-circle, so that two side sections 340*c* with two cut-outs 342*a* from two adjacent end cap components 340 form a through passage or opening 342 to accommodate the needle 112 and catheter tube 110. The through passage 342 formed by the two cut-outs 342*a* provide support and guidance for the needle and catheter to enable venipuncture of an extended length IV catheter, with or without a guidewire, and a short midline catheter of about 8-10 cm length without an integrated guidewire.

Figure 17:
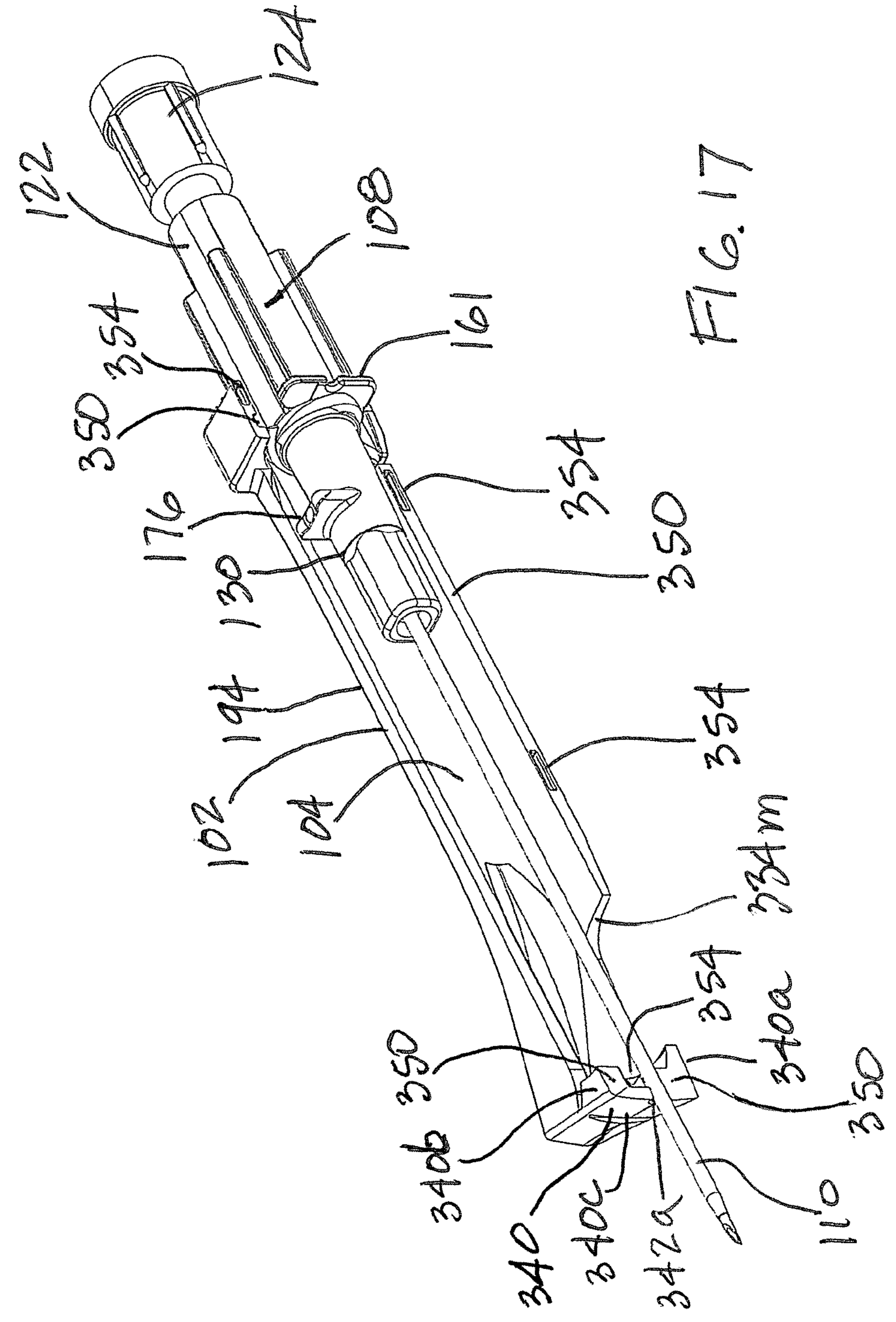
FIG. 17 is a perspective view of the extended dwell catheter assembly of FIG. 15 from a different perspective and shown without one of the housing components.

With continued reference to FIGS. 16 and 17, the lower section 340*a* of the end cap component 340 is separated from the lower wall 230*a* of the housing wall 230 by a gap 344 and the upper or top section 340*b* of the end cap component is separated from the upper wall 230*b* of the housing wall by a gap 344. Thus, each end cap component 340 is attached to the remaining part of the respective left and right frames 193, 194 by a material strip or layer 346, which has a thickness. In an example, the material strip 346 can have the same thickness as the wall thickness of the side section 230*c* and the front section 340*c*. In other examples, the material strip 346 can comprise an indentation 348 to thin out the thickness of the material strip 346 so that it is thinner than the thickness of the side section 230*c* and the front section 340*c*.

In an example, the material strip 346 (FIG. 15) that connects the left end cap component 340 to the left frame 193 and the material strip 346 that connects the right end cap component 340 to the right frame 194 can act as a hinge, such as a living hinge. Thus, the housing 102 of the present embodiment has two gates or end cap components 340 with each gate pivotable or rotatable by a living hinge 346. The living hinge allows the end cap component or gate 340 and the respective frame that it attaches, i.e., the front end wall 347, to pivot, rotate or swing relative to one another. For example, if the first and second frames 193, 194 separate from one another beginning from the proximal end 126 when the assembly is activated due to the catheter hub 130 pushing against the one or more activation ramps 328, as further discussed below, the first and second frames can swing outwardly away from one another and pivot about their respective material strip or living hinge 346. The two end cap components 340 can remain attached to one another as the two frames pivot about the two living hinges 346 until they too are separated to free the catheter hub 130 from the two frames, as further discussed below. In other examples, as discussed below, the two frames remain attached while the two end cap components 340 pivot or rotate about the two living hinges 346, similar to opening a double-gate to provide access out the opening at the distal end of the housing 102.

With reference now to FIG. 17, the ExD catheter assembly of FIG. 15 is shown without the first frame 193 so that the interior space 104 of the now separated housing 102 is more clearly shown. The second frame 194 is shown with joining edges 350 where the seams 232 are formed with the joining edge 350 of the first frame 193. The left frame or first frame 193 and the right frame or second frame 194 can connect to one another along their respective joining edges 350. Engagement slots, tabs, and/or detents 354 may be used for removable securement of the two frames, as further discussed below. The right frame 194 is shown with a cutout 334*m* that forms part of the opening 334 shown in FIG. 16, at the bottom or lower side of the housing 102.

In the figure, the catheter assembly 108 is shown situated in the interior space 104 of the housing 102, which has the needle and catheter tube passing through the cut-out 342, and the catheter hub 130, or at least the push tab 176 of the catheter hub, positioned distally of the base end 190. The needle hub 122 and vent plug 124 project out the proximal opening 101 of the housing 102, with the flange 161 of the needle hub 122 engaging the housing 102 as further discussed below with reference to FIGS. 18A and 18B.

Figure 18A:
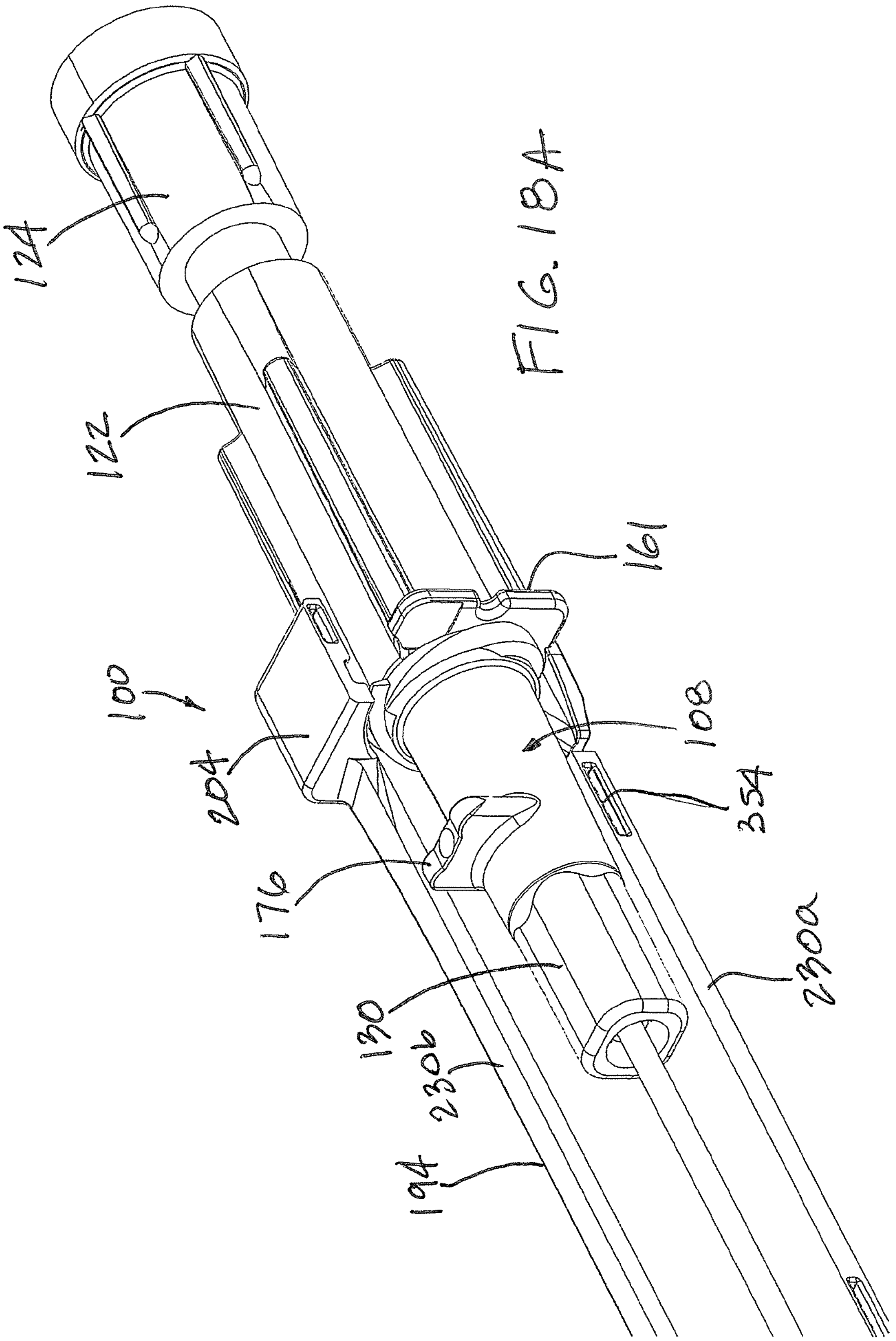
FIGS. 18A and 18B are partial perspective views of the extended dwell catheter assembly of FIG. 15 from a different perspective and shown without one of the housing components.
Figure 18B:
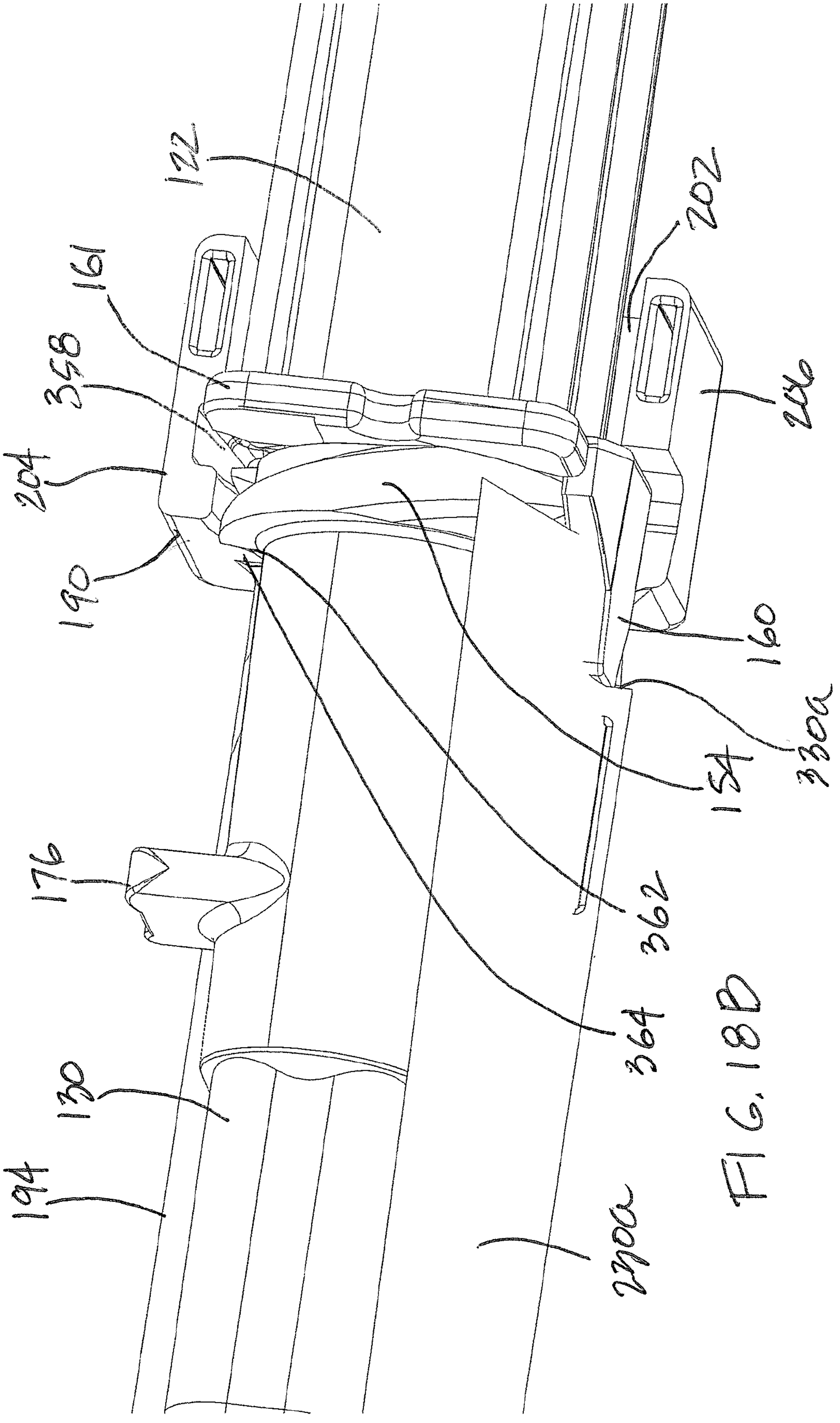

With reference now to FIGS. 18A and 18B, an enlarged partial perspective view of the assembly of FIG. 17 is shown and a further enlarged view of the catheter assembly situated inside the right frame 194 is shown, respectively. As shown, the flange 161 extending from the needle hub 122, which has a generally square or rectangular shape contour, is arranged so that a plane defined by the flange is generally orthogonal to the lengthwise axis of the housing 102 (FIGS. 15 and 16). Portions of the flange 161 that projects outwardly of the exterior profile of the needle hub 122 engages a groove 358 (FIG. 18B) formed with the plurality sides of the base end 190, such as with the first side 200, second side 202, third side 204, and fourth side 206. The groove 358 can be a recessed channel formed into the wall thickness of the plurality of sides of the base end. The groove 358 can be continuously formed across the sides other than where the cut-out 330 (FIG. 16) is provided at the fourth side 206 for accommodating the flange extension 160 of the needle hub 122. The groove 358 can be structured to accept, receive, or accommodate the flange 161 on the needle hub, including where the flange transitions between the various sides, such as the intersections of the sides of the flange 161.

In the ready to use position where the ExD catheter assembly 100 is ready to be used to perform a venipuncture, the needle hub 122 can be held stationary from axial movement by delimiting the flange extension 160 of the needle hub from distal movement via the bottom housing edge 330*a* at the cut-out 330 of the two bottom wall structures 330. To delimit the needle hub 122 from moving in the proximal direction, the flange 161 extending from the exterior of the needle hub 122 is positioned against the proximal lip of the groove 358 of the base end 190. Further, the non-circular structures for coupling the flange 161 and the groove 358, such as by using multi-sided structures, prevents the needle hub from rotating while within the space defined by the sides of the base end 190. This in turn holds the needle hub in the assembled position so that the needle bevel can be oriented in the desire position, as assembled, without prematurely rotating before performing venipuncture.

With continued reference to FIGS. 18A and 18B and particularly FIG. 18B, the exterior threads 154 of the catheter hub 130 comprises a slot 362 for receiving a tab 364 projecting from the interior surface of the top side 204 of the base end 190. In other examples, the arrangement can be reversed and the top side 204 can incorporate a slot and the catheter hub can incorporate a tab. In still other examples, detents can be provided between the catheter hub and the housing at other locations along their respective structures to engage the two. The engagement ensures proper alignment between the catheter hub 130 and the housing 102 in the ready to use position and prevents the catheter hub from rotating while engaged to the housing.

The catheter hub 130 is structured to slide axially in the distal direction following successful placement of the needle and the catheter hub into the vein of a patient while the needle hub remains engaged to the base end 190 of the housing. In an example, the exterior threads 154 are structured to ride on or slide on the interior surfaces of the two lower walls 230*a* of the housing 102. For example, and with further reference to FIG. 15, a user can push on the push tab 176 to advance the needle hub 130 in the distal direction. The push tab 176 is shown located between the two upper wall sections 230*b* of the two frames 193, 194. As shown, the upper edge of the push tab 176 projects above the exterior surfaces of the two upper wall sections 230*b* to present itself for contact and for pushing by a practitioner. In some examples, the push tab 176 can be structured so that the upper edge of the push tab projects further upwardly of the two upper wall sections 230*b* to present itself as a larger target for pushing by a practitioner. As further discussed below, when the practitioner pushes on the push tab 176 in the distal direction following placement of the catheter tube into the vein, and optionally after advancing a guidewire into the vein to guide the catheter tube, the body of the catheter hub 130 abuts the one or more activation ramps 328, on the left frame 193, the right frame 194, or one of each of the two frames 193, 184, to cause the two frames to separate starting from the proximal end 126 of the housing 102. The push tab 176 can be molded with a sufficient length or height to extend above the housing to enable pushing by a practitioner. Optionally, a tab extender can be snap onto a standard push tab to increase the height of the push tab for pushing by a practitioner, as further discussed below.

Figure 19:
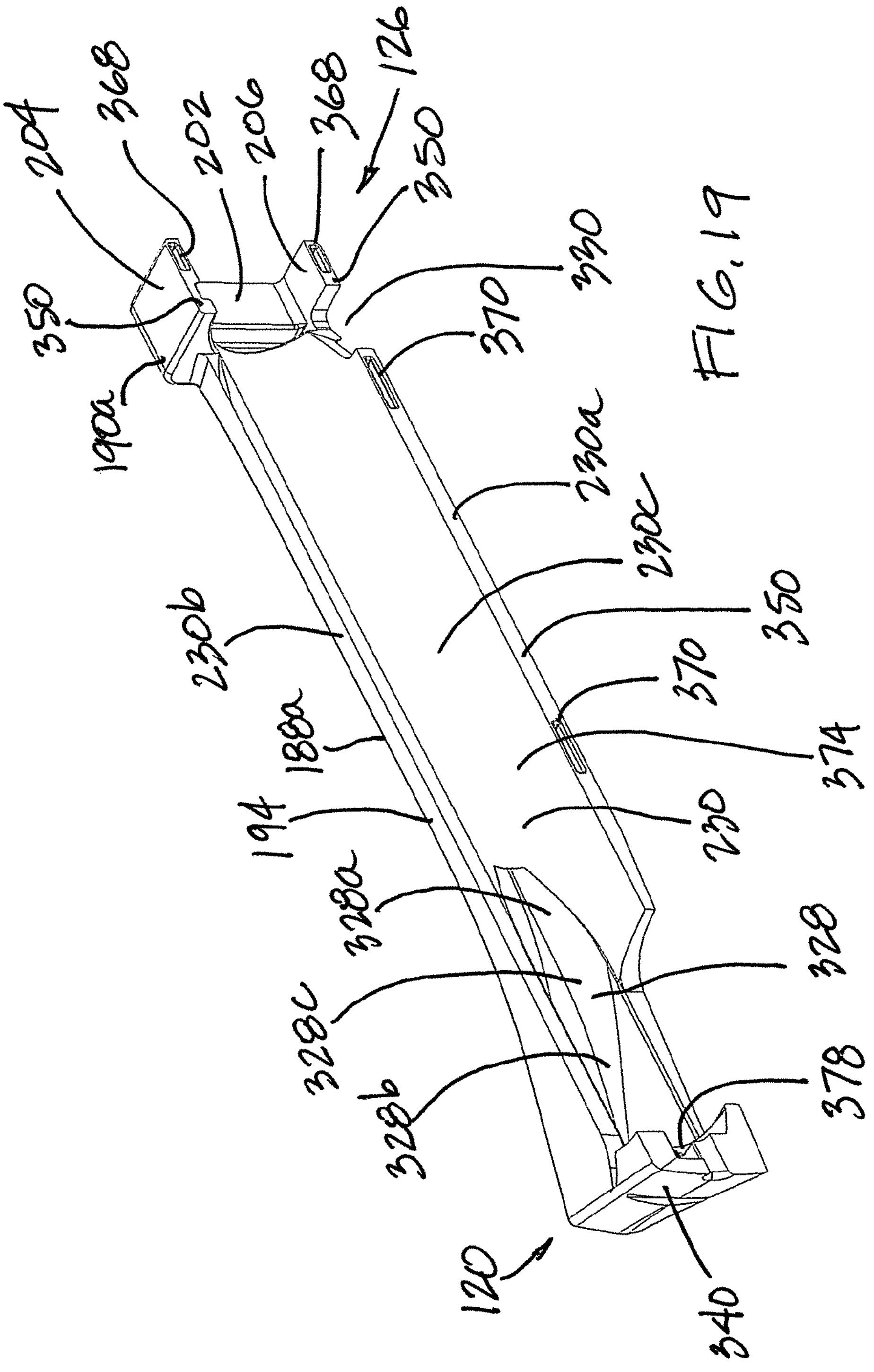
FIG. 19 is a perspective view of one of the housing components of FIG. 18.

FIG. 19 is a perspective view of the right or second frame 194, shown without the left frame 193 and without the catheter assembly 108. The second frame 194 is shown with a base portion 190*a* having a second side 202, top side 204 and bottom side 206. The top side and bottom side are relatively shorter in length than the second side 202. The top side 204 and the bottom side 206 of the right frame 194 can be referred to as partial sides as similar top and bottom side sections are carried by the first or left frame 193 such that when two partial top sections are joined at their respective joining edges 350 and the two partial bottom sections are joined at their respective joining edges 350, they form the top side 204 and bottom side 206 of the base end 190 (FIG. 16).

As shown, the partial top side section 204 incorporates a slot 368 and the partial bottom side section 206 incorporates a slot 368, at the joining edges 350. The slots can be generally rectangular in shape with sharp corners or with radiused corners but can instead embody a round shape, a square shape, a star shape, an oval shape, a polygonal shape, or an irregular shape. The slot 368 on the partial top side section 204 and the slot 368 on the partial bottom side section 206 can be located along the same axial position of the lengthwise axis of the right frame. In other examples, they can be axially offset from the same axial position. As shown, the two slots 368 are both located generally along the proximal end of the two joining edges 350.

The body portion 188*a* is located distal of the base portion 190*a*, which has a wall 230 with a top wall section 230*b*, bottom or lower wall section 230*a* and sidewall section 230*c*, as previously discussed. In an example, two slots 370, similar to the slots 368 at the base portion 190*a*, are provided at the joining edge 350 of the lower wall structure or section 230*a*. The two slots 370 can have the same shape as the two slots 368 on the base portion 190*a* or can be different. In an example, one of the two slots 370 on the lower wall section 230*a* can be located adjacent the housing edge 330*a* (FIG. 18B) of the bottom cutout 330 and the second slot 370 can be located distally thereof. In other examples, there can be just one slot on the lower wall section 230*a* or more than two slots and they can locate elsewhere along the joining edge 350.

With continued reference to FIG. 19, the activation ramp 328 is located on the interior surface 374 of the sidewall section 230*c* of the housing wall 230 closer to the distal end 120 than the proximal end 126, at the activation region 320

(FIG. 15) of the frame 194. The activation ramp 328 has a proximal ramp section 328*a*, a distal ramp section 328*b*, and a central ramp section 328*c*, which is located between the proximal and distal ramp sections. In an example, the proximal ramp section 328*a* comprises a slope that increases from the interior surface 374 of the right frame 194, which can be viewed as a structure having a surface that extends radially away from the interior surface. When assembled with the left frame 193 and the assembled housing having a catheter assembly located therein, the proximal ramp section 328*a* extends away from the interior surface towards the needle, or towards the lengthwise axis passing through the housing. The lengthwise axis passing through the housing can be considered as a referenced line and the proximal ramp section 328 can be understood as having a surface that is furthest from the referenced line and that gradually moves closer to the referenced line as the ramp approaches the central ramp section 328*c*.

The central ramp portion 328*c* has a surface that is closer to the referenced line than the proximal ramp portion 328*a* and can comprise a generally flat area or a surface area with a large radius.

The distal ramp portion 328*b*, in an example, comprises a slope that decreases from the central ramp portion 328*c*, which has a surface that moves away from the referenced line. If the proximal ramp portion 328*a* has a positive slope, then the distal ramp portion 328*b* has a negative slope. Thus, the activation ramp 328 shown in FIG. 8 can be considered a sloping structure that increases to a peak or crest at the central ramp section then has a negative slope. In other examples, the distal ramp portion 328*b* can be constant or flat with the central ramp portion 328*c*, without any slope. In still other examples, the distal ramp portion 328*b* can have a positive slope that continues to extend towards the referenced line. Preferably, the distal ramp portion 328*c* has a negative slope.

When the left and right frames 193, 194 are assembled together to form a housing 102, the gap between the two adjacent activation ramps 328, which can be referred to as an activation gap 400 (FIG. 28), if two activation ramps are incorporated, or between the activation ramp 328 and the interior surface 374 of the adjacent frame, if only one activation ramp is incorporated, can vary. The activation gap can narrow as it extends from the proximal ramp portion 328*a* to a narrower point at the central ramp portion 328*c*, or from two proximal ramp portions to a narrower point at two central ramp portions. As further discussed below, the activation gap 400 can be incorporated as a means for which the catheter hub 130 (FIG. 2) can advance against to impart a pair of components forces to then separate the housing 102 into two or more housing components.

With still further reference to FIG. 19, a recess 378 is provided with the end cap component 340 of the second or right frame 194. The recess 378 can have three sides and a fourth side that is opened. Optionally, the recess 378 can embody a four-sided slot, similar to one of the slots 368, 370 of the body section or the base section. The recess 378 at the end cap component 340 can be sized and shaped to receive a corresponding tab on the adjacent end cap component in an interference or snap fit arrangement. In some examples, the location of the recess 378 and of the tab for coupling with the recess can reverse so that the recess can locate on the end cap component of the first or left frame 193.

Figure 20:
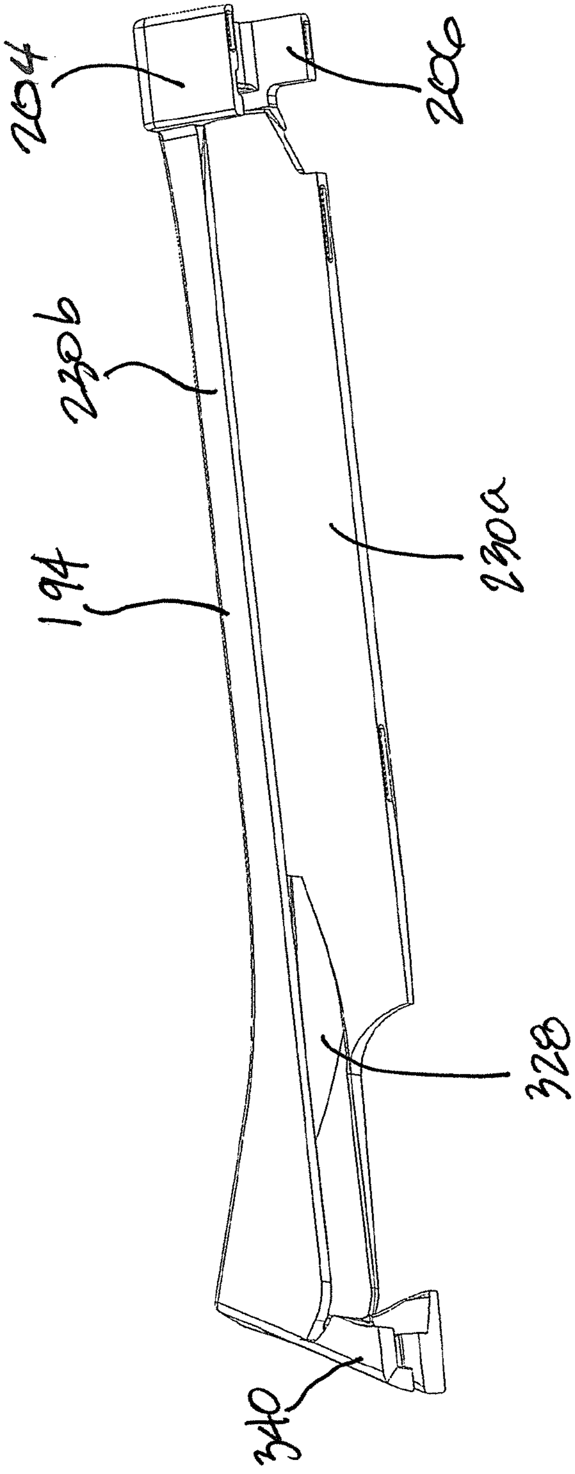
FIG. 20 is a perspective view of one of the housing components of FIG. 18.
Figure 21:
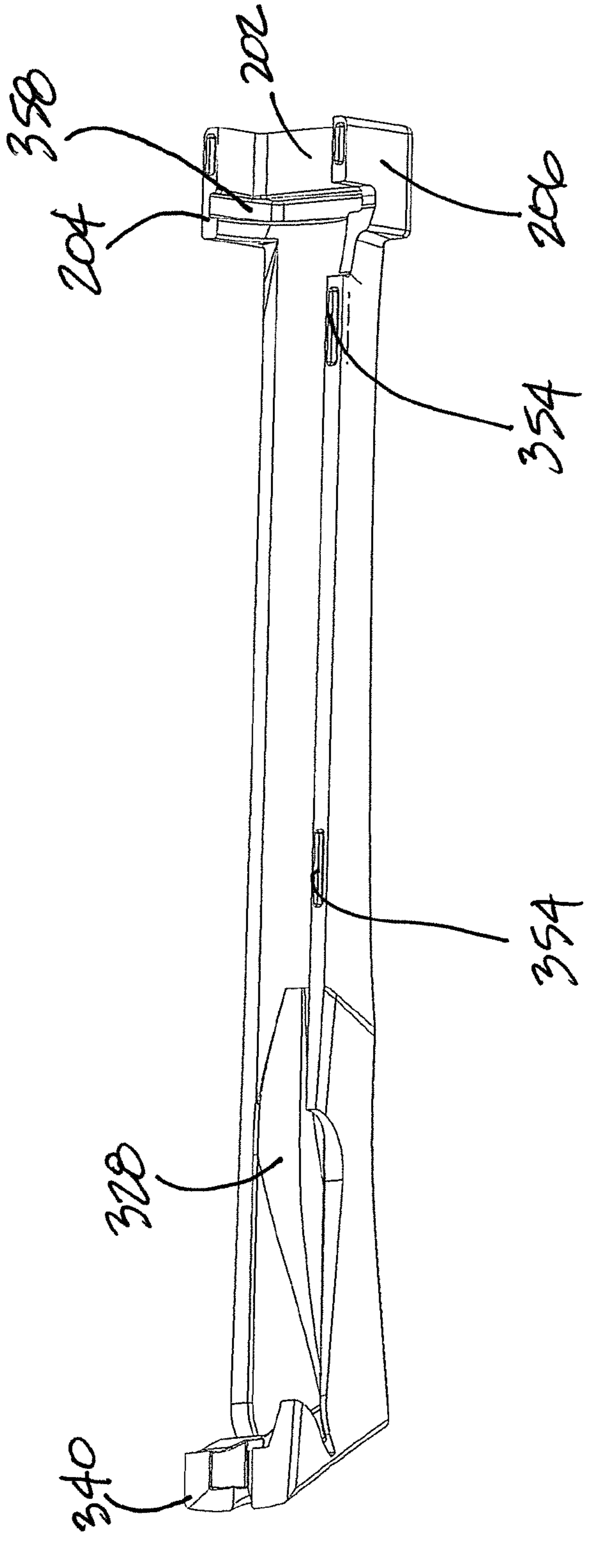
FIG. 21 is a perspective view of one of the housing components of FIG. 18.

FIGS. 20 and 21 are different perspective views of the right frame 194 showing various details.

Figure 22:
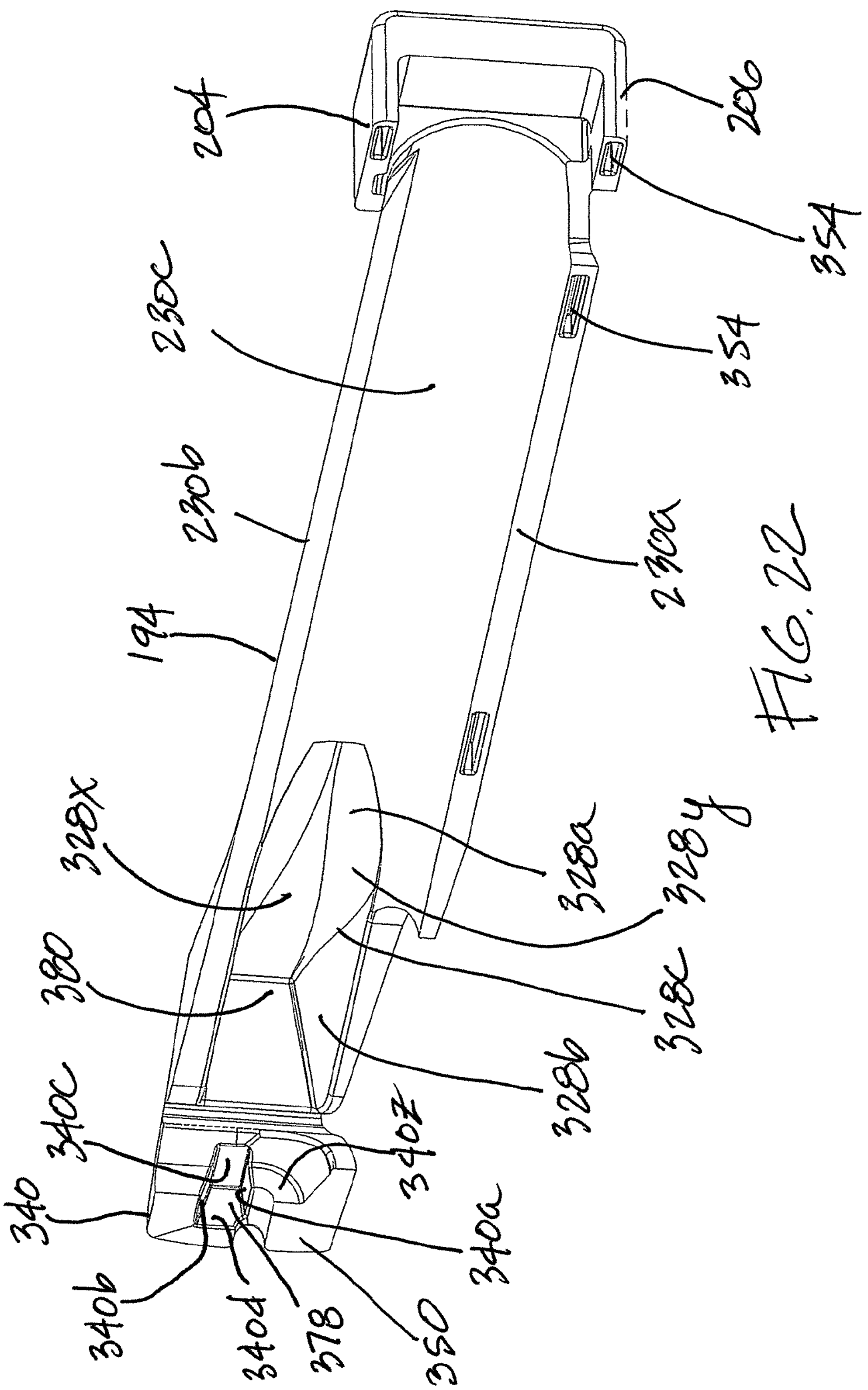
FIG. 22 is a perspective view of one of the housing components of FIG. 18.

FIG. 22 is a further perspective view of the right or second frame 194. In the view shown, the activation ramp 328 is implemented as two separate activation ramp sections 328*x*, 328*y*, each with a proximal ramp portion 328*a*, distal ramp portion 328*b*, and central ramp portion 328*c*. The two separate activation ramp sections 328*x*, 328*y* can operate or function as explained above. A gap or void 380 is provided at the distal ramp sections of the two ramp sections 328*x*, 328*y*, formed by the negative slopes of the two distal ramp sections. A small gap is located between the two ramp sections 328*x*, 328*y*. In other examples, the activation ramp 328 is formed as a single ramp structure without a gap. The surface of the activation ramp 328 can be generally flat or can have a large radius to form a slight curve for accommodating the contour of the catheter hub.

As can be visualized, when the second or right frame 194 is coupled to the first or left frame 193 and the catheter hub 130 is advanced distally to abut the two separate activation ramp sections 328*x*, 328*y*, the nose section of the catheter hub 130 (FIG. 2) initially abuts the two proximal ramp portions 328*a* of the two separate activation ramp sections 328*x*, 328*y* then moves into the gap or void 380 as the nose section continues to move in the distal direction. Then the intermediate portion of the catheter hub, which is larger in diameter or size than the nose section of the catheter hub, moves over the two proximal ramp portions 328*a* to further expand the two frames 193, 194 away from one another. At this point, the two frames 193, 194 are completely separated from one another except for the engagement at the two end cap components 340, at the distal end of the housing. If not completely separated proximal of the two end cap components, further movement of the external threads 154 of the catheter hub 130 against the two proximal ramp portions 328*a* further expands the two frames 193, 194 away from one another so that the tabs and slots of the two frames completely separate from one another, except for the engagement at the two end cap components 340. Finally, the last engagement between the recess 378 and the tab 398 (FIG. 26) on the left frame 193 can separate by physically grasping one of the frames, or both, and pulling one or both frames away from one another. The catheter hub can then be completed, such as connected to a drip line and taped to a patient.

In an example, the recess 378 at the end cap component 340 has two sidewalls 340*a*, 340*b*, a bottom wall 340*c*, and a center wall 340*d*. In an example, the two sidewalls 340*a*, 340*b* each comprises a surface and wherein the two surfaces of the two sidewalls taper or are converging in the direction of the bottom wall 340*c*. Thus, the surface of the center wall 340*d* is trapezoid in shape. The recess 378 is therefore tapered and has a width or gap at the opening of the recess 378 that is larger than the width or gap at the bottom of the recess. This configuration allows the corresponding tab on the end cap component 340 of the first frame 193 to engage the recess 378 and for the engagement to readily separate to facilitate separation of the two frames 193, 194 at the two end cap components to then separate the catheter hub from the housing of the ExD catheter assembly.

Figure 23:
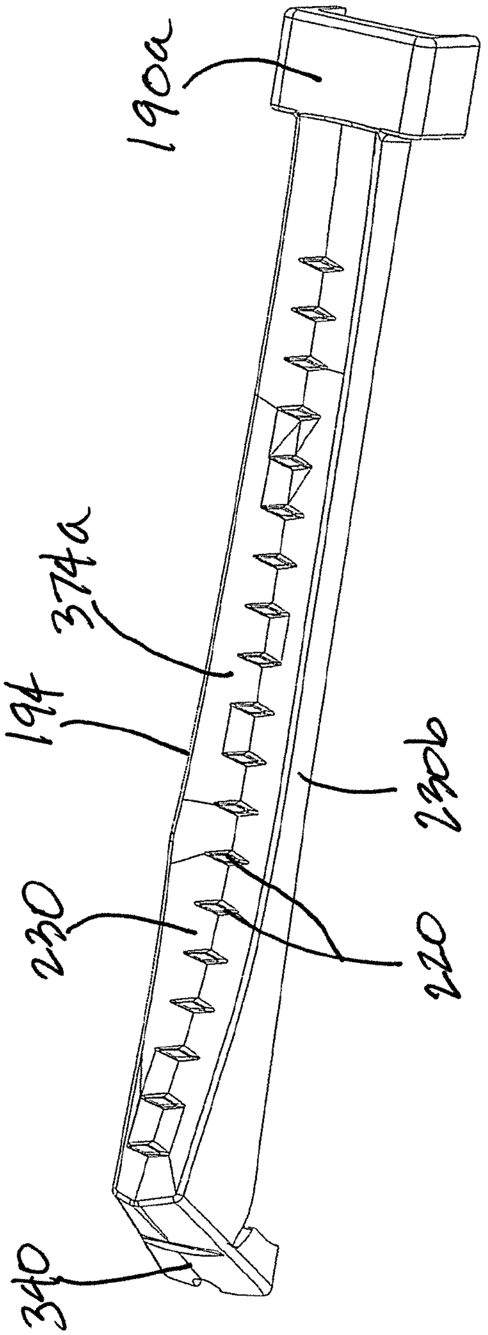
FIG. 23 is a perspective view of one of the housing components of FIG. 18.

FIG. 23 is a perspective view of the second frame 194 of FIG. 22, shown from a reversed view to show the exterior surface 374*a* of the right frame. As shown, the exterior surface is provided with a plurality of spaced apart projections or ornamentations 220, similar to that shown for the left frame of FIG. 15. In an example, the two different sets of projections 220 for the two frames can be the same and can have the same spacing. In other examples, the projections can have different shapes and/or different spacing between two adjacent projections.

Figure 24:
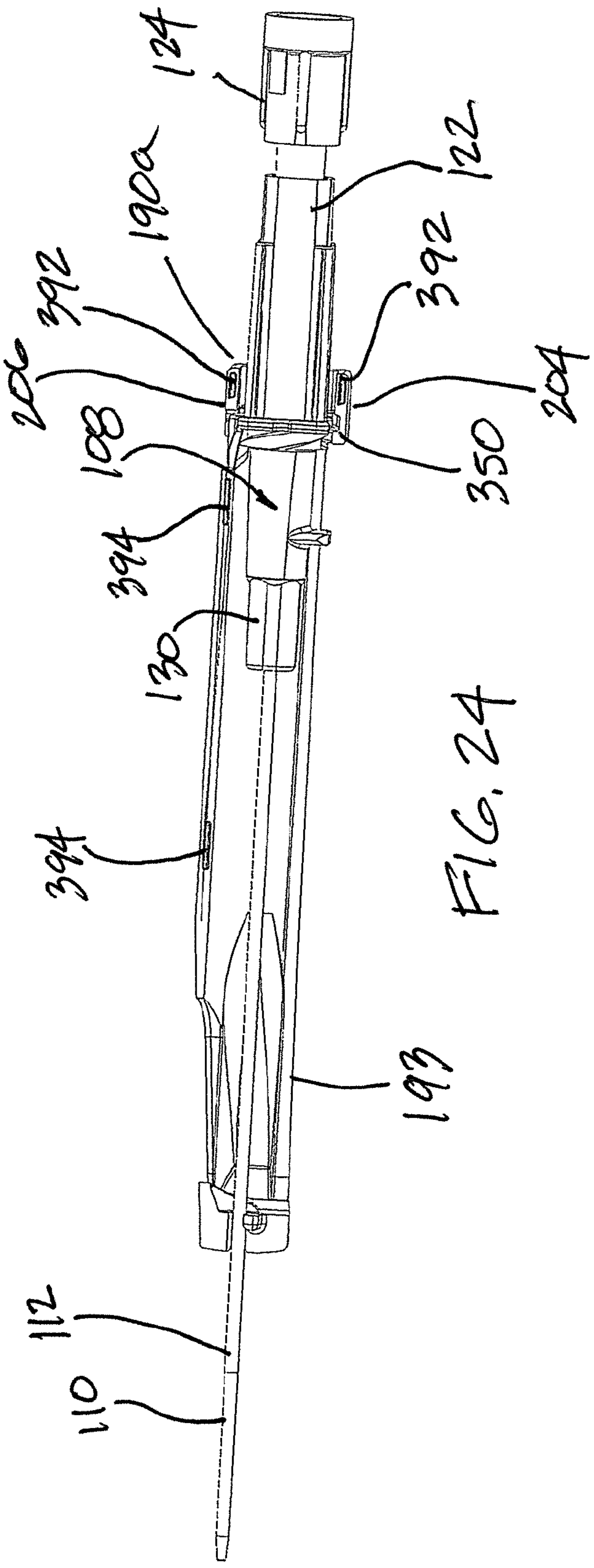
FIG. 24 is a perspective view of the extended dwell catheter assembly of FIG. 15 from a different perspective and shown without one of the housing components.

FIG. 24 is a side view of the ExD catheter assembly 100 of FIG. 15 shown with the catheter assembly 108 mounted with the first frame or left frame 193 and where the second frame 194 has been removed to more clearly show the arrangement, similar to the arrangement of FIG. 17 but with the first frame 193 instead of the second frame 194. The present combination is similar as the previously described combination (such as FIG. 17) except in the present combination, tabs or male detents 392 are provided on the third side 204 of the base portion 190*a* at the joining edge 350 and on the fourth side 206 of the base portion 190*a* at the joining edge 350 to engage the two slots 368 on the base portion 190*a* of the second frame 194 (FIG. 19). Tabs or male detents 394 are also provided at the joining edge 350 on the lower wall structure or section 230*a* for engaging the two slots 370 on the lower wall structure 230*a* of the second frame 194 (FIG. 19). Optionally, the two frames 193, 194 can join one another along adjoining seams via welding or adhesive. If welding or adhesive is used, the upper and lower seams at the distal end of the housing attach to one another via detents so that the detents can disengage to open a distal gate opening to then enable separation of the catheter hub from the housing, as further discussed below.

Figure 25:
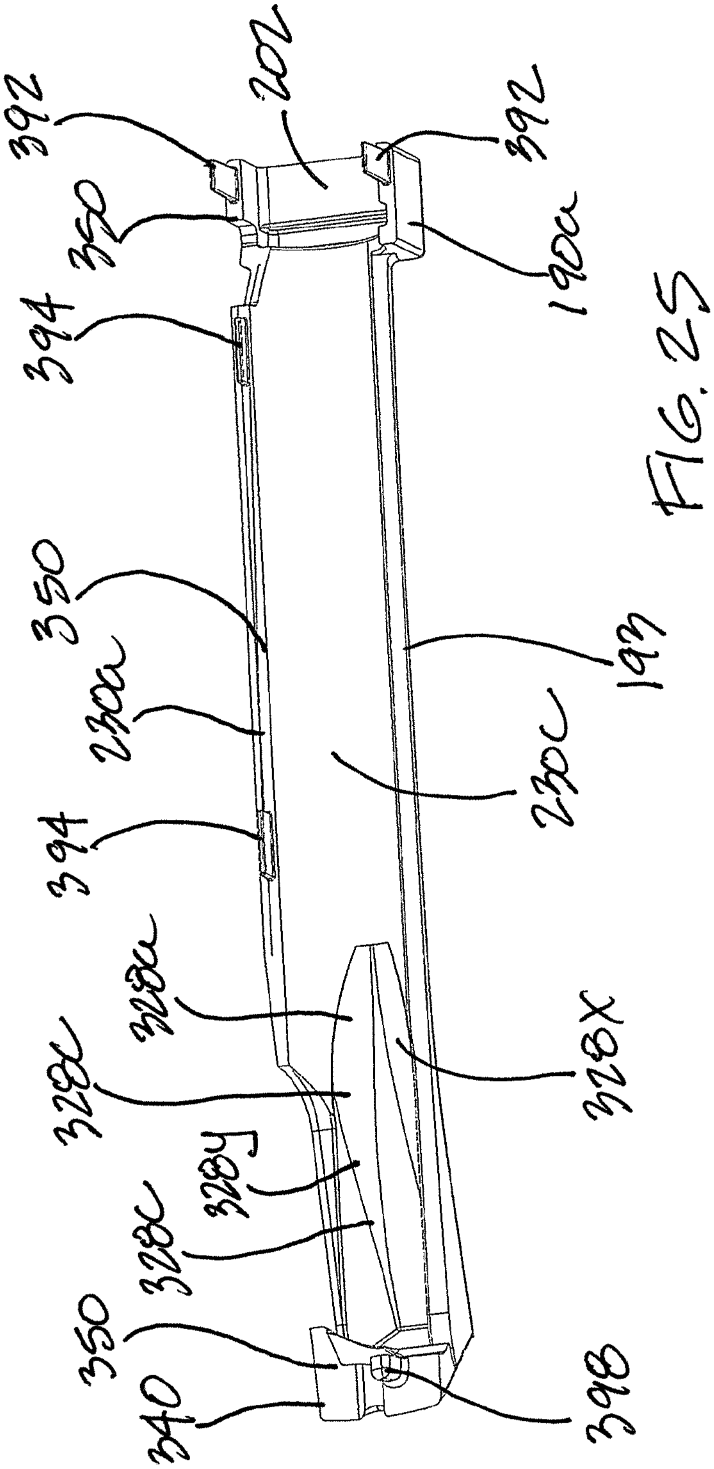
FIG. 25 is a perspective view of the housing component of FIG. 24.

FIG. 25 is a perspective view of the first frame 193 of FIG. 24 shown without the catheter assembly 108. The tabs or male detents 392 on the base portion 190*a* and the tabs or male detents 394 on the lower wall structure or section 230*a* are shown. Also shown are the two activation ramp sections 328*x*, 328*y* located on the sidewall structure or section 230*c* of the frame, the shape and function of which are similar to the two activation ramp sections 328*x*, 328*y* discussed above with reference to FIG. 22. As with the other activation ramp sections 328*x*, 328*y*, each of the activation ramp section comprises a proximal ramp portion 328*a*, a distal ramp portion 328*b*, and a central ramp portion 328*c* located between the proximal and distal ramp portions.

A tab or male detent 398 is provided at the joining edge 350 of the end cap component 340 of the first frame 193. The tab 398 is located on the end cap component 340 at a location to matingly engage the slot on the right frame 194, when the left and right frames are assembled to form the housing of FIG. 15. The tab 398 is sized and shaped to engage the recess 378 on the end cap component 340 of the second frame 194. In an example, the engagement between the tab 398 and the recess 378 is a slight interference.

In an example, the engagement between the tab or male detent 398 and the recess 378 at the two end cap components 340 has a stronger gripping or engagement hold than the engagement between the tabs 392 on the base portion 190*a* and tabs 394 on the lower wall structure 230*a* engaging corresponding slots 368, 370 on the second frame 194. This relative engagement force between the engaging pairs of tabs and slots ensures that when the catheter hub 130 is advanced in the distal direction within the interior space 104 of the housing following initial catheter tube placement, and after advancement of a guidewire when incorporated, upon contact by the catheter hub against the activation ramps, the housing will separate first at the proximal end of the housing before separation at the two end cap components 340. In other examples, the various pairs of tabs and slots open generally at about the same time upon contact by the catheter hub against the activation ramps.

Figure 26:
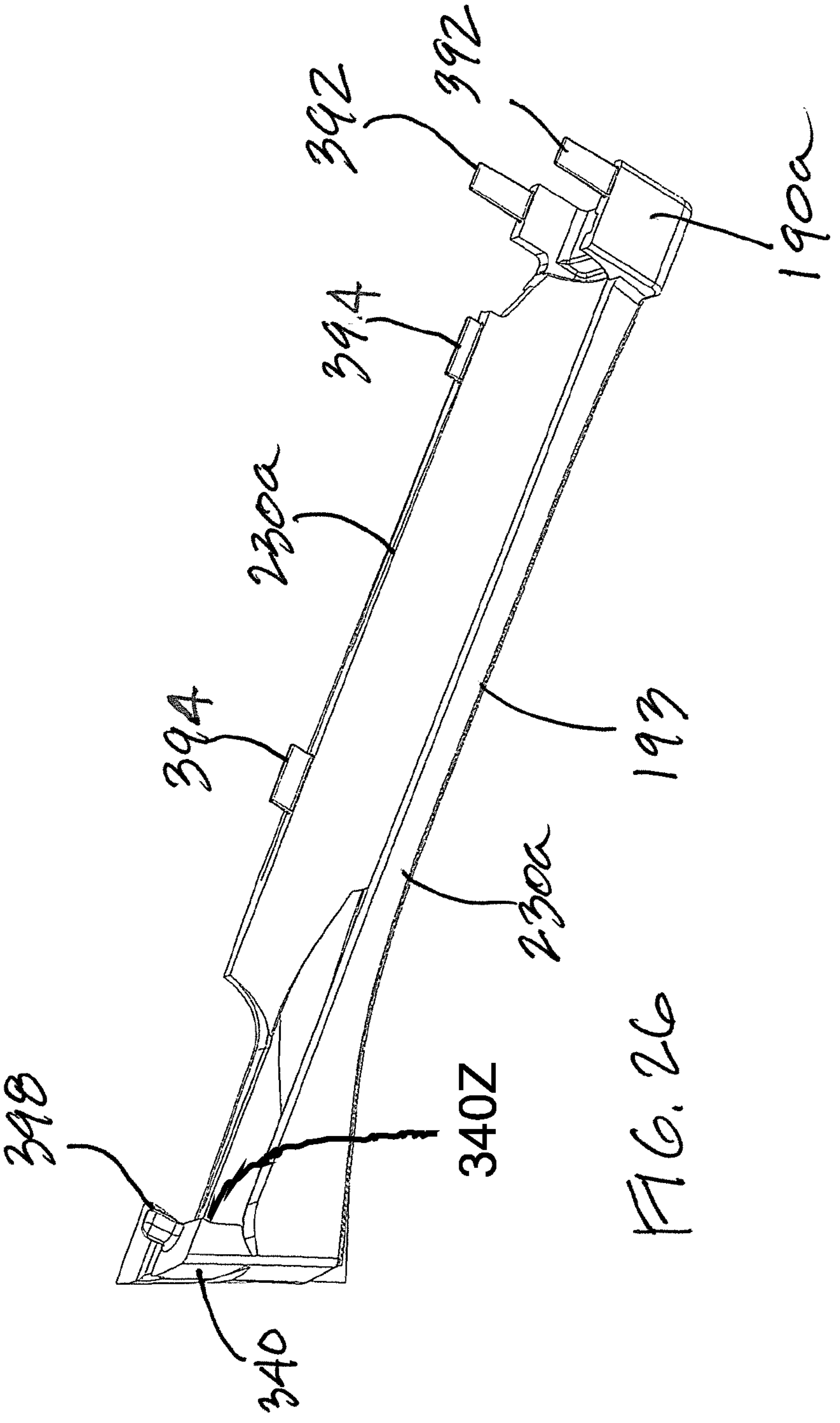
FIG. 26 is a perspective view of one of the housing components of FIG. 25.

FIG. 26 is a perspective view of the first frame 193 of FIG. 25 from a different perspective. In the orientation shown, the tabs 392 on the base portion 190*a* are longer than the tabs 392 on the lower wall structure 230*a* of the body section. The tabs on the base portion 190*a* are also longer than the tab 398 on the end cap component 340. The different lengths of the various tabs mate or engage with slots having different and corresponding depths to engage to ensure a generally tight seam 232 (FIG. 16) when the two housing frames 193, 194 are coupled to form the housing 102. In some examples, each of the left and right frames can have both a slot and a tab to mate with corresponding tabs and slots rather having an arrangement where all the slots are located with one frame and all the tabs are located with another frame.

Figure 27:
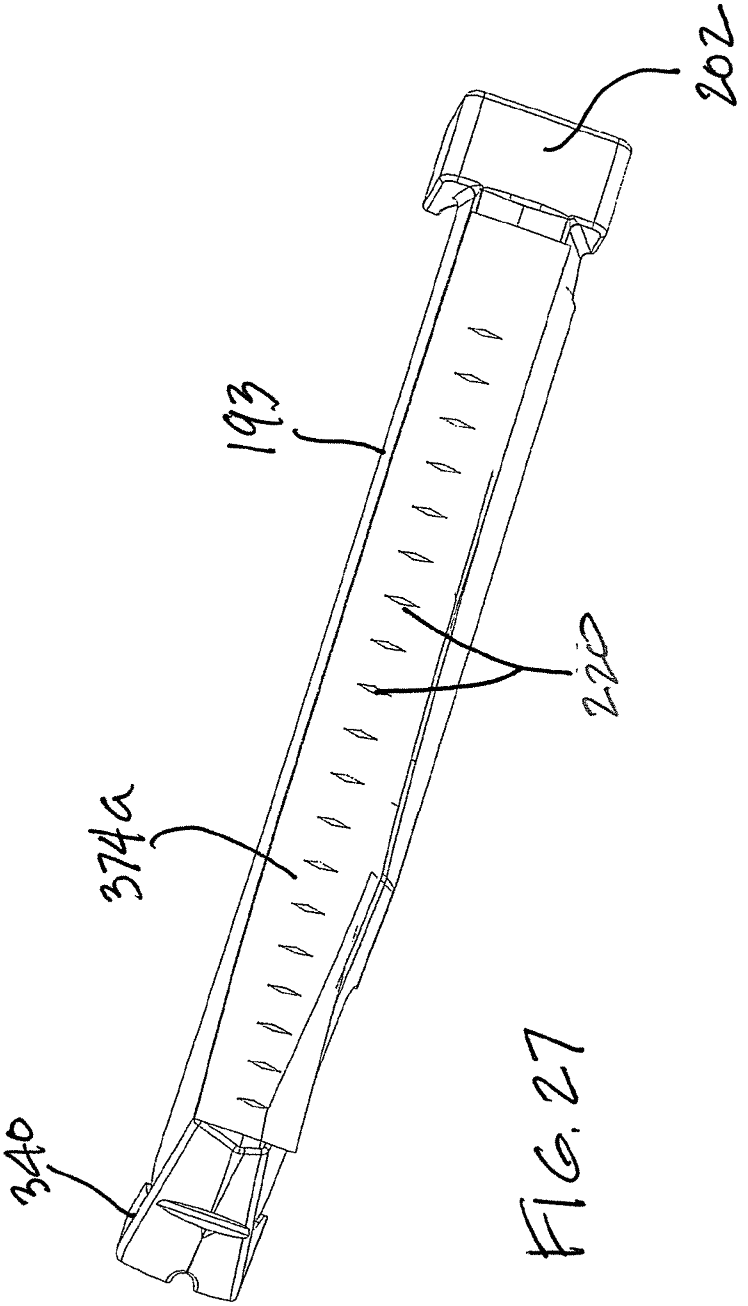
FIG. 27 is a perspective view of one of the housing components of FIG. 25.

FIG. 27 is a perspective view of the first frame 193 shown from a reversed view to show the exterior surface 374*a* of the first frame. As shown, the exterior surface 374*a* is provided with a plurality of spaced apart projections or ornamentations 220, similar to that shown for the second frame. In an example, the two different sets of projections 220 for the two frames can be the same and can have the same spacing. In other examples, the projections can have different shapes and/or different spacing between two adjacent projections.

With reference again to FIGS. 15-17, 24, and 28 for a discussion of the ExD catheter assembly 100 being put to use. The user can use the ExD catheter assembly to puncture a targeted vein with guidance from a visualization device, such as an ultrasound monitor using an ultrasound probe. Primary blood flashback can be observed flowing into the needle hub 122. Next, the angle of insertion of the ExD catheter assembly 100 is lowered prior to further advancing the ExD catheter assembly 100 to locate the catheter tube deep into the vein. In some examples, a guidewire dispenser having a guidewire extending through the lumen of the needle may be used with the ExD catheter assembly. For example, a SonoStik® guidewire dispenser having a housing may be placed into the proximal opening of the catheter hub after removal of the vent plug 124 and the guidewire projecting through the lumen of the needle and advanced in a manner known in the industry. The guidewire may be used to guide the catheter tube to a desired treatment location within the body.

The needle and catheter tube are advanced over the guidewire and stopped at or just before the nose end 184 of the housing 102 contacts the skin. If the ExD catheter assembly is used without a guidewire, then the ExD catheter assembly may be advanced without first advancing the guidewire. The practitioner can then place his or her thumb on the push tab 176 of the catheter hub 130 to advance the catheter hub against the one or more activation ramps 328 on one or both first and second housing frames 193, 194.

Figure 28:
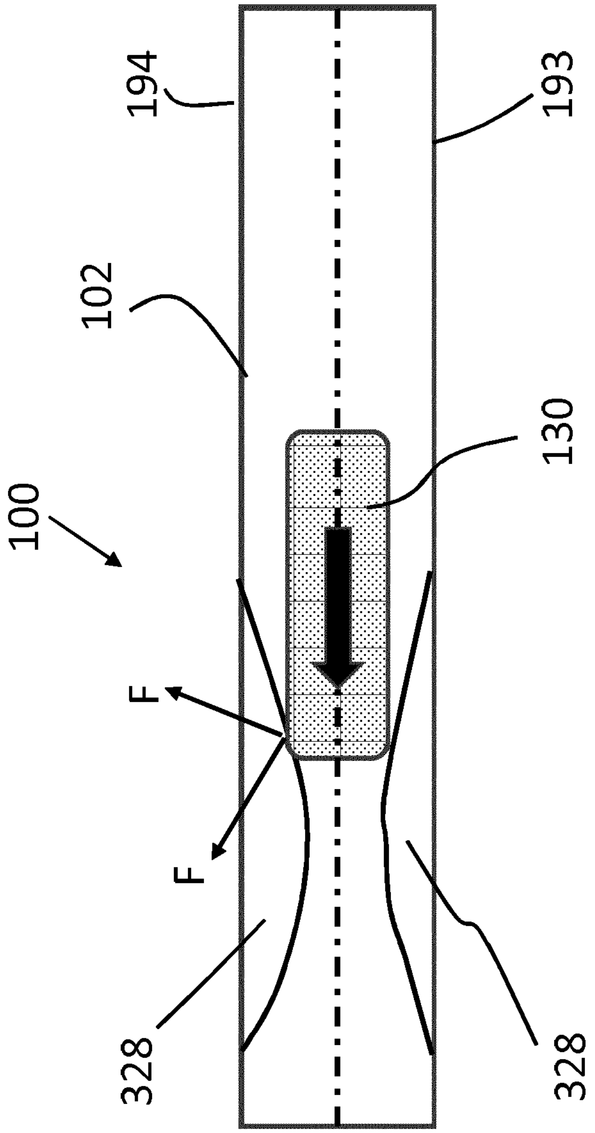
FIG. 28 is a schematic of the extended dwell catheter assembly of FIG. 15, showing the pair of component forces when the catheter hub contacts the activation ramps.

With further reference to the schematic diagram of the ExD catheter assembly 100 of FIG. 28, when the catheter hub 130 is pushed in the distal direction until the nose end of the catheter hub pushes against the two activation ramps 328, a pair of component forces are generated on each of the two frames 193, 194. This then causes the two frames to separate starting at the base end of the housing. As the catheter hub continues to move in the distal direction, the two frames further separate until the tabs and slots on the base end and the body completely separate from one another. At this point with the tab 398 (FIG. 26) and the recess 378 (FIG. 19) on the two end cap components 340 continue to engage, the two frames pivot at their respective living hinges 346. The user can then use a free hand while maintaining a grip on the catheter hub to pull on one of the two frames 193, 194 to separate them at their respective end cap components 340. The catheter hub 130 and the housing 102 are then free of one another. The user can then finish preparing the catheter hub, such as connecting a drip line to the catheter hub and taping it to a patient to secure the puncture site.

With reference again to the ExD catheter assembly 100 of FIGS. 15-27 and particularly to FIGS. 15, 17, 22, and 26, an alternative implementation of the device or assembly is contemplated. In the alternative implementation, the left and right frames, or first and second frames 193, 194 are secured together with the tabs or male detents 392, 394, 398 engaging the corresponding slots or female detents 354, 378. In the present embodiment, the engagement between the tabs or male detents 392, 394 and the slots or female detents 354 at the body 188 and at the base 190 are such that they do not separate upon advancement of the catheter hub 130 in the distal direction within the interior of the housing 102. For example, the engagement between the tabs and the slots can be with interference and/or with adhesive, bonding or welding. Further, the activation ramps 328 (FIG. 28) can be omitted from the first and second frames 193, 194 so that radial forces are not generated by the advancing catheter hub to separate the two housing frames. Thus, when the catheter hub 130 is advanced distally to further place the catheter tube into the vein, the catheter hub can reach the void 380 space (FIG. 22) at the distal end of the body section without imparting any radial forces on the two frames to separate them. Instead, the distal abutment of the catheter hub 130 against the distal gates opens the distal gate opening to then permit separation of the catheter hub 130 from the housing 102.

With specific reference now to FIGS. 22 and 26, the tab 398 at the end cap component 340 of the first frame 193 engages the recess 378 on the second frame 194 in a friction, loose or separable engagement. That is, upon being pushed distally by the advancing catheter hub 130, the male detent or tab 398 on the first frame 193 can release or separate from the recess 378 on the second frame 194. In the detailed view of FIG. 22, the recess 378 is shown with an open slot or recess. This structure allows the tab and recess at the two end cap components 340 of the left and right frames 193, 194 to separate by allowing the tab 398 to pass through the side opening of the recess without a sidewall rather than the opening proximate the joining edge 350. The separation at the two end components 340 can therefore occur by simply providing an axial force when pushing the catheter hub 130 in the distal direction against on the two end cap components without having to generate a radial force as discussed with reference to FIG. 28.

Thus, following cannulation, optionally following guidewire placement and following catheterization, as previously described with the first implementation of the ExD catheter assembly 100 of FIGS. 15-28, the catheter hub 130 can advance against the proximally facing surfaces 340Z of the two end cap components 340 of the left and right frames (FIGS. 22 and 26). The advancing force of the catheter hub 130 forces the tab 398 to separate from the recess 378. This separation is facilitated by the open side between the two sidewalls 340*a*, 340*b* of the recess at the end cap component 340 of the second or right frame 194 (FIG. 22). That is, the tab 398 on the first or left frame 193 can simply slide out through the gap provided by the missing side of the recess 378 between the two sidewalls 340*a*, 340*b*.

With reference now to FIGS. 15 and 16, as the tab 398 and the female detent 378 at the two end components 340 separate and the two frames are held secured by the tabs 392, 394 and slots 354 (FIGS. 22 and 26) at the body portions 188*a* and base portions 190*a* of the two frames 193, 194, the two end components 340 are forced to swing in the distal direction about the two living hinges 346. In an example, the space or distance between the two living hinges 346 is larger than the horizontal dimension or cross-sectional dimension of the catheter hub 130. Thus, as the two end cap components 340 swing in the distal direction about the two living hinges, a gate with a gap, called a gate opening or distal gate opening as defined by the space provided by the distally swinging end components, opens up to provide clearance for the catheter hub 130 to pass therethrough. The swinging end cap components 340 may be referred to as gates that can swing open to open the distal gate opening. In practice, this allows the catheter hub 130 to separate from the needle hub 122 and the housing 102 through the gate opening or distal gate opening to separate from the needle 112, the needle hub 122, the housing 102, and guidewire and guidewire dispenser if used. The catheter hub can then be secured to a patient for fluid administration. The needle 112, the needle hub 122, the housing 102, and the guidewire and guidewire dispenser if used, can be discarded or disposed of per approved protocol.

Thus, an aspect of the present invention is understood to include an ExD catheter assembly comprising a multi-part housing having an interior space having a catheter assembly located therein; said catheter assembly comprising a catheter tube attached to a catheter hub and a needle attached to a needle hub and extending through the catheter tube with a needle tip extending distally of a distal opening of the catheter tube. Said needle and catheter tube projects through an opening at a distal end of the housing. The distal end can comprise two end cap components removably attached to one another, such as by engaging a male detent and a female detent. The female detent can be a recess with three sidewalls and with at least one open side and one open inlet to the recess.

The multi-part housing can comprise a first frame attached to a second frame. The two frames can have a seam therebetween. The two frames can attach along a joining edge. One of the two frames can comprise a tab or a male detent and the other frame can comprise a corresponding slot or female detent for receiving the male detent to removably secure the two frames together. The distal end of the housing can comprise a seam. The opening at the distal end having the needle and catheter tube project thereto can be formed by two cut-outs. The distal end of the housing can include a living hinge. Preferably there are two living hinges at the distal end of the housing. A gate with a gap can be defined by the distance between the two living hinges. When the tab and the female detent with at least one open side separate from one another, two end cap components can swing distally about the two living hinges to open a gate opening or distal gate opening at the distal end of the housing. The catheter hub can exit the gate opening or distal gate opening and separate from the remaining components of the ExD catheter assembly, which can include a needle, a needle hub, a housing, and a guidewire and a guidewire dispenser if used.

Figure 29:
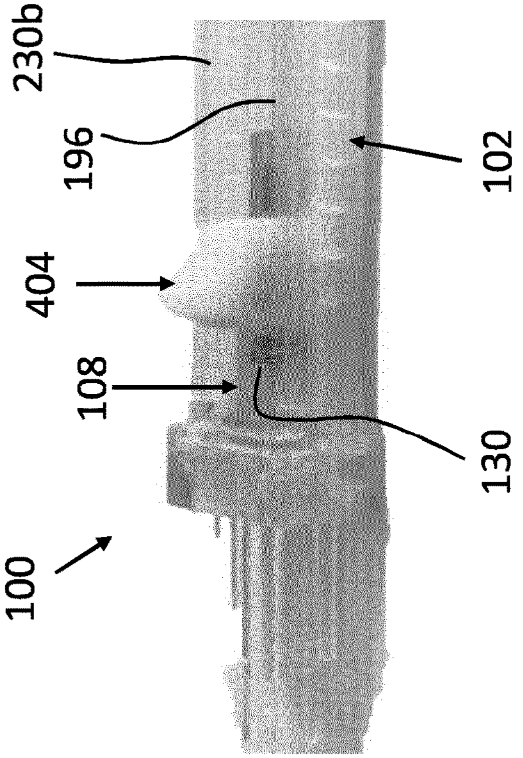
FIGS. 29-31 are different views and a cross-sectional view of a tab adapter for use with a catheter hub to facilitate operation of the ExD catheter assembly.

With reference now to FIG. 29, a partial perspective view of an ExD catheter assembly 100 comprising a housing 102 and a catheter assembly 108 is shown. The ExD catheter assembly 100 can be similar to one of the ExD catheter assemblies disclosed elsewhere herein, such as the assembly 100 of FIGS. 15-16. The ExD catheter assembly of the present embodiment is shown with a tab extender or tab adapter 404 attached to the catheter hub 130 and extends orthogonal to the lengthwise axis of the housing through the housing opening 196 so that an upper portion of the tab adapter 404 rises above the top wall structure 230*b* of the housing to present a surface for pushing or grasping by a practitioner. In an example, the tab adapter 404 is provided to extend the profile of the integrally formed push tab 176

(FIG. 2) of the catheter hub 130 well above the top wall structure **230*b* to facilitate operation of the ExD catheter assembly. Alternatively, the push tab 176 can be formed in an extended configuration and extends above the top wall structure 230*b* of the housing to present itself to be pushed by a practitioner without the separately formed tab adapter 404**.

Figure 30:
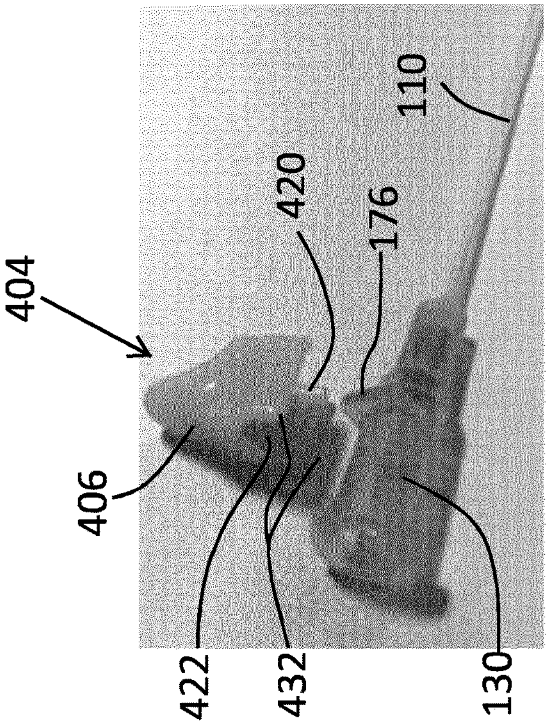
Figure 31:
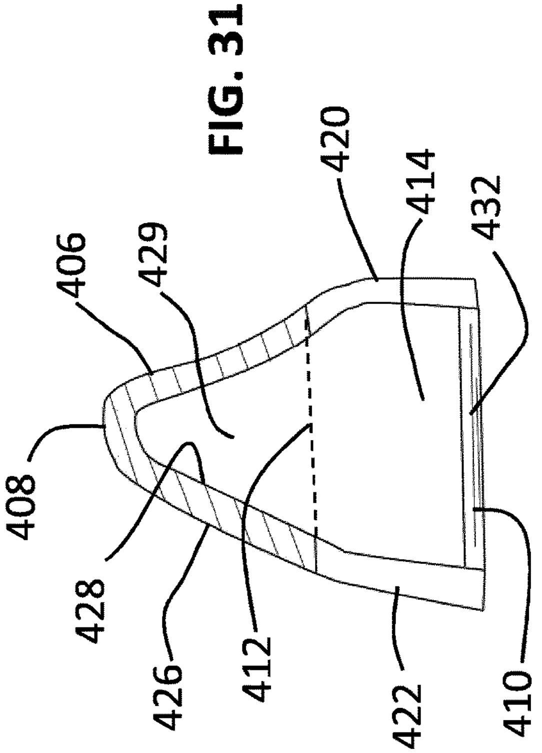

FIG. 30 shows a tab adapter 404 spaced from a catheter hub 130 and FIG. 31 shows a cross-sectional side view of the tab adapter 404. With reference to FIGS. 29-31, and continued reference to FIG. 29, the tab adapter 404 can be formed from a plastic material, such as by plastic injection molding. The tab adapter 404 can comprise a body 406 having a first end 408 and a second end 410. The first end 408 can be located above, elevation-wise, the second end 410. In an example, the body 406 can be formed as a solid structure above the imaginary line 412 and having a tunnel or channel 414 below the imaginary line 412 with an arcuate first opening 420 and an arcuate second opening 422 in communication with one another via the channel 414. In an alternative embodiment, the body 406 is hollow and is formed with a wall structure having an exterior surface 426 and an interior surface 428 defining an interior space or cavity 429. The wall thickness between the exterior surface 426 and an interior surface 428 has a sufficient thickness to provide structural rigidity for carrying a digital load applied by a user to advance the catheter hub 130.

The tab adapter 404 is sized and shaped for mounting over the catheter hub 130. In an example, the tab adapter 404 is configured to seat over the catheter hub 130 and the hub body situated in the channel 414 of the body 406. The first opening 420 and the second opening 422 of the tab adapter 404 are sized to fit snugly around the curved body of the catheter hub 130. Depending on how the tab adapter 404 is situated over the catheter hub 130, such as by placement or location along the axial position of the catheter hub, the first and second openings 420, 422 of the tab adapter 404 can have the same size or different sizes to fit the particular contour of the catheter hub. In an example, as shown in FIG. 30, the first and second openings 420, 422 can have a semi-spherical shape, semi-oval or elliptical shape, or an arcuate shape. Preferably, the two openings 420, 422 are sized and shaped to fit snuggly over the catheter hub body and has a gripping force around the hub body. The two openings can have different shapes from one another and can be selected based on the size and contour of the catheter hub body.

When mounted over the catheter hub 130, the push tab 176 (FIG. 30) is configured to fit within the interior space 429 of the body 406. To secure against slipping, sliding, or moving relative to the catheter hub 130 when digital pressure is applied to the body 406, two gripping bars 432 are provided at the second end 410 of the body 406, on either side of each of the two openings 420, 422. The gripping bars 432 can resemble ribs and can be provided with contoured surfaces to snuggly fit against the catheter hub. Relative to the upper part of the two openings 420, 422, the locations of the gripping bars 432 on the body of the tab adapter 404 should be located so that when mounted to the catheter hub, the two gripping bars 432 are below the centerline of the catheter hub body. The size and shape of the first and second openings 420, 422 and the locations of the two gripping bars 432 are such that the tab adapter 404 fits snuggly and grips the catheter hub body. The adapter 404 may be used by sliding the channel and the two openings over the catheter hub body and ensuring that the push tab on the catheter hub is located within the interior of the tab adapter.

The push tab 176 of the catheter hub 130 can contact the interior surface 428 on the proximal side of the body 406. Thus, when the tab adapter 404 is pushed in the distal direction by a practitioner, the interior surface 428 of the tab adapter 404 pushes against the proximally facing surface of the push tab 176 to advance the push tab 176, and hence the catheter hub 130, in the distal direction. In an example, the interior space 429 of the tab adapter 404 is provided with a socket that receives that push tab 176 in a size-on-size fit or with a slight interference to resist separation from the catheter hub body upon distal advancement of the catheter hub.

Figure 32:
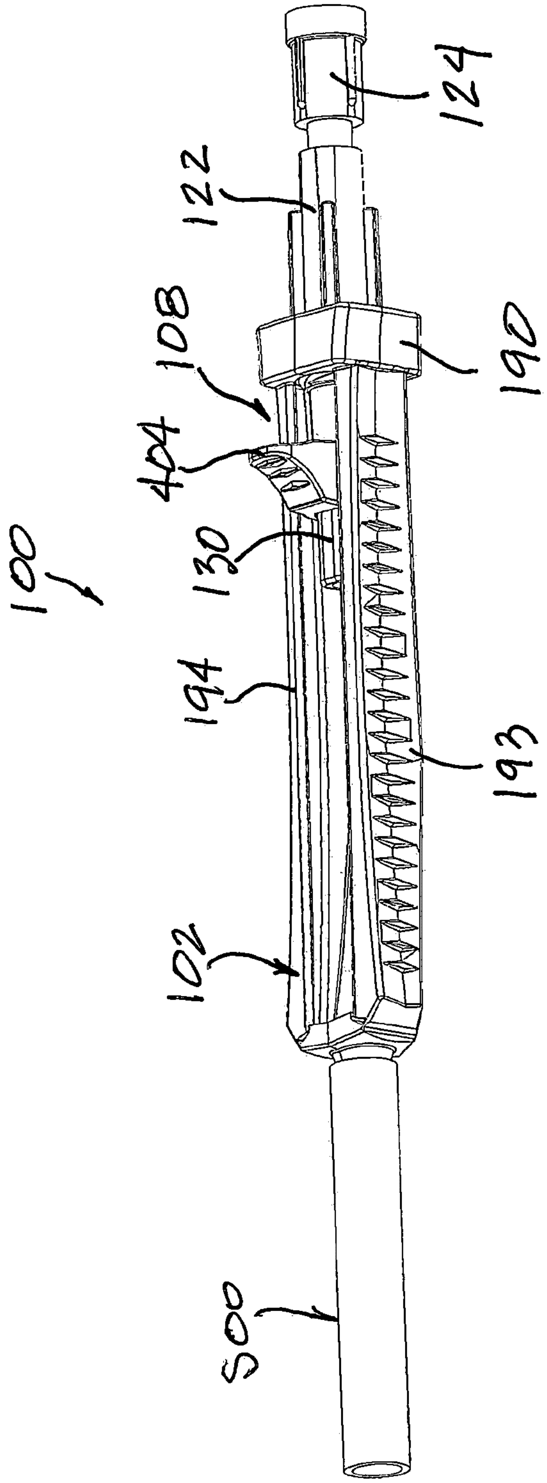
FIG. 32 is a perspective view of an extended dwell catheter assembly provided in accordance with further aspects of the present invention.

With reference now to FIG. 32, an extended dwell catheter assembly 100 provided in accordance with still further aspects of the present invention is shown. The present ExD catheter assembly 100 shares similar aspects with the catheter assembly of FIGS. 1-14 and FIGS. 15-28, and in particular a similar housing 102 configuration in which a first frame or left frame 193 and a second or right frame 194 are attached to form the housing 102 and can separate to release the catheter hub 130 of the catheter assembly 108 from the housing. The first and second frames 193, 194 can attach to one another along a seam by corresponding tabs or male detents and engagement slots. Optionally, the first and second frames 193, 194 can attach to one another along upper and lower seams via adhesive or welding. The catheter hub 130 of the catheter assembly 108 can instead separate from the housing 102 by incorporating a gate assembly at the distal end of the housing 102 that opens to allow the catheter hub to separate.

As shown, the ExD catheter assembly 100 comprises a removable protective cap 500, which is configured to be placed over the needle to cover the needle and the needle tip prior to use. The proximal opening of the protective cap 500 can frictionally engage with the nose section or nose end 184 of the housing 102.

A tab adapter or tab extender 404, similar to the tab extender of FIGS. 29-31, can be positioned over the catheter hub 130 and secured thereto by fitment. A needle hub 122 extends proximally of the base end 190, and outside of the housing 102. A vent plug 124 is attached to the needle hub 122, which can allow air to vent but captures any blood that may flow inside of the needle hub and the vent plug.

Figure 33:
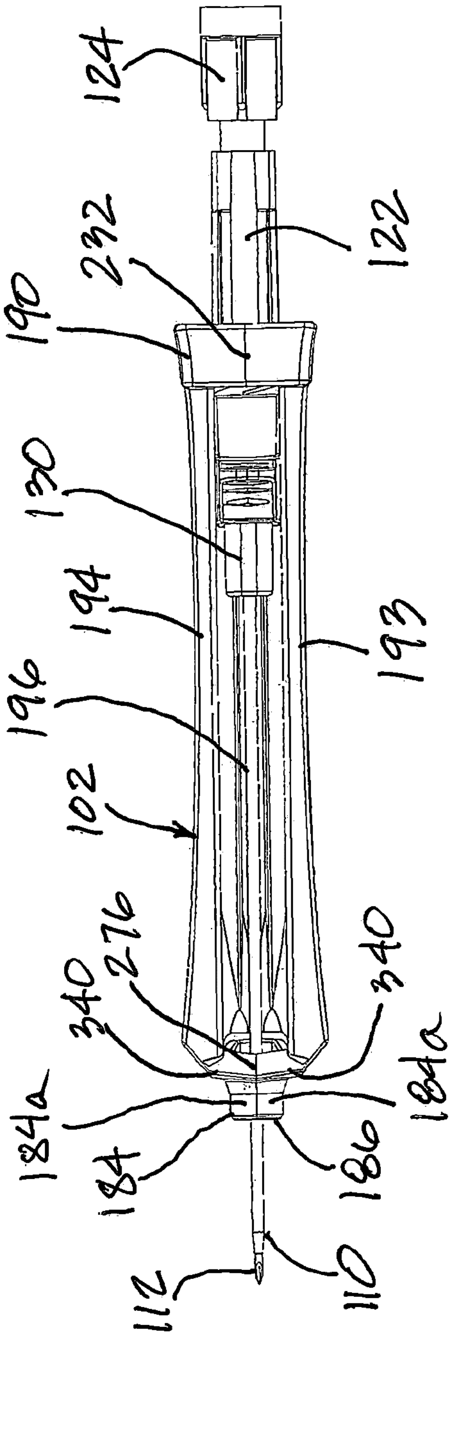
FIG. 33 is a top view of the ExD catheter assembly of FIG. 32.
Figure 36:
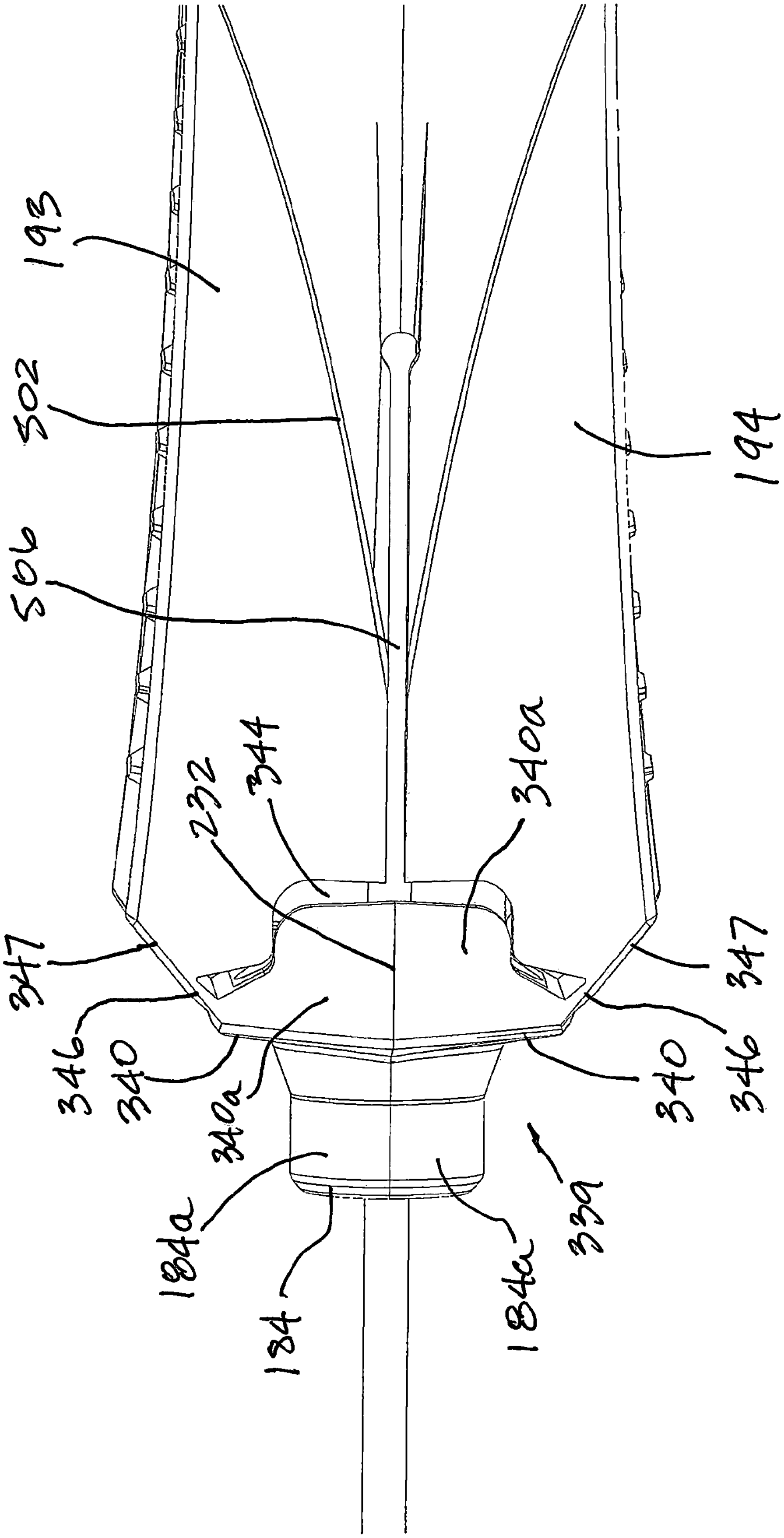

FIG. 33 is a top view of the ExD catheter assembly 100 of FIG. 32, shown without the protective cap 500. The housing 102 is shown with a nose end or nose section 184 having a tip 186 at an end of two nose portions **184*a* having an upper seam 276 extending therebetween. The upper seam 276 extends through the upper part of the nose end 184. A similar corresponding lower seam extends through the lower part of the nose end 184. Each nose portion 184*a* is joined to an end cap component 340 of each respective first or second frame 193, 194, similar to that of FIGS. 15 and 16. Each nose portion 184*a* and each end cap component 340 can be referred to as a gate or rotatable gate 339 (FIG. 36). The two gates 339 from the two end cap components 340 are part of a gate assembly 600. The two gates 339 can swing open to allow the catheter hub 130 to separate from the housing 102 without requiring the first frame 193 and the second frame 194** to separate from one another.

Figure 34:
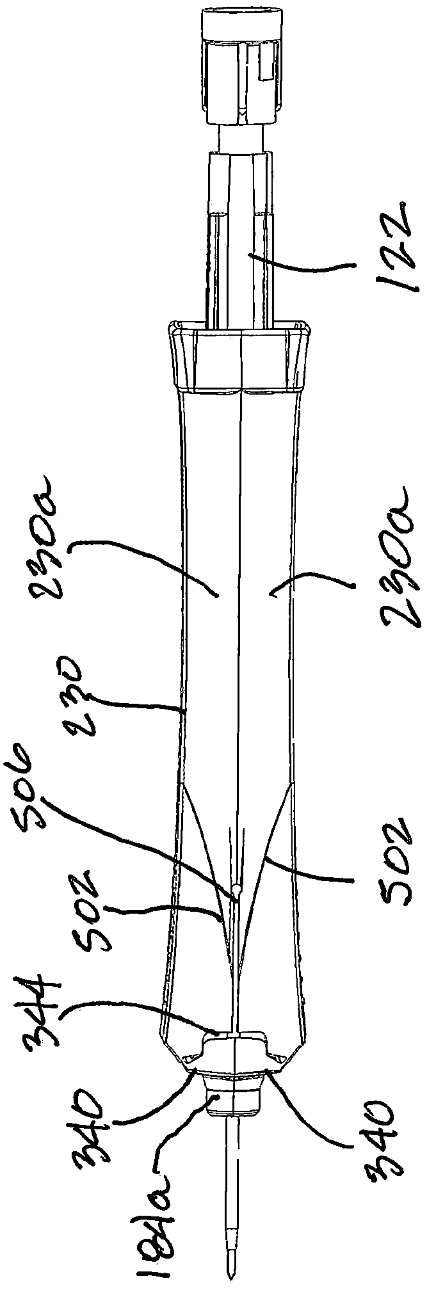
FIG. 34 is a bottom view of the ExD catheter assembly of FIG. 32.

FIG. 34 is a bottom view of the ExD catheter assembly 100 of FIG. 33, which resembles the housing of FIG. 16. In the present embodiment, each of the two first and second frames 193, 194 comprises a wall structure 230 comprising a lower wall section, an upper wall section, and a sidewall section. A plurality of projections or ornamentations are provided on the exterior surface of the sidewall section, which can embody round, elongated, polygonal, or irregular shape projections. The projections can be spaced from one another and provided for aesthetic and to facilitate gripping the housing 102 on the two sidewalls of the housing. The two housing frames have an interior for accommodating the catheter assembly 108 (FIG. 32) having a catheter hub therein.

In the present embodiment, a lower elongated opening is not incorporated, unlike the opening 334 of FIG. 16. The lower wall 230*a* of both housing frames 193, 194 can be solid and can join one another along the seam 232 up to the gap 344 that separates the two end cap components 340 from the remainder of two frames. This allows the two frames to remain attached to one another while the two end cap components 340 along with the two nose portions 184*a* of the nose end 184 swing open about respective living hinges to open a distal gate opening, as further discussed below. In other embodiments, two housing frames 193, 194 are joined to one another up to a lengthwise gap 506 (FIG. 34). The lengthwise gap 506 extends up to and flows or blends into the front gap 344 that allows the two end cap components 340 to swing to open the distal gate opening, as further discussed below. The proximal end of the lengthwise gap 506 can serve as an injection point for the plastic injection gate or inlet.

Optional score lines 502 can be incorporated on the wall surface of each frame. The score lines 502 can be straight, can have curves, or both for aesthetic appeal. Score lines are understood as grooved lines formed into the wall thickness of the lower walls 230*a* of the two frames 193, 194. In other examples, the score lines can be omitted.

Figure 35:
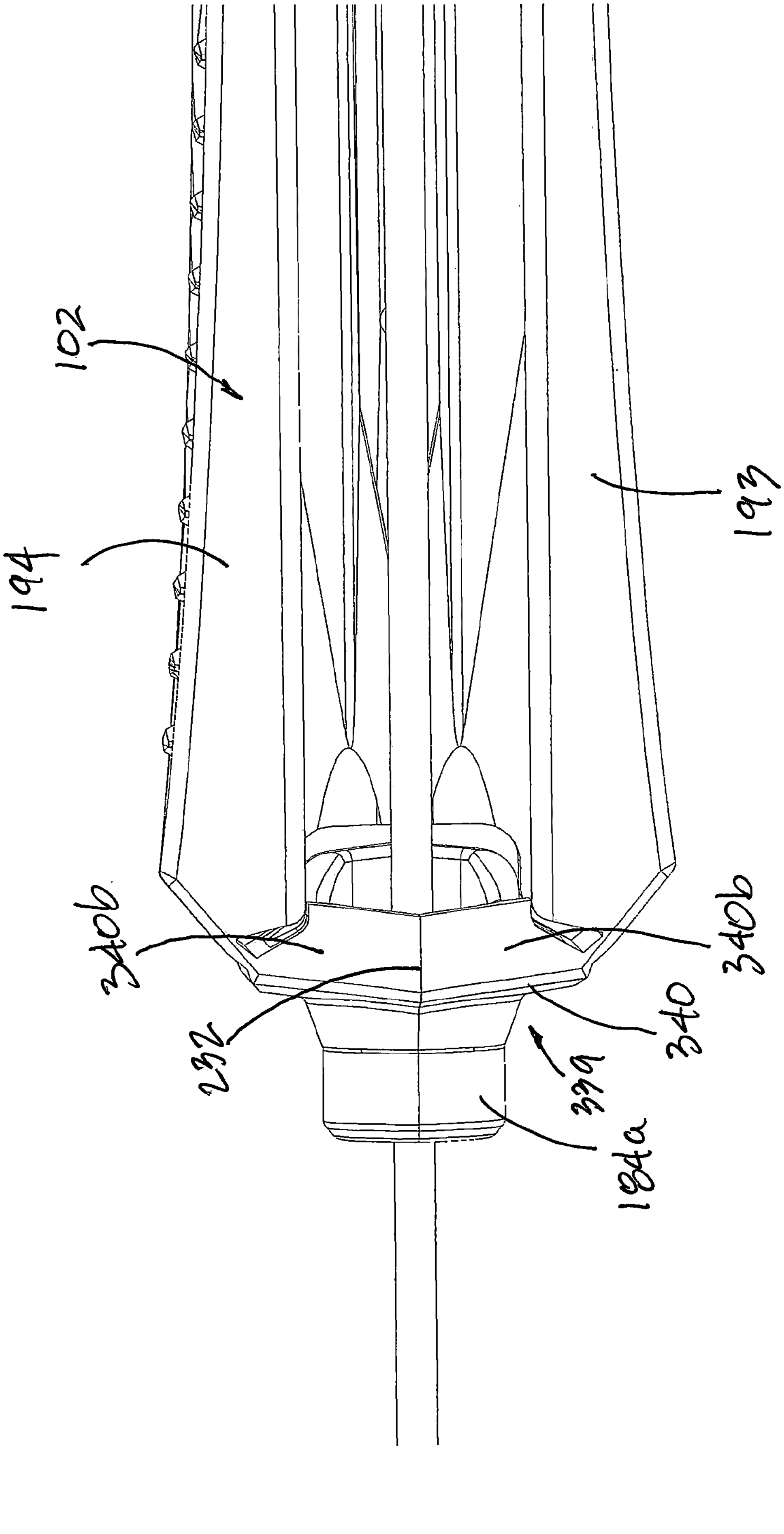
FIGS. 35 and 36 are enlarged top and bottom views of the distal end of the housing of the ExD catheter assembly of FIG. 32.

FIGS. 35 and 36 are close-up top and bottom views, respectively, of the distal end of the housing, showing the end cap components 340, similar to FIGS. 15-17, and the nose portions 184*a* of the nose end 184. Also shown is the distal gap 344, the lengthwise gap 506, and the seams 232 between the two upper sidewalls 340*b* and the lower sidewalls 340*a* of the two end cap components 340.

The two end cap components 340 are attached to the two front end walls 347 via two living hinges 346. Each of the two end cap components 340 is attached to a nose portion 184*a*, which combination may be referred to as a gate or rotatable gate 339. Similar to the embodiment of FIGS. 15-27, the two gates 339 of the gate assembly 600 can swing open when pushed in a distal direction by distal movement of the catheter hub 130 to open a distal gate opening.

Figure 37:
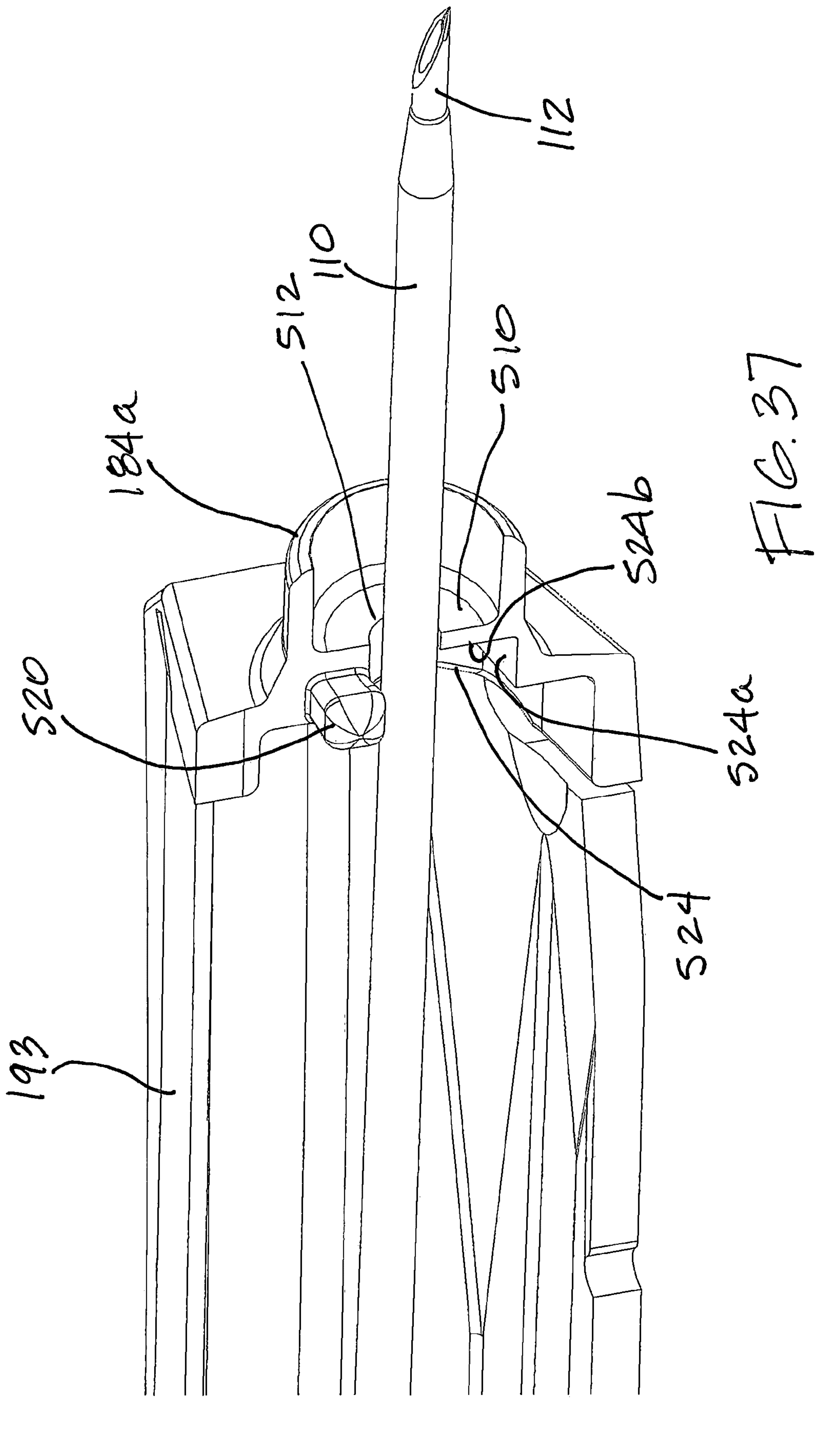
FIG. 37 is an enlarged sectional perspective view of the ExD catheter assembly of FIG. 32 shown with the first frame only.
Figure 38:
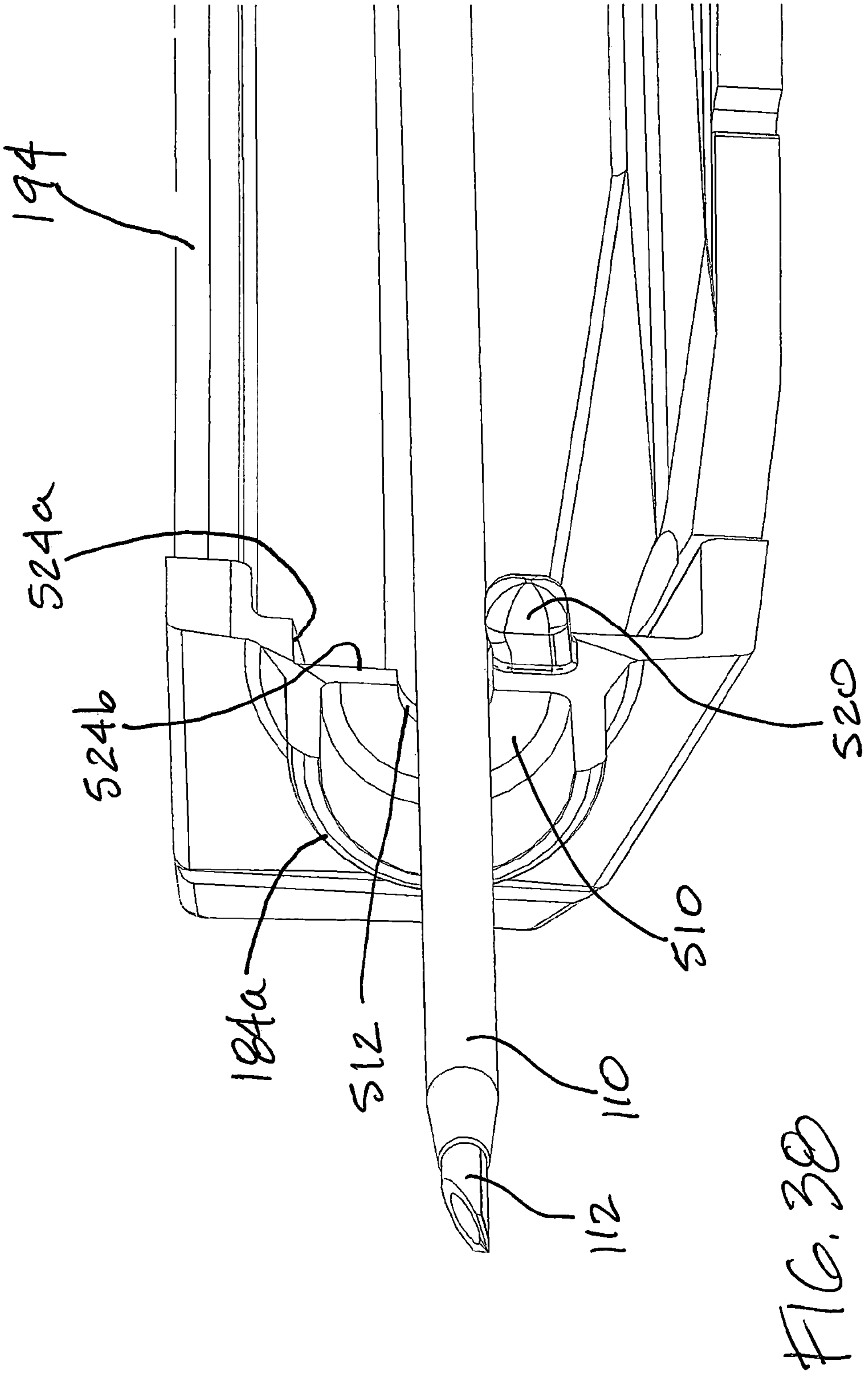
FIG. 38 is an enlarged sectional perspective view of the ExD catheter assembly of FIG. 32 shown with the second frame only.

FIG. 37 is a side view of the first or left frame 193 of the housing shown with the needle and catheter tube and without the second or right frame 194. FIG. 38 is a side view of the second or right frame 194 of the housing shown with the needle and catheter tube and without the first or left frame 193. The two views of FIGS. 37 and 38 will now be discussed to explain the mechanical engagement between the two at the distal end and how they separate when pushed in a distal direction by a catheter hub to open the distal gate opening. As shown, each of the two nose portions 184*a* represents a hollow partial cylinder that when combined form a generally cylindrical cylinder of the nose section or nose end 184 of the housing 102.

A front base wall 510 is provided proximally and inside the boundary defined by the hollow partial cylinder of each nose portion 184*a*. Each front base wall 510 has a cut-out 512 that is sized and shaped to accommodate part of the needle 112 and the catheter tube 110. When the first and second frames 193, 194 are joined, the two cut-outs 512 from the two front base walls 510 form a perimeter defining an opening sized and shaped to receive the circumference of the combination catheter tube with the needle of the catheter assembly located within the housing 102. In an example, the perimeter of the two cut-outs 512 may be referred to as a guide opening that guides the combination needle and catheter tube as the combination advances in the distal direction during cannulation and vascular access. The two base walls 510 can have varying thicknesses, measured along the length of the first frame and/or second frame. A male detent can project from a side part of the base wall 510 that is thicker. In other examples, the base wall 510 can have a uniform thickness.

A male detent 520, which can instead be a stub or stud having an elongated body with a rounded end, is provided on each of the first and second frames 193, 194. As shown in FIG. 37, the male detent 520 of the first frame 193 is located above, elevation-wise, the needle 112 and/or the catheter tube 110 and extends generally orthogonally to the axis defined by the needle. The male detent 520 of the second frame 194, as shown in FIG. 38, is located below, elevation-wise, the needle 112 and extends generally orthogonally to the axis defined by the needle. The arrangement of the two male detents 520 on the two frames 193, 194 can reverse. In an example, the two male detents project radially relative to the lengthwise axis of the needle a sufficient amount such that the tip of each male detent extends beyond the half-way mark of the needle diameter and preferably beyond an edge of the needle on the opposite side from which the male detent extends. In other examples, the male detents 520 can extend a shorter length or distance from the respective side from which the male detents extend. The length of the male detents 520 can be selected to vary the amount of engagement with corresponding receiving slots, as further discussed below.

A receiving slot 524 is provided with the first frame 193 below the male detent 520. Similarly, a receiving slot 524 is provided with the second frame 194 above the male detent 520. Again, the arrangement can reverse. Each receiving slot 524 comprises wall structures configured to frictionally engage a corresponding male detent 520 located on the opposing frame. Thus, the receiving slot 524 on the first frame is configured to frictionally engage the male detent on the second frame and the receiving slot 524 on the second frame is configured to frictionally engage the male detent on the first frame. In an example, the receiving slot has a first wall surface 524*a* and a second wall surface 524*b* configured to frictionally engagement two surface sections of a male detent to be mated therewith. In an example, the first wall surface 524*a* and the second wall surface 524*b* are arranged generally orthogonally to one another. Preferably, each receiving slot 524 does not have wall surface opposite the second wall surface 524*b*, which then provides clearance, or a missing wall, for the male detent 520 to separate from the receiving slot 524 when the catheter hub body 130, such as the nose end of the catheter hub, abuts and pushes against the two base walls 510 in the distal direction. When so pushed, the two gates 339 of the gate assembly 600 rotate about the two living hinges 346 (FIG. 36) to open the distal gate opening to then allow the catheter hub 130 to separate from the housing 102, as previously discussed. In an embodiment, each receiving slot 524 further includes a wall surface opposite the respective first wall surface 524 so that each receiving slot 524 has a three-sided wall structure. Each receiving slot 524 and the rigidity of the end cap component 340 can be sized to grip the corresponding male detent 520 in a slight interference fit.

The user can use the ExD catheter assembly 100 of FIG. 32 to puncture a targeted vein with guidance from a visualization device, such as an ultrasound monitor using an ultrasound probe, after removing the protective cap 500. Primary blood flashback can be observed flowing into the needle hub 122. Next, the angle of insertion of the ExD catheter assembly 100 is lowered prior to further advancing the ExD catheter assembly 100 to locate the catheter tube deep into the vein. In some examples, a guidewire dispenser having a guidewire extending through the lumen of the needle may be used with the ExD catheter assembly. For example, a SonoStik® guidewire dispenser having a housing may be placed into the proximal opening of the catheter hub after removal of the vent plug 124 and the guidewire projecting through the lumen of the needle and advanced in a manner known in the industry. The guidewire may be used to guide the catheter tube to a desired treatment location within the body.

The needle 112 and catheter tube 110 (FIG. 33) are advanced over the guidewire and stopped at or just before the nose end 184 of the housing 102 contacts the skin. If the ExD catheter assembly is used without a guidewire, then the ExD catheter assembly may be advanced without first advancing the guidewire. The practitioner can then place his or her thumb on the tab adapter 404 that is engaged to the catheter hub 130 to advance the catheter hub 130 against the gate assembly 600.

With further reference to the components shown in FIGS. 37 and 38 of the ExD catheter assembly 100 of FIG. 32, when the catheter hub 130 is pushed in the distal direction such that the nose end of the catheter hub 130 pushes against the two gates 339 of the two end components 340, the distally directed force is transferred to the gate assembly 600 and overcomes or exceeds the interference and/or friction forces provided by the engagement between the two male detents 520, or stubs or studs, and the two receiving slots 524. As the catheter hub continues to move in the distal direction, the two gates 339 swing in the distal direction about the living hinges 346 (FIG. 36). The user can continue to move the catheter hub 130 in the distal direction while applying a proximally directed force to or while applying a steady holding force to the housing 102 to move the needle hub 130 completely through the gate opening provided by the two rotated gates 339. The catheter hub 130 and the housing 102 are then free of one another. The user can then finish preparing the catheter hub 130, such as connecting a drip line to the catheter hub and taping it to a patient to secure the puncture site, and optionally removing the tab adapter 404 from the catheter hub 130.

Figure 39:
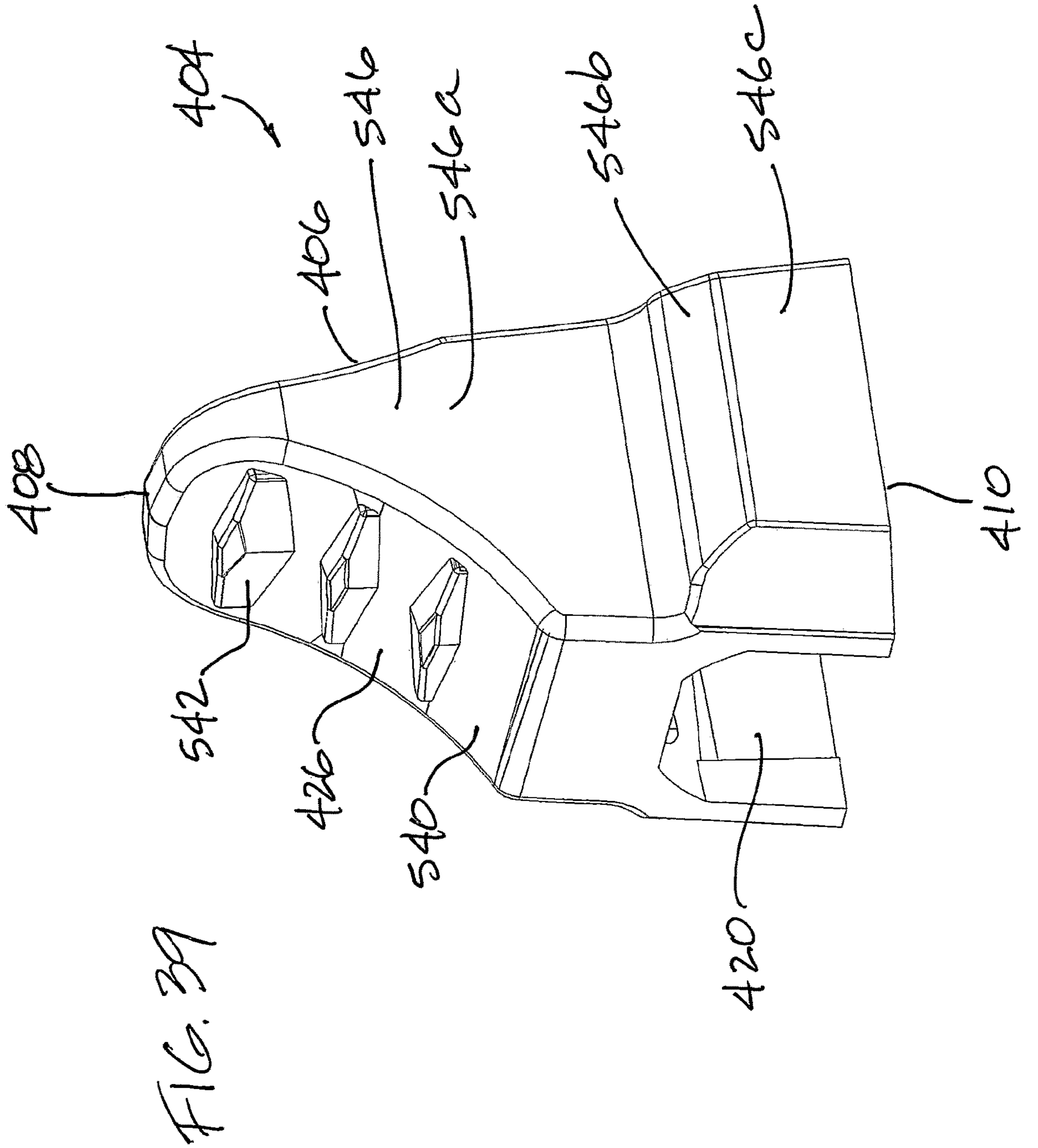
FIGS. 39-42 are different views of a tab adapter for use with a catheter hub to facilitate operation of the ExD catheter assembly in accordance with further aspects of the invention.

With reference now to FIG. 39, a tab adapter 404 in accordance to further aspects of the invention is shown, which is similar to the tab adapter 404 of FIGS. 29-31. The tab adapter 404 of the present embodiment can be formed from a plastic material, such as by plastic injection molding. The tab adapter 404 can comprise a body 406 having a first end 408 and a second end 410. The first end 408 can be located above, elevation-wise, the second end 410. In an example, the body 406 can be formed as a solid structure with a slot to accommodate a push tab extending from the catheter hub and with a hollow tunnel for mounting over the catheter hub body, as further discussed below.

The body 406 can have an exterior surface 426 and an interior surface 428 (FIG. 42), a first opening or distal opening 420 and a second opening 422 (FIG. 41) on the side of the body opposite the first opening. A channel 414 is provided between the two openings 420, 422. The wall thickness between the exterior surface 426 and the interior surface 428 has a sufficient thickness to provide structural rigidity for carrying a digital load applied by a user to advance the catheter hub 130.

The body 406 has a distally facing exterior surface 540 comprising one or more projections or surface features 542 for aesthetic appeal. The distally facing exterior surface can be curved or arcuate. The projections or surface features can optionally be omitted. In other examples, the projections can embody other shapes, such as dimples, round bumps, shaped projections, random projections, etc. The distally facing exterior surface 540 is located between two side surfaces 546. In an example, each of the two side surfaces 546 has a flat or planar wall without varying surface features. In an embodiment, each side surface 546 has a first surface portion 546*a*, a tapered side surface portion 546*b*, and a second surface portion 546*c*. Like the first surface portion, the second surface portion 546*c* has a flat or planar wall. The two second surface portions 546*c* on the two side surfaces 546 define a width that is larger than the width defined by the two first surface portions 546*a*. Thus, the width at the first end 408 of the tab adapter 404 is wider than the width at the second end 410 of the tab adapter.

Figure 40:
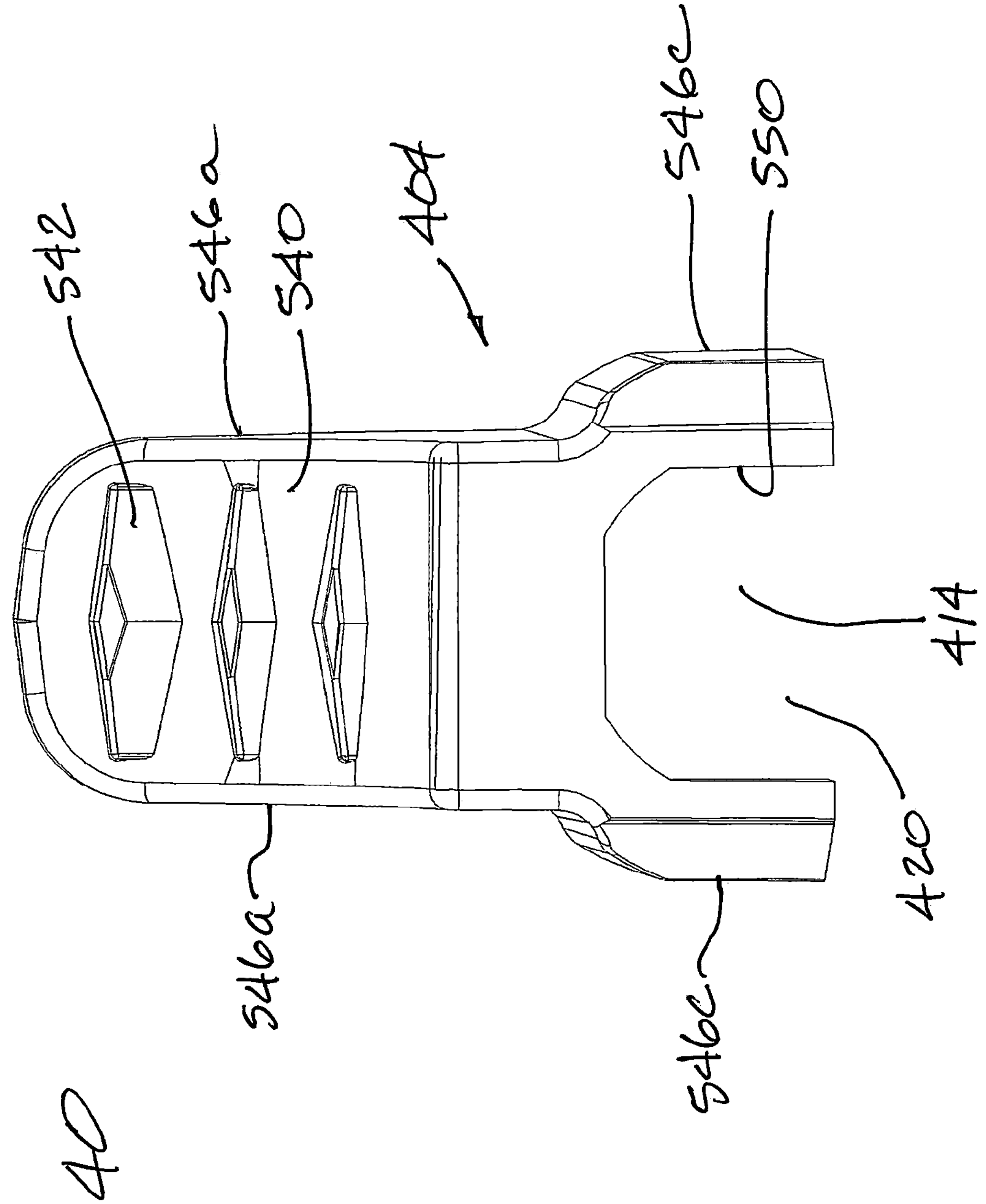

FIG. 40 is a front view of the tab adapter 404, looking at the first or distal opening 420 and the distally facing exterior surface 540. As shown, the distal opening 420 can have a perimeter 550 defined by a plurality of edge sections or segments. The shape of the perimeter 550 can vary depending on the shape of the catheter hub 130 that the tab adapter is configured to mount to. For example, the shape of the perimeter 550 can have only four side edge sections or can be semi-circular or part circle.

Figure 41:
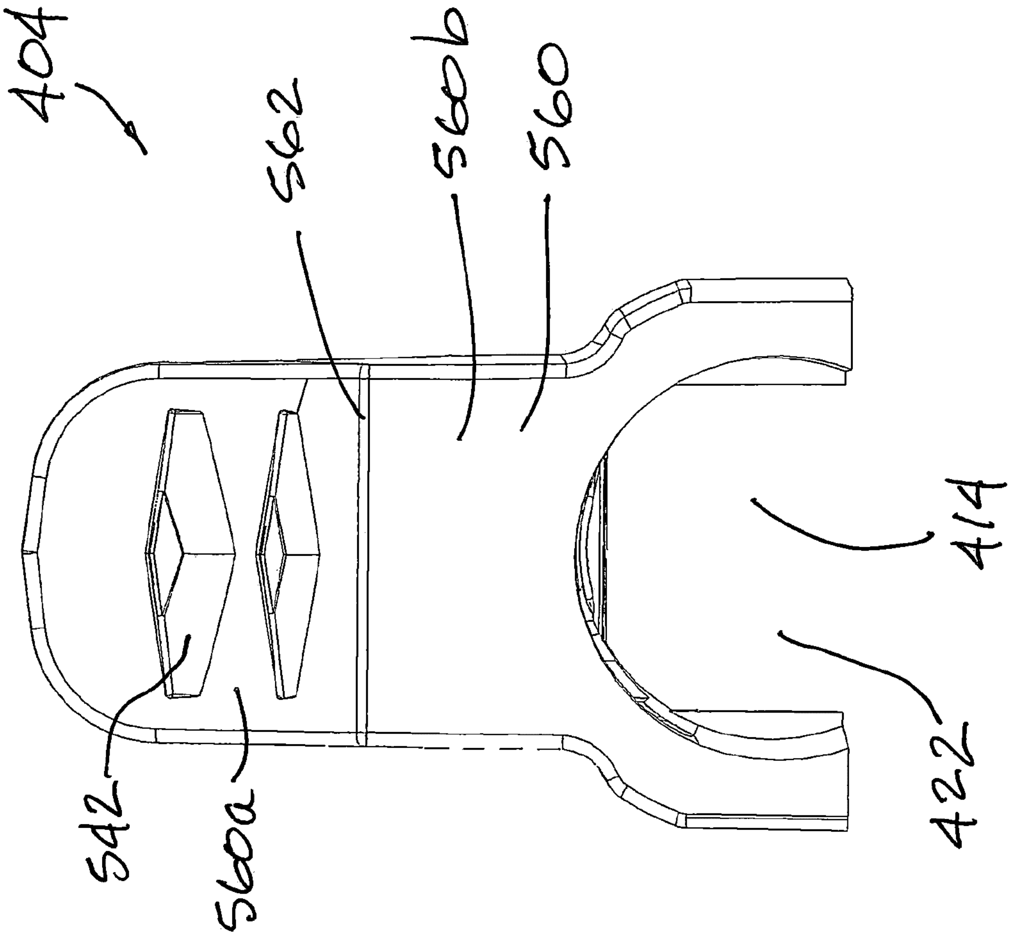

FIG. 41 is a rear view of the tab adapter 404, looking at the proximally facing exterior wall surface 560. In an example, the proximally facing surface 560 has a first surface section 560*a* and a second surface section 560*b*. The first surface section 560*a* can be generally planar but is slanted from the planar surface of the second surface section 560*b* at an inflection line or transition line 562. The first surface section 560*a* can incorporate one or more surface features or projections 542.

As shown, the proximal or second opening 422 can have a perimeter 550 defined by a semi-circular or part circle edge. The shape of the perimeter 550 can vary depending on the shape of the catheter hub 130 that the tab adapter is configured to mount to. For example, the shape of the perimeter 550 can be defined by a plurality of edge segments or sections and can vary depending on the shape of the of the catheter hub 130 that the tab adapter is configured to mount to. The first and the second openings 420, 422 should extend more than the half or median line of the catheter hub body to ensure gripping to more than half of the diameter of the catheter hub body.

Figure 42:
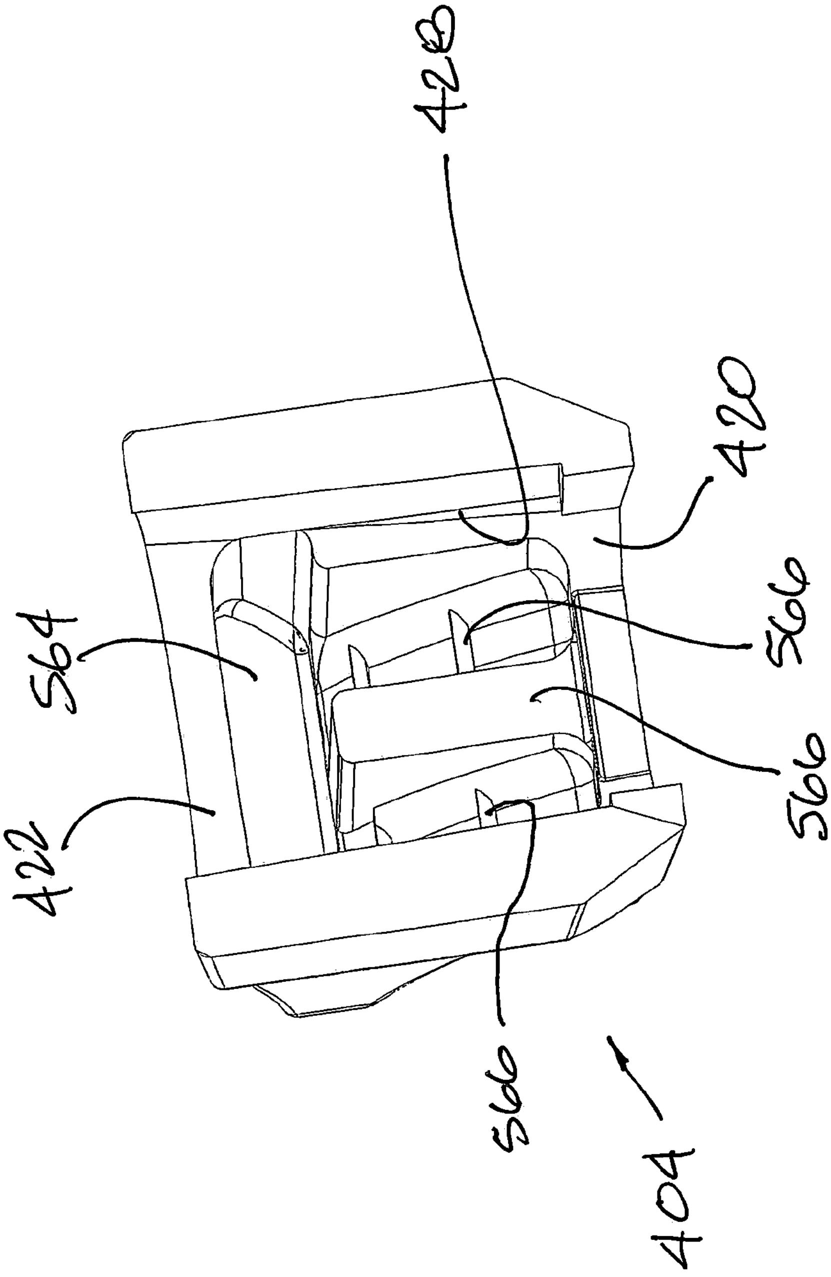

FIG. 42 is a bottom view of the tab adaptor 404, showing the interior surface 428 and the interior cavity 564 defined by the interior surface 428. A plurality of ribs 566 can be incorporated in the interior cavity to provide rigidity.

Figure 43:
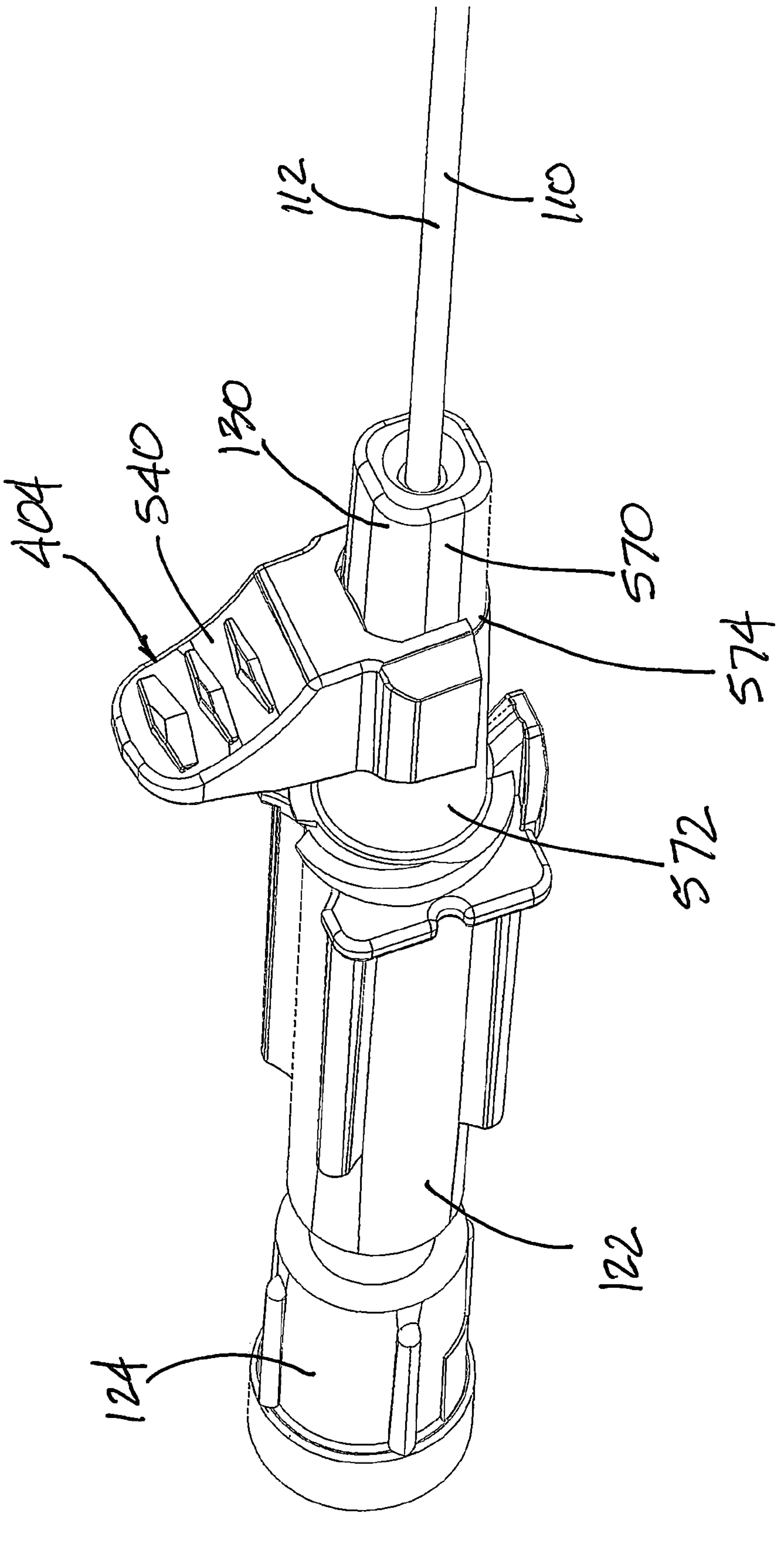
FIG. 43 is a perspective view of the ExD catheter assembly of FIG. 32 shown with the tab adapter of FIGS. 39-42 mounted to a catheter hub.

FIG. 43 is a front perspective view of the tab adaptor 404 mounted onto the catheter hub 130 of the catheter assembly 108, which is also shown with a needle hub 122, a vent plug 123, and a catheter tube 110 and needle 112 extending out the distal end of the catheter hub. As shown, the catheter hub 130 has a nose section 570 at a distal end and a proximal body section 572. The nose section 570 has a generally square shape with rounded corners connecting the four sides. In other examples, the nose section 570 can have other cross-sectional shapes, including generally cylindrical, oval, elliptical, polygonal, etc. The proximal body section 572 is generally round and can be relatively larger in girth or outer contour than the nose section 570. Thus, a step up or a stepped section 574 can be provided between the nose section 270 and the proximal body section 572. The openings on the tab adapter can be sized and shaped accordingly to fit with the contour of the catheter hub body.

In the present embodiment, the tab adapter 404 is sized and shaped for mounting over the catheter hub 130. In an example, the tab adapter 404 is configured to seat over the catheter hub 130 and the hub body situated in the channel 414 of the body 406. The first opening 420 and the second opening 422 of the tab adapter 404 are sized to fit snugly around the curved body of the catheter hub 130. Depending on how the tab adapter 404 is situated over the catheter hub 130, such as by placement or location along the axial position of the catheter hub, the first and second openings 420, 422 of the tab adapter 404 can have the same size or different sizes to fit the particular contour of the catheter hub. In an example, as shown in FIGS. 40 and 41, the first opening 420 can have a shape that fits snuggly around the generally square cross-section of the nose section 570 and the second opening 422 can have a semi-spherical shape, semi-oval or elliptical shape, or an arcuate shape to fit around the proximal body section 572. Preferably, the two openings 420, 422 are sized and shaped to fit snuggly over the catheter hub body and has a gripping force around the hub body.

When mounted over the catheter hub 130, the push tab 176 of the catheter hub is configured to fit within the interior space 429 of the body 406. The push tab 176 of the catheter hub 130 can contact the interior surface 428 on the proximal side of the body 406 or can project into a female detent, recess, or socket within the interior for increased securement between the tab adapter and the catheter hub. Thus, when the tab adapter 404 is pushed in the distal direction by a practitioner, the interior surface 428 of the tab adapter 404, or a recess or female detent within the adapter, pushes against the proximally facing surface of the push tab 176 to advance the push tab 176, and hence the catheter hub 130, in the distal direction. In other examples, the gripping provided by the openings 420, 422 against the catheter hub body can also transfer the distally directed force to the catheter hub to advance the catheter hub when the tab adapter is pushed.

Figure 44:
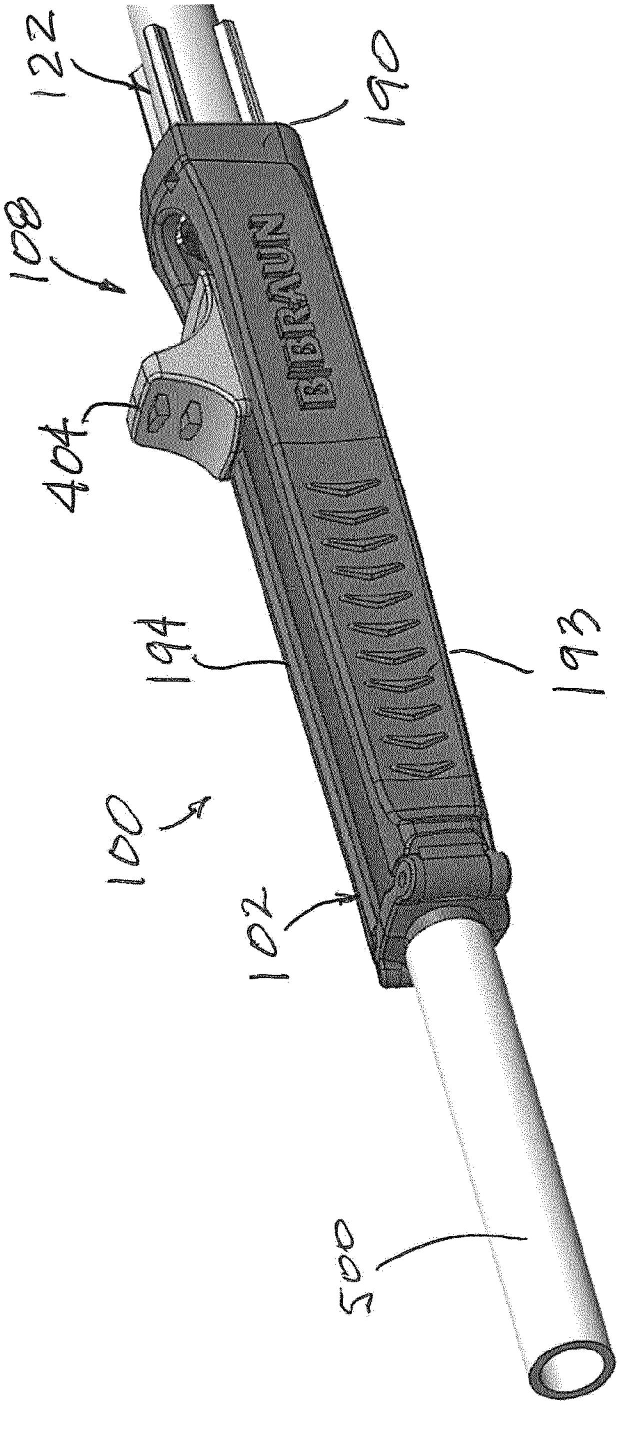
FIG. 44 is a perspective view of an extended dwell catheter assembly in accordance with further aspects of the invention.

With reference now to FIG. 44, an extended dwell catheter assembly 100 provided in accordance with still further aspects of the present invention is shown. The present ExD catheter assembly 100 shares similar aspects with the catheter assembly of FIGS. 1-14, FIGS. 15-28 and FIGS. 32-43. As shown, the present ExD catheter assembly 100 comprises a housing 102 with a first frame or left frame 193 and a second or right frame 194 attached to form the housing 102. The assembly further comprises a catheter assembly 108, which can be similar to other catheter assemblies described herein. The catheter assembly 108 is shown located at least partially within the housing 102. The catheter assembly comprises a catheter hub, a needle hub 122, and a protective cap 500 covering a needle with a needle tip. The first and second frames can separate to release the catheter hub of the catheter assembly 108 from the housing. The first and second frames 193, 194 can attach to one another along a seam by corresponding tabs or male detents and engagement slots, as previously described, and whereby the engagements can separate. Optionally, the first and second frames 193, 194 can attach to one another along upper and lower seams via adhesive or welding, in addition to the tabs and detents or as an alternative. Where the two housing frames 193, 194 do not separate, the housing 102 can be provided with a gate assembly to permit separation of the catheter hub from the housing 102 following cannulation and vascular access, as further discussed below. However, the housing still has an upper seam and a lower seam to separate the housing into a left housing frame and a right housing frame, as opposed to a horizontal frame that separates the housing into an upper frame and a lower frame.

Like the embodiment of FIGS. 32-43, a tab adapter or tab extender 404 can be positioned over the catheter hub 130 and secured thereto by fitment. The needle hub 122 is shown extending proximally of the base end 190 having a vent plug attached thereto (FIG. 32). When using the ExD catheter assembly 100, the protective cap 500 is first removed to expose the needle.

Figure 45B:
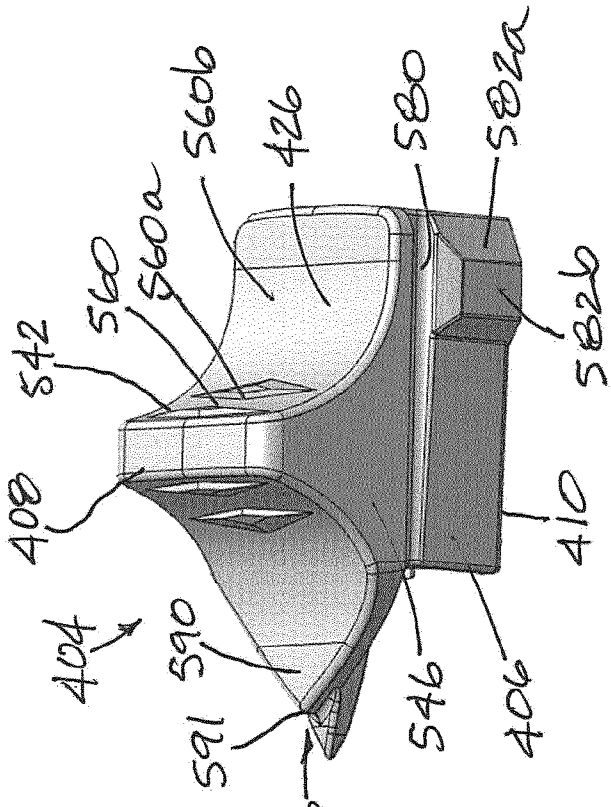
FIGS. 45A-45C show different views of a tab adapter.
Figure 45A:
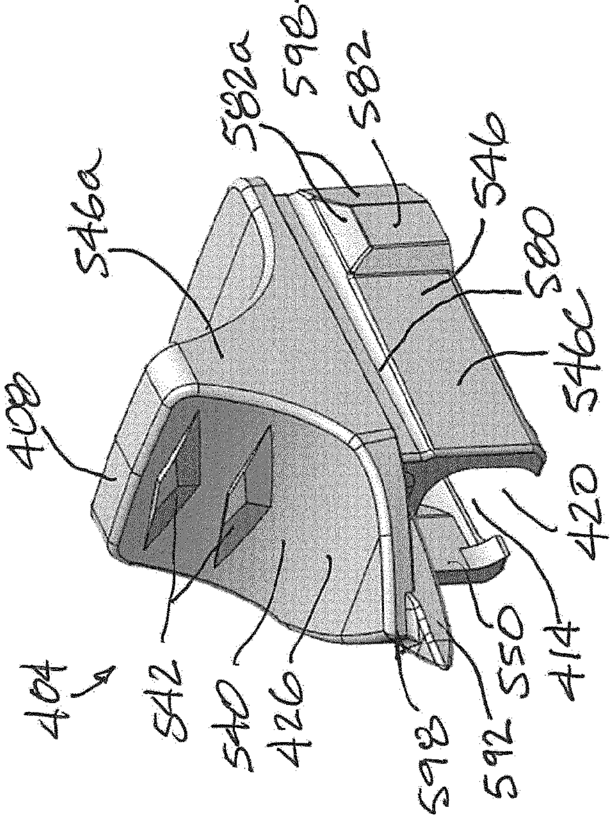
Figure 45C:
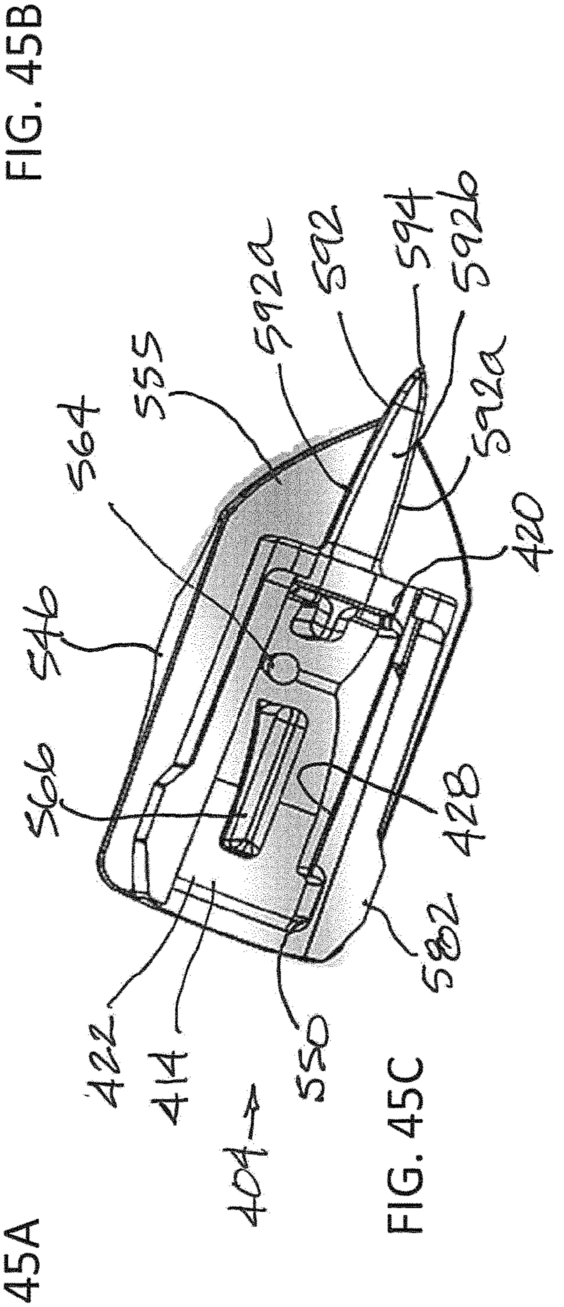

With reference now to FIG. 45A-45C, top perspective views and a bottom view of a tab adapter 404 in accordance with further aspects of the invention are shown. The present tab adapter 404 shares many similarities with the tab adapter 404 of FIGS. 39-43 with some differences. The tab adapter 404 of the present embodiment can be formed from a plastic material, such as by plastic injection molding. The tab adapter 404 can comprise a body 406 having a first end 408 and a second end 410. The first end 408 can be located above, elevation-wise, the second end 410. In an example, the body 406 can be formed as a solid structure with a slot to accommodate a push tab extending from the catheter hub and with a hollow tunnel for mounting over the catheter hub body, as further discussed below.

The body 406 of the adapter can have an exterior surface 426 and an interior surface 428 (FIG. 45C), a first opening or distal opening 420 and a second opening 422 (FIG. 45C) on the end of the body opposite the first opening 420. A channel 414 is provided between the two openings 420, 422. The wall thickness between the exterior surface 426 and the interior surface 428 has a sufficient thickness to provide structural rigidity for carrying a digital load applied by a user to advance the catheter hub 130.

The body 406 has a distally facing exterior surface 540 comprising one or more projections or surface features 542 for aesthetic appeal. The distally facing exterior surface 540 can be arcuate or curved. The projections or surface features 542 can optionally be omitted. In other examples, the projections can embody other shapes, such as dimples, round bumps, shaped projections, random projections, etc. The distally facing exterior surface 540 is located between two side surfaces 546. In an example, each of the two side surfaces 546 can have a flat or planar wall without varying surface features. As shown, a recessed groove or race 580 is located between a first surface portion 546*a* and a second surface portion 546*c* on each of the two side surfaces 546 of the tab adapter 404. The two second surface portions 546*c* of the two side surfaces can be generally planar and parallel to one another, thereby defining a generally constant outside dimension at least along portions of the two side surfaces. The two first surface portions 546*a* can also be generally parallel to one another. As shown, however, the two first surface portions 546*a* of the two side surfaces 546 taper inwardly in the direction from the second end 410 towards the first end 408.

A projection 582 can be incorporated on at least one of the two side surfaces 546 of the tab adapter 404 and extending radially of the lengthwise axis of the tab adapter 404. The projection 582 can include ramped surfaces 582*a* and a planar end surface 582*b* that intersect with the ramped surfaces. In other examples, the projection can be formed from straight sides and a planar end surface of a semi-spherical dome, or a non-spherical dome. In use, the projection 582 can be arranged to abut or contact the gate assembly 600 (FIG. 46) at the distal end of the housing to open the gate wider and allow separation between the housing and the catheter hub, as discussed above with reference to FIGS. 32-43 and further discussed below. In an example, a projection 582 is provided on each of the two side surfaces 546 of the tab adapter 404 so that the gate assembly can be abutted by both projections 582.

The distal opening 420 of the adapter can have a perimeter 550 defined by a plurality of edge sections or segments. The shape of the perimeter 550 can vary depending on the shape of the catheter hub 130 that the tab adapter 404 is configured to mount to or mount on. For example, the shape of the perimeter 550 can have only four side edge sections or can be semi-circular or part circle or any corresponding shape of the catheter hub outer contour. However, the shape of the perimeter 550 does not have to precisely conform to the contour of the catheter hub in order for the tab adapter 404 to be used with the catheter hub and secured thereto by fitment.

In an example, the proximally facing surface 560 has a first surface section 560*a* and a second surface section 560*b*. The first surface section 560*a* can be generally curved, arcuate, or slanted, such as a ramp having a wall that is mostly vertical or extending upwardly. The second surface section 560*b* can be curved or arcuate and mostly horizontal or flat. The first surface section 560*a* and the second surface section 560*b* connect or joined to one another and together resemble a jump or a ramp, similar to the arcuate exterior surface of the distally facing surface. The first surface section 560*a* of the proximally facing surface 560 can incorporate one or more surface features or projections 542.

In an example, the proximal or second opening 422 can have a perimeter 550 defined by a semi-circular or part circle edge. The shape of the perimeter 550 of the second opening 422 can vary depending on the shape of the catheter hub 130 that the tab adapter is configured to mount to. For example, the shape of the perimeter 550 can be defined by a plurality of edge segments or sections and can vary depending on the shape of the of the catheter hub 130 that the tab adapter 404 is configured to mount to. However, the shape of the perimeter 550 of the second opening 422 does not have to precisely conform to the contour of the catheter hub in order for the tab adapter 404 to be used with the catheter hub. The perimeters of the first and second openings 420, 422 can be the same or can differ from one another. The first and the second openings 420, 422 should extend more than the half or median line of the catheter hub body to ensure gripping to more than half of the diameter of the catheter hub body.

FIG. 45C is a bottom view of the tab adaptor 404, showing the interior surface 428 and the interior cavity 564 defined by the interior surface 428. A plurality of ribs 566 can be incorporated in the interior cavity to provide rigidity.

In an embodiment, the distally facing exterior surface 540 is provided with a narrowed tip 590 having a tip end 591 that resembles a spear or arrow. Thus, the distally facing surface 540 and the two side surfaces 546 can converge to define an acute tip that is somewhat pointed but that flares out to resemble a wide arrow. Just below, elevation-wise, the tip 590 of the distally facing exterior surface 540, an extension 592 is provided. In an example, the extension 592 can be molded as an elongated stem or bar formed with the body 406 of the tab adapter 404. The extension 592 can have side edges 592*a* and a bottom edge 592*b* having an elongated shape with a narrowing tip 594. The narrowing tip or tip end 594 of the extension 592 can be located distally of the tip end 591 of the distally facing exterior surface 540. In an alternative embodiment, the extension 592 may be omitted. The extension can be unitarily formed with the tab adapter and can share one of the side edges with the underside surface 555 of the tab adapter 404.

With reference specifically to FIGS. 45A and 45B, an actuating end 598 comprising both the narrowing tip or tip end 594 of the extension 592 and the narrowing tip or tip end 591 of the distally facing surface 540 is provided at the distal end of the tab adapter 404. As further discussed below, the actuating end 598 is configured to separate the two gates of the gate assembly 600 (FIG. 46) located at the distal end 120 of the housing 102 to then provide clearance for the catheter hub, which is attached to the tab adapter 404, to separate from the housing following successful venipuncture.

Figure 46:
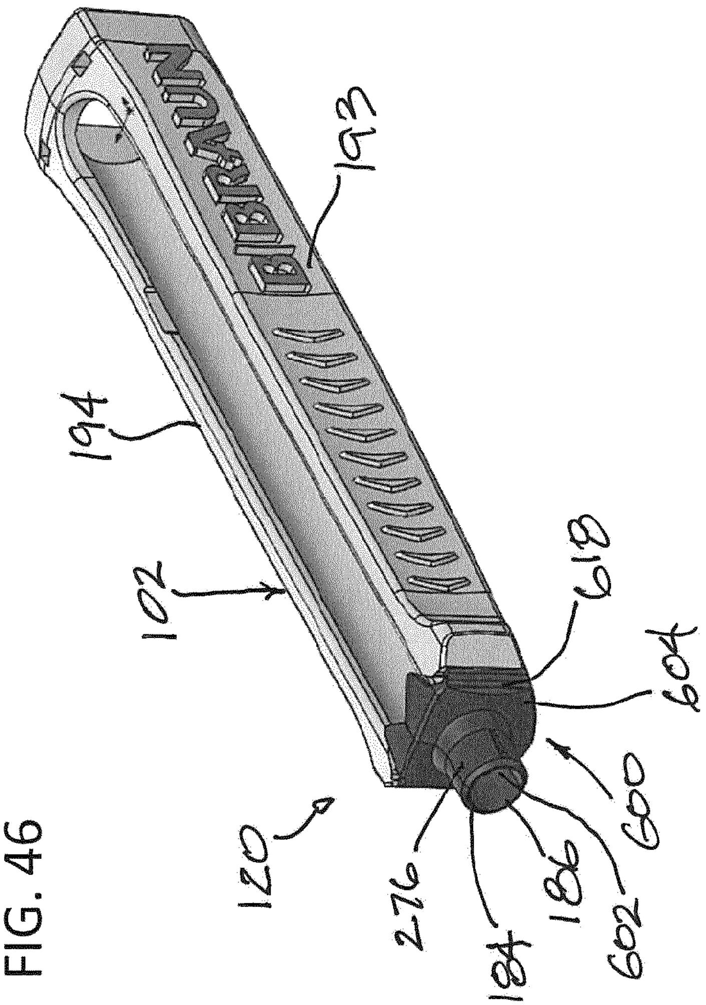
FIG. 46 is a perspective view of a housing with a gate assembly.

FIG. 46 is a front perspective view of the housing 102 of the ExD catheter assembly 100 of FIG. 44, shown without the catheter assembly 108 and the tab adapter 404. The housing 102 is shown with the first or left frame 193 attached to the second or right frame 194, as previously discussed. Also shown attached to the housing 102 is a gate assembly 600, which can attach to the distal end of the housing 102. In an example, the gate assembly 600 comprises a nose end 184 having a tip 186. The nose end 184 is hollow and defines a bore 602. The gate assembly 600 further comprises an upper seam 276 and a lower seam, which allows the gate assembly 600 to separate at the upper and lower seams and swing distally about two pivotable hinges, as further discussed below. The upper seam 276 extends through the upper part of the nose end 184. A similar corresponding lower seam extends through the lower part of the nose end 184.

Figure 47A:
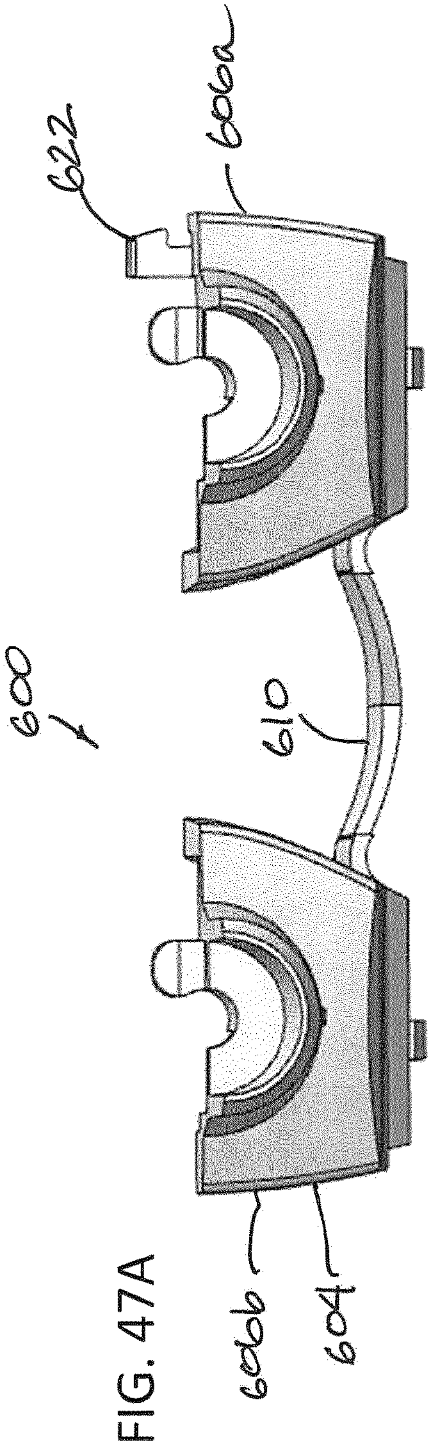
FIGS. 47A and 47B show different views of a gate assembly, in an open state.
Figure 47B:
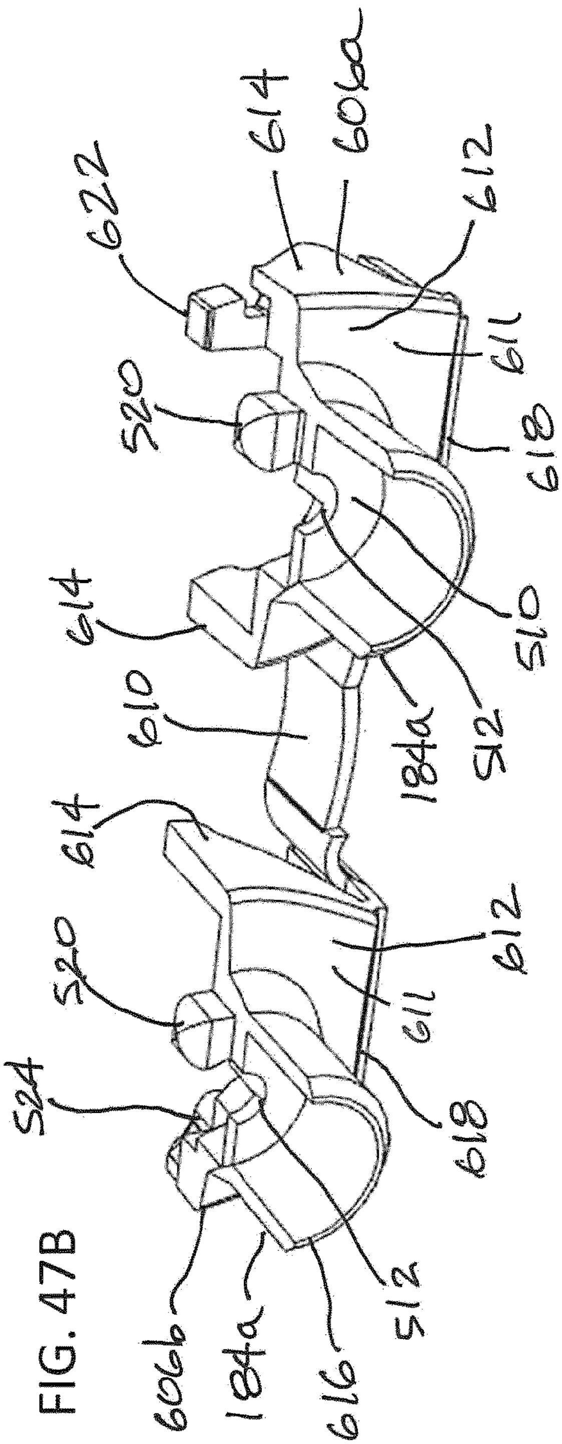

FIGS. 47A and 47B show a pre-assembled front view and a pre-assembled front perspective view of the gate assembly 600 of FIG. 46. As shown, the gate assembly 100 may be clam-shape or clam-shell shape and comprises a body 604 having a first gate 606*a* and a second gate 606*b*, which can be combined to form the assembled gate assembly 600 shown in FIG. 46. In an example, the two gates 606*a*, 606*b* can be formed by molding, such as plastic injection molding, and can include a tie strip 610 for keeping the pair together during manufacturing and assembly. Optionally, the tie strip 610 can be omitted and other tracking and monitoring may be used to associate the corresponding pair of gates.

As shown, both the first and second gates 606*a*, 606*b* have body sections 611 having a barrier wall 612 having wall sections 614 extending proximally thereof and wall sections 646 extending distally thereof. Each gate further comprises a male detent 520, or stem or stud, and a receiving slot 524 for engaging the corresponding receiving slot 524 and male detent 520 of the opposing gate. Each receiving slot 524 can have at least one open or missing side so that the mated male detent 520 can swing out through the missing side, similar to the receiving slot 524 and male detent 520 arrangement of FIGS. 37 and 38. For example, each receiving slot 524 can have three sides and can be sized and shaped to receive the male detent 520 in an interference. Thus, when a load is applied to the gate, such as by the tab adapter of FIGS. 45A-45C, each male detent 520 can slip past the missing wall of the corresponding receiving slot 524 and allow the gate to swing open, as further discussed below. More specifically, the first and second gates 606*a*, 606*b* will swing distally about respective living hinges 618.

Each gate is provided with a front base wall 510 inside the boundary defined by the hollow partial cylinder of each nose portion 184*a* or each distal wall 616. Each front base wall 510 has a cut-out 512 that is sized and shaped to accommodate part of the needle 112 and the catheter tube 110.

When the first and second frames 193, 194 are joined, the two cut-outs 512 from the two front base walls 510 form a perimeter defining an opening 620 (FIG. 48A) sized and shaped to receive the circumference of the combination catheter tube and needle. The opening 620 may be thought of as a guide opening for guiding the catheter tube and needle during advancement of the same during cannulation and vascular access. In an example, the perimeter of the two cut-outs 512 may be referred to as a guide opening that guides the combination needle and catheter tube as the combination advances in the distal direction during cannulation and vascular access. The two base walls 510 can have varying thicknesses, measured along the length of the first frame and/or second frame. A male detent can project from a side part of the base wall 510 that is thicker. In other examples, the base wall 510 can have a uniform thickness.

The male detent 520 is provided on each of the first and second gates 606*a*, 606*b*. As shown, the male detent 520 of each of the first gate 606*a* and the second gate 606*b* are located on the side of the cut-out 512 opposite the receiving slot 524. In an example, the two male detents project radially relative to the lengthwise axis of the needle a sufficient amount such that the tip of each male detent extends beyond the half-way mark of the needle diameter and preferably beyond an edge of the needle on the opposite side from which the male detent extends. In other examples, the male detents can extend a shorter length or distance from the respective side from which the male detents extend. The length of the male detents 520 can be selected to vary the amount of engagement with corresponding receiving slots, as further discussed below.

Each receiving slot 524 of a gate comprises wall structures configured to frictionally engage a corresponding male detent 520 located on the opposing gate. Thus, the receiving slot 524 on the first gate 606*a*, which is located with the first frame or left frame 193, is configured to frictionally engage the male detent on the second gate 606*b*, which is located with the second frame 194, and the receiving slot 524 on the second gate is configured to frictionally engage the male detent on the first gate.

In an example, the receiving slot 524 has a first wall surface and a second wall surface configured to frictionally engage two surface sections of a male detent, similar to that of FIG. 37. In an example, the first wall surface and the second wall surface are arranged generally orthogonally to one another. Preferably, each receiving slot 524 does not have a wall surface opposite the second wall surface, or has a missing wall section so as to define an open slot or channel, which then provides clearance for the male detent to separate from the receiving slot when the tip end 591 of the tab adapter (FIG. 45A) abuts and pushes against the two base walls 510 (FIG. 47B) in the distal direction. When so pushed, the two gates 606*a*, 606*b* rotate about the two living hinges 618 (FIGS. 48B and 48C) to open the gates to then allow the catheter hub to separate from the housing 102 (FIG. 46), as previously discussed. In an embodiment, each receiving slot 524 further includes a wall surface opposite the respective first wall surface so that each receiving slot has a three-sided wall structure. Each receiving slot 524 can be sized to grip the corresponding male detent 520 in a slight interference fit.

Figure 48B:
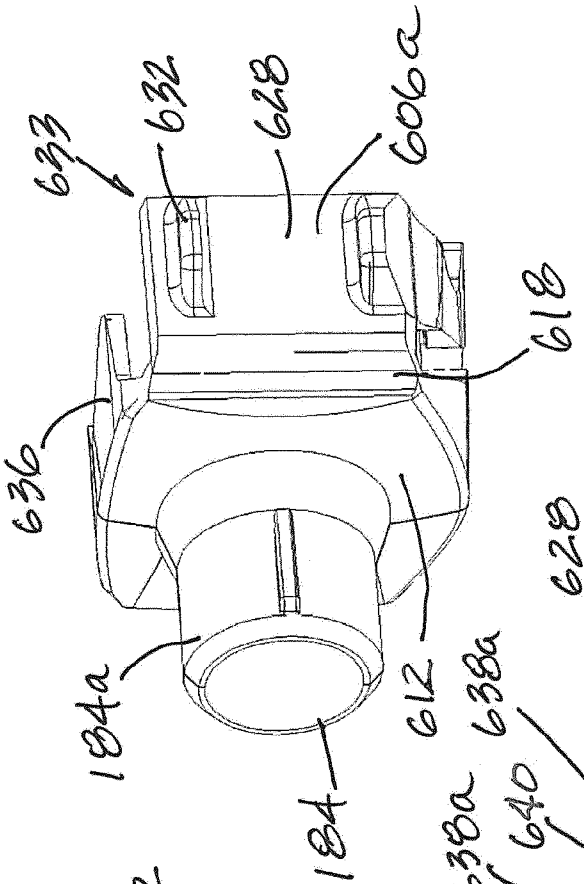
FIGS. 48A-48C show different views of the gate assembly in an assembled state.
Figure 48A:
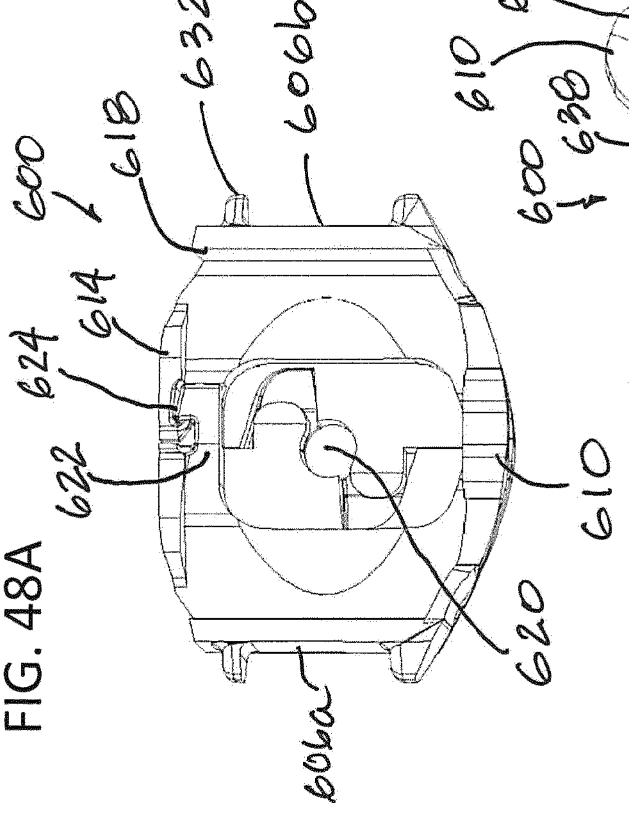
Figure 48C:
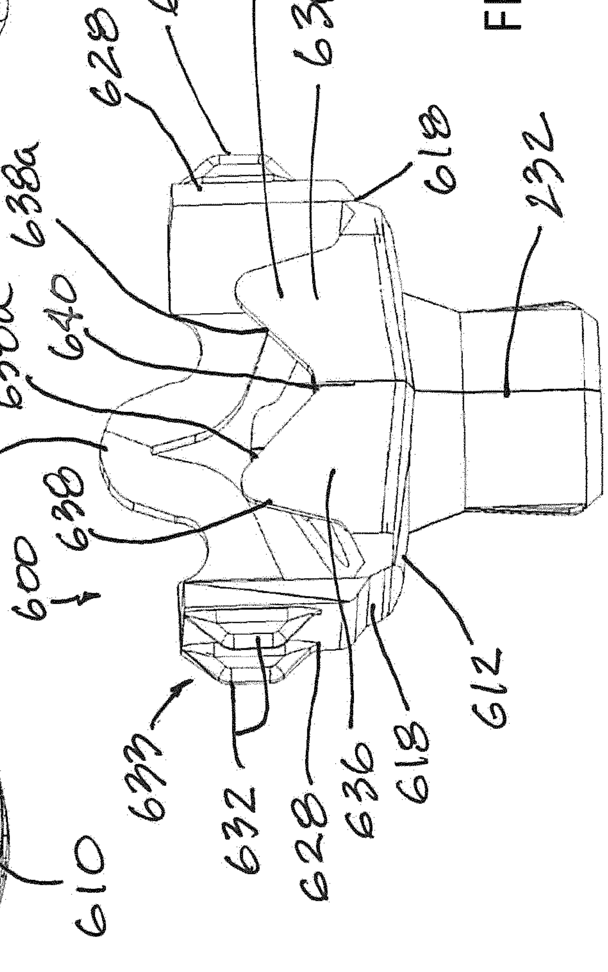

FIG. 48A shows a rear view of the gate assembly 600, FIG. 48B shows a front to side perspective view of the gate assembly, and FIG. 48C shows a top view of the gate assembly when the first and second gates 606*a*, 606*b* (FIGS. 47A and 47B) are assembled or joined to form a gate assembly 600. The assembling of the two gates is facilitated by a hook arm 622 located on the first gate 606*a* hooking or latching to a corresponding female detent 624 on the second gate housing 606*b*. In other examples, the location of the hook arm 622 and the female detent 624 can reverse. Thus, in addition to the friction forces provided by the combination male detents 520 and receiving slots 524 discussed immediately above, the clam-shell structure of the gate assembly 600 can be held together via the hook arm 622 and the female detent 624. In some examples, the hook arm and female detent can be omitted and the interference between the pair of male detents 520 and receiving slots 524 can increase to provide the required engagement to retain the first and second gates 606*a*, 606*b* together, similar to that of FIGS. 37 and 38. In still other examples, positive engagement means, such as barbs, may be incorporated with the pair of male detents 520 and receiving slots 524 to provide added engagement forces.

The combination hook arm 622 and female detent 624 provide holding forces in the radial direction relative to the axis passing through the bore of the nose end. However, upon being abutted and pushed in the distal direction by the actuating end 598 of the tab adapter 404, such as by the tip end 594 of the extension 592 on the tab adapter 404 (FIGS. 45A-45C), such as when the tab adapter 404 moves in the distal direction to advance the catheter tube into the vein of a patient as discussed above, the hook arm 622 deforms and separates from the female detent 624. At about the same time that the hook arm 622 deflects to separate from the female detent 624, the male detents 520 on the two gates 606*a*, 606*b* separate from the corresponding receiving slots 524.

Two of the proximal wall sections 614 that extend proximally of the barrier wall 612 can be referred to as gate sidewalls 628. In an example, the two gate sidewalls 628 are pivotably connected to the corresponding barrier walls 612 of the first and second gates 606*a*, 606*b*. In one example, each pivotable connection is a living hinge 618, which is understood to mean a unitarily formed thin section or thin plastic strip formed during molding to join two adjacent sections, such as to join the gate sidewall 628 and the barrier wall 612. Each gate sidewall 628 can be provided with a flange 632, with more than one flange contemplated, such as two or three spaced apart flanges 632. Each set of two flanges 632, or at least one flange, and gate sidewall 628 define a key 633 for fitting into a slot 644 at the distal end of the housing 102 to retain the gate assembly 600 to the housing, as further discussed below.

With reference to FIG. 48C, the first and second gates 606*a*, 606*b* have a seam 232 passing therebetween. When the two gates are pushed in the distal direction to separate, the separation occurs at the seam 232. The seam 232 extends between two adjacent proximal wall sections 614. The wall sections 614 may be referred to as deflection walls 636. As shown, each deflection wall 636 has a proximal edge 638. The proximal edge 638 can have different edge sections. The different edge sections of the proximal edge 638 can have straight edges or curved edges. As shown, two relatively straight edges are joined by an elbow, radius, or angle, can be an acute or an obtuse angle. Two adjacent straight edge sections 638*a* of the two deflection walls 636 converge at the seam 232. As shown, two adjacent edge sections 638*a* at the seam 232, or bisected by the seam, define an abutting edge 640. The abutting edge 640 is configured to be abutted or pushed by the actuating end 598 of the tab adapter 404, such as by the tip end 591 of the distally facing exterior wall surface 540, when the tab adapter 404 is advanced in the distal direction during use of the ExD catheter assembly 100.

An extended dwell catheter assembly 100 in accordance with aspects of the invention is understood to include a tab adapter 404 having an actuating end 598, such as a narrowed tip or a tip end, for pushing against an abutting edge 640 or against a combination hook arm 622 and female detent 624 of a gate assembly. In an example, the tab adapter 404 has both a tip 590 with a tip end 591 located on a distally facing exterior surface 540 and a tip end 594 located on an extension 592, which is located below, elevation-wise, the exterior surface 426 of the distally facing exterior surface 540. The two tip ends 591, 594 can be part of an actuation end 598 of the tab adapter 404. In some examples, the tip end 591 of the distally facing exterior surface 540 is located proximally of the tip end 594 of the extension so that the two tip ends 591, 594 contact two different surfaces along two different planes. In an example, the tip end 594 of the extension is configured to abut a surface that is located distally of a surface to be abutted by the tip end 591 of the distally facing exterior surface 540.

Figure 49:
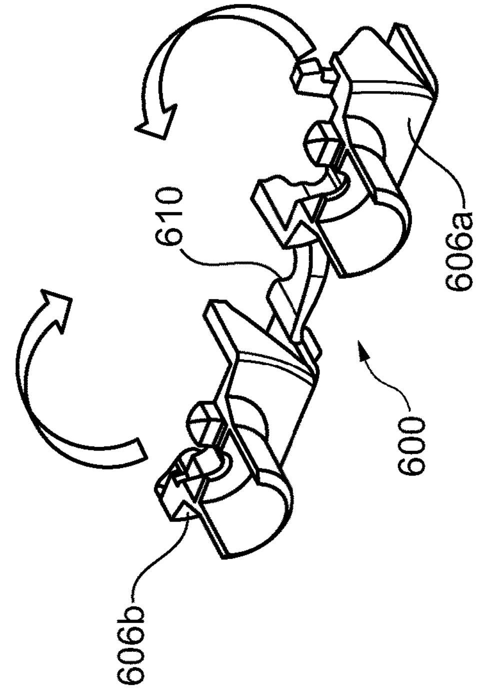
FIG. 49 shows the direction of movement to assemble the gate assembly.

FIG. 49 shows the gate assembly 600 in the open state with arrows showing directions of movement of the first and second gates 606*a*, 606*b* to close the clam-shell gate member into the engaged state shown in FIGS. 48A-48C. As previously discussed, movement of the two gates as shown will cause the hook arm 622 to engage the female detent 624 (FIG. 48A) and the two male detents 520 to engage the two receiving slots 524 (FIG. 47B). The two engaged housing sections can engage without added adhesive glue or bonding.

Figure 50:
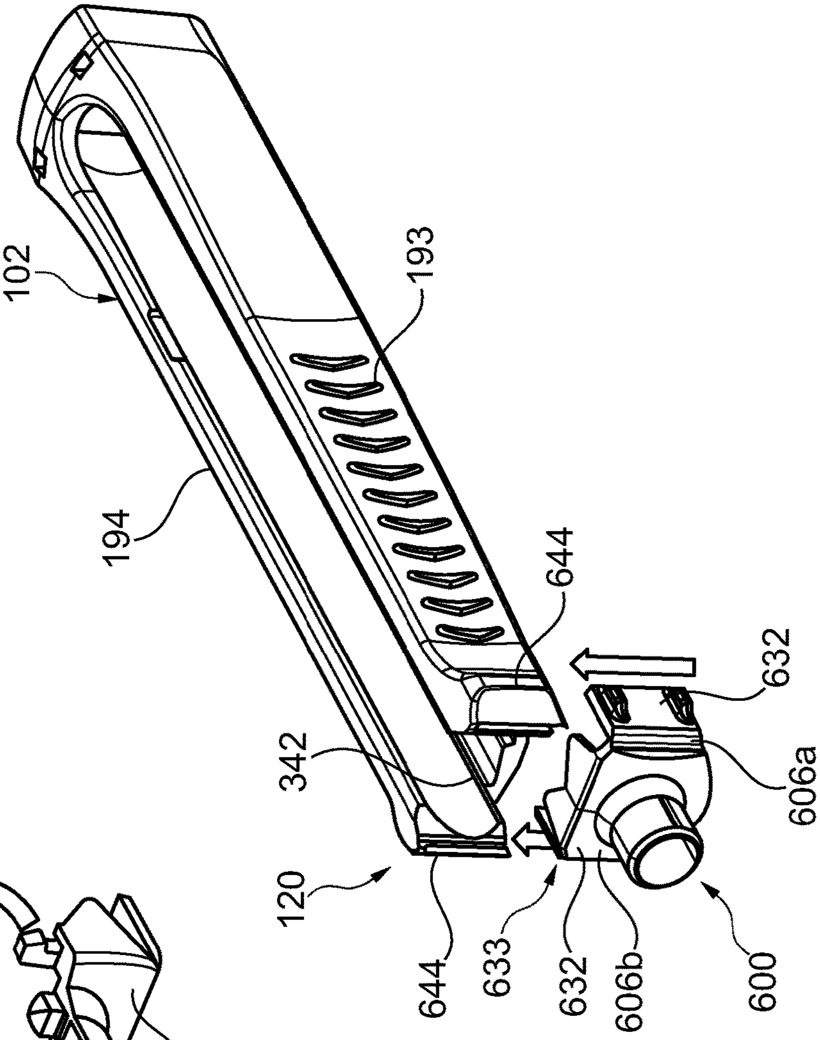
FIG. 50 shows the direction of movement to mount the assembled gate assembly to a housing.
Figure 51:
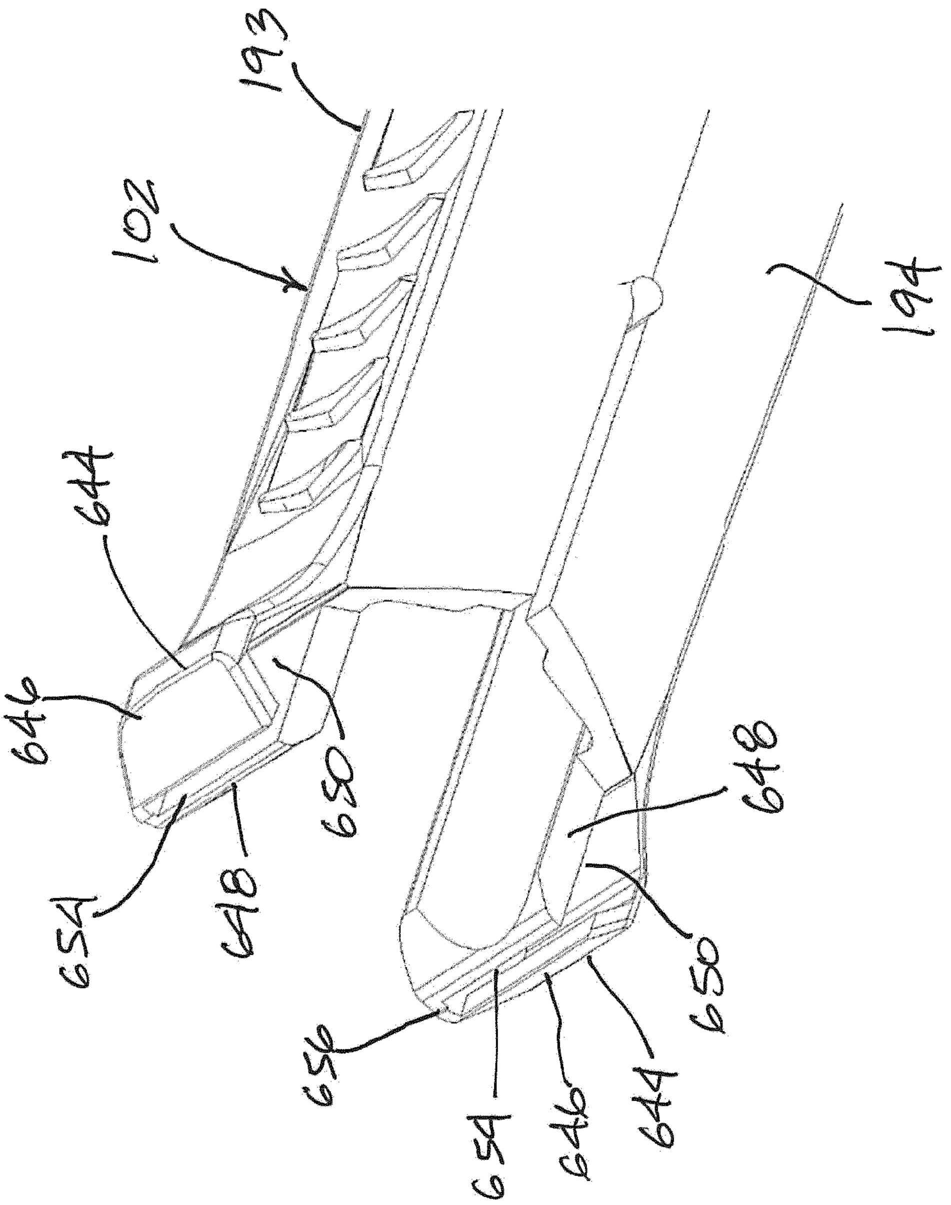
FIG. 51 is a partial bottom perspective view showing the open distal end of the housing.

FIG. 50 shows an assembled gate assembly 600 moving towards the distal end 120 of the housing 102 to secure to the housing. In an example, the housing 102 is provided with two receiving slots 644 at the distal end 120 adjacent the distal opening 342, one on the first or left frame 193 and one on the second or right frame 194. With further reference to FIG. 51, the two receiving slots 644 are shown at the distal end. In an example, each receiving slot 644 is formed by a first wall slab 646 and a second wall slab 648. The first and second wall slabs 646, 648 of each receiving slot define a hollow space 650 therebetween for receiving a key.

As discussed above with reference to FIG. 48C, the gate assembly 600 has a key 633 formed with each of the two gates 606*a*, 606*b*. In particular, each gate comprises a gate sidewall 628 having one or more flanges 632. The combination gate sidewall 628 and the one or more flanges 632 define a profile or contour that is sized and shaped to fit within the hollow space 650 of the receiving slot 644, called a key 633. Thus, as shown in FIG. 50 and with further reference to FIG. 51, when the gate assembly 600 is assembled to the housing 102, the two keys 633 on the first and second gates 606*a*, 606*b* slide into the two receiving slots 644 and are held thereto by frictional and mechanical engagements. Once assembled as shown in FIG. 46, the gate assembly 600 is secured to the distal end 120 of the housing 102 with the two gates 606*a*, 606*b* being pivotable about respective living hinges 618 to swing open, such as to allow a catheter hub assembled to the housing to separate from the housing.

With reference again to FIG. 51, a gap 654 is provided between the first wall slab 646 and the second wall slab 648. The gap 654 is provided to accommodate the wall structure of the gate sidewall 628, adjacent the living hinge 618. The gap 654 is delimited at the end opposite the opening to the hollow space 650 by a rib 656, which joins the first wall slab 646 and the second wall slab 648 together. The first wall slab 646 is shown with a contoured wall structure, which is sized and shaped to receive the profile defined by the at least one flange 632 on the gate sidewall 628 of the gate assembly 600.

Figure 52:
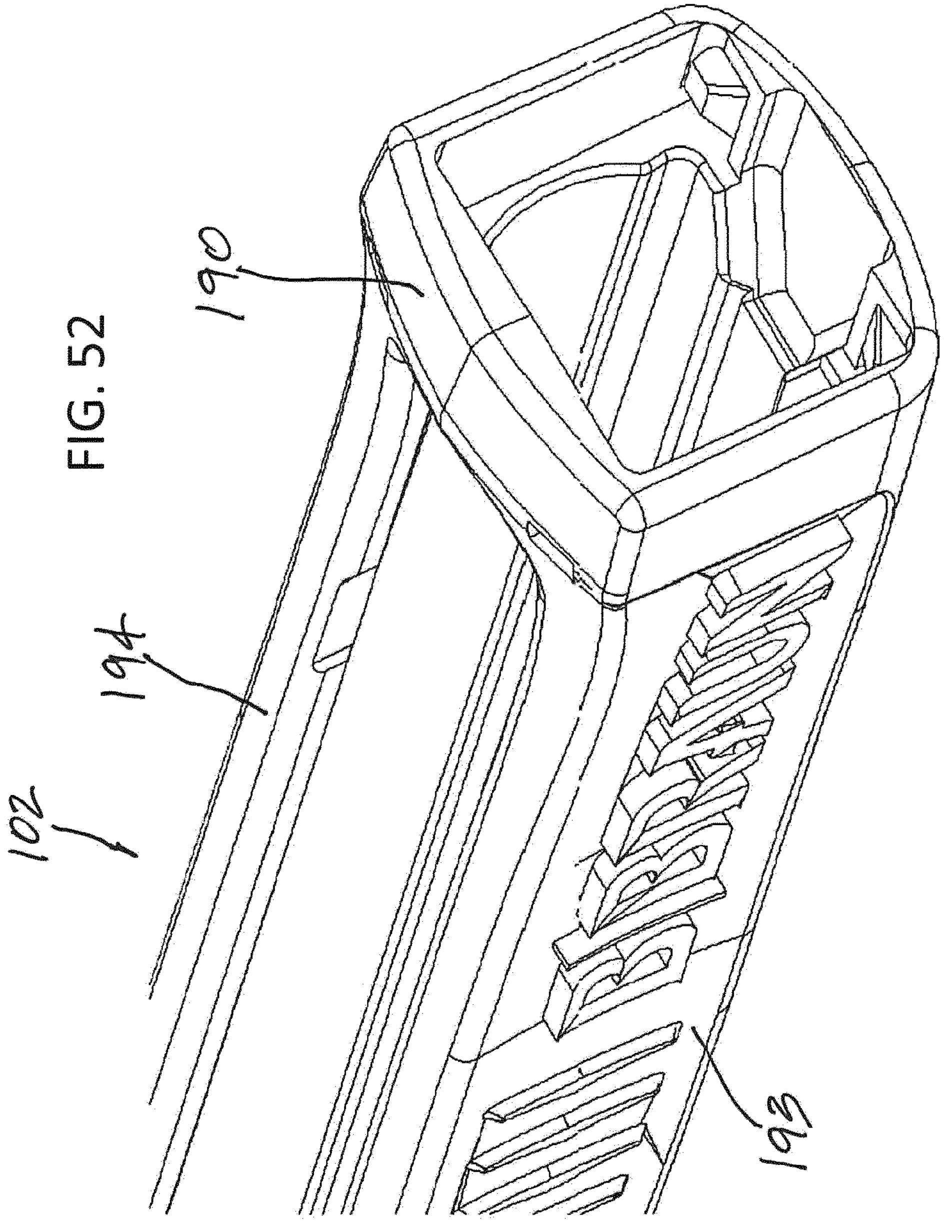
FIG. 52 is a partial rear perspective view of the housing, showing the open proximal end.

FIG. 52 shows a partial rear perspective view of the housing 102 of FIGS. 44-52. The housing has a base end 190 with a proximal opening for accommodating a catheter assembly.

The extended dwell catheter assembly 100 of FIGS. 44-52 may be used as described elsewhere herein for other ExD catheter assemblies.

Figure 53:
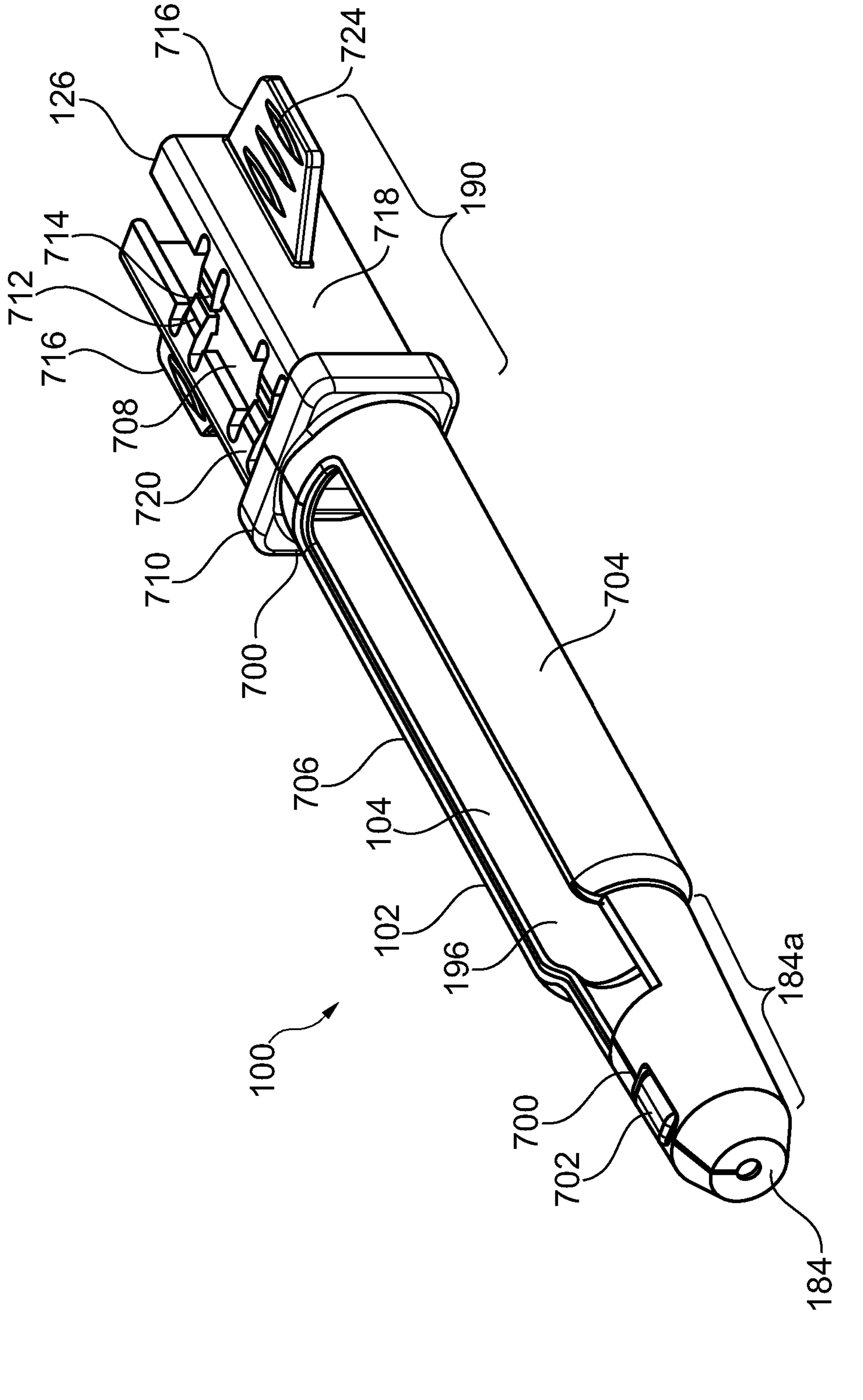
FIG. 53 is a perspective view of a housing component of an extended dwell catheter assembly provided in accordance with further aspects of the present invention.

With reference now to FIG. 53, a perspective view of a housing 102 of an ExD catheter assembly 100 is shown. The ExD catheter assembly 100 can be similar to one of the ExD catheter assemblies disclosed elsewhere herein, such as the assembly 100 of FIGS. 1 and 15. The housing 102 of the ExD catheter assembly 100 may be molded as a single piece. The housing 102 may be cylindrical-in-part and rectangular-in-part. The rectangular portion of the housing 102 may be a base 190. In some embodiments, the housing 102 may be entirely cylindrical. A gate opening 700 on top of the housing 102 may bisect the housing 102 lengthwise. Opening the housing 102 by spreading the gate opening 700 may allow a catheter hub (not shown) to be removed from an interior space 104 of the housing 102 through a body opening 196. In some embodiments, the gate opening 700 may be a living hinge. The living hinge may separate when the gate opening 700 is pulled apart with radial force. In some embodiments, the gate opening 700 may be a frangible living hinge. The frangible living hinge may have perforations that facilitate separation of the living hinge and the gate opening 700 when the gate opening 700 is pulled apart. A lock 702 may serve as additional reinforcement to keep the gate opening 700 intact. The lock 702 may be located on a nose section 184*a* of the housing 102 between a nose end 184 and the body opening 196. In some embodiments, there may be a plurality of locks 702 on the gate opening 700 along its length. The lock 702 may be a detent engagement of two sides 704, 706 created by the bisection of the housing 102 by the gate opening 700. The detent engagement may be disengaged by applying additional radial force on the housing 102 to pull the gate opening 700 apart. In some embodiments, a male detent may be on the side 706 and a female detent may be on the side 704. In some embodiments, the male detent may be on the side 704 and the female detent may be on the side 706. (not shown)

The base 190 of the housing 102 may have a top opening 708 extending from a skirt 710 of the base 190 to a proximal end 126 of the housing 102. The skirt 710 may be rectangular. The skirt 710 may have rounded edges. Other skirt 710 shapes are contemplated, such as round and triangular. A movable bridge 712 or a plurality of movable bridges may extend over the opening 708. The movable bridge 712 may have splitting, or moving, edges 714 that may be colinear to the gate opening 700. In some embodiments, the edges 714 may be connected to each other with a living hinge. In some embodiments, the edges 714 may be connected to each other with a frangible living hinge. The edges 714 may split with application of radial force on the base 190 pointing away from the edges 714. The base 190 may have wings 716 extending out from its sides 718, 720. The wings 716 may be held to advance the ExD catheter assembly 100 towards the patient once the skin is punctured. The wings 716 may have protruding grips 724 for improved handling. The wings 716 may also be pushed downward, meaning opposite direction of the opening 708, to exert radial forces on the housing 102. In some embodiments, pushing down the wings 716 may only exert enough forces to split the movable bridges 712. In some embodiments, pushing down the wings 716 may split one or more components, including the movable bridges 712, the gate opening 700, and unlock the lock 702. In such embodiments, the ability to split one or more components may depend on the length and/or material properties of the housing 102. For example, a shorter housing 102 provides a shorter distance for force travel across the length of the housing 102, in which case less force dissipation occurs between the wings 716 and the nose end 184. In another example, a housing 102 constructed from a material having lower ductility or hardness may allow one or more of the movable bridges 712, the gate opening 700, and the lock 702 to split with more ease.

Figure 54:
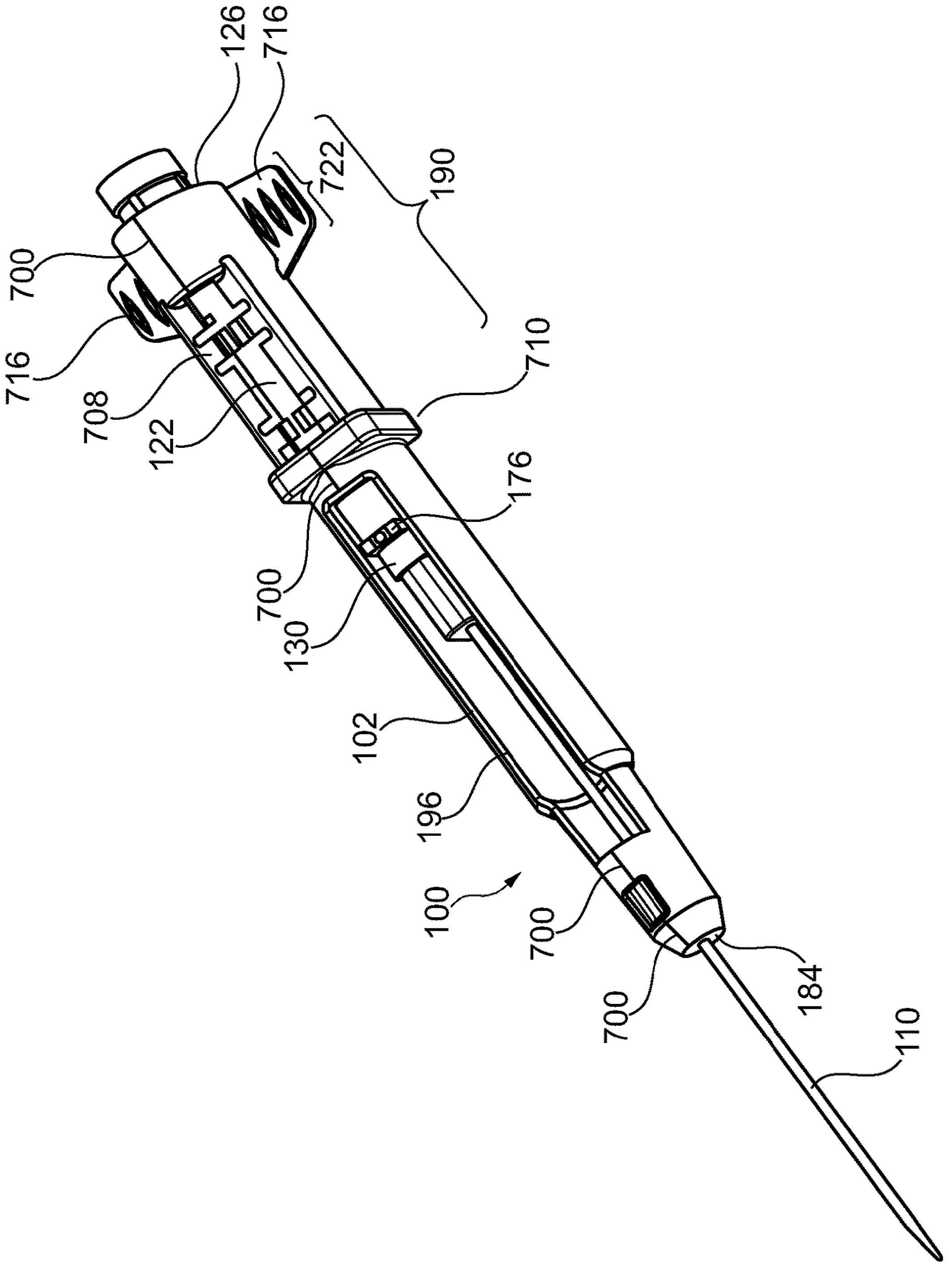
FIG. 54 is a perspective view of an extended dwell catheter assembly provided in accordance with further aspects of the present invention.

With reference now to FIG. 54, a perspective view of an ExD catheter assembly 100 is shown. The ExD catheter assembly 100 can be similar to one of the ExD catheter assemblies disclosed elsewhere herein, such as the assembly 100 of FIG. 53. The catheter assembly 100 may have a housing 102 having a base 190. The base 190 may have a top opening 708 to observe flashback from a needle hub 122. The housing 102 may additionally have a body opening 196 providing access to an interior space 104 housing a catheter hub 130. The catheter hub 130 may be pushed to a distal position via a push tab 176 extending from the catheter hub 130 and out of the body opening 196 to fully advance a catheter tube 110 once in the body. The base opening 708 may extend between a skirt 710 of the base 190 and a proximal section cover 722. The proximal section cover 722 may allow the ExD catheter assembly 100 to be held from a more proximal position in relation to the patient. Hence, larger hands can be accommodated, and availability of more holding positions can provide improved control. The base 190 may be rectangular up until the proximal section cover 722, which may be cylindrical. In some embodiments, the base 190 may be entirely rectangular or entirely cylindrical. A gate opening 700 on top of the housing 102 may bisect the housing 102 lengthwise from a nose end 184 to a proximal end 126. Having the proximal section cover 722 and thus having the gate opening 700 bisect the housing 102 all the way from the nose end 184 to the proximal end 126 may provide added structural reinforcement to the housing 102. Hence, additional force may be required to spread apart the gate opening 700 than in the ExD catheter assembly 100 of FIG. 53 to remove the catheter hub 130 from the interior space 104 of the housing 102. In some embodiments, the gate opening 700 may be a living hinge. In some embodiments, the gate opening 700 may be a frangible living hinge.

The proximal section cover 722 may have wings 716. When the wings 716 are pushed downward, meaning opposite direction of the base opening 708, to remove the catheter hub 130, more force may be required than in the ExD catheter assembly 100 of FIG. 53 because the wings 716 and the nose end 184 are further apart than in FIG. 53, and the gate opening 700 continues to bisect the housing 102 proximal to the base opening 708 unlike in FIG. 53. In some embodiments, if added reinforcement is not desired, the housing 102 may be constructed from a material having lower ductility or hardness than that of FIG. 53 to allow removal of the catheter hub 130 from the housing 102 with more ease despite the aforementioned constraints.

Figure 55:
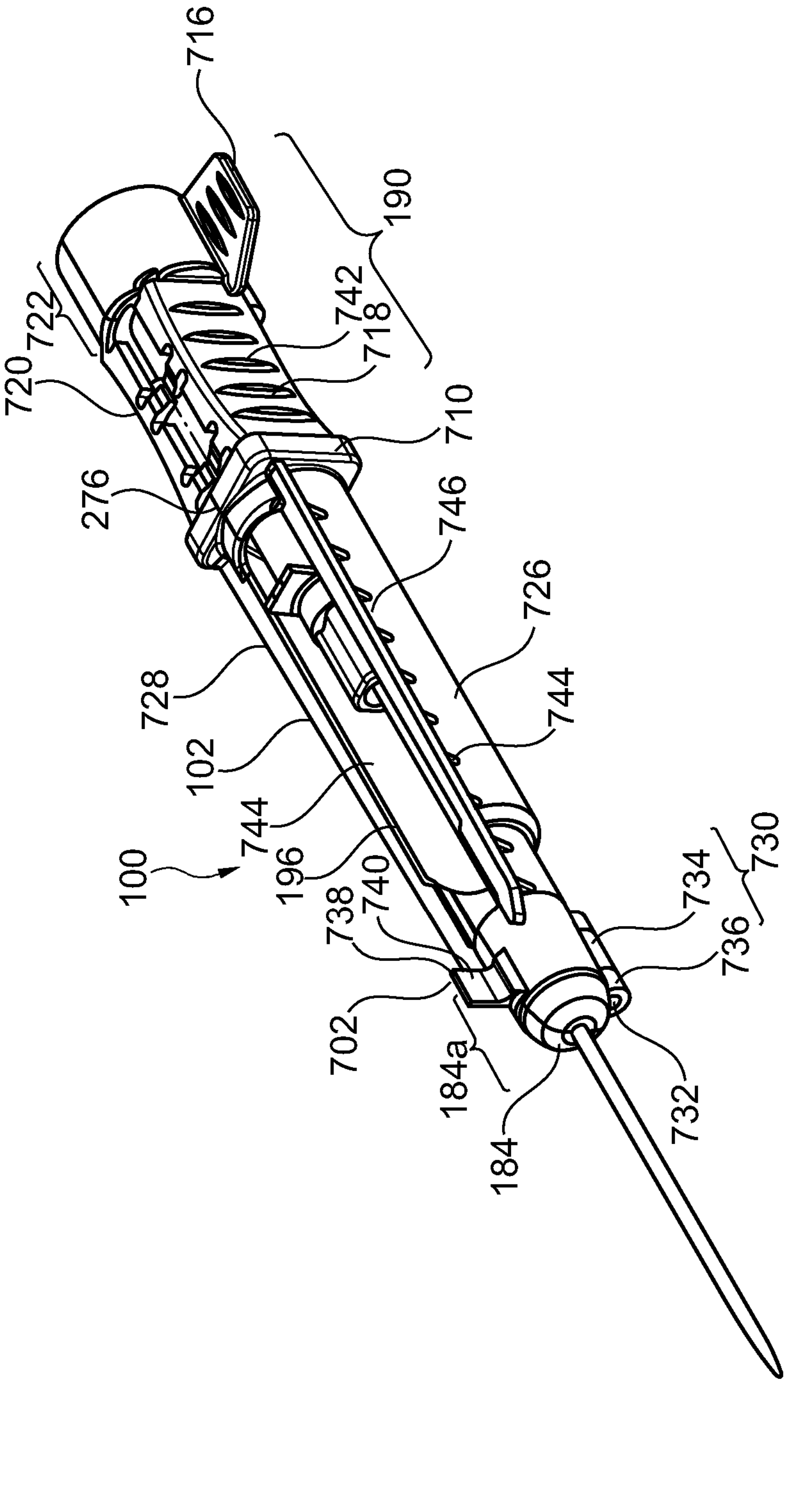
FIG. 55 is a perspective view of an extended dwell catheter assembly provided in accordance with further aspects of the present invention.

With reference now to FIG. 55, a perspective view of an ExD catheter assembly 100 is shown. The ExD catheter assembly 100 can be similar to one of the ExD catheter assemblies disclosed elsewhere herein, such as the assembly 100 of FIG. 54. A housing 102 of the ExD catheter assembly 100 may be constructed from separate parts. The housing 102 may have a first frame 726 and a second frame 728. The first and second frames 726, 728 may be held together by a hinge 730 or a plurality of hinges. The hinge 730 may be located on the bottom of the housing 102. The first frame 726 may have a male part 734 of the hinge 730, and the second frame 728 may have a female part 736 of the hinge 730. In other embodiments, the first frame 726 may have the female part 736 of the hinge 730, and the second frame 728 may have the male part 734 of the hinge 730. A pin 732 may pass through both the male part 734 and the female part 736. In some embodiments, the male part 734 may be insertable into the female part 736 instead of using the pin 732. In some embodiments, the housing 102 may be constructed as a single piece. In such embodiments, the hinge 730 may be a living hinge. In some of such embodiments, the hinge 730 may resemble a conventional hinge, for example hinges generally used in opening and closing doors. The hinge 730 may allow the first frame 726 to open and hang down from the second frame 728 (see FIGS. 57-58) in an open position.

Still referring to FIG. 55, the first and second frames 726, 728 may have an upper seam 276 on top of the housing 102 and a lower seam 277 (see FIGS. 57-58) on the bottom of the housing 102. The upper and lower seams 276, 277 may bisect the housing 102. The upper and lower seams 276, 277 may be living hinges, frangible living hinges, or spaced apart. In some embodiments, only the upper seam 276 may be a living hinge or a frangible living hinge. In some of such embodiments, only the lower seam 277 may be a living hinge or a frangible living hinge. In some embodiments, one of the upper and lower seams 276, 277 may be a living hinge while another one of the upper and lower seams 276, 277 may be a frangible living hinge. In some embodiments, one of the upper and lower seams 276, 277 may be a frangible living hinge while another one of the upper and lower seams 276, 277 may be a living hinge. In some embodiments, some parts of the upper and lower seams 276, 277 may be a living hinge and some parts may be a frangible living hinge. The living hinge and/or the frangible living hinge of the upper seam 276 and/or the lower seam 277 may be separated by applying radial forces on the housing 102 directed away from the upper and lower seams 276, 277 to pull down the first frame 726 from a closed state shown in FIG. 55 to an open state (see FIGS. 57-58). The radial forces may be applied by pushing down wings 716 located on a proximal section cover 722 of a base 190, such as in the ExD catheter assembly 100 of FIG. 54.

The base 190 of the housing 120 may be separated from rest of the housing 120 by a skirt 710. In some embodiments, the proximal section cover 722 may be deleted, and the wings 716 may extend out from sides 718, 720 of the base 190. In some embodiments, the sides 718, 720 may have protrusions 742 to provide improved grip. In addition, or in lieu, the radial forces may be applied by pushing down rails 744 extending out of the housing 102. The rails 744 may extend from the skirt 710 to the nose section **184*a*. The rails 744 may extend out widthwise from a body opening 196 providing access to an interior space 104 of the housing 102. The rails 744 may be supported with a rail leg or rail legs 746 extending between under the rails 744 and the housing 102**.

A lock 702 may serve as additional reinforcement to keep the upper and lower seams 276, 277 intact. The lock 702 may interrupt the upper seam 276. The lock 702 may be located on a nose section **184*a* of the housing 102 between a nose end 184 and the body opening 196. In some embodiments, there may be a plurality of locks 702. In some embodiments, the lock 702 may be a detent engagement of the first and second frames 726, 728. In some embodiments, the detent engagement may be disengaged by pushing a tab 738 away from the engagement to lift up and free a male detent from a female detent. The tab 738 may be located on the same frame as the male detent. In some embodiments, the male detent may be on the second frame 728 and the female detent may be on the first frame 726. In some embodiments, the male detent may be on the first frame 726 and the female detent may be on the second frame 728. The tab 738 may have a curved shape resembling a fin. An inner curve 740 of the tab 738 may have a rough surface. The rough surface may provide improved grip. In some embodiments, the tab 738 may be deleted. In such embodiments, the detent engagement may be disengaged by applying additional radial force on the housing 102 when pulling down the first frame 726** from the closed state to the open state.

Figure 56:
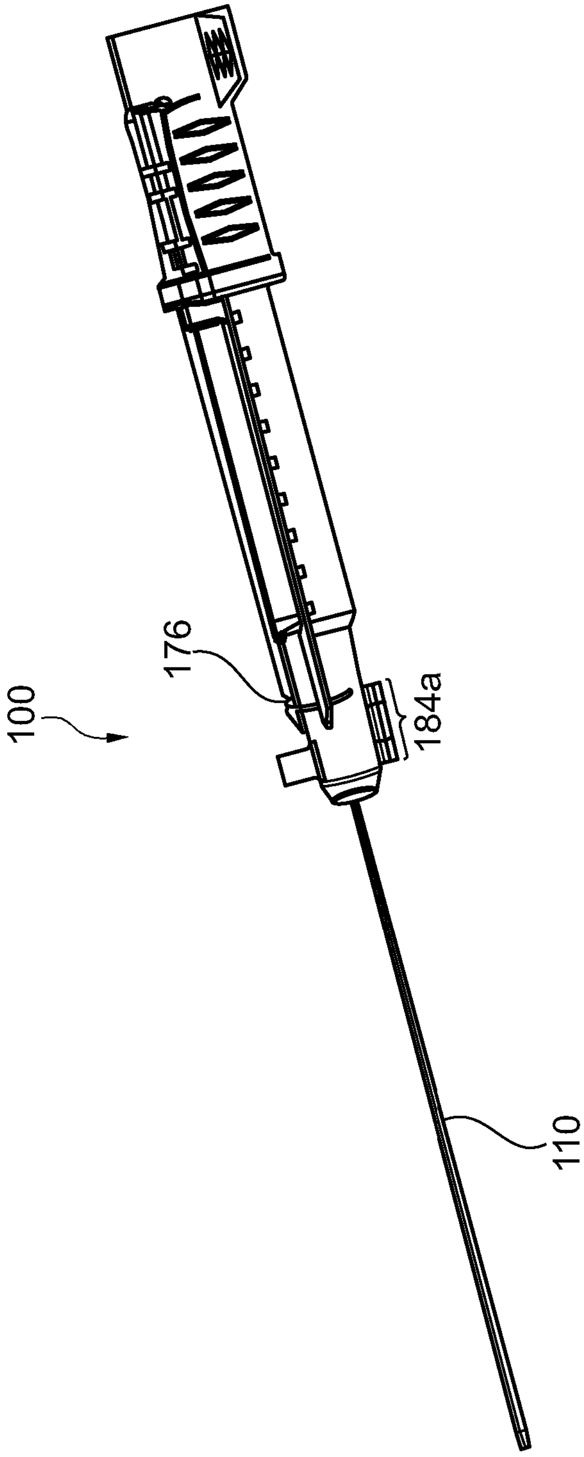
FIG. 56 is a different perspective view of the extended dwell catheter assembly of FIG. 55 with a catheter hub in a distal position.

With reference now to FIG. 56, the ExD catheter assembly 100 is shown with a catheter hub 130 in a distal position. The catheter hub 130 may be pushed to the distal position via a push tab 176 extending from the catheter hub 130 out of the body opening 196 to fully advance a catheter tube 110 once in the body. In the distal position, the catheter hub may be partially covered by the nose section 184*a*. Also, in the distal position, the push tab 176 may abut the nose section 184 to stop further movement of the catheter 130 hub into the nose section 184*a*.

Figure 57:
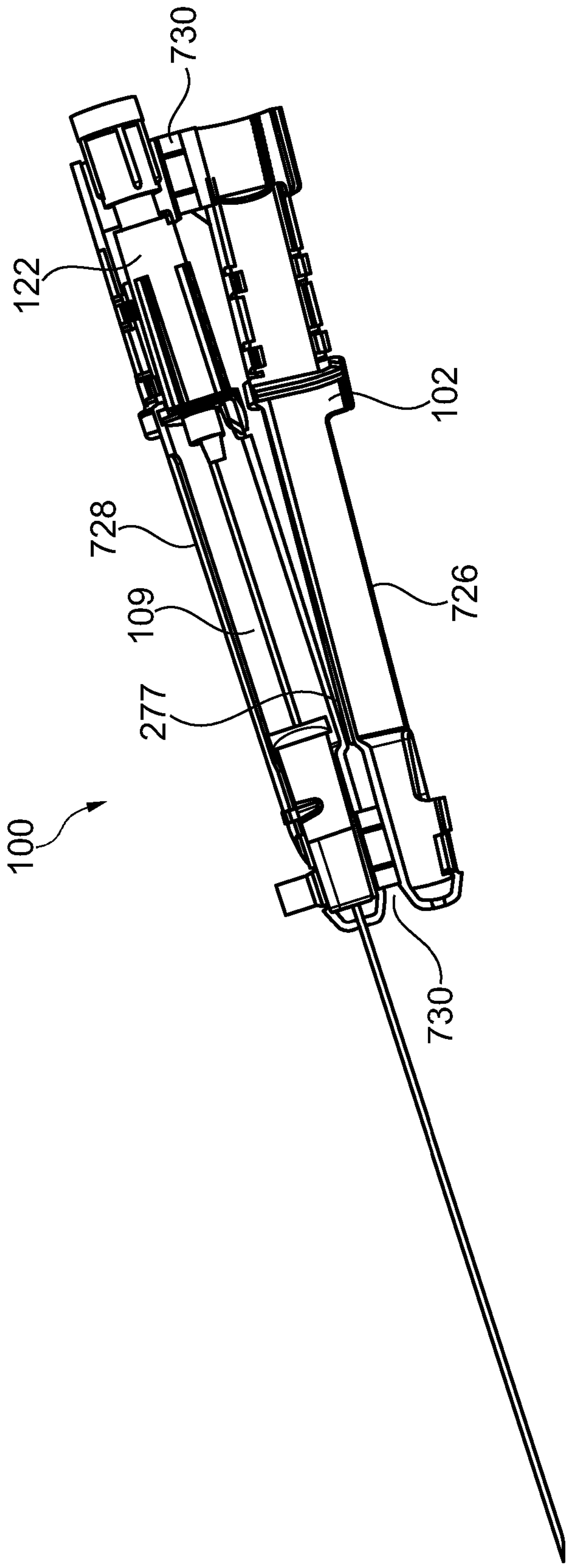
FIG. 57 is a perspective view of the extended dwell catheter assembly of FIG. 55 with the catheter hub in the distal position and a housing component in an open position.

With reference now to FIG. 57, the ExD catheter assembly 100 is shown with the housing 102 in the open state. The first frame 726 may open and hang down from the second frame 728 by hinges 730. The first frame 726 may not contact the second frame 728 at the lower seam 277 except for by the hinges 730. In embodiments having an upper seam 276 that is a living hinge(s) and/or frangible living hinge(s), the upper seam 276 (see FIG. 55) may be torn open by the application of radial forces on the housing 102. A needle hub 122 may be tightly fitted onto the second frame 728 so that the needle hub 122 does not fall out of the interior space 104 once the housing 102 is opened from the first frame 726. In other embodiments, locations(s) of one, some or all feature (s) and/or component(s) of the housing 102 may be switched to the opposing frame so that the housing 102 can be opened from the second frame 728.

Figure 58:
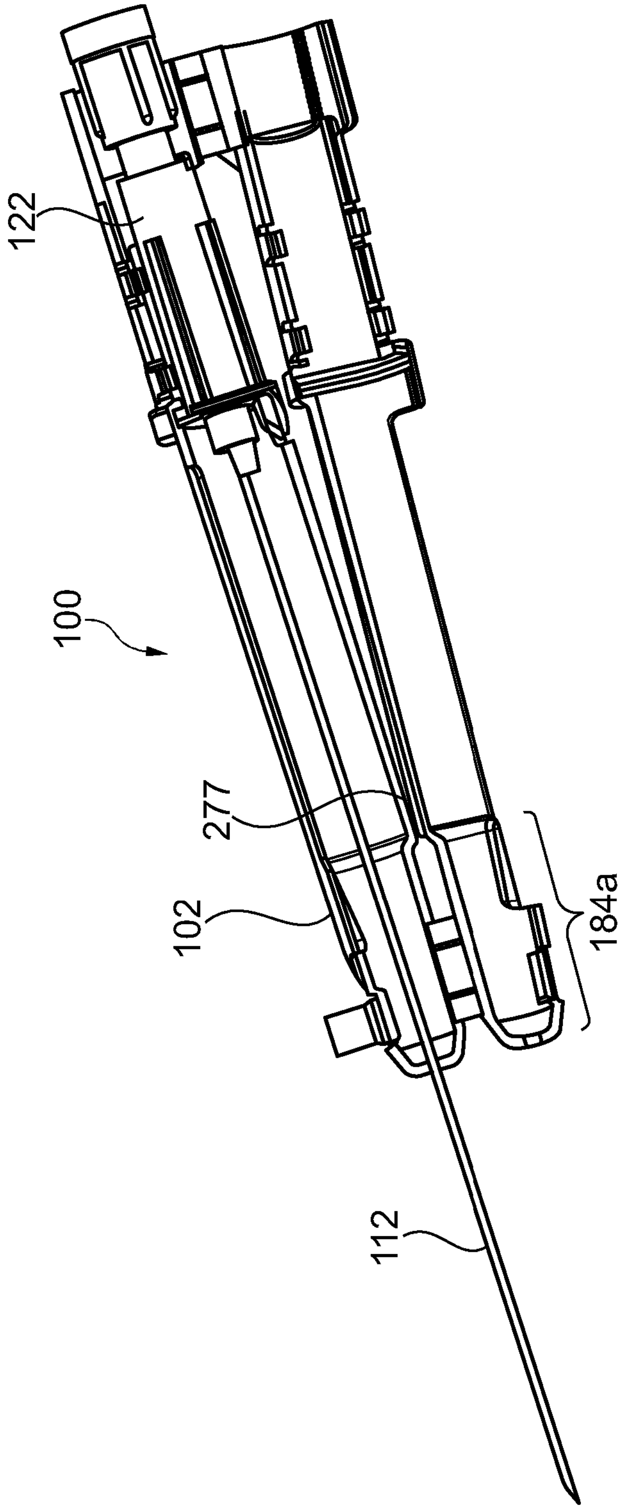
FIG. 58 is a perspective view of the extended dwell catheter assembly of FIG. 55 with the catheter hub removed from the housing component.

With reference now to FIG. 58, the ExD catheter assembly 100 is shown with the catheter hub 130 (see FIG. 56) removed from the housing 102. The catheter hub 130 may be removed from the housing 102 by moving the nose section 184*a* laterally while holding the catheter hub 130 in place. The catheter hub 130 may then stay attached to the patient. A needle 112 may be exposed when the catheter hub 130 is detached from the assembly 100. The needle 112 may engage with a needle guard (not shown) located inside the catheter hub 130 as the needle 112 is withdrawn from the catheter hub 130. The needle guard may prevent needle 112 pokes. The needle 112, the needle hub 122, and the housing 102 may then be safely discarded.

Figure 59:
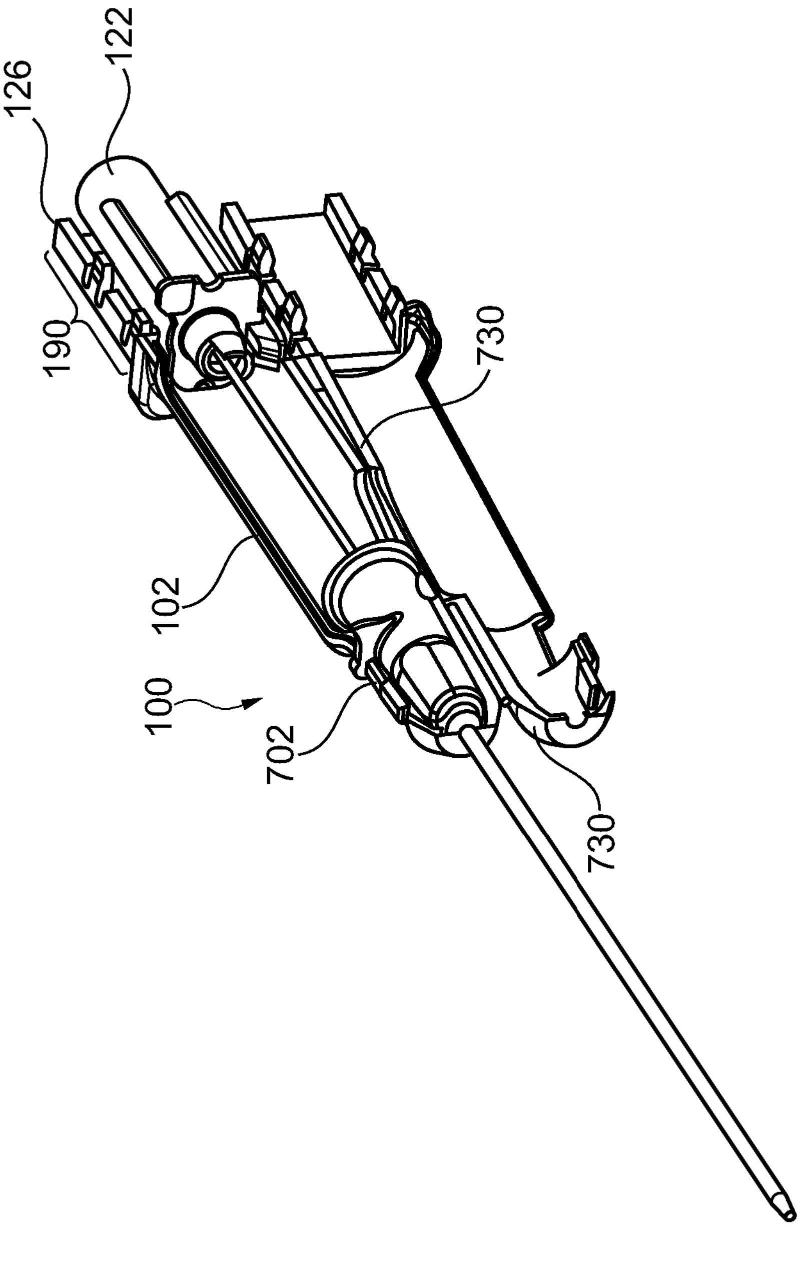
FIG. 59 is a perspective view of an extended dwell catheter assembly provided in accordance with further aspects of the present invention.

With reference now to FIG. 59, a perspective view of an ExD catheter assembly 100 is shown. The ExD catheter assembly 100 can be similar to one of the ExD catheter assemblies disclosed elsewhere herein, such as the assembly 100 of FIG. 54. The assembly 100 may have a housing 102 constructed from a single piece. The housing 102 may have hinges 730. The hinges 730 may be living hinges. The hinges 730 may not resemble the hinges 730 of the ExD catheter assembly 100 of FIG. 55 or have pins 732 like the same. The housing 102 may have a lock 702 or a plurality of locks to keep the housing 102 closed. The lock 702 may not feature a tab, unlike the assembly 100 of FIG. 55. The housing 102 may be held from a base 190 proximal to the housing 102. Wings or a proximal section cover may be omitted, unlike the assembly 100 of FIG. 55. Hence, the base 190 may be open at a proximal end 126. A needle hub 122 may extend out proximally from the base 190.

Figure 60:
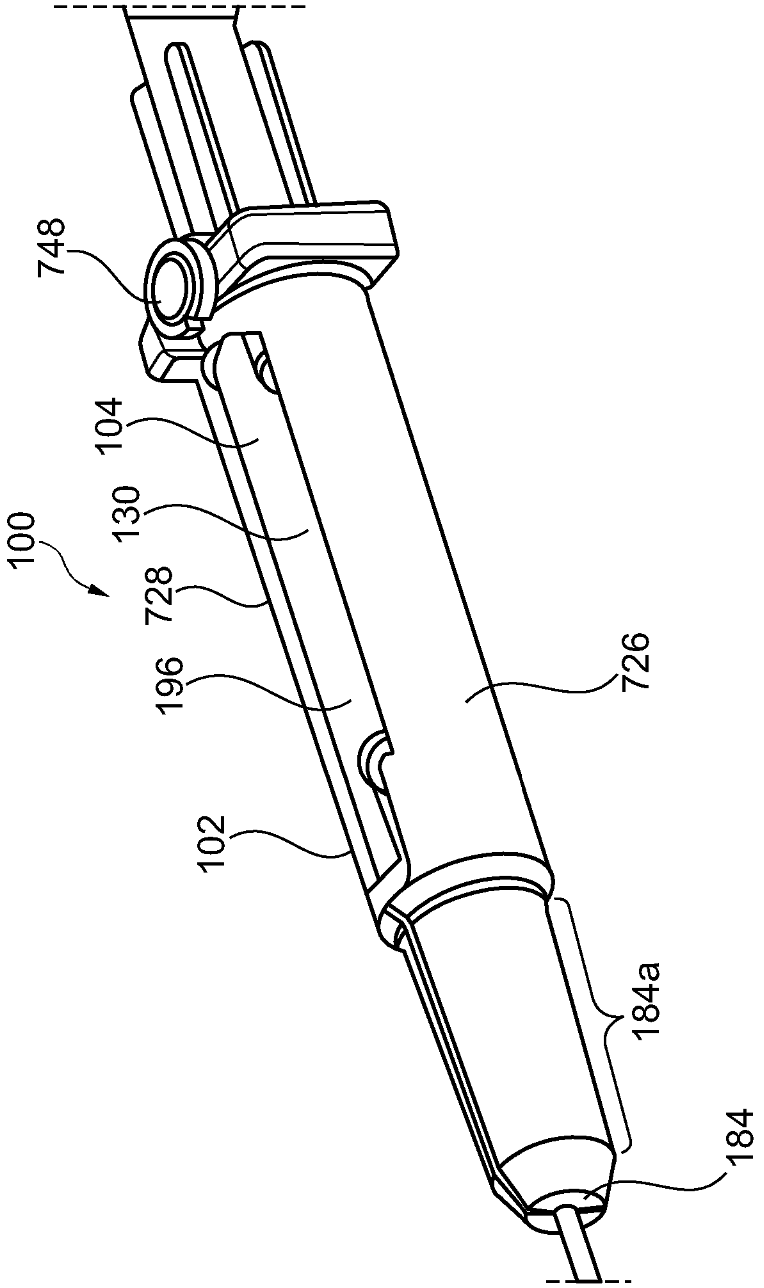
FIG. 60 is a perspective view of an extended dwell catheter assembly provided in accordance with further aspects of the present invention.

With reference now to FIG. 60, a perspective view of an ExD catheter assembly 100 is shown. The ExD catheter assembly 100 can be similar to one of the ExD catheter assemblies disclosed elsewhere herein, such as the assembly 100 of FIG. 55. A housing 102 of the ExD catheter assembly 100 may be constructed from separate parts. The housing 102 may have a first frame 726 and a second frame 728. The first and second frames 726, 728 may be held together by a detent engagement of the first and second frames 726, 728. The detent engagement may be located on a nose section 184*a* of the housing between a nose end 184 and a body opening 196. In some embodiments, there may be a plurality of detent engagements of the first and second frames 726, 728. In some embodiments, the detent engagement may be disengaged by pressing a button 748 on the housing 102 that disconnects the first and second frames 726, 728. Once the first and second frames 726, 728 are disconnected, a catheter hub 130 may be freed from an interior space 104 of the housing 102.

Figure 61:
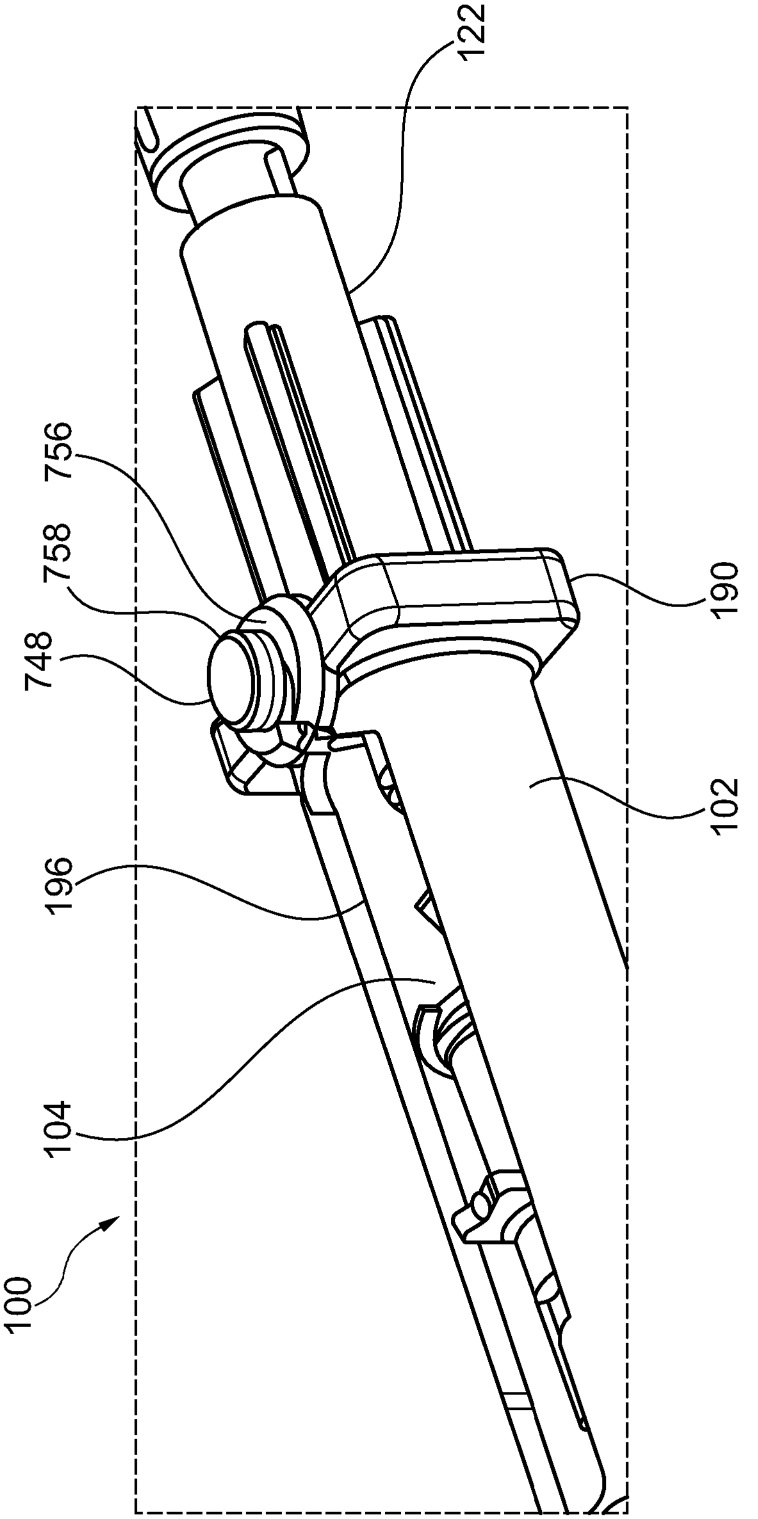
FIG. 61 is an enlarged perspective view of a proximal end of the extended dwell catheter assembly of FIG. 60.

With reference now to FIG. 61, an enlarged perspective view of a proximal end of the ExD catheter assembly 100 is shown. The button 748 may have one or more ramped side surfaces 754 (see FIGS. 64-65) applying radial forces on the housing 102 to disengage the detent engagement when the button 748 is depressed. The button 748 may be housed in a button housing 756. The button may have a top surface 758. The top surface 758 may be directly contacted to press down the button 748. The top surface 758 may be round. Other shapes of the top surface 758 are contemplated, such as oval, square, and rectangle. The button 748 may be located proximal to the body opening 196 on a base 190 of the housing 102. A needle hub 122 may extend from within the interior space 104 and out of the base 190. The base 190 may be dimensioned so that more than half of the needle hub 122 is exposed. In some embodiments, the button 748 may be replaced by a latch (not shown) that is unlatched by applying radial forces on the housing 102 to disengage the detent engagement.

Figure 62:
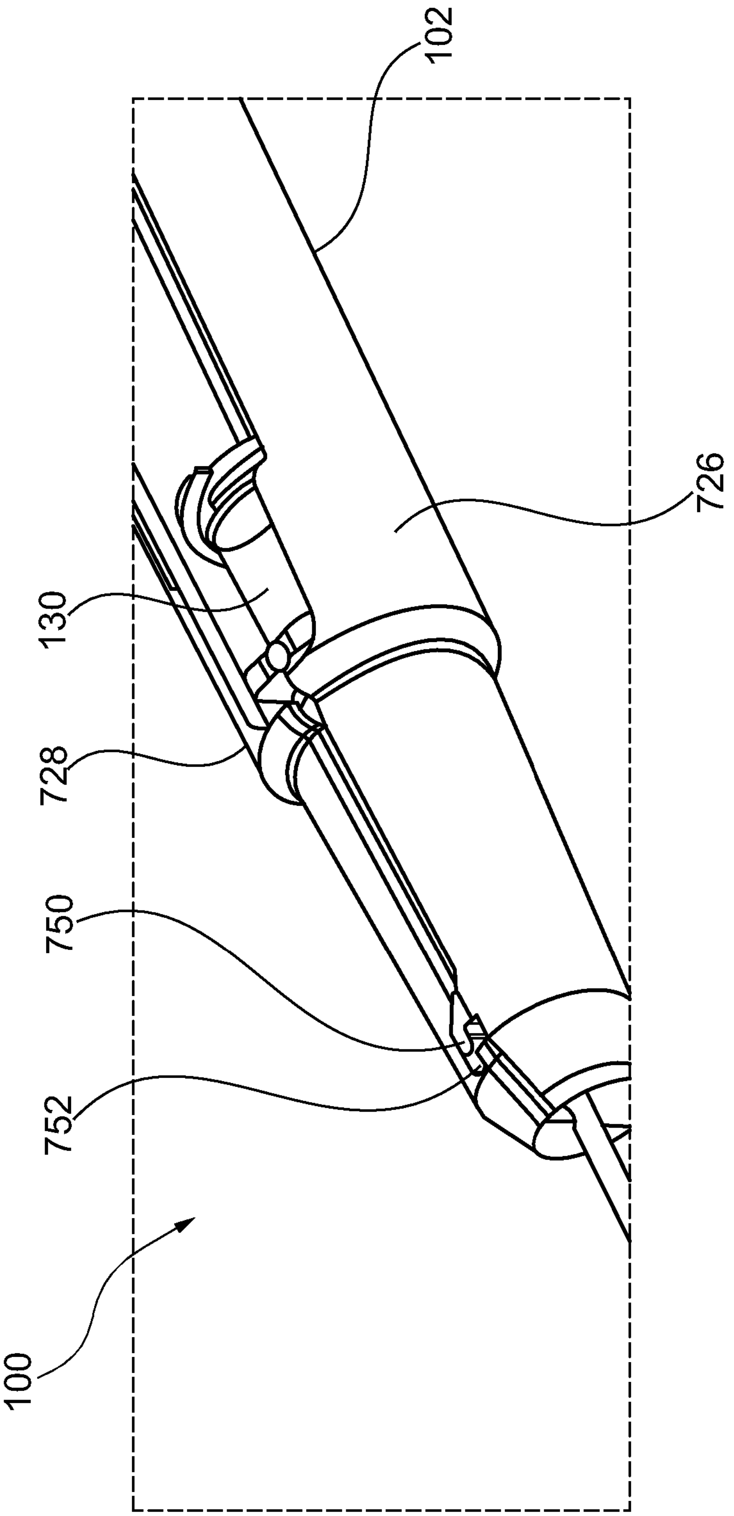
FIG. 62 is an enlarged perspective view of a distal end of the extended dwell catheter assembly of FIG. 60.

With reference now to FIG. 62, an enlarged perspective view of a distal end of the ExD catheter assembly 100 is shown. The detent engagement of the first and second frames 726, 728 is shown in a partially disengaged state with a male detent 750 separating from a female detent 752. In some embodiments, the male detent 750 may be on the second frame 728 and the female detent 752 may be on the first frame 726. In some embodiments, the male detent 750 may be on the first frame 726 and the female detent 752 may be on the second frame 728. The catheter hub 130 is shown in a distal position, and thus ready for extraction from the housing 102 once the detent engagement is fully disengaged and the first and second frames 726, 728 are fully detached from each other. In some embodiments, the partially disengaged state shown may be the result of the button 748 (see FIG. 61) being only partially pressed down. In some embodiments, the partially disengaged state shown may be the result of the button 748 fully pressed down, and the frames 726, 728 may require additional radial force to complete detachment from each other. For example, each one of the frames 726, 728 may be held by one hand and pulled apart from a partially disengaged state.

Figure 63:
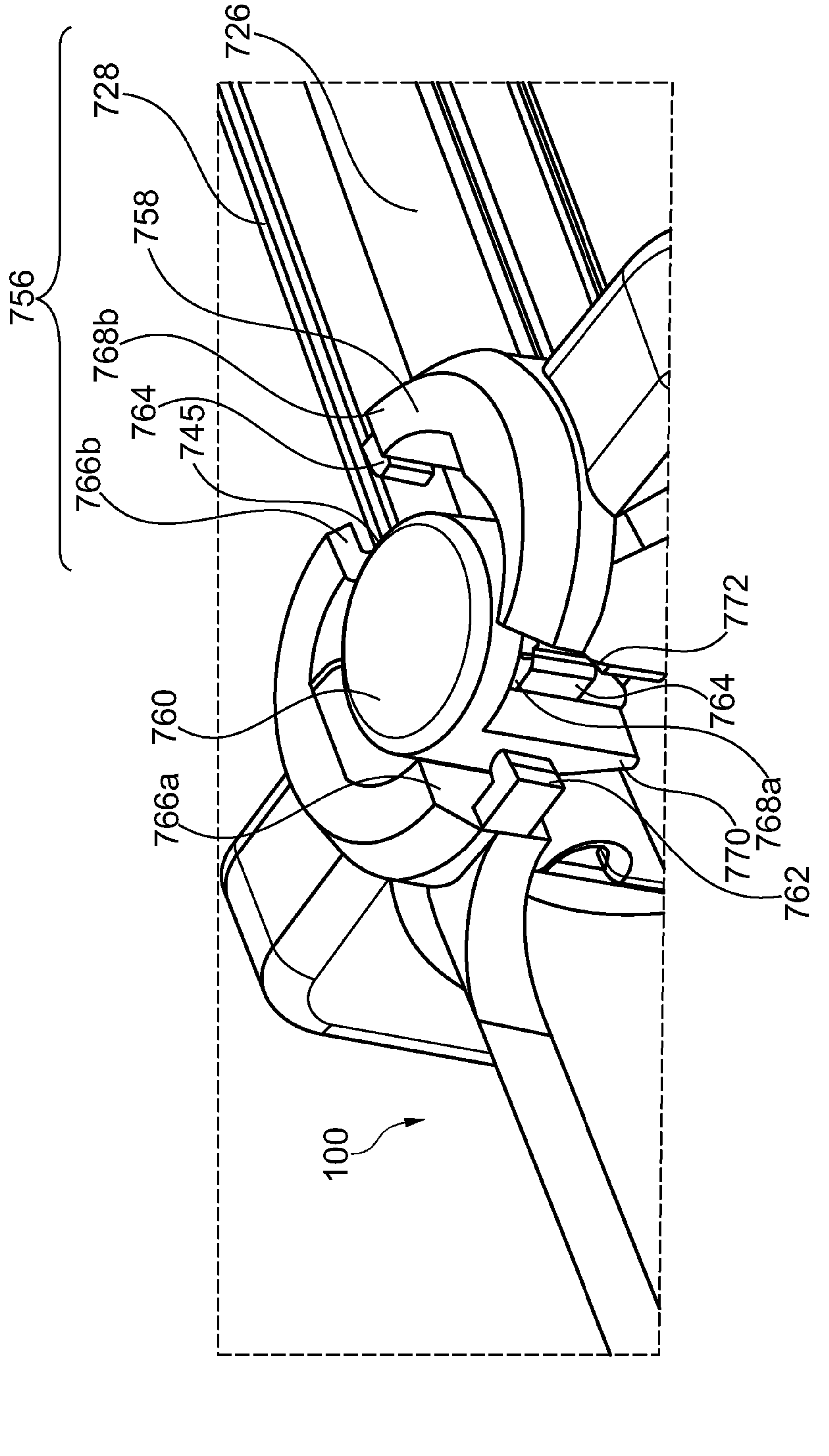
FIG. 63 is an enlarged perspective view of a housing component separation button of the extended dwell catheter assembly of FIG. 60.

With reference now to FIG. 63, an enlarged perspective view of the button 745 of the ExD catheter assembly 100 is shown. The button 745 is shown in a depressed state. When the button 745 is in the depressed state, the button housing 756 may separate, a first half 758 of the button housing 756 being on the first frame 726 and a second half 760 of the button housing 756 being on the second frame 728. The button housing 756 may have one or more ramped sidewalls 760. Each ramped sidewall 760 may slidably receive each side surface 754 (see FIGS. 64-65). When the button 745 is in the depressed state, the ramps of the sidewall 760 and the side surface 754 may align so no space is left for the button 745 to move down unless the button housing 756 separates, so each side surface 754 may exert a force on each ramped sidewall 760. One or more male tabs 762 and one or more female tabs 764 that can engage with the one or more male tabs 762 may extend from the first and second halves 758, 760 of the button housing 756. The male tabs 762 may extend from each side surface 766*a*, 766*b* of the first half 758, and the female tabs 764 may extend from each side surface 768*a*, 768*b* of the second half 760. In other embodiments, the male tabs 762 may extend from each side surface 768*a*, 768*b* of the second half 760, and the female tabs 764 may extend from each side surface 766*a*, 766*b* of the first half 758. In other embodiments, one of the side surfaces 766*a*, 766*b* may have the male tab 762 and the other side surface 766*a*, 766*b* may have the female tab 764, and one of the side surfaces 768*a*, 768*b* may have the female tab 764 and the other side surface 768*a*, 768*b* may have the male tab 762. One of the female tabs 764 may be slidably engageable with a recess 770 of the button 745. When the button 745 is pressed, the male tabs 762 may disengage from the female tabs 764 due to the radial forces applied on the button housing 756 and a roof 772 of the recess 770 pressing down on the female tab 764, which is then freed from its complementing male tab 762. In other embodiments, there may be a plurality of recesses 770 that may be slidably engageable with a plurality of female tabs 764 and plurality of recess roofs 772 that may release the plurality of female tabs 764 from male tabs 762.

Figure 64:
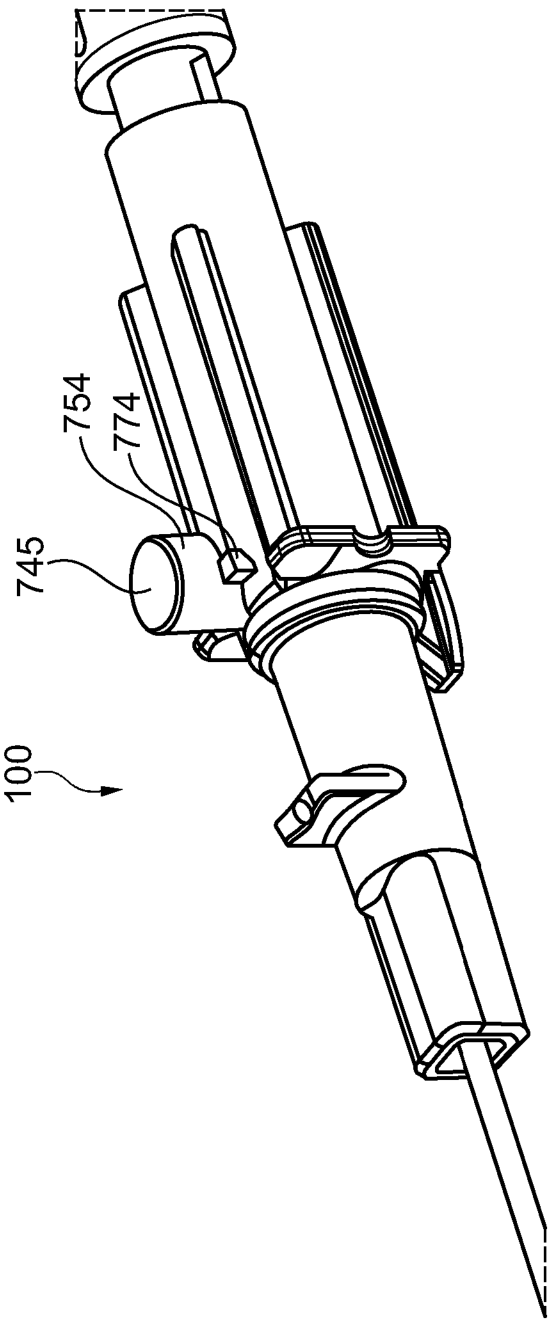
FIG. 64 is a partial perspective view of the extended dwell catheter assembly of FIG. 60 without the housing component.

With reference now to FIG. 64, a partial perspective view of the ExD catheter assembly 100 without the housing 102 (see FIG. 60) is shown. The ramped side surfaces 754 (see also FIG. 65) of the button 745 may have pins 774 (see also FIG. 65) extending out therefrom. The button 745 may attach to the catheter assembly 100 by coupling the pins 774 to seats (not shown) located inside the button housing 756. The pins 774 may move up and down within the seats when the button 745 is pressed until the first and second frames 726, 728 (see FIG. 60) separate along with the button 745 to be safely discarded. In some embodiments, the button 745 may be coupled to one of the first and second frames 726, 728 in such a way that the button 745 stays with that frame after the frames 726, 728 separate from each other. By example and not limitation, such a coupling that allows the button 745 to stay with one of the frames 726, 728 may require tight fitment of one of the pins 774 into its complementing seat.

Figure 65:
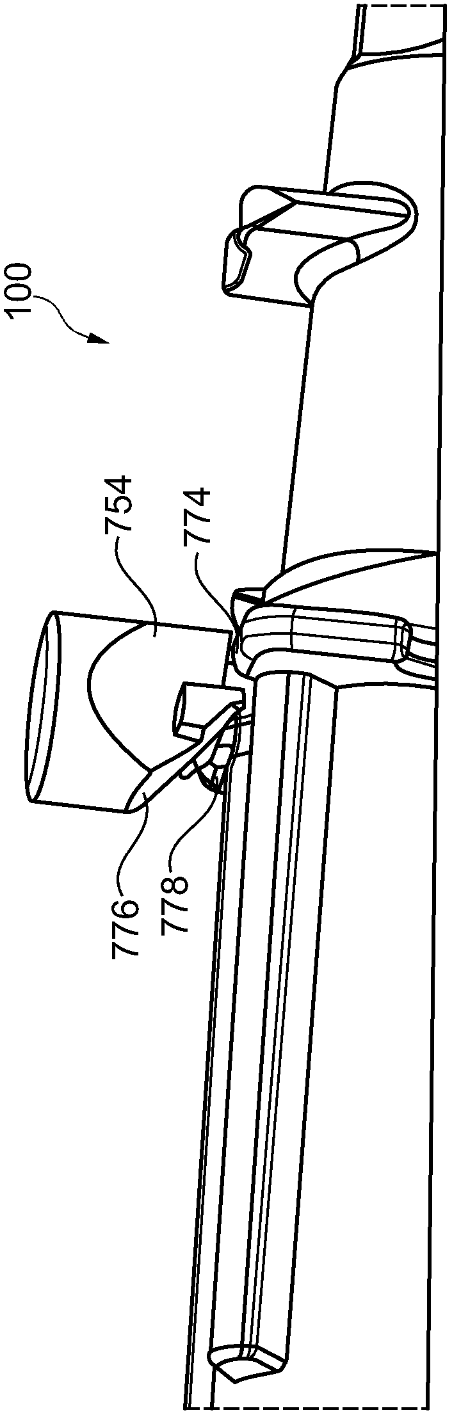
FIG. 65 is an enlarged view of the housing component separation button of the extended dwell catheter assembly of FIG. 60 without the housing component.

With reference now to FIG. 65, a partial perspective view of the ExD catheter assembly 100 without the housing 102 (see FIG. 60) from a proximal angle is shown. The button 745 may have a ramped rear surface 776 in addition to the ramped side surfaces 754. In some embodiments, the ramped rear surface 776 may facilitate sliding of the button 745 when pressed. In some embodiments, the ramped rear surface 776 may apply radial forces on the button housing 756 due to the bulk of the button 745 inside the housing 756 changing when pressed. The pins 774 may have legs 778 that extend below the button 745 and connect from underneath the button 745. The legs 778 may allow for the button 745 to move down evenly when pressed.

Figure 66:
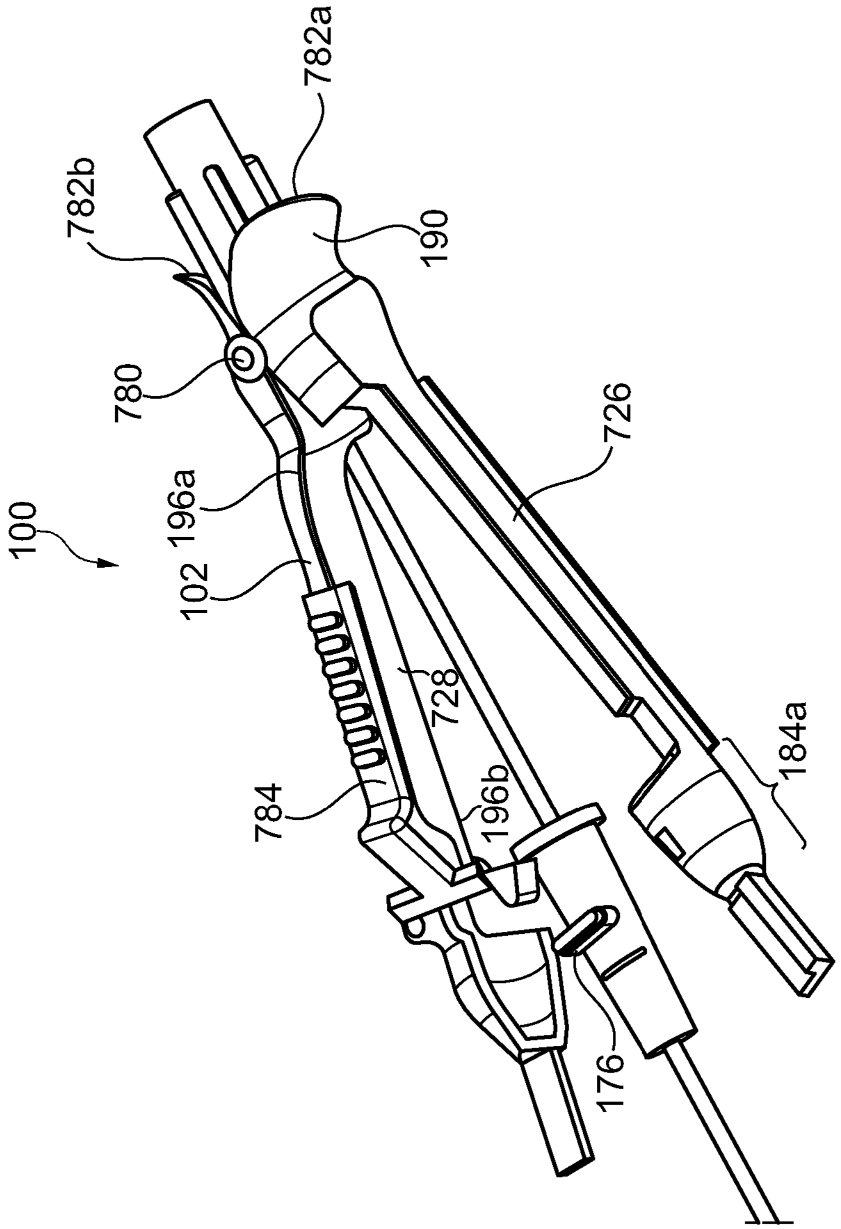
FIG. 66 is a perspective view of an extended dwell catheter assembly provided in accordance with further aspects of the present invention.

With reference now to FIG. 66, a perspective view of an ExD catheter assembly 100 is shown. The ExD catheter assembly 100 can be similar to one of the ExD catheter assemblies disclosed elsewhere herein, such as the assembly 100 of FIG. 60. A housing 102 of the ExD catheter assembly 100 may be constructed from separate parts. The housing 102 may have a first frame 726 and a second frame 728. The first and second frames 726, 728 may be held together by clamp-shaft coupling 780. The first and second frames 726, 728 may pivot away from each other at the clamp-shaft coupling 780 to open the housing 102. The clamp-shaft coupling 780 may be located between upper and lower body openings 196*a*, 196*b* of the housing 102 and a base 190 of the housing 102. The base 190 may have ends 782*a*, 782*b* on each of the first and second frames 726, 728 that proximally curve outward. The curved ends 782*a*, 782*b* may be used as leverage to be pushed together and open the housing 102. Once the housing 102 is opened up, a catheter hub 130 located in an interior space 104 of the housing 102 may be removed. Prior to removal, the catheter hub 130 may be pushed in a distal direction to advance a catheter tube 110 into the patient. The catheter hub 130 may be pushed with a pusher 784. The pusher 784 may have a T-shape. The pusher 784 may be initially proximal to a push tab 176 of the catheter hub 130. The pusher 784 may be pushed in a distal direction to engage with the push tab 176 and push the catheter hub 130 to a nose section 184*a* of the housing 102. Once the catheter hub 130 is fully advanced, the base 190 may be squeezed from the base ends 782*a*, 782*b* to open and detach the housing 102 from the catheter hub 130.

Figure 67:
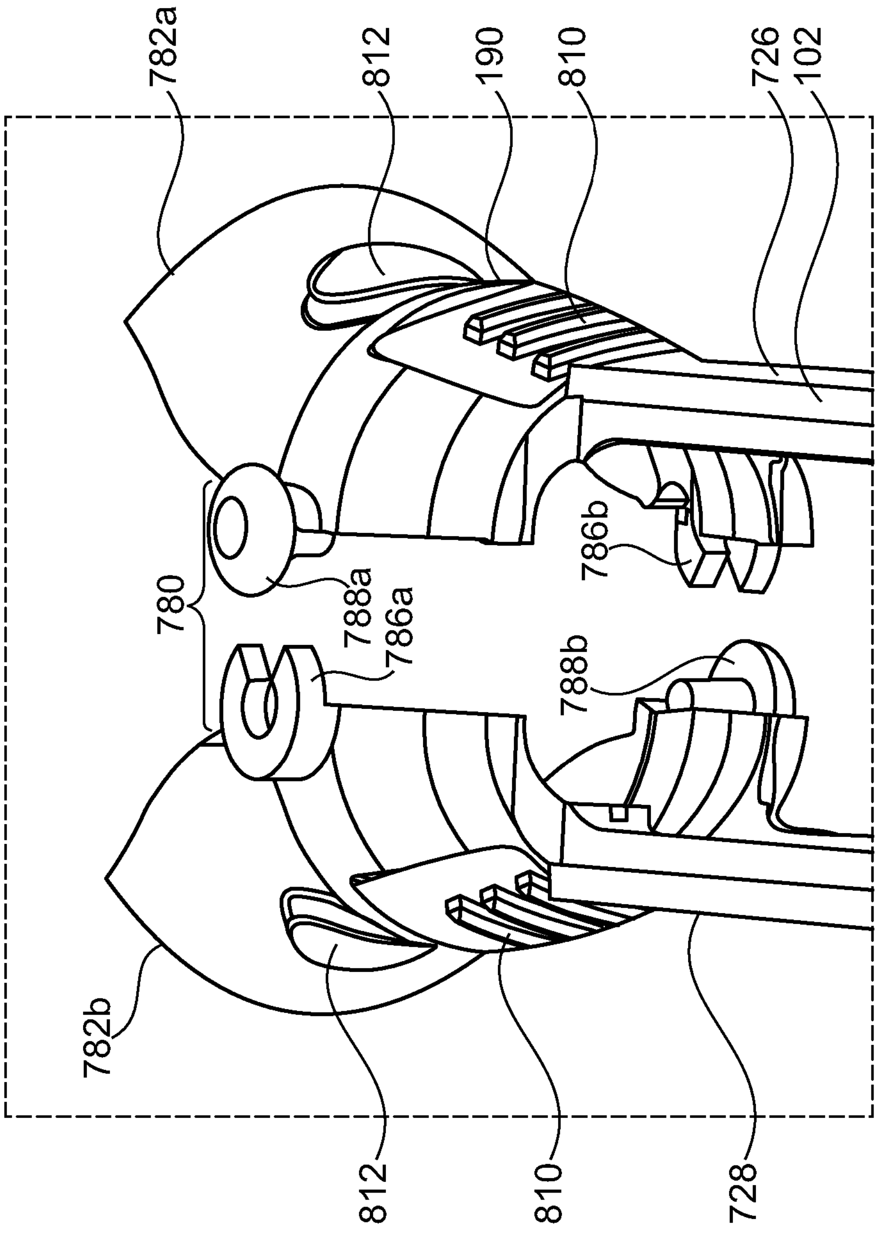
FIG. 67 is an enlarged exploded view of a clamp-shaft connection of a housing component of the extended dwell catheter assembly of FIG. 66.

With reference now to FIG. 67, a proximal section view of the ExD catheter assembly 100 with the clamp-shaft coupling 780 of the first and second frames 726, 728 disconnected is shown. The clamp-shaft coupling may have upper clamp 786*a*-upper shaft 788*a* and lower clamp 786*b*-lower shaft 788*b* pairs. The upper and lower clamps 786*a*, 786*b* may be on alternating frames. Similarly, the upper and lower shafts 788*a*, 788*b* may be on alternating frames. In some embodiments, the upper and lower clams 786*a*, 786*b* may be on the same frame and so may the upper and lower shafts 788*a*, 788*b*. In some embodiments, the clamp-shaft coupling 780 may be replaced with another connection that the first and second frames 726, 728 may pivot or rotate from. By example and not limitation, such a connection may be a hinge like the hinge 730 of FIG. 55.

Still referring to FIG. 67, the base 190 may have a plurality of grips 810 protruding from each of the first and second frames 726, 728. The grips 810 may improve gripping when holding the catheter assembly 100 from the base 190. The grips 810 may be shaped and arranged like gills. The base 190 may also have a second type of grips 812 protruding from each of the first and second frames 726, 728. The grips 812 may be located more proximally on the housing 102 relative to the grips 810. The grips 812 may have a circular shape. The grips 812 may have a curved surface that complements fingertips of the user. The grips 812 may allow the user to have improved grip when squeezing the base ends 782*a*, 782*b* to open the housing 102.

Figure 68:
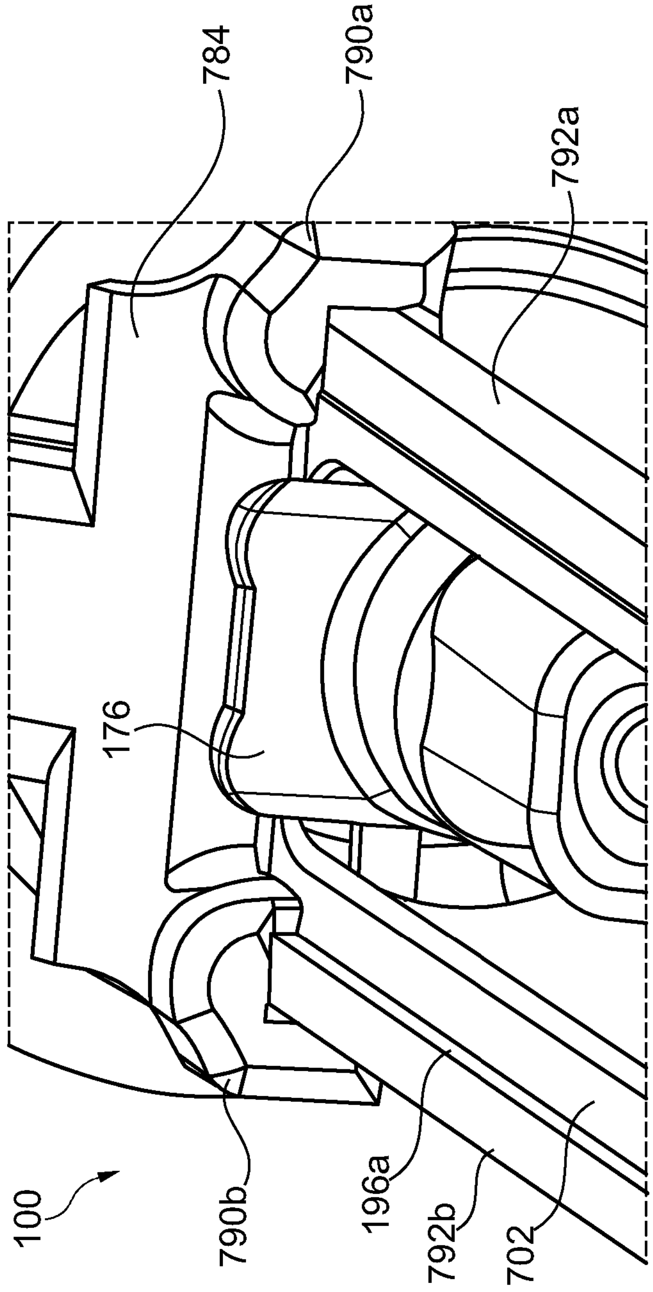
FIG. 68 is an enlarged view of clamps of a catheter hub pusher and a catheter hub with a push tab of the extended dwell catheter assembly of FIG. 66.

With reference now to FIG. 68, an enlarged view of sections of the catheter hub 130 and the pusher 784 of the ExD catheter assembly 100 is shown. The pusher 784 may have a pair of legs 790*a*, 790*b*, one at each end of the hat of its T-shape. The legs 790*a*, 790*b* may have hook shapes. The hook shape of the legs 790*a*, 790*b* may slidably engage with tracks 792*a*, 792*b* of the housing 102, respectively. The tracks 792*a*, 792*b* may extend along each side of the upper body opening 196*a*. The pusher 784 may be slid on the tracks 792*a*, 792*b* in a distal direction to first engage with the push tab 176 of the catheter hub 130 and then push the catheter hub towards the nose section 184*a*.

Figure 69:
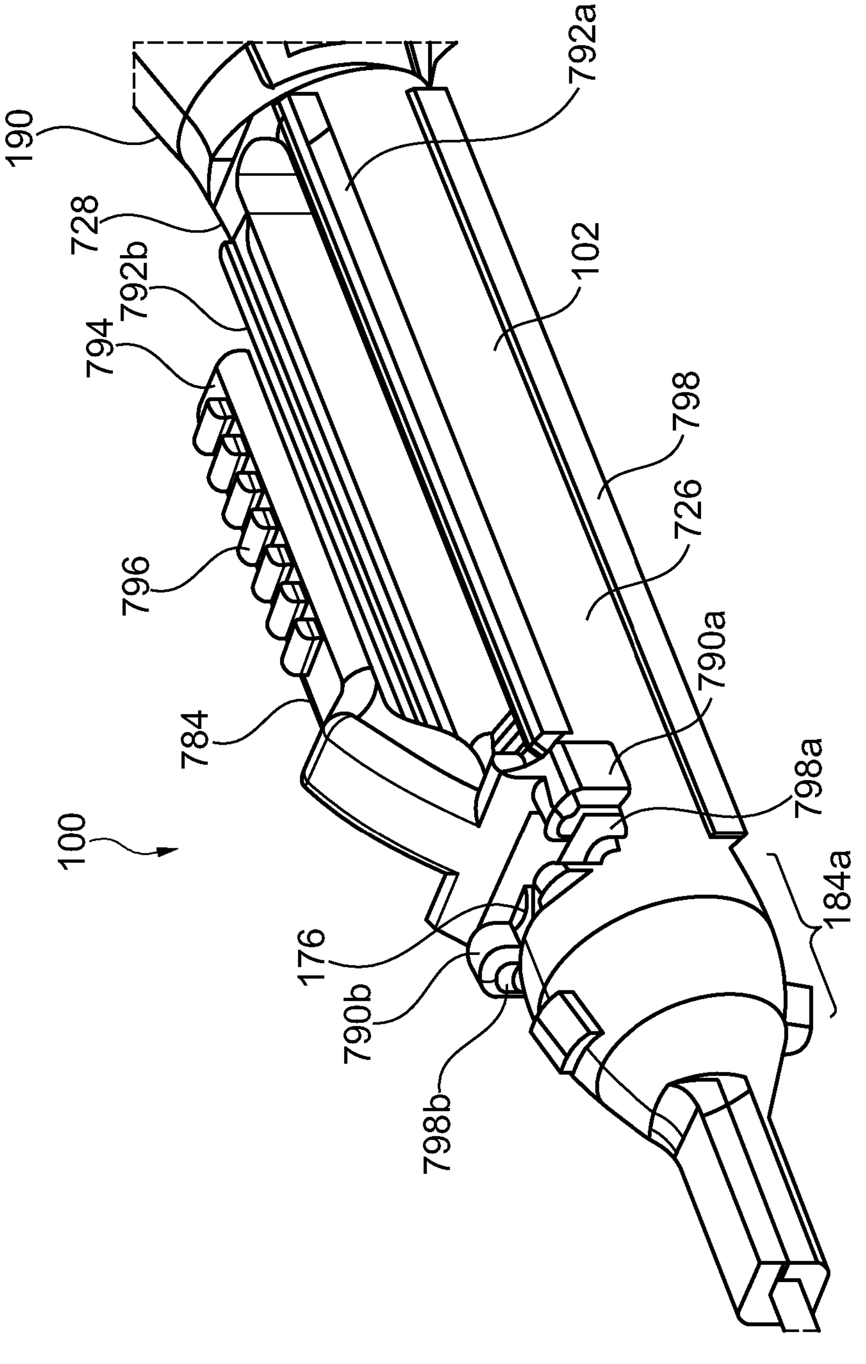
FIG. 69 is a partial perspective view of the extended dwell catheter assembly of FIG. 66 with the catheter hub pusher and the catheter hub in a distal position.

With reference now to FIG. 69, the pusher 784 of the ExD catheter assembly 100 in a fully advanced or distal position is shown. In this position, the push tab 176 may be sandwiched between the nose section 184*a* and the pusher 784 The pusher 784 may be slid to this position by holding and guiding the pusher 784 from a handle 794. The handle 794 may be leveled above the legs 790*a*, 790*b*. The handle 794 being further out from the housing 102 may make it easier to grip the pusher 784 as well as allow the handle 794 of the pusher 784 to sit above the base 190 when in a proximal position. The handle 794 may have protrusions 796 for increased grip. In the distal position, each leg of the legs 790*a*, 790*b* may be above a track end of track ends 798*a*, 798*b*. The track ends 798*a*, 798*b* may be recesses between the nose section 184*a* and the tracks 792*a*, 792*b* on each side of the upper body opening 196*a*. The track ends 798*a*, 798*b* may be dimensioned so that the hook-like legs 790*a*, 790*b* of the pusher 794 do not grab onto the housing 102 and have space to be detached from the housing 102. The first and second frames 726, 728 may each have grips 798 (only one shown) that extend across the nose section 184*a* and the base 190. The grips 798 may be used to hold the catheter assembly 100 with one hand while pushing or removing the pusher 784 with the other hand.

Figure 70:
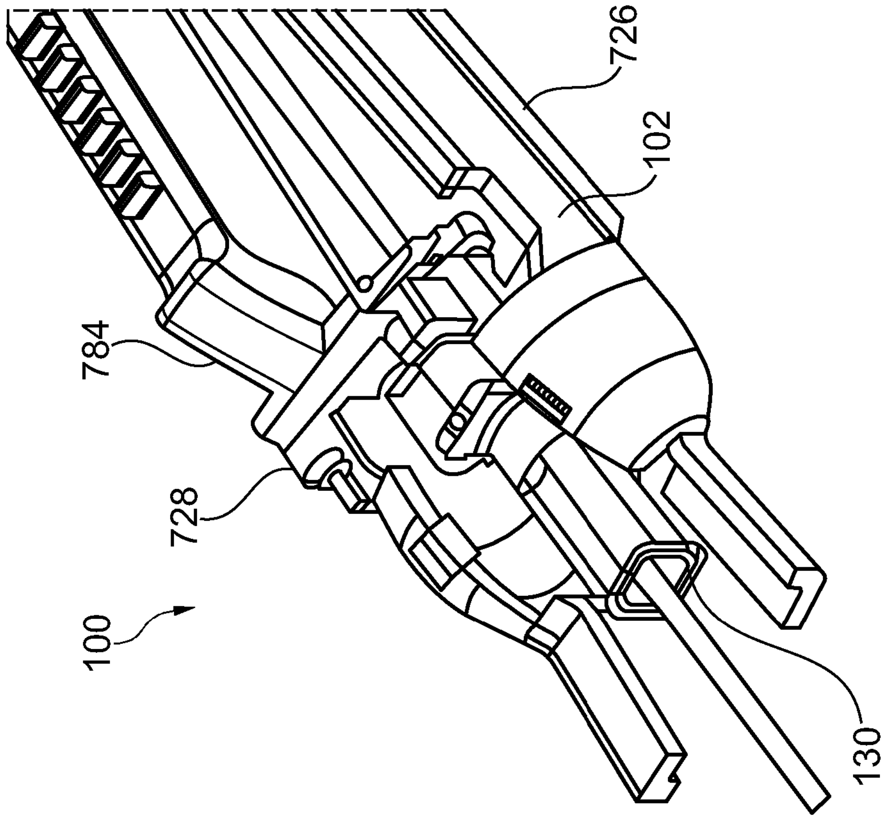
FIG. 70 is a partial perspective view of the extended dwell catheter assembly of FIG. 66 with the housing component in an open position and the catheter hub pusher removed from the housing component.

With reference now to FIG. 70, the housing 102 of the ExD catheter assembly 100 in an open position and the pusher 784 being removed from the housing 102 are shown. The opening between the first and second frames 726, 728 may decrease proximally due to the pivot point clamp-shaft coupling 780 (see FIG. 66) being located in a proximal section of the housing 102. The pusher 784 and the housing 102 may be discarded, and the catheter hub 130 may be left attached to the patient.

Figure 71:
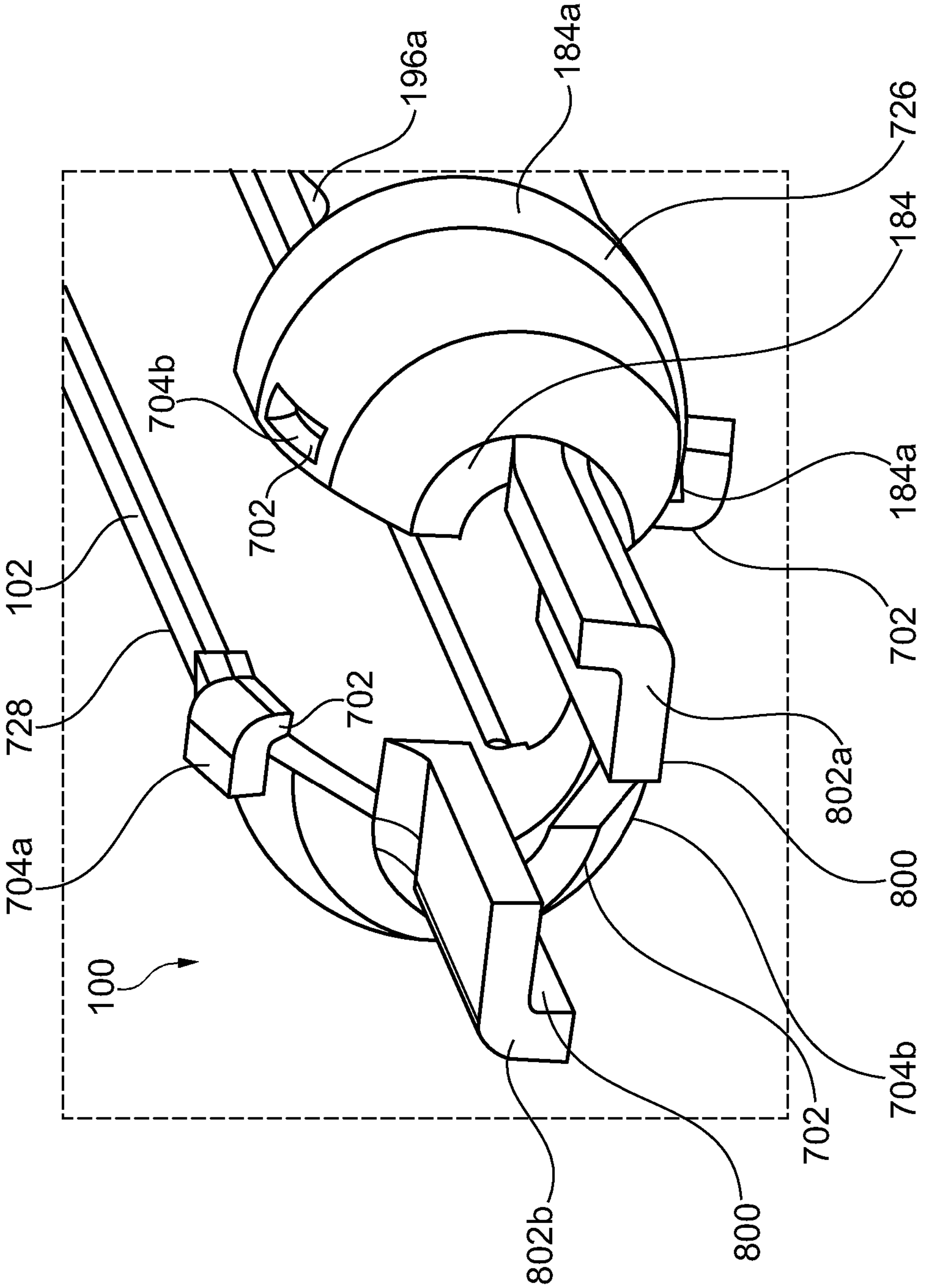
FIG. 71 is an enlarged perspective view of a distal end of the housing component of the dwell catheter assembly of FIG. 66.

With reference now to FIG. 71, a section of the ExD catheter assembly 100 is shown with the housing 102 in an open position from a distal angle. At the most distal end of the housing 102, a tip 800 may extend out of a nose end 184. The tip 800 may have two separable sections 802*a*, 802*b*, one at each of the first and second frames 726, 728, respectively. The sections 802*a*, 802*b* may form a double butt lap joint when the housing 102 is closed. The section 802*b* of the tip 800 may be on top of the section 802*a* when joined together. In other embodiments, the section 802*a* may be on top of the section 801*b* when joined together. A lock 702 may serve as additional reinforcement to keep the sections 802*a*, 802*b* joined, and generally the first and second frames 726, 728 intact. The lock 702 may interrupt the upper seam 276. The lock 702 may be located on the nose section 184*a* of the housing 102 between the nose end 184 and the upper body opening 196*a*. In some embodiments, there may be a plurality of locks 702. In such embodiments, one of the locks 702 may be between the nose end 184 and the lower body opening 196*b*. In some embodiments, the lock 702 may be a detent engagement of the first and second frames 726, 728. In some embodiments, the detent engagement may be disengaged by squeezing the curved based ends 782*a*, 782*b* (see FIG. 66) together. The resulting radial forces on the housing 102 may lift up and free a male detent 704*a* from a female detent 704*b*. In some embodiments, the male detent 704*a* may be on the second frame 728 and the female detent 704*b* may be on the first frame 726. In some embodiments, the male detent 704*a* may be on the first frame 726 and the female detent 704*b* may be on the second frame 728. In embodiments having a plurality of locks 702, the male and female detents 704*a*, 704*b* may each alternate between the first and second frames 726, 728.

Figure 72:
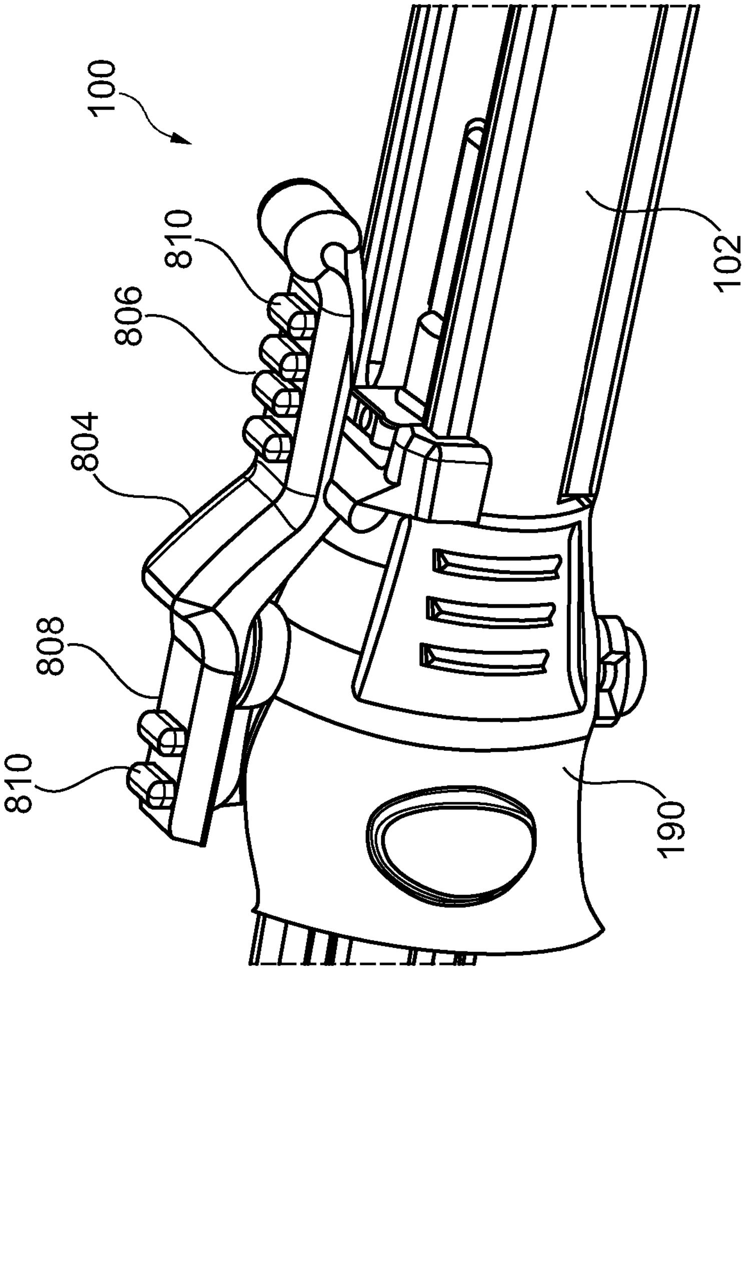
FIG. 72 is an enlarged perspective view of a proximal end of the housing component of the dwell catheter assembly of FIG. 66 featuring another embodiment of the catheter hub pusher.

With reference now to FIG. 72, a pusher 804 attached to the ExD catheter assembly 100 is shown. The pusher 804 may be similar to the pusher 784 of FIG. 66 and may replace the pusher 784. The pusher 804 may have a distal handle 806 and a proximal handle 808. The distal and proximal handles 806, 808 may provide multiple options for holding the pusher 804. Depending on the user's hand size or position of the catheter assembly 100 relative to the user or the patient, holding the pusher 804 from the distal handle 806 or the proximal handle 808 may be easier. The proximal handle 808 may be elevated relative to the distal handle 806. The elevated position of the proximal handle 808 may allow it to sit on the base 190 of the housing 102 when the pusher 804 is in a proximal position. The distal and proximal handles 806, 808 may be the same size or different sizes. The distal and proximal handles 806, 808 may each have a grip or grips 810 protruding from thereon. The distal handle 806 may have a tip 812 extending distally therefrom. The tip 812 may be curved upwards. The curvature of the tip 812 may allow the user's finger to engage with the distal handle 806 without slipping and leverage the tip 812 when sliding the pusher 804 in a distal direction.

Figure 73:
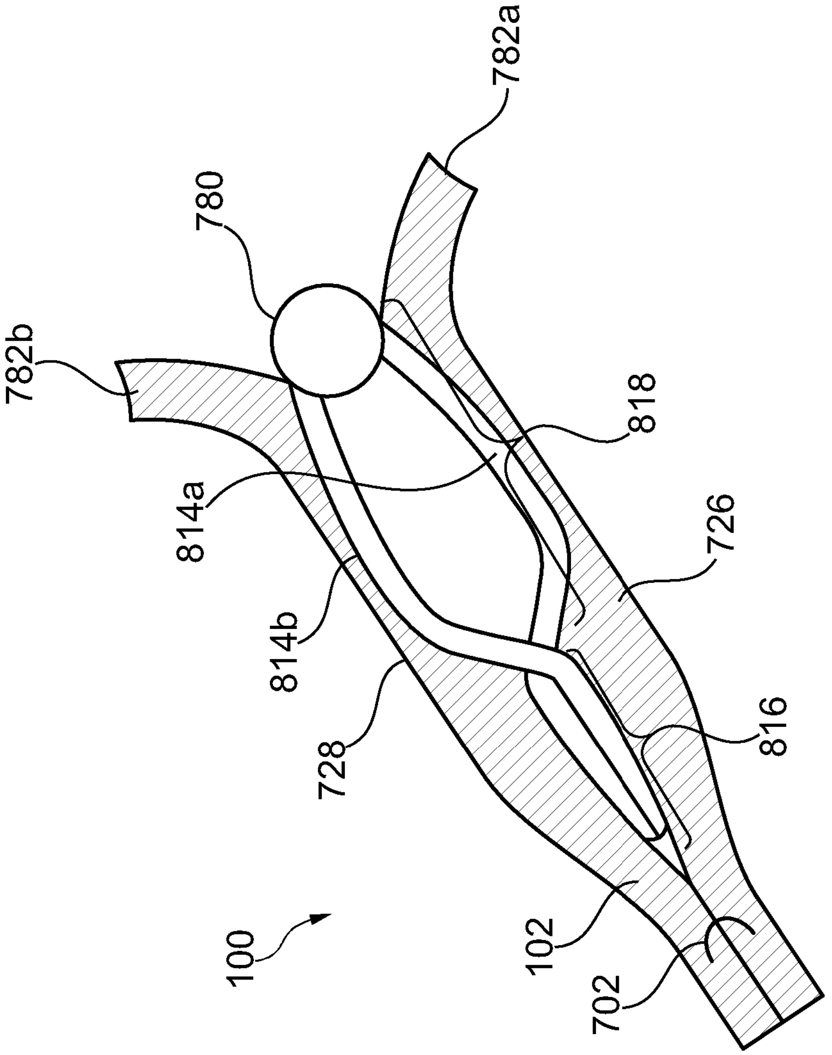
FIG. 73 is a top view of an extended dwell catheter assembly provided in accordance with further aspects of the present invention.

With reference now to FIG. 73, a top view of an ExD catheter assembly 100 is shown. The ExD catheter assembly 100 can be similar to one of the ExD catheter assemblies disclosed elsewhere herein, such as the assembly 100 of FIG. 66. A housing 102 of the ExD catheter assembly 100 may be constructed from separate parts. The housing 102 may have a first frame 726 and a second frame 728. The first and second frames 726, 728 may be held together by clamp-shaft coupling 780. A first arm 814*a* and a second arm 814*b* may be pivotably attached to the clamp-shaft coupling 780. The first and second arms 814*a*, 814*b* may overlap each other. Due to the overlap, the first and second arms 814*a*, 814*b* may resemble a pair of scissors. The first and second arms 814*a*, 814*b* may have a distal section 816 and a proximal section 818. The distal section 816 may be within an interior space 104 of the housing 102 while the proximal section 818 may be extending out of the interior space 104. (see FIG. 73) The distal section 816 may push the first and second frames 726, 728 apart when the first and second arms 814*a,b* pivot away from each other at the clamp-shaft coupling 780 to open the housing 102 when ends 782*a*, 782*b* of the housing 102 are squeezed. The first and second arms 814*a*, 814*b* may make opening the housing 102 is easier by providing additional leverage. Lock or locks 702 keeping the first and second frames 726, 728 intact may be easier to unlock due to the radial forces applied on the housing 102 by the first and second arms 814*a*, 814*b*.

Figure 74:
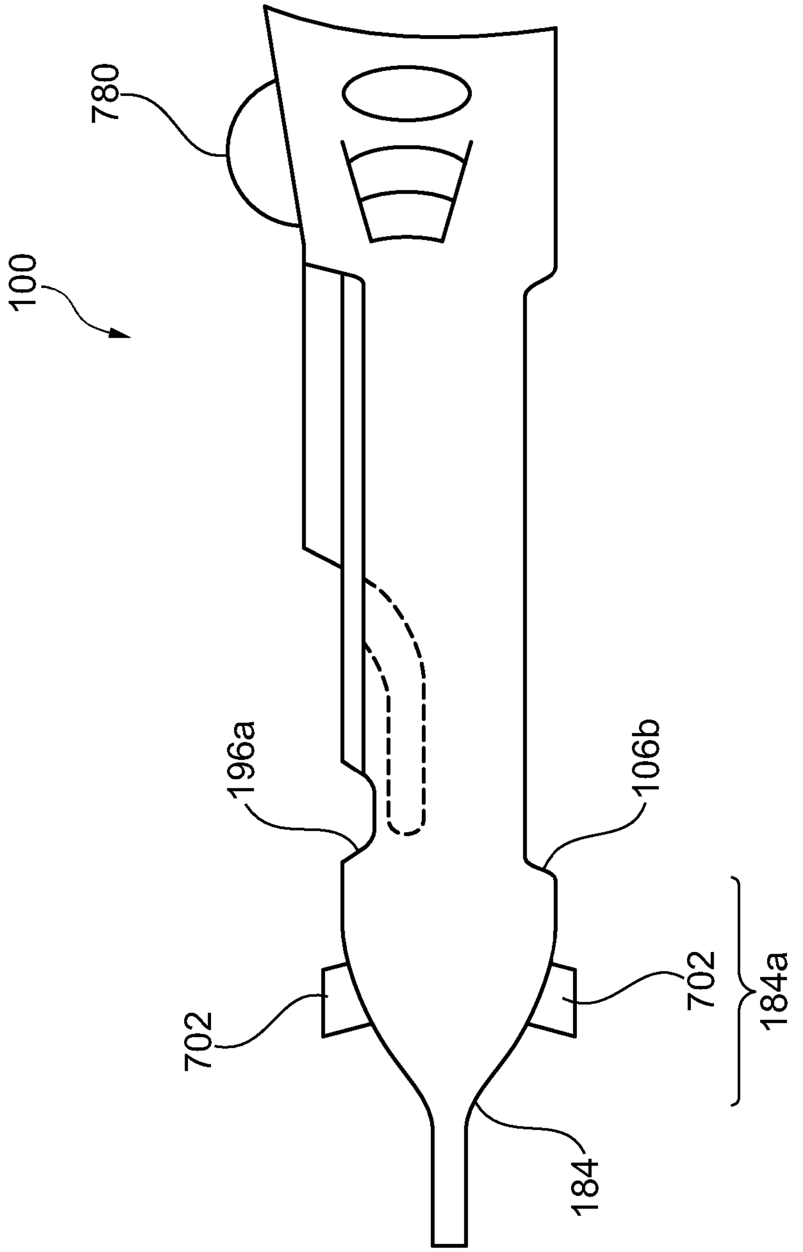
FIG. 74 is a side view of the extended dwell catheter assembly of FIG. 73.

With reference now to FIG. 74, a side view of the ExD catheter assembly 100 is shown. The distal section 816 of the first and second arms 814*a*, 814*b* within the interior space 104 of the housing 102 is shown with dashed lines. The clamp-shaft coupling 780 may be larger in size than in the catheter assembly 100 of FIG. 66. The larger size may allow for the first and second arms 814*a*, 814*b* to pivot with less application of force. A plurality of locks 702 is shown, one located on a nose section 184*a* of the housing 102 between a nose end 184 and an upper body opening 196*a* and another between the nose end 184 and a lower body opening 196*b*.

Figure 75:
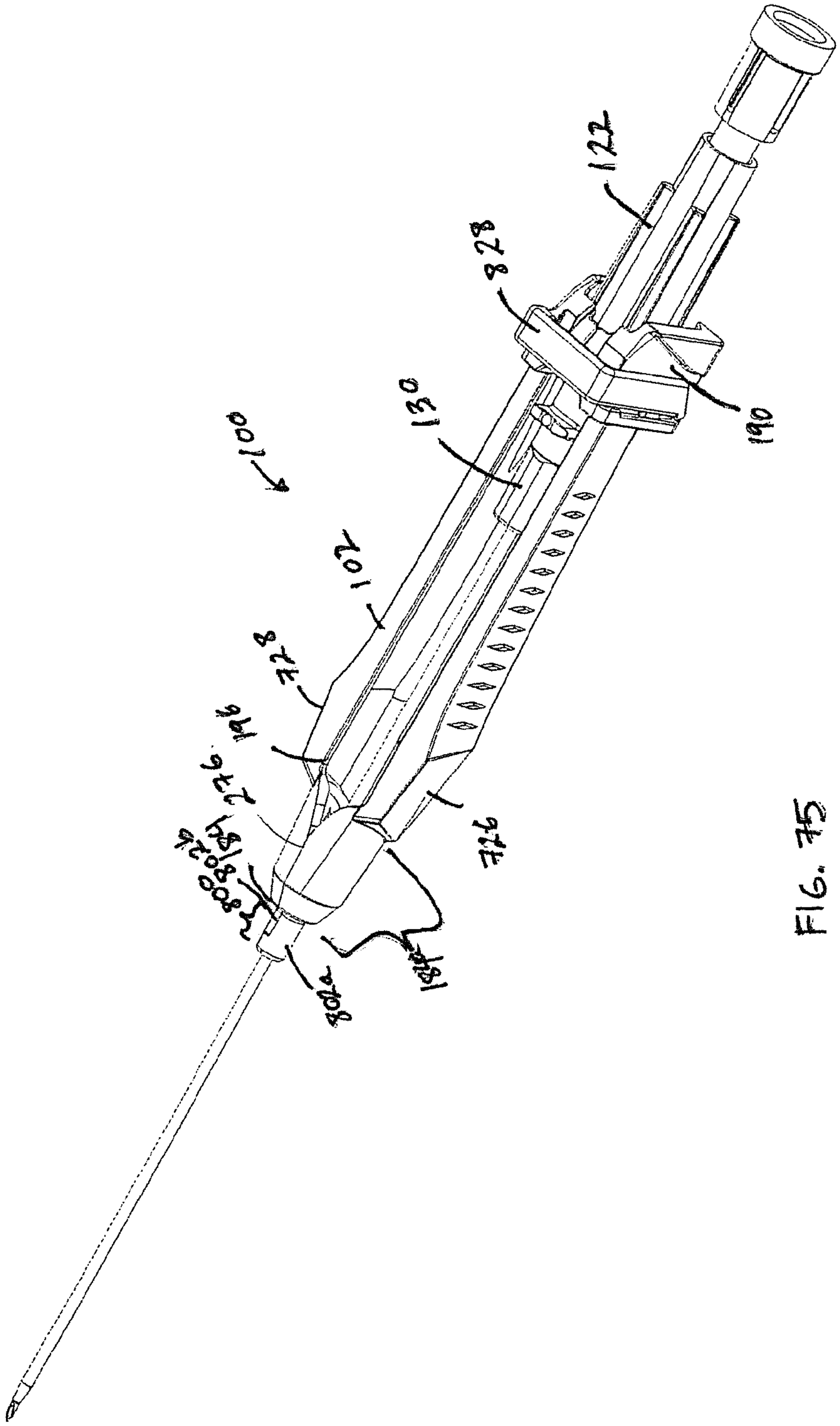
FIG. 75 is a perspective view of an extended dwell catheter assembly provided in accordance with further aspects of the present invention.

With reference now to FIG. 75, a perspective view of an ExD catheter assembly 100 is shown. The ExD catheter assembly 100 can be similar to one of the ExD catheter assemblies disclosed elsewhere herein, such as the assemblies 100 of FIGS. 1 and 55. A housing 102 of the ExD catheter assembly 100 may be constructed from separate parts. The housing 102 may have a first frame 726 and a second frame 728. The first and second frames 726, 728 may have an upper seam 276 and a lower seam 278 (see FIG. 76). The upper seam 276 may be at a nose section 184*a* of the housing 102. The upper seam 276 may curve out and widen into a body opening 196. At the most distal end of the housing 102, a tip 800 may extend out of a nose end 184. The tip 800 may have two separable sections 802*a*, 802*b*, one at each of the first and second frames 726, 728, respectively. The sections 802*a*, 802*b* may form two finger joints, one extending from the upper seam 276 and one extending from the lower seam 278, when the first and second frames 726, 728 are intact. The first and second frames 726, 728 may be held together by a bottom plate 820 (see FIG. 79). The bottom plate 820 may have long tabs 822*a*, 822*b* engageable with slots 826*a*, 828*a* of the first frame 726, respectively, and short tabs 824*a*, 824*b* engageable with slots 826*b*, 828*b* of the second frame 728, respectively. (see FIG. 77) A latch 828 pivotably attachable to the bottom plate 820 and the first frame 726 may pull the bottom plate 820 in a proximal direction when activated, thereby releasing the short tabs 824*a*, 824*b* from their slots 826*b*, 828*b*. At the same time, the long tabs 822*a*, 822*b* may still be engaged to the slots 826*a*, 828*a*, and thus the second frame 728 may separate from the first frame 726, which remains attached to the bottom plate 820 and the latch 828. The latch 828 may go over a base 190 of the housing 102. A needle hub 122 may be ejected proximally out of the base 190 once a catheter hub 130 is pushed to a distal position.

Figure 76:
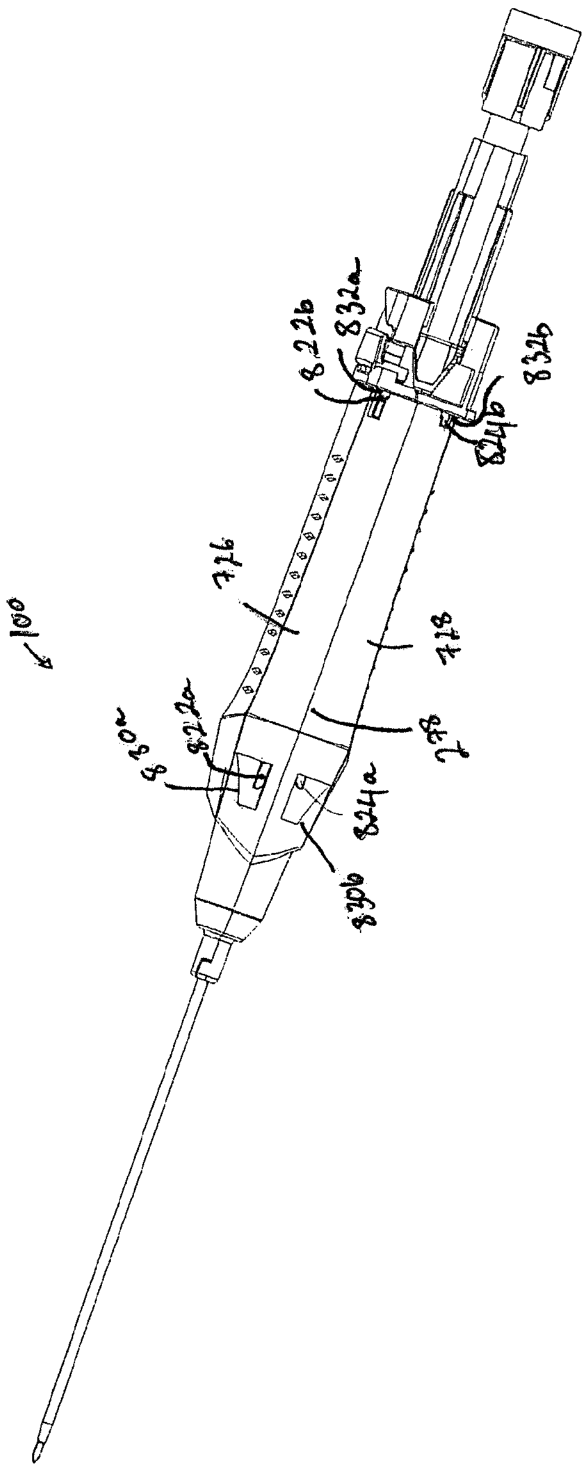
FIG. 76 is a bottom perspective view of the extended dwell catheter assembly of FIG. 75.

With reference now to FIG. 76, a bottom view of the ExD catheter assembly 100 is shown. The long tab 822*a* and the short tab 824*a* may be distal to the long tab 822*b* and the short tab 824*b*. The long tab 822*a* and the short tab 824*a* may extend out of their respective slots 826*a,b* (see FIG. 77) out to a first frame distal slot recess 830*a* and a second frame distal slot recess 830*b* when engaged with the first and second frames 726, 728, respectively. The first and second frame distal slot recesses 830*a*, 830*b* may have the same dimensions. The first and second frame distal slot recesses 830 may have a trapezoidal shape. Other shapes are also contemplated, for example, rectangular, square, and triangular. The long tab 822*b* and the short tab 824*b* may extend out of their respective slots 828*a*, 828*b* (see FIG. 77) out to a first frame proximal slot recess 832*a* and a second frame proximal slot recess 832*b* when engaged with the first and second frames 726, 728, respectively. The first frame proximal slot recess 832*a* may be dimensioned larger than the second frame proximal slot recess 832*b*. The larger dimensions of the first frame proximal slot recess 832*a* may accommodate the long tab 822*b*. The first and second frame proximal slot recesses 832*a*, 832*b* may provide a snug fitment for the tabs 822*b*, 824*b*. In other embodiments, the first and second frame proximal slot recesses 832*a*, 832*b* may have the same dimensions. In such embodiments, fitment of the tab 824*b* may not be snug.

Figure 77:
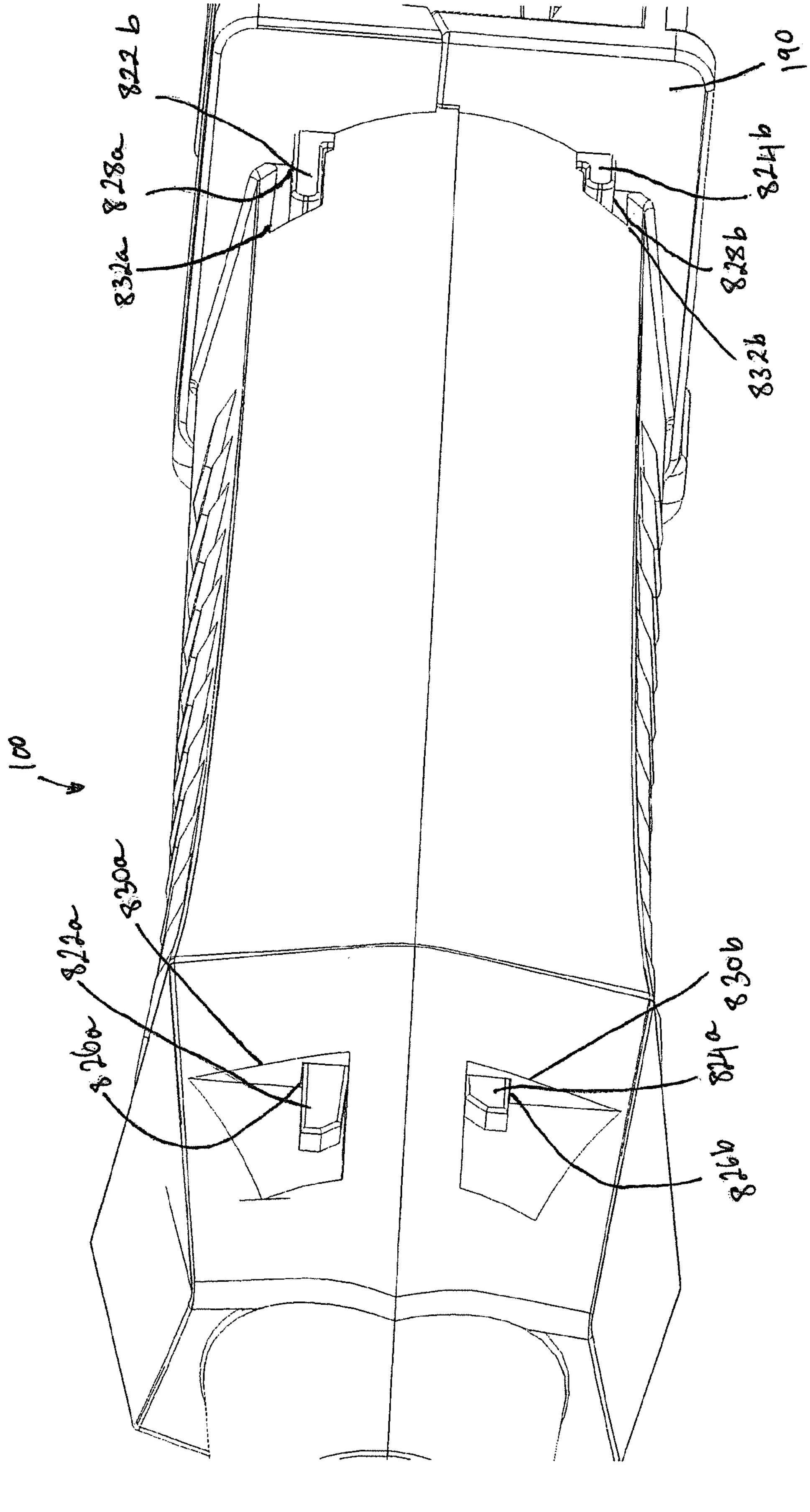
FIG. 77 is an enlarged bottom perspective view of the extended dwell catheter assembly of FIG. 75.

With reference now to FIG. 77, an enlarged bottom view of the ExD catheter assembly 100 is shown. The tabs 822*a*, 824*a* may have chamfered distal ends. The tabs 822*b*, 824*b* may have rounded distal ends. In other embodiments, all distal ends may be rounded, chamfered, or squared off. The slots 826*a*, 826*b*, 828*a*, 828*b* may have widths just enough to accommodate their respective tabs 822*a*, 824*a*, 822*b*, 824*b*. The tabs 822*b*, 824*b* may be directly adjacent to the base 190.

Figure 78:
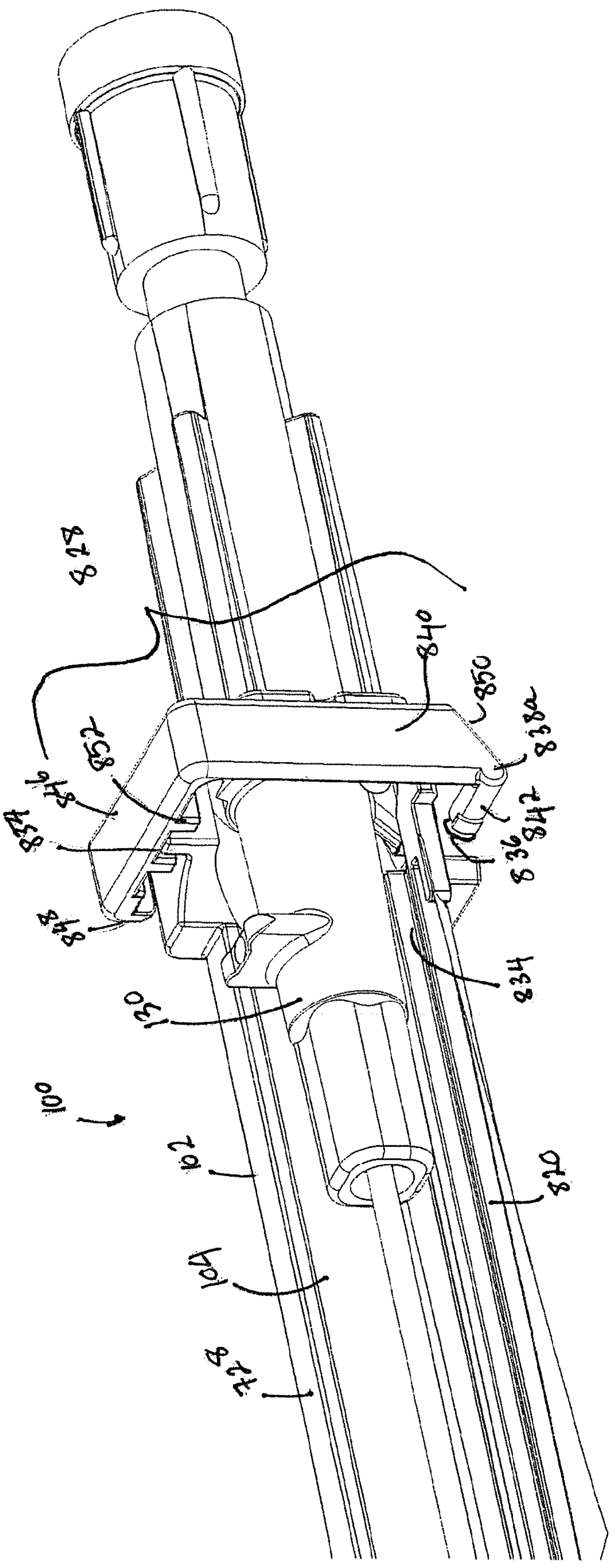
FIG. 78 is a section view of the extended dwell catheter assembly of FIG. 75 without a first housing component frame.

With reference now to FIG. 78, a proximal section of the ExD catheter assembly 100 without the first frame 726 (see FIG. 75) is shown. The bottom plate 820 may lay inside an interior space 104 of the housing 102 under the catheter hub 130. The tabs 822*a*, 822*b* engageable with the first frame 726 and the tabs 824*a*, 824*b* engageable with the second frame 728 may be separated by a groove 834. The groove 834 may run along an entire length of the bottom plate 820 on its surface facing up, or toward the catheter hub 130 when assembled. The latch 828 may pivotably connect with the first frame 726 from under the bottom plate 820. The connection may be facilitated with a connection pin 836. The connection pin 836 may extend out inwards, or towards the interior space 104, from a distal bottom corner 838*a* of a first side 840 of the latch 828. The connection pin 836 may have a generally cylindrical shape with a protrusion 842 on its outer surface that extends along its length. The protrusion 842 may engage with a slot (not shown) inside the base 190 of the first frame 726 that limits the rotation of the connection pin 836 to allow the latch 828 to pivot only a certain amount in the proximal direction. The latch 828 may have a top 846 and a second side 848. The top 846 may have teeth 852 that extend down from an inside surface facing the base 190 when assembled. The teeth 852 may form a finger joint with an opposing tooth 854 that goes in between the teeth 852. A first half of the tooth 854 may be on the first frame 726 (not shown) and a second half may be on the second frame 728. In some embodiments, there may be a plurality of teeth 854 receivable by multiple sets of the teeth 852. The top 846 and the first side 840 may extend across an entirety of a height and width of the base 190. The second side 848 may partially extend across the height of the base 190. The first side 840 may have a proximal bottom corner 838*b*. An edge 850 may extend across bottom corners 838*a*, 838*b*. The edge 850 may be sloped, the proximal bottom corner 838*b* being higher, elevation-wise, than the distal bottom corner 838*a*.

Figure 79:
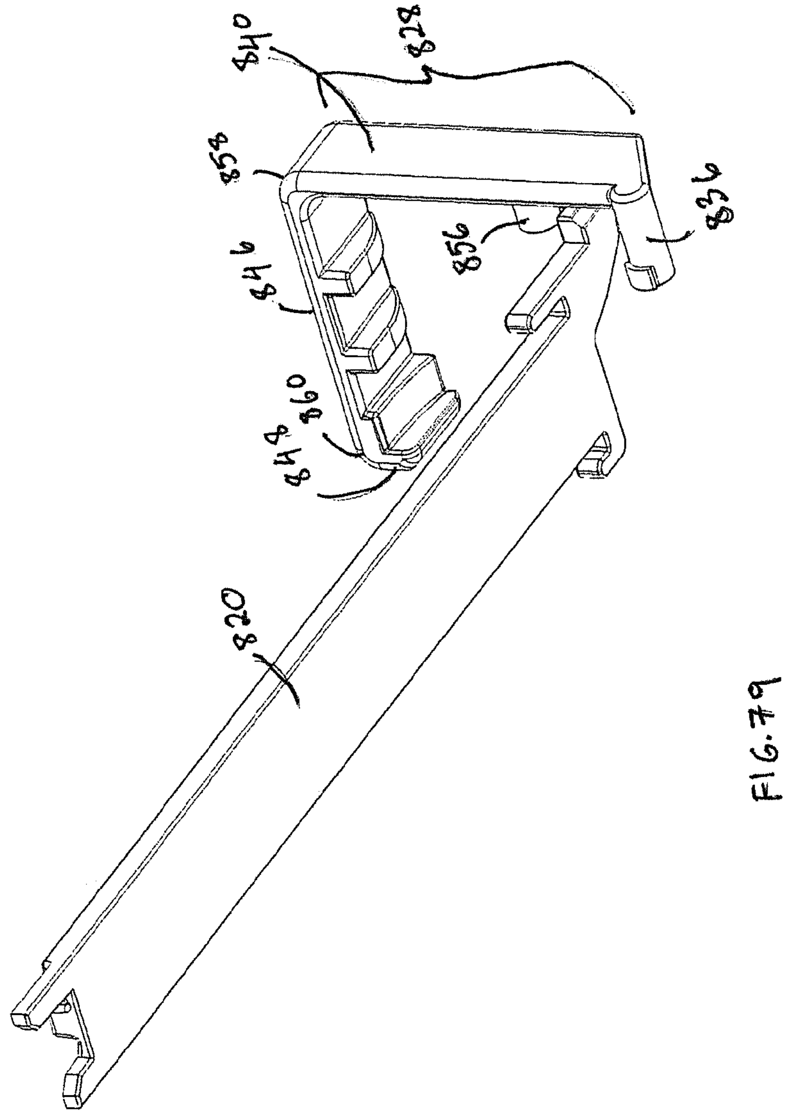
FIG. 79 is an isolated perspective view of a latch and a bottom plate of the extended dwell catheter assembly of FIG. 75.

With reference now to FIG. 79, the bottom plate 820 and the latch 828 are shown. The latch 828 may be movably connected to the bottom plate 820 with a shaft 856 extending inwards, or towards the base 190 (see FIG. 78). The shaft 856 may be cylindrical. The shaft 856 may move laterally in a proximal direction when the latch 828 is pulled in the same direction. The lateral movement of the shaft 856 may be limited by the limited rotation of the connection pin 836 as explained in discussing FIG. 78. The first and second sides 840, 848 of the latch 828 may form filleted corners 858, 860 with the top 846 of the latch 828, respectively. In other embodiments, the corners 858, 860 may be straight.

Figure 80:
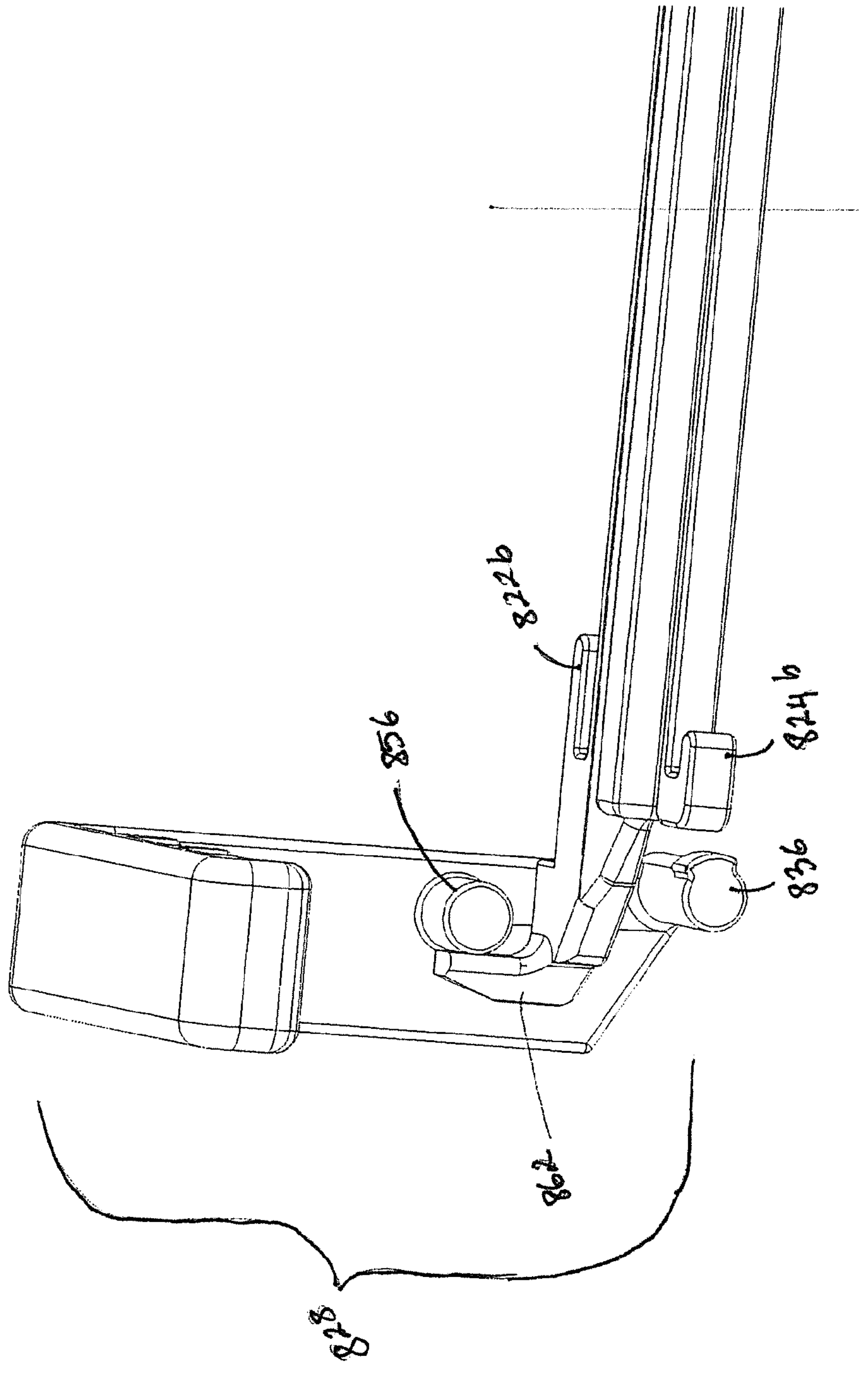
FIG. 80 is an isolated side view of the latch and bottom plate of the extended dwell catheter assembly of FIG. 75

With reference now to FIG. 80, a section view of the bottom plate 820 and the latch 828 are shown. The bottom plate may have a proximal hook 862 attached to the shaft 856 of the latch 828. When the latch 828 is pulled in a proximal direction, the shaft 856 may pull the bottom plate 820 proximally from the proximal hook 862. When the bottom plate 820 is pulled in a proximal direction, the short tab 824*b* and the short tab 824*a* (see FIG. 77) will disengage with their respective slots 828*b*, 826*b* (see FIG. 77) while the long tab 822*b* and the long tab 822*a* (see FIG. 77) remain engaged with their respective slots 828*a*, 826*a* (see FIG. 77). As a result, the second frame 728 (see FIG. 75) will detach from the first frame 726 (see FIG. 75), which will remain attached to the latch 828 and the bottom plate 820. The first and second frames 726, 728 may be separated from the catheter hub 130 (see FIG. 78), which may remain attached to the patient. The first and second frames 726, 728 may then be discarded.

Methods of making and of using the extended dwell catheter assemblies and components thereof are within the scope of the present invention.

Although limited embodiments of the extended dwell catheter assemblies and their components have been specifically described and illustrated herein, many modifications and variations will be apparent to those skilled in the art. For example, the locations and placements of the male and female detents can be reversed at the joining edges, the gripping surfaces can be non-symmetrical, and the materials can be modified, such as with insert molding or co-molding. Accordingly, it is to be understood that the extended dwell catheter assemblies and their components constructed according to principles of the disclosed device, system, and method may be embodied other than as specifically described herein. The disclosure is also defined in the following claims.

What is claimed is:

1. An extended dwell catheter assembly comprising:

a housing comprising a first frame attached to a second frame and having an interior space, said housing having a distal opening and a proximal opening;

a catheter assembly located in the interior space of the housing, said catheter assembly comprising a catheter tube attached to a catheter hub and a needle attached to a needle hub, wherein the needle and the catheter tube project out the distal opening of the housing and the needle hub projects out the proximal opening of the housing, and wherein the catheter hub is slidable within the interior space of the housing from a proximal position to a distal position within the interior space;

an upper seam located between the first frame and the second frame along a first side of the housing and a lower seam located between the first frame and the second frame along a second side of the housing, the upper seam located above, elevation-wise, the lower seam; and wherein the first frame and the second frame are separable from one another along the upper seam and the lower seam.

2. The extended dwell catheter assembly of claim 1, wherein the catheter hub comprises an interior cavity and wherein a needle guard comprising a proximal wall and two arms is located in the interior cavity of the catheter hub.

3. The extended dwell catheter assembly of claim 1, wherein the first frame or the second frame comprises a plurality of tabs and the other one of the first frame or the second frame comprises a plurality of receiving slots engaging the plurality of tabs.

4. The extended dwell catheter assembly of claim 1, wherein the housing comprises a base end comprising a plurality of side walls.

5. The extended dwell catheter assembly of claim 4, further comprising a first lever and a second lever, the first lever and the second lever projecting from different surfaces of base end of the housing.

6. The extended dwell catheter assembly of claim 5, wherein the first lever is attached to a three-sided cut-out on the second frame.

7. The extended dwell catheter assembly of claim 6, wherein the second lever comprises a curved proximally facing surface.

8. The extended dwell catheter assembly of claim 5, wherein the first lever and the second lever move relative to one another to separate the first frame and the second frame.

9. The extended dwell catheter assembly of claim 1, wherein the housing comprises a body opening and wherein a push tab on the catheter hub is located in the body opening.

10. The extended dwell catheter assembly of claim 1, wherein the first frame comprises a gate having a living hinge and the second frame comprises a gate having a living hinge.

11. The extended dwell catheter assembly of claim 10, wherein a tab engages a recess to engage two end cap components at a distal end of the housing.

12. The extended dwell catheter assembly of claim 1, wherein the first frame has an activation structure and the second frame has an activation structure and wherein a gap defined by the two activation structures are sized and shaped to be pushed by the catheter hub to separate the first frame from the second frame.

13. The extended dwell catheter assembly of claim 1, further comprising a tab adapter fitted around the catheter hub.

14. The extended dwell catheter assembly of claim 1, further comprising a guidewire extending through the needle.

15. The extended dwell catheter assembly of claim 1, further comprising a vent plug attached to the needle hub, the vent plug comprising a vent filter.

16. The extended dwell catheter assembly of claim 15, wherein the vent plug is entirely located externally of the housing.

17. A method of manufacturing an extended dwell catheter assembly comprising:

forming a housing, the housing comprising a first frame attached to a second frame and having an interior space, said housing having a distal opening and a proximal opening, an upper seam located between the first frame and the second frame along a first side of the housing and a lower seam located between the first frame and the second frame along a second side of the housing, the upper seam located above, elevation-wise, the lower seam;

placing a catheter assembly in the interior space of the housing, said catheter assembly comprising a catheter tube attached to a catheter hub and a needle attached to a needle hub, wherein the needle and the catheter tube project out the distal opening of the housing and the needle hub projects out the proximal opening of the housing, and wherein the catheter hub is slidable within the interior space of the housing from a proximal position to a distal position within the interior space; and wherein the first frame and the second frame are separable from one another along the upper seam and the lower seam.

18. The method of claim 17, wherein the first frame and the second frame are separable by moving the first frame in a first direction and the second frame in a second direction.

19. The method of claim 17, wherein the first frame and the second frame are separable by advancing the catheter hub in a distal direction to push apart two activation structures located inside the interior space of the housing.

20. The method of claim 17, wherein the catheter hub is separable from the housing by displacing two end cap components about two living hinges.

21. The method of claim 17, further comprising a vent plug attached to the needle hub, the vent plug comprising a vent filter.

22. The method of claim 21, wherein the vent plug is entirely located externally of the housing.

23. An extended dwell catheter assembly comprising:

a housing comprising a first frame attached to a second frame and having an interior space, said housing having a distal opening and a proximal opening;

a catheter assembly located in the interior space of the housing, said catheter assembly comprising a catheter tube attached to a catheter hub and a needle attached to a needle hub, wherein the needle and the catheter tube project out the distal opening of the housing and the needle hub projects out the proximal opening of the housing, and wherein the catheter hub is slidable within the interior space of the housing from a proximal position to a distal position within the interior space; and a gate assembly attached to the housing, the gate assembly comprising a first gate attached to a living hinge and a second gate attached to a living hinge;

wherein the first gate and the second gate are rotatable about the two living hinges to open the two gates for separating the catheter assembly from the housing.

24. The extended dwell catheter assembly of claim 23, further comprising a tie strip connecting the first gate and the second gate together.

25. The extended dwell catheter assembly of claim 24, wherein the gate assembly comprises a key comprising a flange for attaching to a slot on the housing.

26. The extended dwell catheter assembly of claim 23, further comprising a vent plug attached to the needle hub, the vent plug comprising a vent filter.

27. The extended dwell catheter assembly of claim 26, wherein the vent plug is entirely located externally of the housing.

* * * * *